(12) United States Patent
Suzuki et al.

(10) Patent No.: US 8,648,103 B2
(45) Date of Patent: Feb. 11, 2014

(54) NITROGEN-CONTAINING AROMATIC HETEROCYCLYL COMPOUND

(75) Inventors: Keiko Suzuki, Tokyo (JP); Takahiro Yamaguchi, Tokyo (JP); Akihiro Tamura, Kanagawa (JP); Tomohiro Nishizawa, Tokyo (JP); Mitsuhiro Yamaguchi, Tokyo (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 166 days.

(21) Appl. No.: 13/001,806

(22) PCT Filed: Jul. 7, 2009

(86) PCT No.: PCT/JP2009/062331
§ 371 (c)(1),
(2), (4) Date: Dec. 29, 2010

(87) PCT Pub. No.: WO2010/004972
PCT Pub. Date: Jan. 14, 2010

(65) Prior Publication Data
US 2012/0108639 A1    May 3, 2012

(30) Foreign Application Priority Data
Jul. 8, 2008  (JP) .................................. 2008-178377

(51) Int. Cl.
*A61K 31/427*  (2006.01)
*C07D 277/20*  (2006.01)
*A61K 31/422*  (2006.01)
*C07D 261/06*  (2006.01)

(52) U.S. Cl.
USPC ............ 514/365; 514/378; 548/205; 548/247

(58) Field of Classification Search
USPC .......................... 514/365, 378; 548/205, 247
See application file for complete search history.

(56) References Cited

U.S. PATENT DOCUMENTS 7,893,098 B2    2/2011  Fang

FOREIGN PATENT DOCUMENTS

| RU | 2 361 862 C2 | 7/2009 |
|---|---|---|
| WO | 2006/052555 A2 | 5/2006 |
| WO | 2006/052569 A1 | 5/2006 |
| WO | 2006/057922 A2 | 6/2006 |
| WO | 2006/085113 A2 | 8/2006 |
| WO | 2006/100106 A1 | 9/2006 |
| WO | 2007/002557 A1 | 1/2007 |
| WO | 2007/015744 A1 | 2/2007 |
| WO | 2007/060164 A1 | 5/2007 |
| WO | 2007/075749 A2 | 7/2007 |
| WO | 2007/092364 A2 | 8/2007 |
| WO | 2007/120575 A2 | 10/2007 |

OTHER PUBLICATIONS

Hotzel, Christian. Design, synthesis, DNA-binding and cytotoxicity evaluation of new potential combilexines. Eur. J. Med. Chem. 37 (2002) 367-378.*
International Search Report mailed Oct. 6, 2009, issued in corresponding International Application No. PCT/JP2009/062331, filed Jul. 7, 2009, 4 pages.
Havel, R.J., "Conversion of Plasma Free Fatty Acids Into Triglycerides of Plasma Lipoprotein Fractions in Man," Metabolism 10(12):1031-1034, Dec. 1961.
International Preliminary Report on Patentability [in Japanese], issued Jan. 11, 2011, in corresponding International Application No. PCT/JP2009/062331, filed Jul. 7, 2009, 7 pages.
Shen, H.C., et al., "Discovery of Biaryl Anthranilides as Full Agonists for the High Affinity Niacin Receptor," Journal of Medicinal Chemistry 50(25):6303-6306, Dec. 2007.
Shen, H.C., et al., "Discovery of Novel Tricyclic Full Agonists for the G-Protein-Coupled Niacin Receptor 109A With Minimized Flushing in Rats," Journal of Medicinal Chemistry 52(8):2587-2602, Apr. 2009.
Decision on Grant mailed Nov. 29, 2012, issued in corresponding Russian Application No. 2011104223, filed Jul. 7, 2009, 14 pages.

* cited by examiner

*Primary Examiner* — Samantha Shterengarts
(74) *Attorney, Agent, or Firm* — Christensen O'Connor Johnson Kindess PLLC

(57) ABSTRACT

The present invention provides a compound having excellent regulating action on blood lipid level that is represented by the following general formula (I) or a pharmacologically acceptable salt thereof, wherein, in one embodiment, A represents a 5-membered nitrogen-containing aromatic heterocyclyl group; $R^1$ represents COOH; each $R^2$ represents an alkyl; each $R^3$ represents an optionally substituted phenyl, an optionally substituted phenylalkyl; m represents 0, 1, 2, or 3; n represents 0 or 1; each of $R^4$, $R^5$, $R^6$, and $R^7$ represents H, an alkyl; and B represents an optionally substituted naphthyl, an optionally substituted aromatic heterocyclyl, or a group represented by the following formula (II) wherein each of $B^1$ and $B^2$ represents an optionally substituted phenyl or an optionally substituted aromatic heterocyclyl.

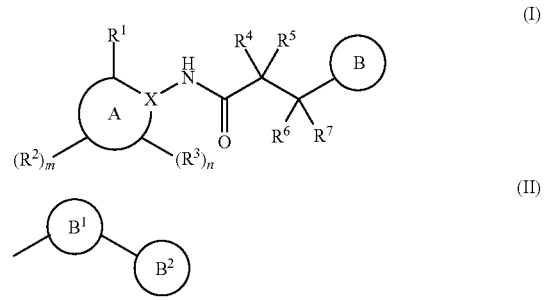

44 Claims, No Drawings

NITROGEN-CONTAINING AROMATIC HETEROCYCLYL COMPOUND

TECHNICAL FIELD

The present invention relates to a novel nitrogen-containing aromatic heterocyclyl compound or a pharmacologically acceptable salt thereof useful as a pharmaceutical agent, a pharmaceutical composition comprising the same as an active ingredient; or a method for the treatment or prophylaxis of a disease, which comprises administering a pharmaceutically effective amount of such compound or salt thereof to a warm-blooded animal; and the like.

BACKGROUND ART

Lipolysis in adipocytes has been known to cause an increase in the level of triglyceride (TG), low density lipoprotein (LDL), and the like (for example, see Non Patent Literature 1). Such abnormality in blood lipid levels causes hyperlipidemia, arteriosclerosis, diabetes, metabolic syndrome, and the like. Accordingly, suppression of lipolysis in adipocytes is useful for regulation of blood lipid levels, such as (i) an increase in the level of high density lipoprotein (HDL), or (ii) a decrease in the level of total cholesterol (TC), low density lipoprotein (LDL), very low density lipoprotein (VLDL), nonesterified fatty acid (NEFA), or triglyceride (TG). It is anticipated that a compound having lipolysis-suppressive activity will be useful for the treatment or prophylaxis of dyslipidemia with low HDL cholesterol, hypercholesterolemia, dyslipidemia with high LDL cholesterol, dyslipidemia with high VLDL cholesterol, dyslipidemia with high triglyceride (hypertriglyceridemia), hyperlipidemia, dyslipidemia, lipid metabolism abnormality, arteriosclerosis, type I diabetes mellitus, type II diabetes mellitus, metabolic syndrome, insulin resistance, cardiac failure, myocardial infarction, cardiovascular disease, coronary heart disease, apoplectic stroke, adiposity, angina, chronic renal failure, peripheral vascular disorder, non-alcoholic steatohepatitis, anorexia nervosa, metabolic syndrome, Alzheimer's disease, schizophrenia, amyotrophic lateral sclerosis, and the like, or for reduction in event occurrence or mortality due to cardiovascular disease or coronary heart disease (for example, see Example E of Patent Literature 7, or Example 4 of Patent Literature 8).

There is known an anthranilic acid derivative having regulating action on blood lipids level (for example, see Patent Literatures 1 to 7). However, the compound of the present invention differs from the above-described anthranilic acid derivative in terms of the structure of a heterocyclyl ring to which an amide group is bound.

PRIOR ART LITERATURE

Patent Literature

Patent literature 1: International publication pamphlet WO2006/052555 (US2007/0299101)
Patent Literature 2: International Publication Pamphlet WO2006/057922 (US2007/0281969)
Patent literature 3: International publication pamphlet WO2007/002557 (US2006/0293364)
Patent literature 4: International publication pamphlet WO2007/092364 (US2009/0062269)
Patent literature 5: International publication pamphlet WO2007/120575
Patent literature 6: International publication pamphlet WO2006/085113 (US2008/0200468)
Patent literature 7: International publication pamphlet WO2007/015744
Patent literature 8: International publication pamphlet WO2006/052569

Non Patent Literature

Non patent literature 1: Havel R J., Metabo Clin Exp, 1961, Vol. 10, pp. 1031-1036

SUMMARY OF THE INVENTION

Subject to be Solved by the Invention

The present inventors have conducted studies regarding compounds having excellent regulating action on blood lipid levels. As a result, the inventors have found that a nitrogen-containing aromatic heterocyclyl compound having a specific structure or a pharmacologically acceptable salt thereof has excellent properties such as lipolysis-suppressive activity, blood lipid level-regulating action (for example, reducing action on the level of NEFA or TG), in vivo activity, solubility, oral absorption property, metabolic stability, blood concentration, bioavailability (BA), tissue transitivity, physical stability, drug interaction, and safety [for example, flushing], and that such compound or salt thereof is useful as a pharmaceutical agent (preferably, a pharmaceutical agent for the treatment or prophylaxis of dyslipidemia or lipid metabolism abnormality). Based on the above-described findings, the present invention has been completed.

Solution to the Problem

The present invention provides: a novel nitrogen-containing aromatic heterocyclyl compound useful as a pharmaceutical agent, or a pharmacologically acceptable salt thereof;

a pharmaceutical composition comprising, as an active ingredient, the nitrogen-containing aromatic heterocyclyl compound or a pharmacologically acceptable salt thereof, preferably, a pharmaceutical composition for the treatment or prophylaxis of dyslipidemia with low HDL cholesterol, hypercholesterolemia, dyslipidemia with high LDL cholesterol, dyslipidemia with high VLDL cholesterol, dyslipidemia with high triglyceride (hypertriglyceridemia), hyperlipidemia, dyslipidemia, lipid metabolism abnormality, arteriosclerosis, type I diabetes mellitus, type II diabetes mellitus, insulin resistance, cardiac failure, myocardial infarction, cardiovascular disease, apoplectic stroke, adiposity, angina, chronic renal failure, peripheral vascular disorder, non-alcoholic steatohepatitis, anorexia nervosa, metabolic syndrome, Alzheimer's disease, schizophrenia, or amyotrophic lateral sclerosis, or for reduction in event occurrence or mortality due to cardiovascular disease or coronary heart disease, more preferably a pharmaceutical composition for the treatment or prophylaxis of hyperlipidemia, dyslipidemia, lipid metabolism abnormality, arteriosclerosis, or type II diabetes mellitus, and even more preferably a pharmaceutical composition for the treatment or prophylaxis (preferably, treatment) of dyslipidemia or lipid metabolism abnormality;

use of the nitrogen-containing aromatic heterocyclyl compound or a pharmacologically acceptable salt thereof in the manufacture of a pharmaceutical composition for the treatment or prophylaxis (preferably, treatment) of diseases (preferably, the above-described diseases);

a method for the treatment or prophylaxis (preferably, treatment) of diseases (preferably, the above-described diseases), which comprises administering a pharmaceutically effective amount of the nitrogen-containing aromatic heterocyclyl compound or a pharmacologically acceptable salt thereof to a warm-blooded animal (preferably, a human); and a method for the production of the nitrogen-containing aromatic heterocyclyl compound or a pharmacologically acceptable salt thereof.

In one aspect, the present invention provides the following.
(1) A compound represented by the following general formula (I) or a pharmaceutically acceptable salt thereof

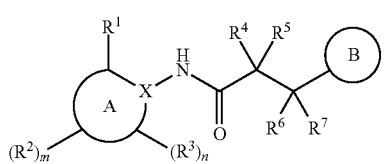

(I)

[wherein A including X represents a nitrogen-containing 5-membered aromatic heterocyclyl group, and X represents a carbon atom or a nitrogen atom, except that A is not a thiazolyl group, $R^1$ represents a carboxy group, a carboxymethyl group, or a tetrazolyl group, each $R^2$ independently represents a group selected from substituent group α, each $R^3$ independently represents a phenyl group, a substituted phenyl group (wherein the substituent(s) represent 1 to 4 groups independently selected from substituent group α), a 5- or 6-membered aromatic heterocyclyl group, a substituted 5- or 6-membered aromatic heterocyclyl group (wherein the substituent(s) represent 1 to 4 groups independently selected from substituent group α), a phenyl($C_1$-$C_6$ alkyl) group, a substituted phenyl($C_1$-$C_6$ alkyl) group (wherein the substituent(s) represent 1 to 4 groups independently selected from substituent group α), a 5- or 6-membered aromatic heterocyclyl($C_1$-$C_6$ alkyl) group, or a substituted 5- or 6-membered aromatic heterocyclyl($C_1$-$C_6$ alkyl) group (wherein the substituent(s) represent 1 to 4 groups independently selected from substituent group α), m represents 0, 1, 2, or 3, n represents 0 or 1, provided that when m is 3, n is 0, each of $R^4$, $R^5$, $R^6$, and $R^7$ independently represents a hydrogen atom, a $C_1$-$C_6$ alkyl group, a halogeno($C_1$-$C_6$ alkyl) group, a hydroxy group, a $C_1$-$C_6$ alkoxy group, or a halogeno group, B represents a naphthyl group, a substituted naphthyl group (wherein the substituent(s) represent 1 to 4 groups independently selected from substituent group α), a 9- or 10-membered aromatic heterocyclyl group, a substituted 9- or 10-membered aromatic heterocyclyl group (wherein the substituent(s) represent 1 to 4 groups independently selected from substituent group α), or a group represented by the following formula (II)

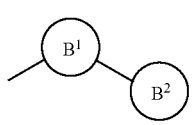

(II)

[wherein each of $B^1$ and $B^2$ independently represents a phenyl group, a substituted phenyl group (wherein the substituent(s) represent 1 to 4 groups independently selected from substituent group α), a 5- or 6-membered aromatic heterocyclyl group, or a substituted 5- or 6-membered aromatic heterocyclyl group (wherein the substituent(s) represent 1 to 4 groups independently selected from substituent group α)], and substituent group α represents the group consisting of a $C_1$-$C_6$ alkyl group, a hydroxy($C_1$-$C_6$ alkyl) group, a ($C_1$-$C_6$ alkoxy)-($C_1$-$C_6$ alkyl) group, a halogeno($C_1$-$C_6$ alkyl) group, a ($C_3$-$C_8$ cycloalkyl)-($C_1$-$C_6$ alkyl) group, a $C_3$-$C_8$ cycloalkyl group, a $C_2$-$C_6$ alkenyl group, a $C_2$-$C_6$ alkynyl group, a hydroxy group, a $C_1$-$C_6$ alkoxy group, a halogeno($C_1$-$C_6$ alkoxy) group, a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group, a formylamino group, a ($C_1$-$C_6$ alkyl)carbonylamino group, a ($C_1$-$C_6$ alkoxy)carbonylamino group, a ($C_1$-$C_6$ alkyl)sulfonylamino group, a formyl group, a ($C_1$-$C_6$ alkyl)carbonyl group, a carboxy group, a ($C_1$-$C_6$ alkoxy)carbonyl group, a carbamoyl group, a ($C_1$-$C_6$ alkylamino)carbonyl group, a di($C_1$-$C_6$ alkyl)aminocarbonyl group, an aminosulfonyl group, a ($C_1$-$C_6$ alkylamino)sulfonyl group, a di($C_1$-$C_6$ alkyl)aminosulfonyl group, a cyano group, a nitro group, and a halogeno group].

(2) The compound according to (1) above or a pharmacologically acceptable salt thereof, wherein A is a pyrrolyl group and X is a carbon atom.

(3) The compound according to (1) above or a pharmacologically acceptable salt thereof, which is represented by the following general formula (I-1)

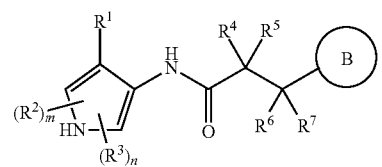

(I-1)

(4) The compound according to (1) above or a pharmacologically acceptable salt thereof, which is represented by the following general formula (I-3)

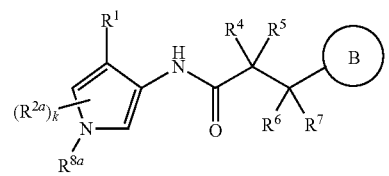

(I-3)

[wherein $R^{8a}$ represents a hydrogen atom, a $C_1$-$C_6$ alkyl group, a hydroxy($C_1$-$C_6$ alkyl) group, a ($C_1$-$C_6$ alkoxy)-($C_1$-$C_6$ alkyl) group, a halogeno($C_1$-$C_6$ alkyl) group, a ($C_3$-$C_8$ cycloalkyl)-($C_1$-$C_6$ alkyl) group, a $C_3$-$C_8$ cycloalkyl group, a $C_2$-$C_6$ alkenyl group, a $C_2$-$C_6$ alkynyl group, a $C_1$-$C_6$ alkylsulfonyl group, a formyl group, a ($C_1$-$C_6$ alkyl)carbonyl group, a ($C_1$-$C_6$ alkoxy)carbonyl group, a carbamoyl group, a ($C_1$-$C_6$ alkylamino)carbonyl group, a di($C_1$-$C_6$ alkyl)aminocarbonyl group, an aminosulfonyl group, a ($C_1$-$C_6$ alkylamino)sulfonyl group, or a di($C_1$-$C_6$ alkyl)aminosulfonyl group, each $R^{2a}$ independently represents a $C_1$-$C_4$ alkyl group, a halogeno($C_1$-$C_4$ alkyl) group, a ($C_3$-$C_6$ cycloalkyl)-($C_1$-$C_4$ alkyl) group, a $C_3$-$C_6$ cycloalkyl group, a $C_2$-$C_4$ alkenyl group, a $C_2$-$C_4$ alkynyl group, a hydroxy group, a $C_1$-$C_4$ alkoxy group, a formyl group, a ($C_1$-$C_4$ alkyl)carbonyl group, a cyano group, or a halogeno group, and k represents 0, 1, or 2].

(5) The compound according to (4) above or a pharmacologically acceptable salt thereof, wherein $R^{8a}$ represents a hydrogen atom, a $C_1$-$C_4$ alkyl group, a ($C_1$-$C_2$ alkoxy)-($C_1$-$C_4$ alkyl) group, a ($C_3$-$C_6$ cycloalkyl)-($C_1$-$C_4$ alkyl) group, a halogeno($C_1$-$C_4$ alkyl) group, a $C_3$-$C_6$ cycloalkyl group, a $C_2$-$C_4$ alkenyl group, or a $C_2$-$C_4$ alkynyl group, each $R^{2a}$ represents a $C_1$-$C_2$ alkyl group, a halogeno($C_1$-$C_2$ alkyl) group (wherein the halogeno group(s) represent 1 to 5 groups selected from the group consisting of a fluoro group and a chloro group), a $C_3$-$C_4$ cycloalkyl group, a cyano group, a fluoro group, or a chloro group, and k represents 0 or 1.

(6) The compound according to (4) above or a pharmacologically acceptable salt thereof, wherein $R^{8a}$ represents a $C_1$-$C_4$ alkyl group, and k represents 0.

(7) The compound according to (4) above or a pharmacologically acceptable salt thereof, wherein $R^{8a}$ represents an ethyl group, and k represents 0.

(8) The compound according to (1) above or a pharmacologically acceptable salt thereof, which is represented by the following general formula (I-4)

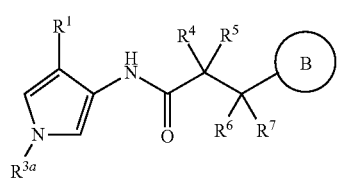

(I-4)

[wherein $R^{3a}$ represents a phenyl($C_1$-$C_2$ alkyl) group or a substituted phenyl($C_1$-$C_2$ alkyl) group (wherein the substituent(s) represent 1 to 3 groups independently selected from substituent group α1), and substituent group α1 represents the group consisting of a $C_1$-$C_2$ alkyl group, a halogeno($C_1$-$C_2$ alkyl) group (wherein the halogeno group(s) represent 1 to 5 groups selected from the group consisting of a fluoro group and a chloro group), a fluoro group, and a chloro group].

(9) The compound according to (8) above or a pharmacologically acceptable salt thereof, wherein $R^{3a}$ represents a phenylmethyl group or a substituted phenylmethyl group (wherein the substituent(s) represent 1 to 3 groups independently selected from substituent group α2), and substituent group α2 represents the group consisting of a methyl group, a trifluoromethyl group, and a fluoro group.

(10) The compound according to (1) above or a pharmacologically acceptable salt thereof, which is represented by the following general formula (I-2)

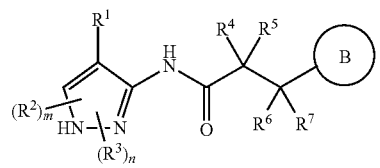

(I-2)

(11) The compound according to (1) above or a pharmacologically acceptable salt thereof, which is represented by the following general formula (I-5)

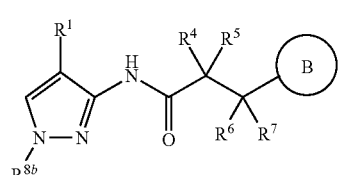

(I-5)

[wherein $R^{8b}$ represents a hydrogen atom, a $C_1$-$C_4$ alkyl group, a ($C_1$-$C_2$ alkoxy)-($C_1$-$C_4$ alkyl) group, a halogeno($C_1$-$C_4$ alkyl) group, a $C_3$-$C_6$ cycloalkyl group, a $C_2$-$C_4$ alkenyl group, or a $C_2$-$C_4$ alkynyl group].

(12) The compound according to (11) above or a pharmacologically acceptable salt thereof, wherein $R^{8b}$ represents a $C_1$-$C_4$ alkyl group.

(13) The compound according to any one of (1) to (12) above or a pharmacologically acceptable salt thereof, wherein $R^1$ represents a carboxy group.

(14) The compound according to any one of (1) to (13) above or a pharmacologically acceptable salt thereof, wherein each of $R^4$, $R^5$, $R^6$, and $R^7$ independently represents a hydrogen atom, a $C_1$-$C_2$ alkyl group, a halogeno($C_1$-$C_2$ alkyl) group (wherein the halogeno group(s) represent 1 to 5 groups selected from the group consisting of a fluoro group and a chloro group), a fluoro group, or a chloro group.

(15) The compound according to any one of (1) to (13) above or a pharmacologically acceptable salt thereof, wherein each of $R^4$, $R^5$, $R^6$, and $R^7$ independently represents a hydrogen atom or a fluoro group.

(16) The compound according to any one of (1) to (13) above or a pharmacologically acceptable salt thereof, wherein each of $R^4$ and $R^5$ independently represents a hydrogen atom or a fluoro group, and $R^6$ and $R^7$ each represent a hydrogen atom.

(17) The compound according to any one of (1) to (16) above or a pharmacologically acceptable salt thereof, wherein B represents a naphthyl group or a substituted naphthyl group (wherein the substituent(s) represent 1 to 3 groups independently selected from substituent group α3), and substituent group α3 represents the group consisting of a $C_1$-$C_2$ alkyl group, a halogeno($C_1$-$C_2$ alkyl) group (wherein the halogeno group(s) represent 1 to 5 groups selected from the group consisting of a fluoro group and a chloro group), a hydroxy group, a $C_1$-$C_2$ alkoxy group, a fluoro group, and a chloro group.

(18) The compound according to any one of (1) to (16) above or a pharmacologically acceptable salt thereof, wherein B represents a group represented by the following formula (IIa)

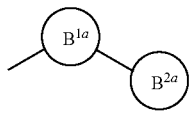

(IIa)

[wherein $B^{1a}$ represents a phenyl group, a substituted phenyl group (wherein the substituent(s) represent 1 to 3 groups independently selected from substituent group α4), a 5-membered aromatic heterocyclyl group, or a substituted 5-membered aromatic heterocyclyl group (wherein the substituent(s) represent 1 to 3 groups independently selected from substituent group α4), $B^{2a}$ represents a phenyl group, a substituted phenyl group (wherein the substituent(s) represent 1 to 3 groups independently selected from substituent group α5), a pyridyl group, or a substituted pyridyl group (wherein the substituent(s) represent 1 to 3 groups independently selected from substituent group α5), substituent group α4 represents the group consisting of a $C_1$-$C_4$ alkyl group, a halogeno($C_1$-$C_4$ alkyl) group, a ($C_3$-$C_6$ cycloalkyl)-($C_1$-$C_4$ alkyl) group, a $C_3$-$C_6$ cycloalkyl group, a $C_1$-$C_4$ alkoxy group, a formyl group, a ($C_1$-$C_4$ alkyl)carbonyl group, a cyano group, a fluoro group, a chloro group, and a bromo group, and substituent group α5 represents the group consisting of a $C_1$-$C_4$ alkyl group, a halogeno($C_1$-$C_4$ alkyl) group, a hydroxy group, a $C_1$-$C_4$ alkoxy group, a fluoro group, a chloro group, and a bromo group].

(19) The compound according to any one of (1) to (16) above or a pharmacologically acceptable salt thereof, wherein B represents a group represented by the following formula (IIb)

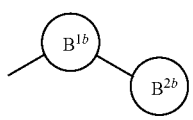

(IIb)

[wherein $B^{1b}$ represents a nitrogen-containing 5-membered aromatic heterocyclyl group or a substituted nitrogen-containing 5-membered aromatic heterocyclyl group (wherein the substituent(s) represent 1 or 2 groups independently selected from substituent group α6), $B^{2b}$ represents a phenyl group, a substituted phenyl group (wherein the substituent(s) represent 1 or 2 groups independently selected from substituent group α7), a pyridyl group, or a substituted pyridyl group (wherein the substituent(s) represent 1 or 2 groups independently selected from substituent group α7), substituent group α6 represents the group consisting of a $C_1$-$C_4$ alkyl group, a halogeno($C_1$-$C_2$ alkyl) group (wherein the halogeno group(s) represent 1 to 5 groups selected from the group consisting of a fluoro group and a chloro group), a ($C_3$-$C_4$ cycloalkyl)-($C_1$-$C_2$ alkyl) group, a $C_3$-$C_4$ cycloalkyl group, a ($C_1$-$C_2$ alkyl)carbonyl group, a cyano group, a fluoro group, and a chloro group, and substituent group α7 represents the group consisting of a $C_1$-$C_2$ alkyl group, a hydroxy group, a fluoro group, and a chloro group].

(20) The compound according to any one of (1) to (16) above or a pharmacologically acceptable salt thereof, wherein B represents a group represented by the following formula (IIc)

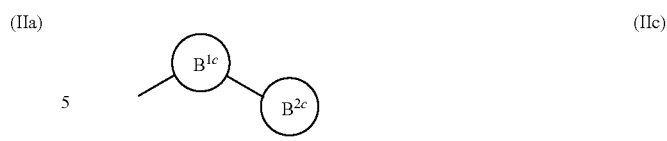

(IIc)

[wherein $B^{1c}$ represents a group selected from the following groups or a group which is selected from the following groups and substituted (wherein the substituent represents one group independently selected from substituent group α8)

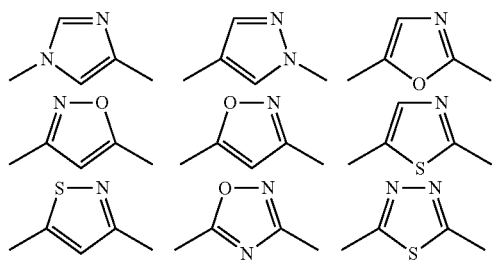

$B^{2c}$ represents a phenyl group or a 4-hydroxyphenyl group, and substituent group α8 represents the group consisting of a $C_1$-$C_4$ alkyl group, a halogeno($C_1$-$C_2$ alkyl) group (wherein the halogeno group(s) represent 1 to 5 groups selected from the group consisting of a fluoro group and a chloro group), a cyclopropyl group, a methylcarbonyl group, a cyano group, a fluoro group, and a chloro group].

(21) The compound according to any one of (1) to (16) above or a pharmacologically acceptable salt thereof, wherein B represents a group represented by the following formula (IId)

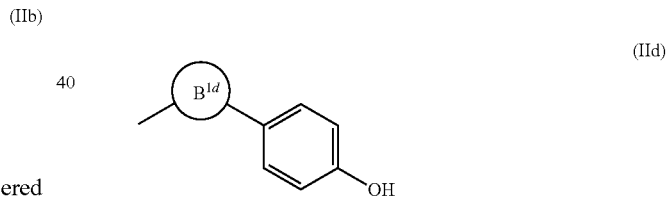

(IId)

[wherein $B^{1d}$ represents a group selected from the following groups or a group which is selected from the following groups and substituted (wherein the substituent represents one group selected from substituent group α9)

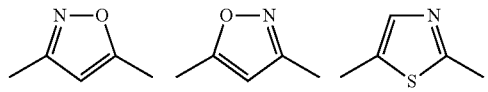

and substituent group α9 represents the group consisting of a methyl group, an ethyl group, and a chloro group].

(22) The compound according to (1) above or a pharmacologically acceptable salt thereof, which is selected from the group consisting of 4-{3-[2-(4-hydroxyphenyl)thiazol-5-yl]propanoyl}amino-1-ethylpyrrole-3-carboxylic acid;

4-{3-[2-(4-hydroxyphenyl)thiazol-5-yl]-2-fluoropropanoyl}amino-1-ethylpyrrole-3-carboxylic acid;

4-{3-[3-(4-hydroxyphenyl)-4-ethylisoxazol-5-yl]propanoyl}amino-1-ethylpyrrole-3-carboxylic acid;

4-{3-[4-chloro-(4-hydroxyphenyl)isoxazol-5-yl]
propanoyl}amino-1-ethylpyrrole-3-carboxylic acid;
4-{3-[4-ethyl-(4-hydroxyphenyl)isoxazol-5-yl]
propanoyl}amino-1-ethylpyrrole-3-carboxylic acid;
4-{3-[(4-hydroxyphenyl)-4-methylisoxazol-5-yl]
propanoyl}amino-1-ethylpyrrole-3-carboxylic acid;
4-{3-[2-(4-hydroxyphenyl)thiazol-5-yl]-2,2-
difluoropropanoyl}amino-1-ethylpyrrole-3-carboxylic
acid;
4-{3-[4-ethyl-3-(4-hydroxyphenyl)isoxazol-5-yl]-2,2-
difluoropropanoyl}amino-1-ethylpyrrole-3-carboxylic
acid;
4-{3-[4-ethyl-5-(4-hydroxyphenyl)isoxazol-3-yl]-2,2-
difluoropropanoyl}amino-1-ethylpyrrole-3-carboxylic
acid;
4-{3-[4-chloro-5-(4-hydroxyphenyl)isoxazol-3-yl]-2,2-
fluoropropanoyl}amino-1-ethylpyrrole-3-carboxylic acid;
4-{3-[3-(4-hydroxyphenyl)isoxazol-5-yl]-2-
fluoropropanoyl}amino-1-ethylpyrrole-3-carboxylic acid; and
4-{3-[3-(4-hydroxyphenyl)isoxazol-5-yl]-2,2-
difluoropropanoyl}amino-1-ethylpyrrole-3-carboxylic
acid.

In the present invention, the compounds of Examples 13, 22, 25, 33, 35, 38, 39, 40, 41, 46, 62, and 63, which are described in (22) above, are preferable.

In the general formula (I) of the present invention, any given combinations of the groups described in (1) to (21) above are preferable. For example, the following combinations are preferable.

(23) A, $R^{2a}$, $R^{8a}$, k: (4); $R^1$: (13); $R^4$, $R^5$, $R^6$, $R^7$: (14); B: (18).
(24) A, $R^{2a}$, $R^{8a}$, k: (5); $R^1$: (13); $R^4$, $R^5$, $R^6$, $R^7$: (15); B: (19).
(25) A, $R^{2a}$, $R^{8a}$, k: (6); $R^1$: (13); $R^4$, $R^5$, $R^6$, $R^7$: (16); B: (20).
(26) A, $R^{2a}$, $R^{8a}$, k: (7); $R^1$: (13); $R^4$, $R^5$, $R^6$, $R^7$: (16); B: (21).
(27) A, $R^{2a}$, $R^{8a}$, k: (7); $R^1$: (13); $R^4$, $R^5$, $R^6$, $R^7$: (16); B: (17).

In another aspect, the present invention provides the following.

(28) A pharmaceutical composition comprising, as an active ingredient, the compound according to any one of (1) to (22) above or a pharmacologically acceptable salt thereof.
(29) The pharmaceutical composition according to (28) above, which is for the treatment or prophylaxis of hyperlipidemia, dyslipidemia, lipid metabolism abnormality, arteriosclerosis, or type II diabetes mellitus.
(30) The pharmaceutical composition according to (28) above, which is for the treatment or prophylaxis of dyslipidemia.
(31) The pharmaceutical composition according to (28) above, which is for the treatment or prophylaxis of lipid metabolism abnormality.
(32) Use of the compound according to any one of (1) to (22) above or a pharmacologically acceptable salt thereof in the manufacture of a pharmaceutical composition for the treatment or prophylaxis of a disease.
(33) The use according to (32) above, wherein the disease is hyperlipidemia, dyslipidemia, lipid metabolism abnormality, arteriosclerosis, or type II diabetes mellitus.
(34) The use according to (32) above, wherein the disease is dyslipidemia.
(35) The use according to (32) above, wherein the disease is lipid metabolism abnormality.
(36) A method for the treatment or prophylaxis of a disease, which comprises administering a pharmaceutically effective amount of the compound according to any one of (1) to (22) above or a pharmacologically acceptable salt thereof to a warm-blooded animal.
(37) The method according to (36) above, wherein the disease is hyperlipidemia, dyslipidemia, lipid metabolism abnormality, arteriosclerosis, or type II diabetes mellitus.
(38) The method according to (36) above, wherein the disease is dyslipidemia.
(39) The method according to (36) above, wherein the disease is lipid metabolism abnormality.
(40) The compound according to any one of (1) to (22) above or a pharmacologically acceptable salt thereof for use in a method for the treatment or prophylaxis of a disease.
(41) The compound described in any one of (1) to (22) above or a pharmacologically acceptable salt thereof for use in a method according to (40) above, wherein the disease is hyperlipidemia, dyslipidemia, lipid metabolism abnormality, arteriosclerosis, or type II diabetes mellitus.
(42) The compound described in any one of (1) to (22) above or a pharmacologically acceptable salt thereof for use in a method according to (40) above, wherein the disease is dyslipidemia.
(43) The compound described in any one of (1) to (22) above or a pharmacologically acceptable salt thereof for use in a method according to (40) above, wherein the disease is lipid metabolism abnormality.

In the general formula (I) of the present invention, the "nitrogen-containing 5-membered aromatic heterocyclyl group" means a 5-membered aromatic heterocyclyl group that contains one nitrogen atom and may further contain 1 to 3 atoms selected from the group consisting of a nitrogen atom, an oxygen atom, and a sulfur atom and may be for example, a pyrrolyl group, a pyrazolyl group, an imidazolyl group, an oxazolyl group, an isoxazolyl group, an isothiazolyl group, a triazolyl group, an oxadiazolyl group, or a thiadiazolyl group. The nitrogen-containing 5-membered heterocyclyl group represented by A is preferably a pyrrolyl group, a pyrazolyl group, an imidazolyl group, an oxazolyl group, an isoxazolyl group, or an isothiazolyl group, more preferably a pyrrolyl group, a pyrazolyl group, or an imidazolyl group, even more preferably a pyrroyl group or a pyrazolyl group, and most preferably a pyrrolyl group.

The "5- or 6-membered aromatic heterocyclyl group" means a 5- or 6-membered aromatic heterocyclic group containing 1 to 4 atoms selected from the group consisting of a nitrogen atom, an oxygen atom, and a sulfur atom and may be for example, a pyrrolyl group, a furyl group, a thienyl group, a pyrazolyl group, an imidazolyl group, an oxazolyl group, an isoxazolyl group, a thiazolyl group, an isothiazolyl group, a triazolyl group, an oxadiazolyl group, a thiadiazolyl group, a tetrazolyl group, a pyranyl group, a pyridyl group, a pyridazinyl group, a pyrimidinyl group, or a pyrazinyl group. In the case of $R^3$ and $R^{3a}$, the 5- or 6-membered aromatic heterocyclyl group is preferably a pyrrolyl group, an imidazolyl group, an oxazolyl group, a thiazolyl group, a triazolyl group, or a pyridyl group, and more preferably a pyridyl group. In the case of $B^1$, the 5- or 6-membered aromatic heterocyclyl group is preferably a 5-membered aromatic heterocyclyl group, more preferably a pyrrolyl group, a furyl group, a thienyl group, a pyrazolyl group, an imidazolyl group, an oxazolyl group, an isoxazolyl group, a thiazolyl group, an isothiazolyl group, a triazolyl group, an oxadiazolyl group, or a thiadiazolyl group, even more preferably a pyrazolyl group, an imidazolyl group, an oxazolyl group, an isoxazolyl group, a thiazolyl group, an isothiazolyl group, an oxadiazolyl group, or a thiadiazolyl group, and still further preferably an isoxazolyl group or a thiazolyl group. In the case of $B^2$, the 5- or 6-membered aromatic heterocyclyl group is preferably a pyrrolyl group, a furyl group, a thienyl group, an imidazolyl group, an oxazolyl group, a thiazolyl group, a triazolyl group, an oxadiazolyl group, a thiadiazolyl group, or a pyridyl group, more preferably a furyl group, a thienyl group, or a pyridyl group, and even more preferably a pyridyl group.

The "phenyl($C_1$-$C_6$ alkyl) group" means the below-described $C_1$-$C_6$ alkyl group which is substituted with a phenyl group and may be for example, a phenylmethyl group (benzyl group), a phenylethyl group, a phenylpropyl group, a phenylbutyl group, a phenylpentyl group, or a phenylhexyl group, preferably a phenyl($C_1$-$C_4$ alkyl) group, more preferably a phenyl($C_1$-$C_2$ alkyl) group, and most preferably a phenylmethyl group.

The "5- or 6-membered aromatic heterocyclyl($C_1$-$C_6$ alkyl) group" means the below-described $C_1$-$C_6$ alkyl group which is substituted with a 5- or 6-membered aromatic heterocyclyl group as described above and is preferably a 5- or 6-membered aromatic heterocyclyl($C_1$-$C_4$ alkyl) group, more preferably a 5- or 6-membered aromatic heterocyclyl($C_1$-$C_2$ alkyl) group, even more preferably a pyrrolylmethyl group, a pyrrolylethyl group, an imidazolylmethyl group, an imidazolylethyl group, an oxazolylmethyl group, an oxazolylethyl group, a thiazolylmethyl group, a thiazolylethyl group, a triazolylmethyl group, a triazolylethyl group, a pyridylmethyl group, or a pyridylethyl group, and still further preferably a pyrrolylmethyl group, an imidazolylmethyl group, an oxazolylmethyl group, a thiazolylmethyl group, a triazolylmethyl group, or a pyridylmethyl group.

The "$C_1$-$C_6$ alkyl group" means a straight-chain or branched-chain alkyl group containing 1 to 6 carbon atoms and may be for example, a methyl group, an ethyl group, a 1-propyl group, a 2-propyl group, a 1-butyl group, a 2-butyl group, a 2-methyl-1-propyl group, a 2-methyl-2-propyl group, a 1-pentyl group, a 2-pentyl group, a 3-pentyl group, a 3-methyl-1-butyl group, a 2-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 2-ethyl-1-butyl group, a 2,2-dimethyl-1-butyl group, or a 2,3-dimethyl-1-butyl group, preferably a $C_1$-$C_4$ alkyl group, more preferably a $C_1$-$C_2$ alkyl group, and most preferably a methyl group. Moreover, in the case of one of the $R^2$ groups, $R^{8a}$ and $R^{8b}$, the $C_1$-$C_6$ alkyl group is preferably a $C_1$-$C_5$ alkyl group, more preferably a $C_1$-$C_4$ alkyl group, still further preferably a $C_2$-$C_4$ alkyl group, and most preferably an ethyl group.

The "halogeno($C_1$-$C_6$ alkyl) group" means the above-described $C_1$-$C_6$ alkyl group which is substituted with the same or different 1 to 7 halogeno groups as described below and may be, for example, a fluoromethyl group, a difluoromethyl group, a dichloromethyl group, a dibromomethyl group, a trifluoromethyl group, a trichloromethyl group, a 2-fluoroethyl group, a 2-bromoethyl group, a 2-chloroethyl group, a 2-iodoethyl group, a 2,2-difluoroethyl group, a 2,2,2-trifluoroethyl group, a trichloroethyl group, a pentafluoroethyl group, a 3-fluoropropyl group, a 3,3,3-trifluoropropyl group, a 3-chloropropyl group, a 4-fluorobutyl group, a 4,4,4-trifluorobutyl group, a 5-fluoropentyl group, a 5,5,5-trifluoropentyl group, a 6-fluorohexyl group, or a 6,6,6-trifluorohexyl group, preferably a halogeno($C_1$-$C_4$ alkyl) group, more preferably a halogeno($C_1$-$C_4$ alkyl) group (wherein the halogeno group(s) represent 1 to 7 groups selected from the group consisting of a fluoro group and a chloro group), even more preferably a halogeno($C_1$-$C_2$ alkyl) group (wherein the halogeno group(s) represent 1 to 5 groups selected from the group consisting of a fluoro group and a chloro group), still further preferably a trifluoromethyl group, a 2,2,2-trifluoroethyl group, or a pentafluoroethyl group, and most preferably a trifluoromethyl group. Moreover, in the case of one of the $R^2$ groups, $R^{8a}$ and $R^{8b}$, the halogeno($C_1$-$C_6$ alkyl) group is preferably a halogeno($C_1$-$C_5$ alkyl) group, more preferably a halogeno($C_1$-$C_4$ alkyl) group, even more preferably a halogeno($C_1$-$C_4$ alkyl) group (wherein the halogeno group(s) represent 1 to 7 groups selected from the group consisting of a fluoro group and a chloro group), and still further preferably a halogeno($C_2$-$C_4$ alkyl) group (wherein the halogeno group(s) represent 1 to 7 groups selected from the group consisting of a fluoro group and a chloro group).

The "$C_1$-$C_6$ alkoxy group" means a hydroxy group which is substituted with a $C_1$-$C_6$ alkyl group as described above and may be for example, a methoxy group, an ethoxy group, a 1-propoxy group, a 2-propoxy group, a 1-butoxy group, a 2-butoxy group, a 2-methyl-1-propoxy group, a 2-methyl-2-propoxy group, a 1-pentyloxy group, a 2-pentyloxy group, a 3-pentyloxy group, a 2-methyl-2-butoxy group, a 3-methyl-2-butoxy group, a 1-hexyloxy group, a 2-hexyloxy group, a 3-hexyloxy group, a 2-methyl-1-pentyloxy group, a 3-methyl-1-pentyloxy group, a 2-ethyl-1-butoxy group, a 2,2-dimethyl-1-butoxy group, or a 2,3-dimethyl-1-butoxy group, preferably a $C_1$-$C_4$ alkoxy group, more preferably a $C_1$-$C_2$ alkoxy group, and most preferably a methoxy group. Moreover, in the case of one of the $R^2$ groups, the $C_1$-$C_6$ alkoxy group is preferably a $C_1$-$C_5$ alkoxy group, more preferably a $C_1$-$C_4$ alkoxy group, and even more preferably a $C_2$-$C_4$ alkoxy group.

The "halogeno group" may be a fluoro group, a chloro group, a bromo group, or an iodo group, preferably a fluoro group, a chloro group, or a bromo group, more preferably a fluoro group or a chloro group, and most preferably a fluoro group.

The "9- or 10-membered aromatic heterocyclyl group" means a 9- or 10-membered aromatic heterocyclyl group containing 1 to 4 atoms selected from the group consisting of a nitrogen atom, an oxygen atom, and a sulfur atom and may be for example, an indolyl group, a benzofuranyl group, a benzothienyl group, a benzimidazolyl group, a benzoxazolyl group, a benzisoxazolyl group, a benzothiazolyl group, a benzisothiazolyl group, a quinolyl group, an isoquinolyl group, a quinoxalinyl group, or a quinazolinyl group, preferably a quinolyl group, an isoquinolyl group, a quinoxalinyl group, or a quinazolinyl group.

The "hydroxy($C_1$-$C_6$ alkyl) group" means the above-described $C_1$-$C_6$ alkyl group which is substituted with a hydroxy group and may be for example, a hydroxymethyl group, a hydroxyethyl group, a hydroxy(1-propyl) group, a hydroxy(2-propyl) group, a hydroxy(1-butyl) group, a hydroxy(2-butyl) group, a hydroxy(2-methyl-1-propyl) group, a hydroxy(2-methyl-2-propyl) group, a hydroxy(1-pentyl) group, or a hydroxy(1-hexyl) group, preferably a hydroxy($C_1$-$C_4$ alkyl) group, more preferably a hydroxy($C_1$-$C_2$ alkyl) group, and most preferably a hydroxymethyl group. Moreover, in the case of one of the $R^2$ groups, $R^{8a}$ and $R^{8b}$, the hydroxy($C_1$-$C_6$ alkyl) group is preferably a hydroxy($C_1$-$C_5$ alkyl) group, more preferably a hydroxy($C_1$-$C_4$ alkyl) group, and even more preferably a hydroxy($C_2$-$C_4$ alkyl) group.

The "($C_1$-$C_6$ alkoxy)-($C_1$-$C_6$ alkyl) group" means the above-described $C_1$-$C_6$ alkyl group which is substituted with a $C_1$-$C_6$ alkoxy group as described above and may be for example, a methoxymethyl group, an ethoxymethyl group, a propoxymethyl group, a butoxymethyl group, a pentyloxymethyl group, a hexyloxymethyl group, a methoxyethyl group, a methoxypropyl group, a methoxybutyl group, a methoxypentyl group, or a methoxyhexyl group, preferably a ($C_1$-$C_4$ alkoxy)-($C_1$-$C_4$ alkyl) group, and more preferably a ($C_1$-$C_2$ alkoxy)-($C_1$-$C_2$ alkyl) group. Moreover, in the case of one of the $R^2$ groups, $R^{8a}$ and $R^{8b}$, the ($C_1$-$C_6$ alkoxy)-($C_1$-$C_6$ alkyl)

group is preferably a ($C_1$-$C_4$ alkoxy)-($C_1$-$C_5$ alkyl) group, more preferably a ($C_1$-$C_2$ alkoxy)-($C_1$-$C_4$ alkyl) group, and even more preferably a ($C_1$-$C_2$ alkoxy)-($C_2$-$C_4$ alkyl) group.

The "($C_3$-$C_8$ cycloalkyl)-($C_1$-$C_6$ alkyl) group" means the above-described $C_1$-$C_6$ alkyl group which is substituted with a $C_3$-$C_8$ cycloalkyl group as described below and may be for example, a cyclopropylmethyl group, a cyclobutylmethyl group, a cyclopentylmethyl group, a cyclohexylmethyl group, a cycloheptylmethyl group, a cyclooctylmethyl group, a cyclopropylethyl group, a cyclobutylethyl group, a cyclopentylethyl group, a cyclohexylethyl group, a cyclopropylpropyl group, a cyclobutylpropyl group, a cyclopentylpropyl group, a cyclohexylpropyl group, a cyclopropylbutyl group, a cyclobutylbutyl group, a cyclopropylpentyl group, or a cyclopropylhexyl group, preferably a ($C_3$-$C_6$ cycloalkyl)-($C_1$-$C_4$ alkyl) group, and more preferably a ($C_3$-$C_5$ cycloalkyl)-($C_1$-$C_2$ alkyl) group. Moreover, in the case of one of the $R^2$ groups and $R^{8a}$, the ($C_3$-$C_8$ cycloalkyl)-($C_1$-$C_6$ alkyl) group is preferably a ($C_3$-$C_6$ cycloalkyl)-($C_1$-$C_5$ alkyl) group, more preferably a ($C_3$-$C_5$ cycloalkyl)-($C_1$-$C_4$ alkyl) group, and even more preferably a ($C_3$-$C_4$ cycloalkyl)-($C_2$-$C_4$ alkyl) group.

The "$C_3$-$C_8$ cycloalkyl group" means a cyclic alkyl group containing 3 to 8 carbon atoms and may be for example, a cyclopropyl group, a cyclobutyl group, a cyclopentyl group, a cyclohexyl group, a cycloheptyl group, or a cyclooctyl group, preferably a $C_3$-$C_6$ cycloalkyl group, more preferably a $C_3$-$C_5$ cycloalkyl group, even more preferably a $C_3$-$C_4$ cycloalkyl group, and most preferably a cyclopropyl group.

The "$C_2$-$C_6$ alkenyl group" means a straight-chain or branched-chain alkenyl group containing 2 to 6 carbon atoms, which may have one or more carbon-carbon double bonds and may be, for example, a vinyl group, a 2-propenyl group (an allyl group), a 2-butenyl group, a 2-pentenyl group, a 3-methyl-2-butenyl group, a 2-hexenyl group, or a 3-methyl-2-pentenyl group, preferably a $C_2$-$C_4$ alkenyl group, and more preferably a $C_2$-$C_3$ alkenyl group. Moreover, in the case of one of the $R^2$ groups, $R^{8a}$ and $R^{8b}$, the $C_2$-$C_6$ alkenyl group is preferably a $C_2$-$C_5$ alkenyl group, and more preferably a $C_2$-$C_4$ alkenyl group.

The "$C_2$-$C_6$ alkynyl group" means a straight-chain or branched-chain alkynyl group containing 2 to 6 carbon atoms which may have one or more carbon-carbon triple bonds and may be for example, an ethynyl group, a 1-propynyl group, a 2-propynyl group, a 1-butynyl group, a 2-butynyl group, a 1-pentynyl group, a 2-pentynyl group, or a 1-hexynyl group, preferably a $C_2$-$C_4$ alkynyl group, and more preferably a $C_2$-$C_3$ alkynyl group. Moreover, in the case of one of the $R^2$ groups, $R^{8a}$ and $R^{8b}$, the $C_2$-$C_6$ alkynyl group is preferably a $C_2$-$C_5$ alkynyl group, and more preferably a $C_2$-$C_4$ alkynyl group.

The "halogeno($C_1$-$C_6$ alkoxy) group" means the above-described $C_1$-$C_6$ alkoxy group which is substituted with 1 to 7 halogeno groups as described above and may be for example, a fluoromethoxy group, a difluoromethoxy group, a dichloromethoxy group, a dibromomethoxy group, a trifluoromethoxy group, a trichloromethoxy group, a 2-fluoroethoxy group, a 2-bromoethoxy group, a 2-chloroethoxy group, a 2-iodoethoxy group, a 2,2-difluoroethoxy group, a 2,2,2-trifluoroethoxy group, a trichloroethoxy group, a pentafluoroethoxy group, a 3-fluoropropoxy group, a 3,3,3-trifluoropropoxy group, a 3-chloropropoxy group, a 4-fluorobutoxy group, a 4,4,4-trifluorobutoxy group, a 5-fluoropentyloxy group, a 5,5,5-trifluoropentyloxy group, a 6-fluorohexyloxy group, or a 6,6,6-trifluorohexyloxy group, preferably a halogeno($C_1$-$C_4$ alkoxy) group, more preferably a halogeno($C_1$-$C_4$ alkoxy) group (wherein the halogeno group(s) represent 1 to 7 groups selected from the group consisting of a fluoro group and a chloro group), even more preferably a halogeno ($C_1$-$C_2$ alkoxy) group (wherein the halogeno group(s) represent 1 to 5 groups selected from the group consisting of a fluoro group and a chloro group), still further preferably a trifluoromethoxy group, a 2,2,2-trifluoroethoxy group, or a pentafluoroethoxy group, and most preferably a trifluoromethoxy group. Moreover, in the case of one of the $R^2$ groups, the halogeno($C_1$-$C_6$ alkoxy) group is preferably a halogeno($C_1$-$C_5$ alkoxy) group, more preferably a halogeno ($C_1$-$C_4$ alkoxy) group, even more preferably a halogeno($C_1$-$C_4$ alkoxy) group (wherein the halogeno group(s) represent 1 to 7 groups selected from the group consisting of a fluoro group and a chloro group), and still further preferably a halogeno($C_2$-$C_4$ alkoxy) group (wherein the halogeno group(s) represent 1 to 7 groups selected from the group consisting of a fluoro group and a chloro group).

The "$C_1$-$C_6$ alkylthio group" means a mercapto group which is substituted with a $C_1$-$C_6$ alkyl group as described above and may be, for example, a methylthio group, an ethylthio group, a 1-propylthio group, a 2-propylthio group, a 1-butylthio group, a 2-butylthio group, a 2-methyl-1-propylthio group, a 2-methyl-2-propylthio group, a 1-pentylthio group, a 2-pentylthio group, a 3-pentylthio group, a 2-methyl-2-butylthio group, a 3-methyl-2-butylthio group, a 1-hexylthio group, a 2-hexylthio group, a 3-hexylthio group, a 2-methyl-1-pentylthio group, a 3-methyl-1-pentylthio group, a 2-ethyl-1-butylthio group, a 2,2-dimethyl-1-butylthio group, or a 2,3-dimethyl-1-butylthio group, preferably a $C_1$-$C_4$ alkylthio group, more preferably a $C_1$-$C_2$ alkylthio group, and most preferably a methylthio group. Moreover, in the case of one of the $R^2$ groups, the $C_1$-$C_6$ alkylthio group is preferably a $C_1$-$C_5$ alkylthio group, more preferably a $C_1$-$C_4$ alkylthio group, and even more preferably a $C_2$-$C_4$ alkylthio group.

The "$C_1$-$C_6$ alkylsulfinyl group" means a sulfinyl group (—SO—) which is substituted with a $C_1$-$C_6$ alkyl group as described above and may be, for example, a methylsulfinyl group, an ethylsulfinyl group, a 1-propylsulfinyl group, a 2-propylsulfinyl group, a 1-butylsulfinyl group, a 2-butylsulfinyl group, a 2-methyl-1-propylsulfinyl group, a 2-methyl-2-propylsulfinyl group, a 1-pentylsulfinyl group, a 2-pentylsulfinyl group, a 3-pentylsulfinyl group, a 2-methyl-2-butylsulfinyl group, a 3-methyl-2-butylsulfinyl group, a 1-hexylsulfinyl group, a 2-hexylsulfinyl group, a 3-hexylsulfinyl group, a 2-methyl-1-pentylsulfinyl group, a 3-methyl-1-pentylsulfinyl group, a 2-ethyl-1-butylsulfinyl group, a 2,2-dimethyl-1-butylsulfinyl group, or a 2,3-dimethyl-1-butylsulfinyl group, preferably a $C_1$-$C_4$ alkylsulfinyl group, more preferably a $C_1$-$C_2$ alkylsulfinyl group, and most preferably a methylsulfinyl group. Moreover, in the case of one of the $R^2$ groups, the $C_1$-$C_6$ alkylsulfinyl group is preferably a $C_1$-$C_5$ alkylsulfinyl group, more preferably a $C_1$-$C_4$ alkylsulfinyl group, and even more preferably a $C_2$-$C_4$ alkylsulfinyl group.

The "$C_1$-$C_6$ alkylsulfonyl group" means a sulfonyl group (—$SO_2$—) which is substituted with a $C_1$-$C_6$ alkyl group as described above and may be for example, a methanesulfonyl group, an ethanesulfonyl group, a 1-propanesulfonyl group, a 2-propanesulfonyl group, a 1-butanesulfonyl group, a 2-butanesulfonyl group, a 2-methyl-1-propanesulfonyl group, a 2-methyl-2-propanesulfonyl group, a 1-pentanesulfonyl group, a 2-pentanesulfonyl group, a 3-pentanesulfonyl group, a 2-methyl-2-butanesulfonyl group, a 3-methyl-2-butanesulfonyl group, a 1-hexanesulfonyl group, a 2-hexanesulfonyl group, a 3-hexanesulfonyl group, a 2-methyl-1-pentanesulfonyl group, a 3-methyl-1-pentanesulfonyl group, a 2-ethyl-1-butanesulfonyl group, a 2,2-dimethyl-1-butanesulfonyl group, or a 2,3-dimethyl-1-butanesulfonyl group, preferably a $C_1$-$C_4$ alkylsulfonyl group, more preferably a $C_1$-$C_2$ alkylsulfonyl group, and most preferably a methanesulfonyl group. Moreover, in the case of one of the $R^2$ groups and $R^{8a}$, the $C_1$-$C_6$ alkylsulfonyl group is preferably a $C_1$-$C_5$ alkylsulfonyl group, more preferably a $C_1$-$C_4$ alkylsulfonyl group, and even more preferably a $C_2$-$C_4$ alkylsulfonyl group.

The "$C_1$-$C_6$ alkylamino group" means an amino group which is substituted with a $C_1$-$C_6$ alkyl group as described above and may be for example, a methylamino group, an ethylamino group, a 1-propylamino group, a 2-propylamino group, a 1-butylamino group, a 2-butylamino group, a 2-methyl-1-propylamino group, a 2-methyl-2-propylamino group, a 1-pentylamino group, a 2-pentylamino group, a 3-pentylamino group, a 1-hexylamino group, a 2-hexylamino group, or a 3-hexylamino group, preferably a $C_1$-$C_4$ alkylamino group, more preferably a $C_1$-$C_2$ alkylamino group, and most preferably a methylamino group. Moreover, in the case of one of the $R^2$ groups, the $C_1$-$C_6$ alkylamino group is preferably a $C_1$-$C_5$ alkylamino group, more preferably a $C_1$-$C_4$ alkylamino group, and even more preferably a $C_2$-$C_4$ alkylamino group.

The "di($C_1$-$C_6$ alkyl)amino group" means an amino group which is substituted with the same or different two $C_1$-$C_6$ alkyl groups as described above and may be for example, a dimethylamino group, a methylethylamino group, a methylpropylamino group [for example, an N-methyl-N-(1-propyl)amino group, etc.], a methylbutylamino group [for example, an N-(1-butyl)-N-methylamino group, etc.], a methylpentylamino group, a methylhexylamino group, a diethylamino group, an ethylpropylamino group [for example, an N-ethyl-N-(1-propyl)amino group, etc.], an ethylbutylamino group, a dipropylamino group, a propylbutylamino group, a dibutylamino group, a dipentylamino group, or a dihexylamino group, preferably a di($C_1$-$C_4$ alkyl)amino group, more preferably a di($C_1$-$C_2$ alkyl)amino group, and most preferably a dimethylamino group. Moreover, in the case of one of the $R^2$ groups, the di($C_1$-$C_6$ alkyl)amino group is preferably a di($C_1$-$C_5$ alkyl)amino group, more preferably a di($C_1$-$C_4$ alkyl)amino group, and even more preferably a di($C_2$-$C_4$ alkyl)amino group.

The "($C_1$-$C_6$ alkyl)carbonylamino group" means an amino group which is substituted with a ($C_1$-$C_6$ alkyl)carbonyl group as described below and may be for example, a methylcarbonylamino group, an ethylcarbonylamino group, a 1-propylcarbonylamino group, a 2-propylcarbonylamino group, a 1-butylcarbonylamino group, a 2-butylcarbonylamino group, a 2-methyl-1-propylcarbonylamino group, a 2-methyl-2-propylcarbonylamino group, a 1-pentylcarbonylamino group, a 2-pentylcarbonylamino group, a 3-pentylcarbonylamino group, a 2-methyl-2-butylcarbonylamino group, a 3-methyl-2-butylcarbonylamino group, a 1-hexylcarbonylamino group, a 2-hexylcarbonylamino group, a 3-hexylcarbonylamino group, a 2-methyl-1-pentylcarbonylamino group, a 3-methyl-1-pentylcarbonylamino group, a 2-ethyl-1-butylcarbonylamino group, a 2,2-dimethyl-1-butylcarbonylamino group, or a 2,3-dimethyl-1-butylcarbonylamino group, preferably a ($C_1$-$C_4$ alkyl)carbonylamino group, more preferably a ($C_1$-$C_2$ alkyl)carbonylamino group, and most preferably a methylcarbonylamino group. Moreover, in the case of one of the $R^2$ groups, the ($C_1$-$C_6$ alkyl)carbonylamino group is preferably a ($C_1$-$C_5$ alkyl)carbonylamino group, more preferably a ($C_1$-$C_4$ alkyl)carbonylamino group, and even more preferably a ($C_2$-$C_4$ alkyl)carbonylamino group.

The "($C_1$-$C_6$ alkoxy)carbonylamino group" means an amino group which is substituted with a ($C_1$-$C_6$ alkoxy)carbonyl group as described below and may be for example, a methoxycarbonylamino group, an ethoxycarbonylamino group, a 1-propoxycarbonylamino group, a 2-propoxycarbonylamino group, a 1-butoxycarbonylamino group, a 2-butoxycarbonylamino group, a 2-methyl-1-propoxycarbonylamino group, a 2-methyl-2-propoxycarbonylamino group, a 1-pentyloxycarbonylamino group, a 2-pentyloxycarbonylamino group, a 3-pentyloxycarbonylamino group, a 2-methyl-2-butoxycarbonylamino group, a 3-methyl-2-butoxycarbonylamino group, a 1-hexyloxycarbonylamino group, a 2-hexyloxycarbonylamino group, a 3-hexyloxycarbonylamino group, a 2-methyl-1-pentyloxycarbonylamino group, a 3-methyl-1-pentyloxycarbonylamino group, a 2-ethyl-1-butoxycarbonylamino group, a 2,2-dimethyl-1-butoxycarbonylamino group, or a 2,3-dimethyl-1-butoxycarbonylamino group, preferably a ($C_1$-$C_4$ alkoxy)carbonylamino group, more preferably a ($C_1$-$C_2$ alkoxy)carbonylamino group, and most preferably a methoxycarbonylamino group. Moreover, in the case of one of the $R^2$ groups, the ($C_1$-$C_6$ alkoxy)carbonylamino is preferably a ($C_1$-$C_5$ alkoxy)carbonylamino group, more preferably a ($C_1$-$C_4$ alkoxy)carbonylamino group, and even more preferably a ($C_2$-$C_4$ alkoxy)carbonylamino group.

The "$C_1$-$C_6$ alkylsulfonylamino group" means an amino group which is substituted with a $C_1$-$C_6$ alkylsulfonyl group as described above and may be for example, a methanesulfonylamino group, an ethanesulfonylamino group, a 1-propanesulfonylamino group, a 2-propanesulfonylamino group, a 1-butanesulfonylamino group, a 2-butanesulfonylamino group, a 2-methyl-1-propanesulfonylamino group, a 2-methyl-2-propanesulfonylamino group, a 1-pentanesulfonylamino group, a 2-pentanesulfonylamino group, a 3-pentanesulfonylamino group, a 2-methyl-2-butanesulfonylamino group, a 3-methyl-2-butanesulfonylamino group, a 1-hexanesulfonylamino group, a 2-hexanesulfonylamino group, a 3-hexanesulfonylamino group, a 2-methyl-1-pentanesulfonylamino group, a 3-methyl-1-pentanesulfonylamino group, a 2-ethyl-1-butanesulfonylamino group, a 2,2-dimethyl-1-butanesulfonylamino group, or a 2,3-dimethyl-1-butanesulfonylamino group, preferably a $C_1$-$C_4$ alkylsulfonylamino group, more preferably a $C_1$-$C_2$ alkylsulfonylamino group, and most preferably a methanesulfonylamino group. Moreover, in the case of one of the $R^2$ groups, the $C_1$-$C_6$ alkylsulfonylamino group is preferably a $C_1$-$C_5$ alkylsulfonylamino group, more preferably a $C_1$-$C_4$ alkylsulfonylamino group, and even more preferably a $C_2$-$C_4$ alkylsulfonylamino group.

The "($C_1$-$C_6$ alkyl)carbonyl group" means a carbonyl group which is substituted with a $C_1$-$C_6$ alkyl group as described above and may be for example, a methylcarbonyl group (an acetyl group), an ethylcarbonyl group, a 1-propylcarbonyl group, a 2-propylcarbonyl group, a 1-butylcarbonyl group, a 2-butylcarbonyl group, a 2-methyl-1-propylcarbonyl group, a 2-methyl-2-propylcarbonyl group, a 1-pentylcarbonyl group, a 2-pentylcarbonyl group, a 3-pentylcarbonyl group, a 2-methyl-2-butylcarbonyl group, a 3-methyl-2-butylcarbonyl group, a 1-hexylcarbonyl group, a 2-hexylcarbonyl group, a 3-hexylcarbonyl group, a 2-methyl-1-pentylcarbonyl group, a 3-methyl-1-pentylcarbonyl group, a 2-ethyl-1-butylcarbonyl group, a 2,2-dimethyl-1-butylcarbonyl group, or a 2,3-dimethyl-1-butylcarbonyl group, preferably a ($C_1$-$C_4$ alkyl)carbonyl group, more preferably a ($C_1$-$C_2$ alkyl)carbonyl group, and most preferably a methylcarbonyl group. Moreover, in the case of one of the $R^2$ groups and $R^{8a}$, the ($C_1$-$C_6$ alkyl)carbonyl group is preferably a ($C_1$-$C_5$ alkyl)carbonyl group, more preferably a ($C_1$-$C_4$ alkyl)carbonyl group, and even more preferably a ($C_2$-$C_4$ alkyl)carbonyl group.

The "($C_1$-$C_6$ alkoxy)carbonyl group" means a carbonyl group which is substituted with a $C_1$-$C_6$ alkoxy group as described above and may be for example, a methoxycarbonyl group, an ethoxycarbonyl group, a 1-propoxycarbonyl group, a 2-propoxycarbonyl group, a 1-butoxycarbonyl group, a 2-butoxycarbonyl group, a 2-methyl-1-propoxycarbonyl group, a 2-methyl-2-propoxycarbonyl group, a 1-pentyloxycarbonyl group, a 2-pentyloxycarbonyl group, a 3-pentyloxycarbonyl group, a 2-methyl-2-butoxycarbonyl group, a 3-methyl-2-butoxycarbonyl group, a 1-hexyloxycarbonyl group, a 2-hexyloxycarbonyl group, a 3-hexyloxycarbonyl group, a 2-methyl-1-pentyloxycarbonyl group, a 3-methyl-1-pentyloxycarbonyl group, a 2-ethyl-1-butoxycarbonyl group, a 2,2-dimethyl-1-butoxycarbonyl group, or a 2,3-dimethyl-1-butoxycarbonyl group, preferably a ($C_1$-$C_4$ alkoxy)carbonyl group, more preferably a ($C_1$-$C_2$ alkoxy)carbonyl group, and most preferably a methoxycarbonyl group. Moreover, in the case of one of the $R^2$ groups and $R^{8a}$, the ($C_1$-$C_6$ alkoxy)carbonyl group is preferably a ($C_1$-$C_5$ alkoxy)carbonyl group, more preferably a ($C_1$-$C_4$ alkoxy)carbonyl group, and even more preferably a ($C_2$-$C_4$ alkoxy)carbonyl group.

The "($C_1$-$C_6$ alkylamino)carbonyl group" means a carbonyl group which is substituted with a $C_1$-$C_6$ alkylamino group as described above and may be for example, a methylaminocarbonyl group, an ethylaminocarbonyl group, a 1-propylaminocarbonyl group, a 2-propylaminocarbonyl group, a 1-butylaminocarbonyl group, a 2-butylaminocarbonyl group, a 2-methyl-1-propylaminocarbonyl group, a 2-methyl-2-propylaminocarbonyl group, a 1-pentylaminocarbonyl group, a 2-pentylaminocarbonyl group, a 3-pentylaminocarbonyl group, a 1-hexylaminocarbonyl group, a 2-hexylaminocarbonyl group, or a 3-hexylaminocarbonyl group, preferably a ($C_1$-$C_4$ alkylamino)carbonyl group, more preferably a ($C_1$-$C_2$ alkylamino)carbonyl group, and most preferably a methylaminocarbonyl group. Moreover, in the case of one of the $R^2$ groups and $R^{8a}$, the ($C_1$-$C_6$ alkylamino)carbonyl group is preferably a ($C_1$-$C_5$ alkylamino)carbonyl group, more preferably a ($C_1$-$C_4$ alkylamino)carbonyl group, and even more preferably a ($C_2$-$C_4$ alkylamino)carbonyl group.

The "di($C_1$-$C_6$ alkyl)aminocarbonyl group" means a carbonyl group which is substituted with a di($C_1$-$C_6$ alkyl)amino group as described above and may be for example, a dimethylaminocarbonyl group, a methylethylaminocarbonyl group, a methylpropylaminocarbonyl group [for example, an N-methyl-N-(1-propyl)aminocarbonyl group, etc.], a methylbutylaminocarbonyl group [for example, an N-(1-butyl)-N-methylaminocarbonyl group, etc.], a methylpentylaminocarbonyl group, a methylhexylaminocarbonyl group, a diethylaminocarbonyl group, an ethylpropylaminocarbonyl group [for example, an N-ethyl-N-(1-propyl)aminocarbonyl group, etc.], an ethylbutylaminocarbonyl group, a dipropylaminocarbonyl group, a propylbutylaminocarbonyl group, a dibutylaminocarbonyl group, a dipentylaminocarbonyl group, or a dihexylaminocarbonyl group, preferably a di($C_1$-$C_4$ alkyl)aminocarbonyl group, more preferably a di($C_1$-$C_2$ alkyl)aminocarbonyl group, and most preferably a dimethylaminocarbonyl group. Moreover, in the case of one of the $R^2$ groups and $R^{8a}$, the di($C_1$-$C_6$ alkyl)aminocarbonyl group is preferably a di($C_1$-$C_5$ alkyl)aminocarbonyl group, more preferably a di($C_1$-$C_4$ alkyl)aminocarbonyl group, and even more preferably a di($C_2$-$C_4$ alkyl)aminocarbonyl group.

The "($C_1$-$C_6$ alkylamino)sulfonyl group" means a sulfonyl group (—$SO_2$—) which is substituted with a $C_1$-$C_6$ alkylamino group as described above and may be for example, a (methylamino)sulfonyl group, an (ethylamino)sulfonyl group, a (1-propylamino)sulfonyl group, a (2-propylamino)sulfonyl group, a (1-butylamino)sulfonyl group, a (2-butylamino)sulfonyl group, a (2-methyl-1-propylamino)sulfonyl group, a (2-methyl-2-propylamino)sulfonyl group, a (1-pentylamino)sulfonyl group, a (2-pentylamino)sulfonyl group, a (3-pentylamino)sulfonyl group, a (1-hexylamino)sulfonyl group, a (2-hexylamino)sulfonyl group, or a (3-hexylamino)sulfonyl group, preferably a ($C_1$-$C_4$ alkylamino)sulfonyl group, more preferably a ($C_1$-$C_2$ alkylamino)sulfonyl group, and most preferably a (methylamino)sulfonyl group. Moreover, in the case one of $R^2$ groups and $R^{8a}$, the ($C_1$-$C_6$ alkylamino)sulfonyl group is preferably a ($C_1$-$C_5$ alkylamino)sulfonyl group, more preferably a ($C_1$-$C_4$ alkylamino)sulfonyl group, and even more preferably a ($C_2$-$C_4$ alkylamino)sulfonyl group.

The "di($C_1$-$C_6$ alkyl)aminosulfonyl group" means a sulfonyl group (—$SO_2$—) which is substituted with a di($C_1$-$C_6$ alkyl)amino group as described above and may be for example, a (dimethylamino)sulfonyl group, a (methylethylamino)sulfonyl group, a (methylpropylamino)sulfonyl group [for example, an N-methyl-N-(1-propyl)amino]sulfonyl group, etc.], a (methylbutylamino)sulfonyl group [for example, an N-(1-butyl)-N-methylamino]sulfonyl group, etc.], a (methylpentylamino)sulfonyl group, a (methylhexylamino)sulfonyl group, a (diethylamino)sulfonyl group, an (ethylpropylamino)sulfonyl group [for example, an N-ethyl-N-(1-propyl)amino]sulfonyl group, etc.], an (ethylbutylamino)sulfonyl group, a (dipropylamino)sulfonyl group, a (propylbutylamino)sulfonyl group, a (dibutylamino)sulfonyl group, a (dipentylamino)sulfonyl group, or a (dihexylamino)sulfonyl group, preferably a di($C_1$-$C_4$ alkyl)aminosulfonyl group, more preferably a di($C_1$-$C_2$ alkyl)aminosulfonyl group, and most preferably a (dimethylamino)sulfonyl group. Moreover, in the case of one of the $R^2$ groups and $R^{8a}$, the di($C_1$-$C_6$ alkyl)aminosulfonyl group is preferably a di($C_1$-$C_5$ alkyl)aminosulfonyl group, more preferably a di($C_1$-$C_4$ alkyl)aminosulfonyl group, and even more preferably a di($C_2$-$C_4$ alkyl)aminosulfonyl group.

The symbols "m" and "n" indicate the number of $R^2$ groups and the number of $R^3$ groups, respectively. The symbol "m" represents 0, 1, 2, or 3, preferably 0, 1, or 2, more preferably 1 or 2, and most preferably 1. The symbol "n" represents 0 or 1. Preferably, when m is 1 or 2, n is 0, and when m is 0, n is 1. When m is 3, n is 0.

X is an atom that forms A. X represents a carbon atom or a nitrogen atom, and preferably represents a carbon atom.

In general formula (I), the group represented by the following formula (III)

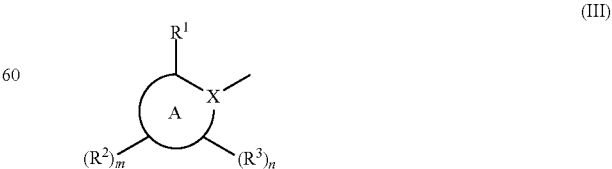

is preferably a group represented by the following formula (III-1) or (III-2),

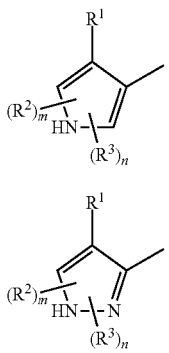

(III-1)

(III-2)

more preferably a group represented by the following formula (III-3), (III-4), or (III-5),

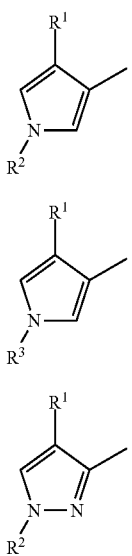

(III-3)

(III-4)

(III-5)

even more preferably a group represented by formula (III-3) or (III-4), and most preferably a group represented by formula (III-3).

Moreover, in general formula (I), the group represented by the above-described formula (III) is preferably a group represented by the following formula (III-6), (III-7), or (III-8),

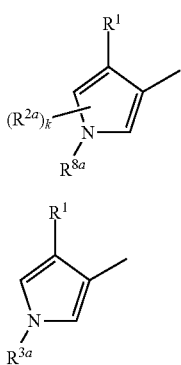

(III-6)

(III-7)

(III-8)

more preferably a group represented by formula (III-6) or (III-7), and most preferably a group represented by formula (III-6).

The compound represented by general formula (I) of the present invention has an acidic group, and it can be combined with a base to form salts. Such salts are also included in the present invention. Examples of such salts may include metal salts, inorganic amine salts, organic amine salts, and amino acid salts. Examples of such metal salts may include alkali metal salts such as sodium salts, potassium salts, or lithium salts; alkaline-earth metal salts such as calcium salts or magnesium salts; aluminum salts; iron salts; zinc salts; copper salts; nickel salts; and cobalt salts. Examples of such inorganic amine salts may be ammonium salts. Examples of such organic amine salts may include morpholine salts, glucosamine salts, ethylenediamine salts, guanidine salts, diethylamine salts, triethylamine salts, dicyclohexylamine salts, diethanolamine salts, piperazine salts, and tetramethylammonium salts. Examples of such amino acid salts may include glycine salts, lysine salts, arginine salts, ornithine salts, glutamic acid salts, and aspartic acid salts.

When the compound represented by general formula (I) of the present invention has a basic group, it can be combined with an acid to form salts. Such salts are also included in the present invention. Examples of such salts may include inorganic acid salts, organic acid salts, and sulfonic acid salts. Examples of such inorganic acid salts may include hydrochloride, hydrobromide, sulfate, nitrate, and phosphate. Examples of such organic acid salts may include acetate, oxalate, malonate, fumarate, maleate, phthalate, and trifluoroacetate. Examples of such sulfonic acid salts may include methanesulfonate, benzenesulfonate, p-toluenesulfonate, 2,4-dimethylbenzenesulfonate, 2,4,6-trimethylbenzenesulfonate, 4-ethylbenzenesulfonate, and naphthalenesulfonate.

The compound represented by general formula (I) of the present invention or a pharmacologically acceptable salt thereof can form a hydrate or a solvate. Such hydrates, solvates, and mixtures thereof are also included in the present invention.

When the compound represented by general formula (I) of the present invention or a pharmacologically acceptable salt thereof has at least one asymmetric center, carbon-carbon double bond, and the like, optical isomers (including enantiomers and diastereoisomers) or geometric isomers may exist. Such isomers and mixtures thereof are represented by a single formula such as formula (I). The present invention also includes such isomers and mixtures thereof that are mixed at any given ratios (including a racemate).

The compound represented by general formula (I) of the present invention or a pharmacologically acceptable salt thereof can form an isotopic compound in which one or more constituent atoms have been substituted with isotopic atoms in a non-native ratio. Such isotopic atoms may be radioactive or nonradioactive atoms. Examples of such isotopic atoms include deuterium ($^2H$; D), tritium ($^3H$; T), carbon-14 ($^{14}C$), and iodine-125 ($^{125}I$). A compound labeled with radioactive isotopic atoms can be used as an agent for the treatment or prophylaxis of diseases, a reagent used for research (for example, a reagent used for an assay), a diagnostic agent (for example, a diagnostic imaging agent), or the like. The present invention also includes a radioactive or nonradioactive, isotopic compound.

The compound represented by general formula (I) of the present invention can be produced according to the following method A to method T. Hereinafter, the compound represented by general formula (I) is also referred to as compound (I) at times. The same applies to cases of using other formulae.

Method A

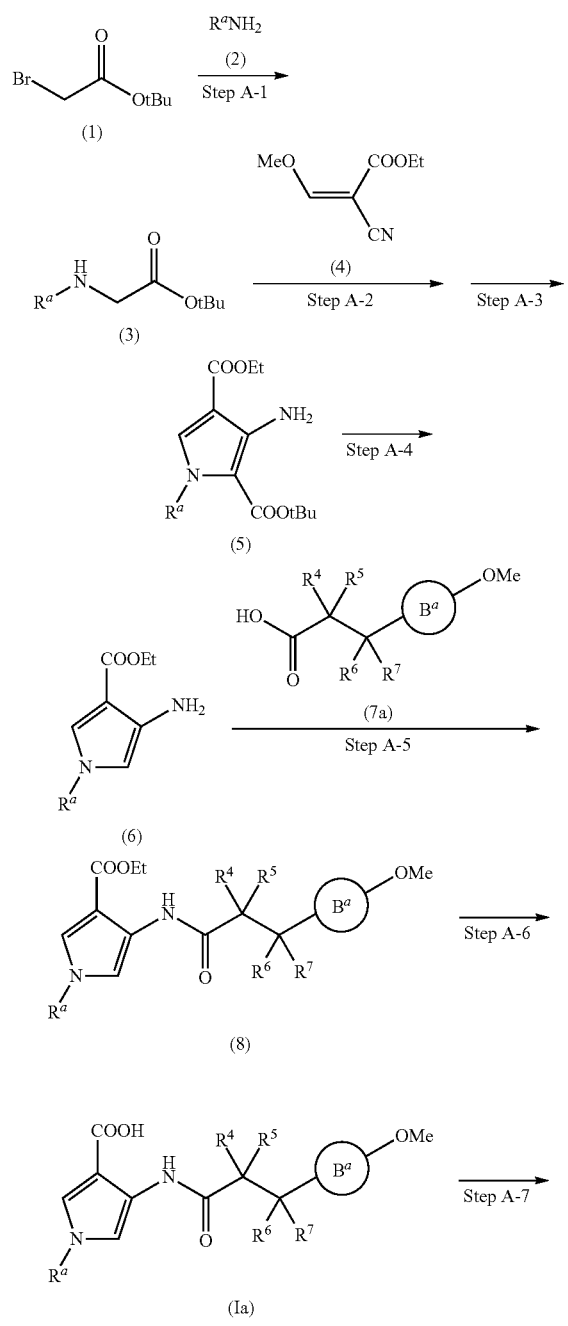

Method B

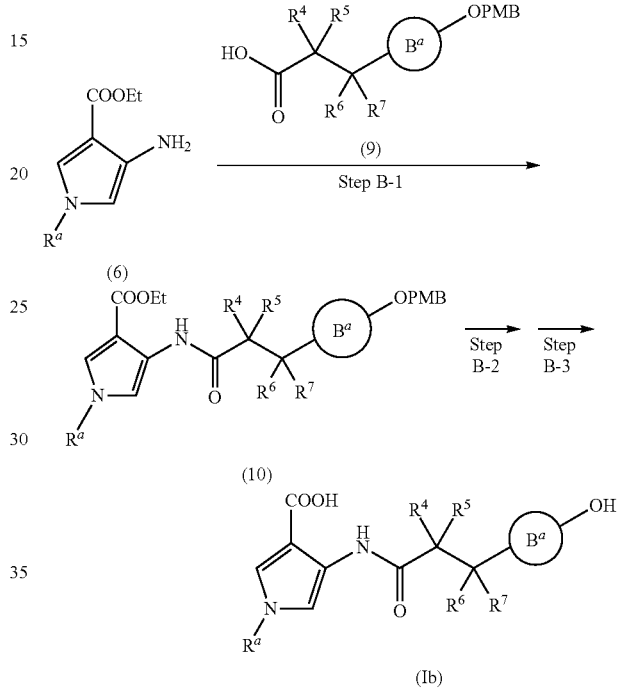

Method C

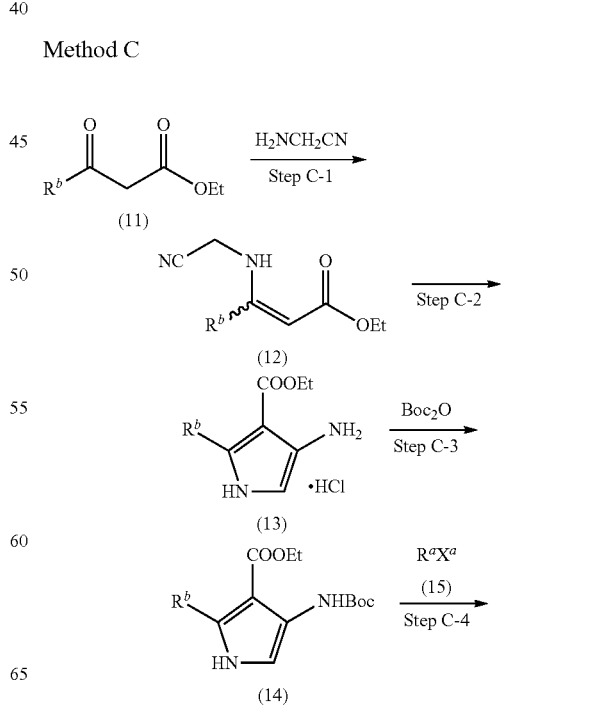

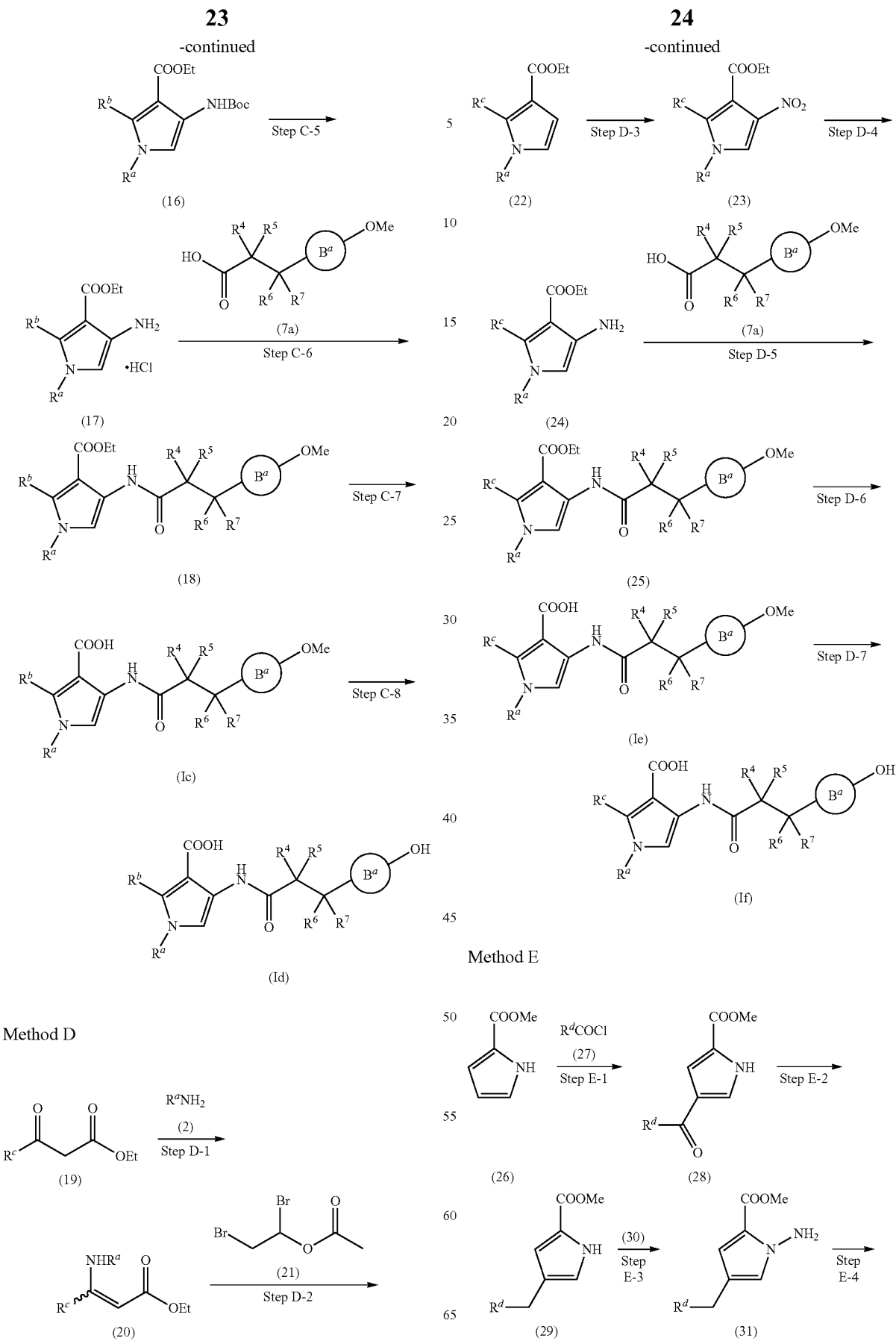

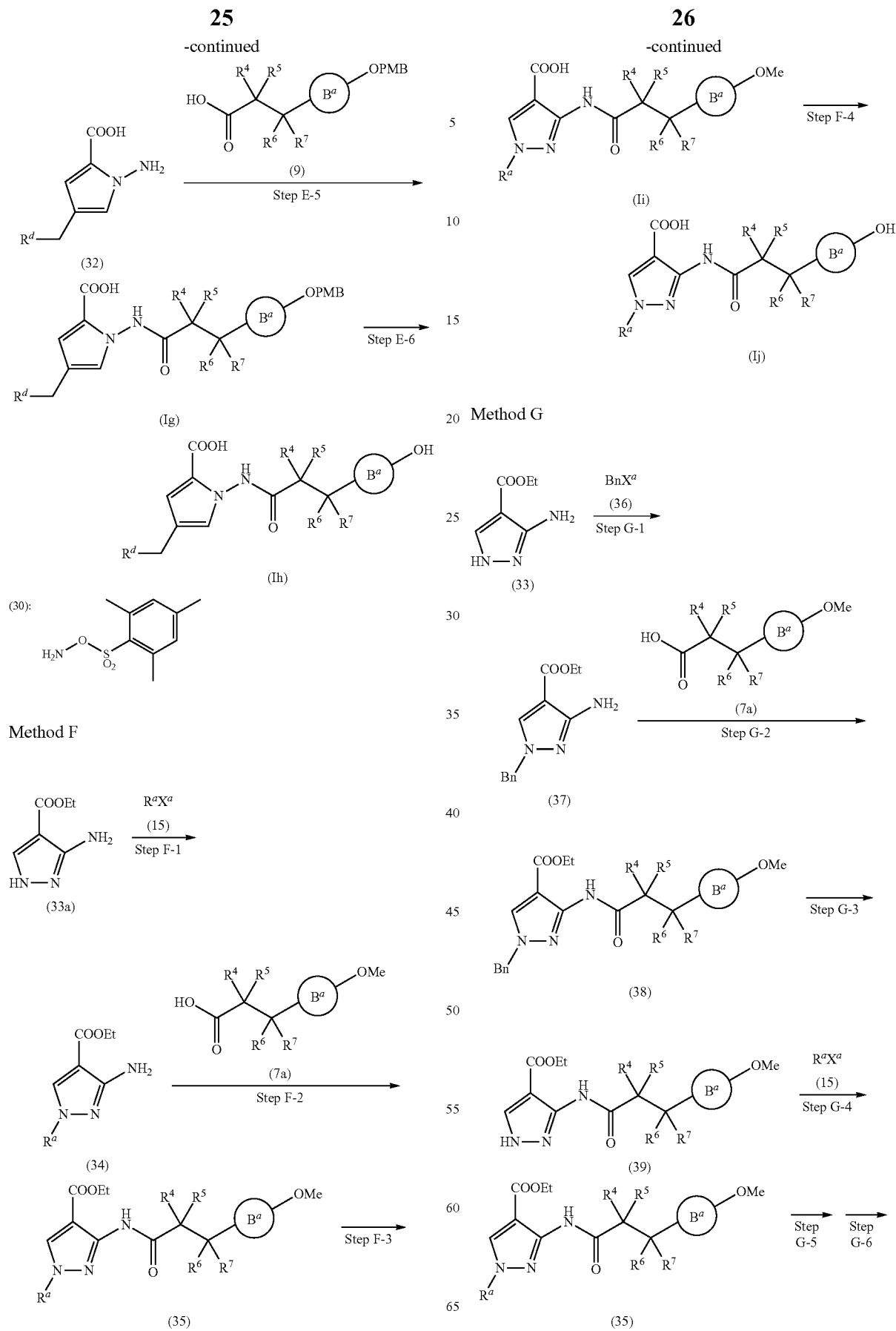

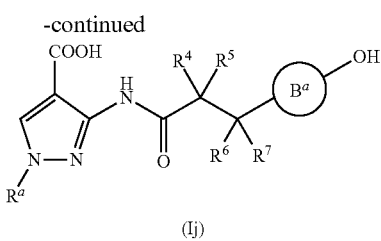
(Ij)
Method H
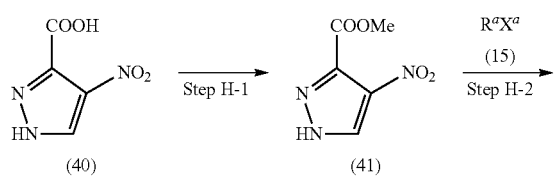
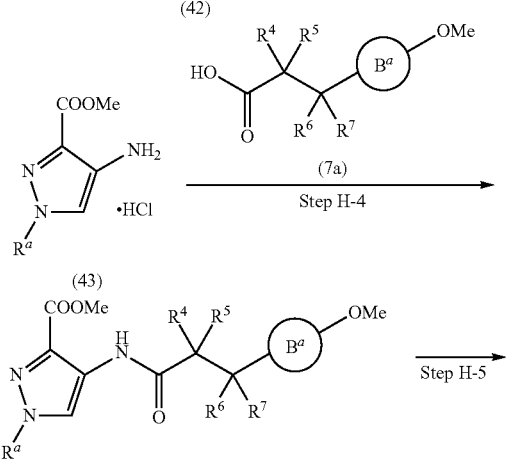
(Ik)
Method I
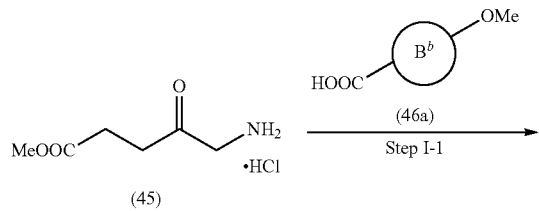
-continued
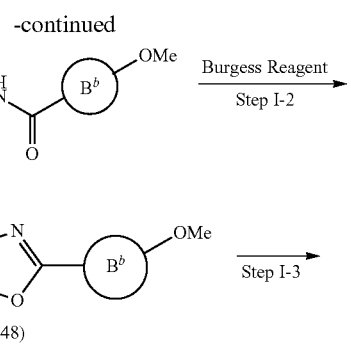
Method J
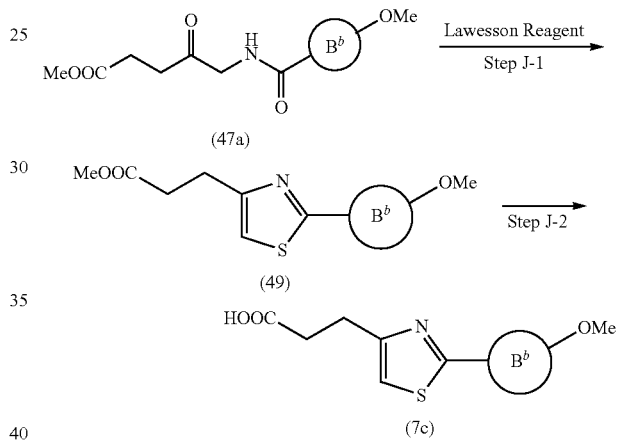
Method K
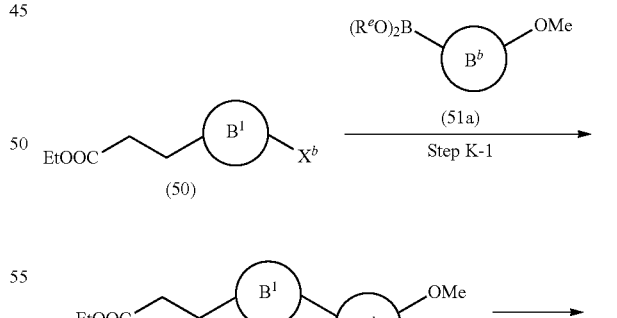

Method L
Method M
Method N
Method O
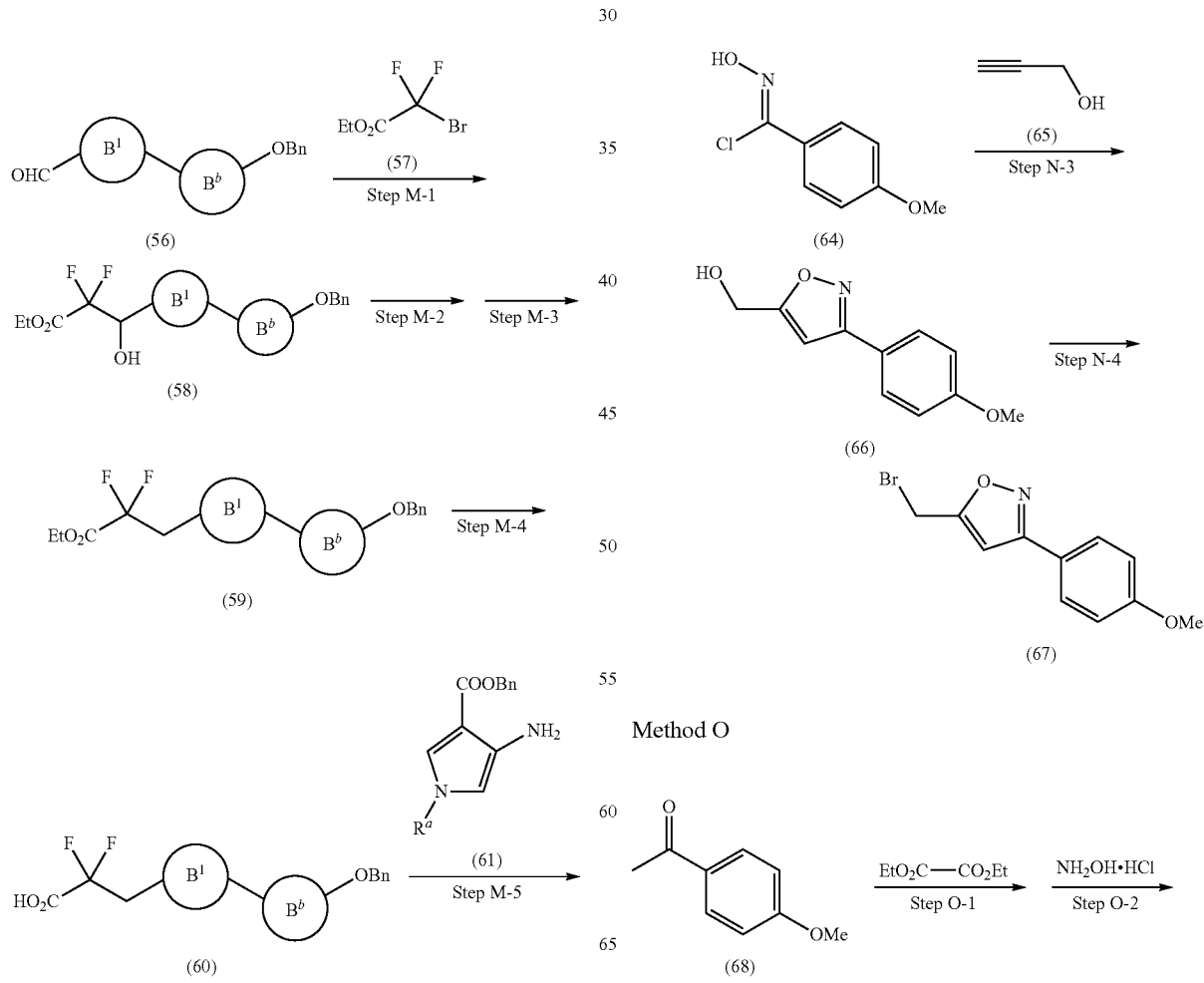

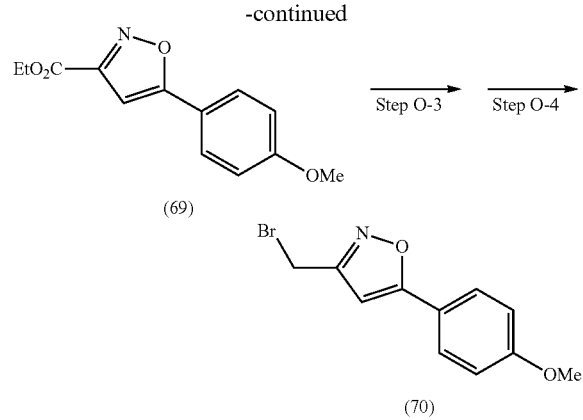
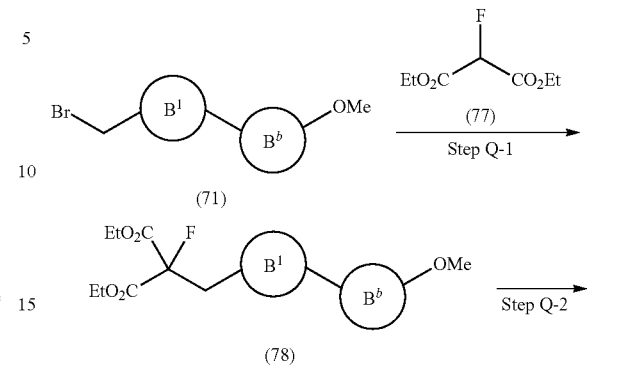
Method P
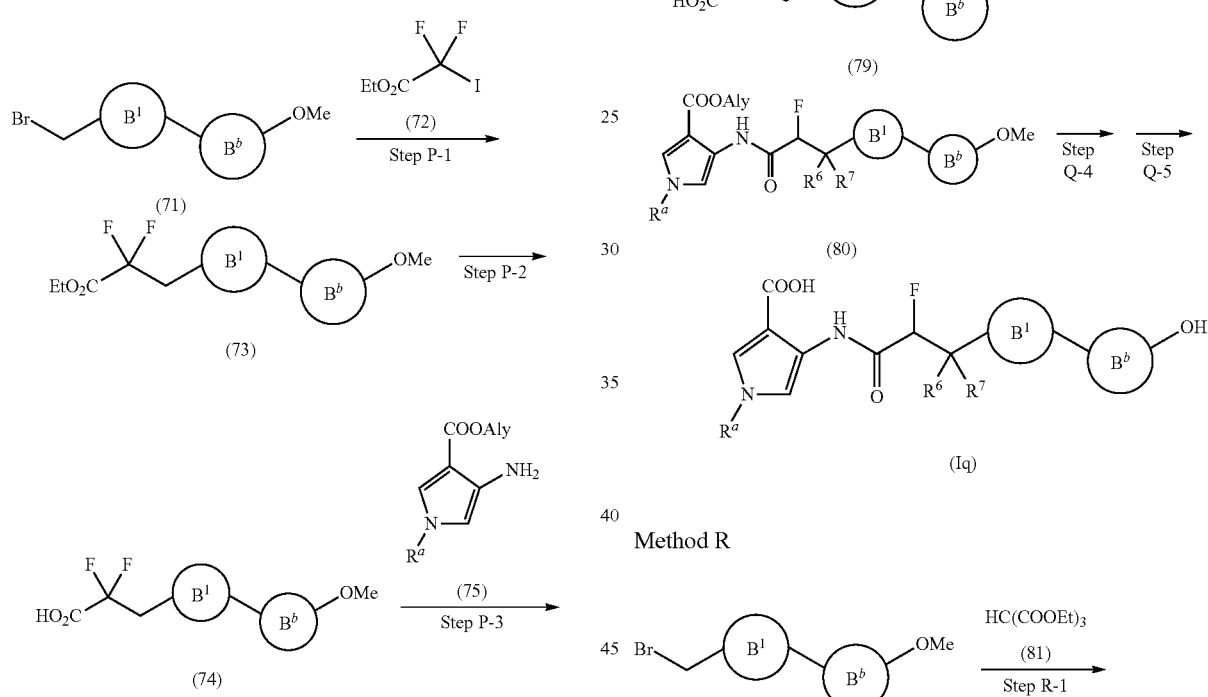
Method Q
Method R
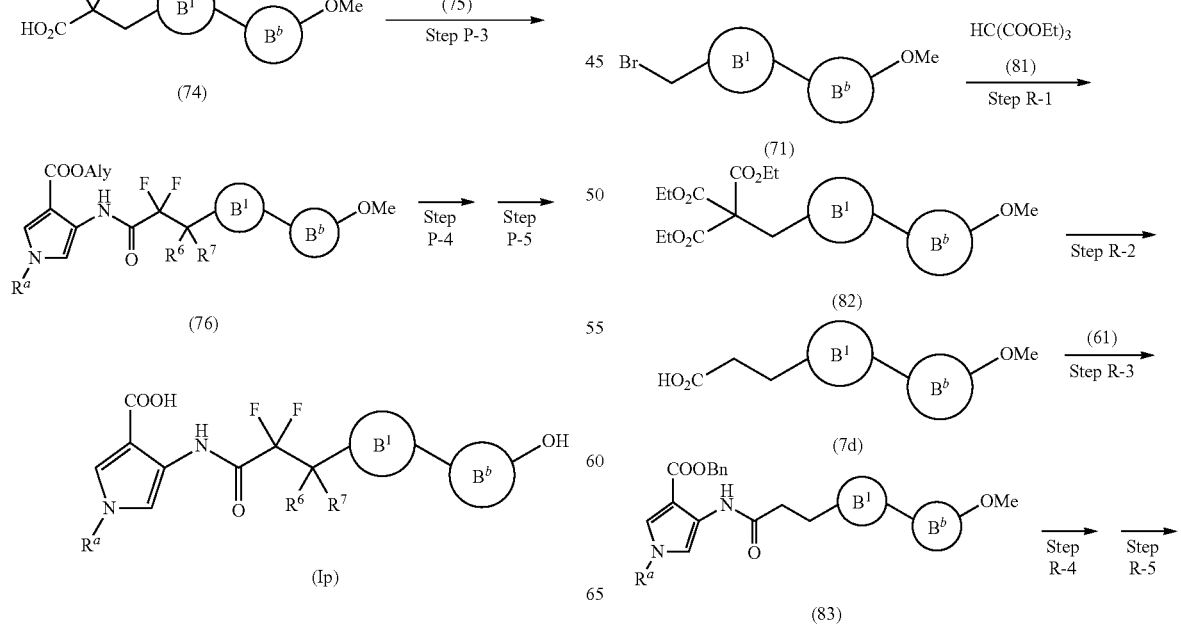

33
34
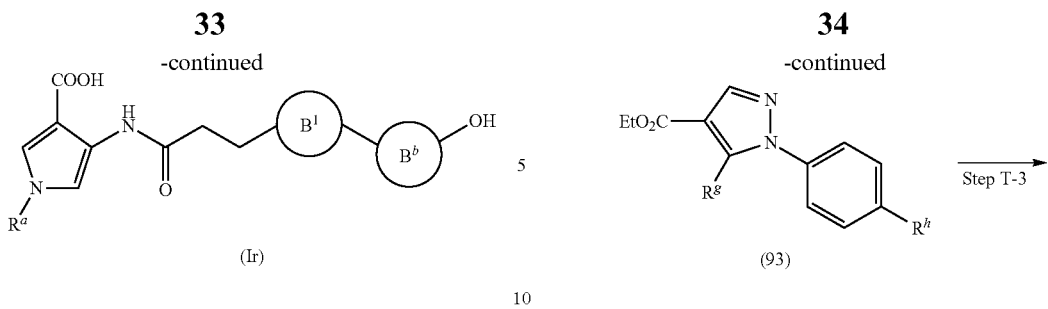
Method S
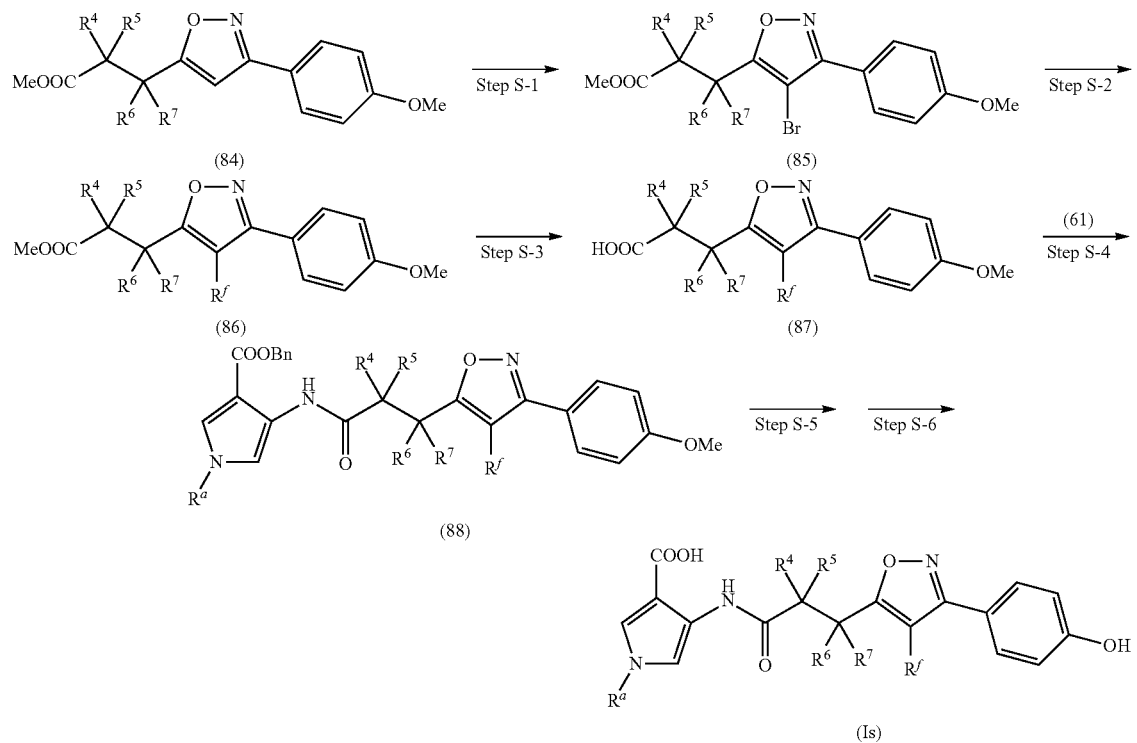
Method T
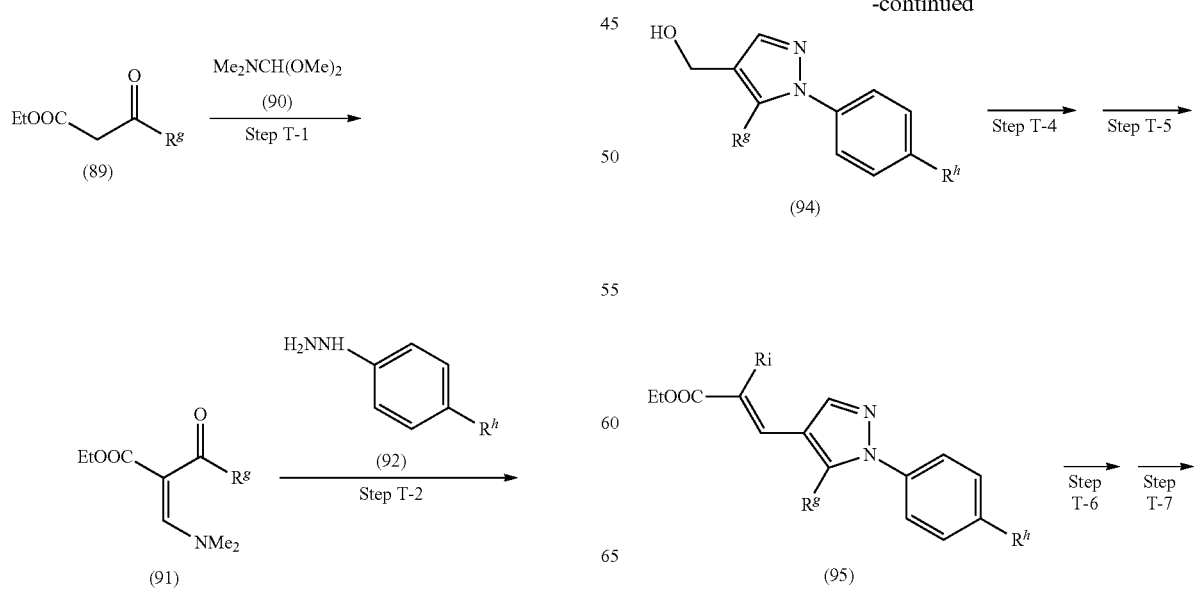

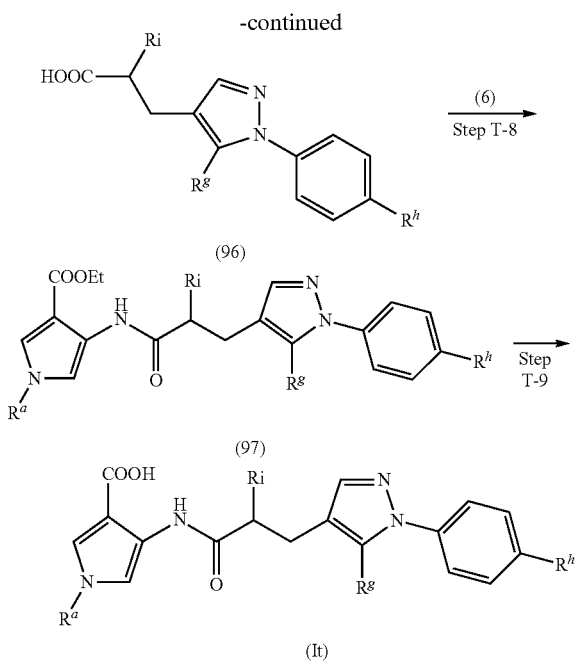

In the structural formulae of the compounds in the above-described method A to method T, $R^4$, $R^5$, $R^6$, $R^7$, and B have the same meanings as those in formula (I). In addition, $B^a$ represents the group obtained by removing a hydroxy group from a group B which has such a hydroxy group; and $B^b$ represents the group obtained by removing a hydroxy group from a group $B^2$ which has such a hydroxy group. $R^a$ has the same meaning as those of $R^2$ or $R^3$ (wherein groups incapable of binding to a nitrogen atom are excluded); $R^b$ and $R^c$ have the same meanings as those of $R^2$ or $R^3$; and $R^d$, together with a methylene group bound thereto, has the same meaning as those of $R^2$ or $R^3$. $R^e$ represents a hydrogen atom or a lower alkyl group; $R^f$ represents a group that is selected from substituent group α and can be used in a carbon-carbon bond forming reaction in the presence of a palladium catalyst (for example, a vinyl group, a cyclopropyl group, etc.); and each of $R^g$ and $R^h$ independently represents a group selected from substituent group α. $R^i$ represents a hydrogen atom or a fluorine atom; $X^a$ represents a chloro group, a bromo group, an iodo group, a methanesulfonyloxy group, or a p-toluenesulfonyloxy group; and $X^b$ represents a bromo group, an iodo group, or a trifluoromethanesulfonyloxy group. Aly represents an allyl group; Bn represents a benzyl group; Boc represents a tert-butoxycarbonyl group; tBu represents a 2-methyl-2-propyl group; and PMB represents a p-methoxybenzyl group.

In the reactions in each step of methods A to T as described below, when a compound serving as a reaction substrate has a group that inhibits the reaction, such as an amino group, a hydroxy group, or a carboxy group, introduction of a protecting group into such group, and the subsequent removal of the introduced protecting group, may be carried out, as necessary. Such protecting group is not particularly limited as long as it is a commonly used protecting group and may be, for example, protecting groups described in T. W. Greene, P. G. Wuts, Protective Groups in Organic Synthesis. Third Edition, 1999, John Wiley & Sons, Inc. Reactions for introducing and removing such protecting groups can be carried out according to well known methods, such as those described in the above-described reference.

The solvent(s) used in the reactions in each step of methods A to T as described below is not particularly limited, as long as it does not inhibit the reaction and dissolves a starting material in part, and is, for example, selected from the following group of solvents. The group of solvents consists of aliphatic hydrocarbons such as hexane, pentane, petroleum ether, or cyclohexane; aromatic hydrocarbons such as benzene, toluene, or xylene; halogenated hydrocarbons such as methylene chloride, chloroform, carbon tetrachloride, dichloroethane, chlorobenzene, or dichlorobenzene; ethers such as diethyl ether, diisopropyl ether, tetrahydrofuran, dioxane, dimethoxyethane, or diethylene glycol dimethyl ether; ketones such as acetone, methyl ethyl ketone, methyl isobutyl ketone, or cyclohexanone; esters such as ethyl acetate, propyl acetate, or butyl acetate; nitriles such as acetonitrile, propionitrile, butyronitrile, or isobutyronitrile; carboxylic acids such as acetic acid or propionic acid; alcohols such as methanol, ethanol, 1-propanol, 2-propanol, 1-butanol, 2-butanol, 2-methyl-1-propanol, or 2-methyl-2-propanol; amides such as formamide, dimethylformamide, dimethylacetamide, N-methyl-2-pyrrolidone, or hexamethylphosphorotriamide; sulfoxides such as dimethyl sulfoxide or sulfolane; water; and mixtures thereof.

The acid(s) used in the reactions in each step of methods A to T as described below is not particularly limited as long as it does not inhibit the reaction and is selected from the following groups of acids. The group of acids consists of inorganic acids such as hydrochloric acid, hydrobromic acid, hydriodic acid, phosphoric acid, sulfuric acid, or nitric acid; organic acids such as acetic acid, propionic acid, trifluoroacetic acid, or pentafluoropropionic acid; and organic sulfonic acids such as methanesulfonic acid, trifluoromethane sulfonic acid, p-toluenesulfonic acid, or camphorsulfonic acid.

The base(s) used in the reactions in each step of methods A to T as described below is not particularly limited as long as it does not inhibit the reaction and is selected from the following group of bases. The group of bases consists of alkali metal carbonates such as lithium carbonate, sodium carbonate, potassium carbonate, or cesium carbonate; alkali metal hydrogencarbonates such as lithium hydrogencarbonate, sodium hydrogencarbonate, or potassium hydrogencarbonate; alkali metal hydroxides such as lithium hydroxide, sodium hydroxide, or potassium hydroxide; alkaline-earth metal hydroxides such as calcium hydroxide or barium hydroxide; alkali metal hydrides such as lithium hydride, sodium hydride, or potassium hydride; alkali metal amides such as lithium amide, sodium amide, or potassium amide; alkali metal alkoxides such as lithium methoxide, sodium methoxide, sodium ethoxide, sodium tert-butoxide, or potassium tert-butoxide; lithium alkyl amides such as lithium diisopropyl amide; silylamides such as lithium bis(trimethylsilyl)amide or sodium bis(trimethylsilyl)amide; alkyl lithiums such as n-butyl lithium, sec-butyl lithium, or tert-butyl lithium; and organic amines such as triethylamine, tributylamine, diisopropylethylamine, N-methyl piperidine, N-methyl morpholine, N-ethyl morpholine, pyridine, picoline, 4-(N,N-dimethylamino)pyridine, 4-pyrrolidinopyridine, 2,6-di(tert-butyl)-4-methylpyridine, quinoline, N,N-dimethylaniline, N,N-diethylaniline, 1,5-diazabicyclo[4,3,0]non-5-ene (DBN), 1,4-diazabicyclo[2,2,2]octane (DABCO), or 1,8-diazabicyclo[5,4,0]undec-7-ene (DBU).

In the reactions in each step of methods A to T as described below, the reaction temperature differs depending on the solvent(s), the starting material(s), the reagent(s), and the like, and the reaction times differ depending on the solvent(s), the starting material(s), the reagent(s), the reaction temperature, and the like.

In the reactions in each step of methods A to T as described below, the desired compound in each step may be isolated from the reaction mixture according to a well known method after completion of the reaction. The desired compound may be obtained, for example, by (i) removing insoluble materials such as a catalyst by filtration, as necessary, (ii) adding water and a water-immiscible solvent (for example, ethyl acetate, etc.) to the reaction mixture to extract the desired compound, (iii) washing an organic layer with water and drying it over a drying agent such as anhydrous magnesium sulfate, and (iv) distilling away the solvent. The desired compound obtained above may be purified, as necessary, according to a well known method such as recrystallization, reprecipitation, or silica gel column chromatography. In addition, the desired compound obtained in each step may be directly used in the subsequent reaction without being purified.

(Method A)

Method A is a method for producing compound (Ia) or (Ib) included in compound (I).

(Step A-1)

Step A-1 is a step of allowing compound (1) to react with compound (2) in the presence of a base. Compound (1) and compound (2) are publicly known or can be easily produced from publicly known compounds.

The base used is preferably an organic amine, and most preferably triethylamine. In step A-1, an excess of compound (2) can be used instead of a base.

The solvent used is preferably an ether, and more preferably diethyl ether or t-butyl methyl ether.

The reaction temperature is preferably between −20° C. and 50° C.

The reaction time is preferably between 30 minutes and 24 hours.

(Step A-2)

Step A-2 is a step of allowing compound (3) to react with compound (4). Compound (4) is publicly known or can be easily produced from a publicly known compound.

The solvent used is preferably an ether, and more preferably tetrahydrofuran.

The reaction temperature is preferably between −20° C. and 100° C.

The reaction time is preferably between 30 minutes and 24 hours.

(Step A-3)

Step A-3 is a step of treating the compound obtained in step A-2 with a base.

The base used is preferably an alkali metal hydride, and most preferably sodium hydride.

The solvent used is preferably an ether, and most preferably tetrahydrofuran.

The reaction temperature is preferably between −20° C. and 100° C.

The reaction time is preferably between 30 minutes and 12 hours.

(Step A-4)

Step A-4 is a step of treating compound (5) with an acid.

The acid used is preferably hydrochloric acid.

The solvent used is preferably an ether, and most preferably 1,4-dioxane.

The reaction temperature is preferably between −20° C. and 150° C.

The reaction time is preferably between 30 minutes and 12 hours.

(Step A-5)

Step A-5 is a step of allowing compound (6) to react with compound (7a) in the presence of a condensing reagent and a base. Compound (7a) is publicly known or can be easily produced from a publicly known compound. Otherwise, compound (7a) can be produced by method I, method J, or method K.

The condensing reagent used is not limited as long as it can be used in an amidation reaction of a carboxy group and is preferably a tetramethyluronium compound such as O-(7-azabenzotriazol-1-yl)-N,N,N',N'-tetramethyluronium hexafluorophosphate (HATU), or O-(benzotriazol-1-yl)-N,N,N',N'-tetramethyluronium hexafluorophosphate (HBTU), and most preferably O-(7-azabenzotriazol-1-yl)-N,N,N',N'-tetramethyluronium hexafluorophosphate.

The base used is preferably an organic amine, and most preferably triethylamine.

The solvent used is preferably an amide, and most preferably dimethylformamide.

The reaction temperature is preferably between −20° C. and 100° C.

The reaction time is preferably between 5 minutes and 6 hours.

(Step A-6)

Step A-6 is a step of hydrolyzing compound (8) in the presence of a base.

The base used is preferably an alkali metal hydroxide, and more preferably lithium hydroxide or sodium hydroxide.

The solvent used is preferably an ether, an alcohol, or a mixture thereof, more preferably tetrahydrofuran, methanol, or a mixture thereof, and most preferably a mixture of tetrahydrofuran and methanol. Step A-6 is carried out in the presence of water.

The reaction temperature is preferably between −20° C. and 100° C.

The reaction time is preferably between 30 minutes and 12 hours.

(Step A-7)

Step A-7 is a step of converting a methoxy group in compound (Ia) to a hydroxy group.

The reagent used is not limited as long as it can convert a methoxy group to a hydroxy group and is preferably a halogenated boron such as boron trifluoride, boron trichloride or boron tribromide, or trimethylsilyl iodide, and most preferably boron tribromide.

The solvent used is preferably a halogenated hydrocarbon, and most preferably methylene chloride.

The reaction temperature is preferably between −20° C. and 100° C.

The reaction time is preferably between 30 minutes and 12 hours.

In method A, compound (Im) included in compound (I), which is represented by the following formula

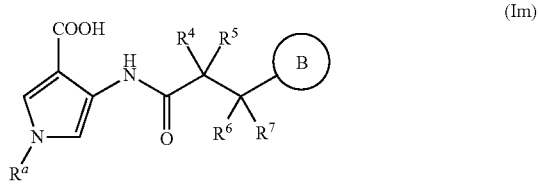

(Im)

can be produced by using compound (7) represented by the following formula

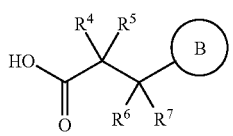

(7)

instead of compound (7a).

(Method B)

Method B is a method for producing compound (Ib) included in compound (I).

(Step B-1)

Step B-1 is a step of allowing compound (5) to react with compound (9) in the presence of a base. Compound (9) is publicly known or can be easily produced from a publicly known compound.

Step B-1 can be carried out according to a method similar to the method applied in step A-5.

(Step B-2)

Step B-2 is a step of treating compound (10) with a silane compound in the presence of an acid, so as to remove the p-methoxybenzyl group in the compound (10).

The silane compound used is not limited as long as it can remove a p-methoxybenzyl group and is preferably a trialkylsilane, and most preferably triethylsilane.

The acid used is preferably an organic acid, and most preferably trifluoroacetic acid.

The solvent used is preferably a halogenated hydrocarbon, and most preferably methylene chloride.

The reaction temperature is preferably between −20° C. and 50° C.

The reaction time is preferably between 30 minutes and 12 hours.

(Step B-3)

Step B-3 is a step of hydrolyzing the compound obtained in step B-2 in the presence of a base.

Step B-3 can be carried out according to a method similar to the method applied in step A-6.

(Method C)

Method C is a method for producing compound (Ic) or (Id) included in compound (I).

(Step C-1)

Step C-1 is a step of allowing compound (11) to react with aminoacetonitrile in the presence of a base. Compound (11) is publicly known or can be easily produced from a publicly known compound.

The base used is preferably an organic amine, and most preferably triethylamine.

The solvent used is preferably an alcohol, and most preferably ethanol.

The reaction temperature is preferably between 0° C. and 150° C.

The reaction time is preferably between 30 minutes and 6 hours.

(Step C-2)

Step C-2 is a step of treating compound (12) with a base.

The base used is preferably an alkali metal alkoxide, and most preferably sodium ethoxide.

The solvent used is preferably an alcohol, and most preferably ethanol.

The reaction temperature is preferably between 0° C. and 100° C.

The reaction time is preferably between 6 hours and 3 days.

In step C-2, compound (13) may be obtained in the form of free amine.

(Step C-3)

Step C-3 is a step of allowing compound (13) to react with di-tert-butyl dicarbonate in the presence of a base.

The base used is preferably an organic amine, and most preferably a mixture of triethylamine and 4-(N,N-dimethylamino)pyridine.

The solvent used is preferably a halogenated hydrocarbon, and most preferably methylene chloride.

The reaction temperature is preferably between −20° C. and 50° C.

The reaction time is preferably between 30 minutes and 24 hours.

(Step C-4)

Step C-4 is a step of allowing compound (14) to react with compound (15) in the presence of a base. Compound (15) is publicly known or can be easily produced from a publicly known compound.

The base used is preferably an alkali metal hydride, and most preferably sodium hydride.

The solvent used is preferably a nitrile or an amide, and more preferably acetonitrile or dimethylformamide.

The reaction temperature is preferably between −20° C. and 100° C.

The reaction time is preferably between 5 minutes and 2 hours.

(Step C-5)

Step C-5 is a step of treating compound (16) with an acid to remove a tert-butoxycarbonyl group in compound (16).

The acid used is preferably an organic solvent solution of hydrogen chloride, and most preferably a hydrogen chloride-ethyl acetate solution.

The solvent used is preferably an ester, and most preferably ethyl acetate.

The reaction temperature is preferably between 0° C. and 50° C.

The reaction time is preferably between 30 minutes and 12 hours.

In step C-5, compound (17) may be obtained in the form of free amine.

(Step C-6)

Step C-6 is a step of allowing compound (17) to react with compound (7a) in the presence of a base.

Step C-6 can be carried out according to a method similar to the method applied in step A-5.

(Step C-7)

Step C-7 is a step of hydrolyzing compound (18) in the presence of a base.

Step C-7 can be carried out according to a method similar to the method applied in step A-6.

(Step C-8)

Step C-8 is a step of converting a methoxy group in compound (Ic) to a hydroxy group.

Step C-8 can be carried out according to a method similar to the method applied in step A-7.

Production of compound (Id) from compound (17) in method C can also be carried out according to a method similar to method B using compound (9).

In method C, compound (In) included in compound (I), which is represented by the following formula

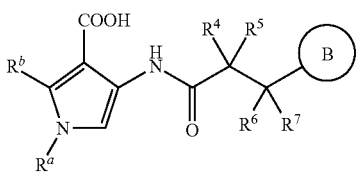

(In)

can be produced by using compound (7) instead of compound (7a).

(Method D)

Method D is a method for producing compound (Ie) or (If) included in compound (I).

(Step D-1)

Step D-1 is a step of allowing compound (19) to react with compound (2) in the presence of an acid. Compound (19) is publicly known or can be easily produced from a publicly known compound.

The acid used is preferably an organic acid, and most preferably acetic acid.

The solvent used is preferably an aromatic hydrocarbon, and most preferably toluene.

The reaction temperature is preferably between 0° C. and 150° C.

The reaction time is preferably between 30 minutes and 12 hours.

(Step D-2)

Step D-2 is a step of allowing compound (20) to react with compound (21). Compound (21) can be produced by allowing vinyl acetate to react with bromine.

The solvent used is preferably an aromatic hydrocarbon, and most preferably toluene.

The reaction temperature is preferably between 0° C. and 150° C.

The reaction time is preferably between 30 minutes and 12 hours.

(Step D-3)

Step D-3 is a step of treating compound (22) with nitric acid in the presence of acetic anhydride.

The solvent used is preferably acetic anhydride.

The reaction temperature is preferably between −20° C. and 50° C.

The reaction time is preferably between 30 minutes and 6 hours.

(Step D-4)

Step D-4 is a step of reducing compound (23) in the presence of a palladium catalyst under a hydrogen atmosphere.

The palladium catalyst used is not limited as long as it can be used in a reduction reaction under a hydrogen atmosphere and is preferably a palladium compound such as palladium-carbon, palladium black, palladium hydroxide, palladium hydroxide-carbon or palladium-barium sulfate, or a platinum compound such as platinum oxide or platinum black, and more preferably palladium-carbon or palladium hydroxide-carbon.

The solvent used is preferably an alcohol, and most preferably ethanol.

The reaction temperature is preferably between 0° C. and 100° C.

The reaction time is preferably between 30 minutes and 12 hours.

(Step D-5)

Step D-5 is a step of allowing compound (24) to react with compound (7a) in the presence of a base.

Step D-5 can be carried out according to a method similar to the method applied in step A-5.

(Step D-6)

Step D-6 is a step of hydrolyzing compound (25) in the presence of a base.

Step D-6 can be carried out according to a method similar to the method applied in step A-6.

(Step D-7)

Step D-7 is a step of converting a methoxy group in compound (Ie) to a hydroxy group.

Step D-7 can be carried out according to a method similar to the method applied in step A-7.

Production of compound (If) from compound (24) in method D can also be carried out according to a method similar to method B using compound (9).

(Method E)

Method E is a method for producing compound (Ig) or (Ih) included in compound (I).

(Step E-1)

Step E-1 is a step of allowing compound (26) to react with compound (27) in the presence of an aluminum compound. Compound (26) and compound (27) are publicly known or can be easily produced from publicly known compounds.

The aluminum compound used is not limited as long as it can be used in a Friedel-Crafts reaction and is preferably a halogenated aluminum such as aluminum chloride or aluminum bromide, and most preferably aluminum chloride.

The solvent used is preferably a halogenated hydrocarbon, and most preferably 1,2-dichloroethane.

The reaction temperature is preferably between −20° C. and 150° C.

The reaction time is preferably between 30 minutes and 12 hours.

(Step E-2)

Step E-2 is a step of reducing compound (28) with a silane compound in the presence of an acid.

The silane compound used is not limited as long as it can reduce a carbonyl group and is preferably a trialkylsilane, and most preferably triethylsilane.

The acid used is preferably an organic acid, and most preferably trifluoroacetic acid.

The solvent used is preferably trifluoroacetic acid.

The reaction temperature is preferably between −20° C. and 50° C.

The reaction time is preferably between 30 minutes and 24 hours.

(Step E-3)

Step E-3 is a step of allowing compound (29) to react with compound (30) in the presence of a base. Compound (30) can be produced by allowing N-(tert-butoxycarbonyl)hydroxylamine to react with 2,4,6-trimethylbenzene sulfonyl chloride and removing the tert-butoxycarbonyl group.

The base used is preferably an alkali metal hydride, and most preferably sodium hydride.

The solvent used is preferably an amide, and most preferably dimethylformamide.

The reaction temperature is preferably between −20° C. and 50° C.

The reaction time is preferably between 30 minutes and 12 hours.

(Step E-4)

Step E-4 is a step of hydrolyzing compound (31) in the presence of a base.

The base used is preferably an alkali metal hydroxide, and most preferably sodium hydroxide.

The solvent used is preferably an alcohol, and most preferably methanol. Step E-4 is carried out in the presence of water.

The reaction temperature is preferably between 0° C. and 100° C.

The reaction time is preferably between 30 minutes and 24 hours.

(Step E-5)

Step E-5 is a step of allowing compound (32) to react with compound (9) in the presence of a base.

Step E-5 can be carried out according to a method similar to the method applied in step A-5.

(Step E-6)

Step E-6 is a step of treating compound (Ig) with a silane compound in the presence of an acid to remove the p-methoxybenzyl group in the compound (Ig).

Step E-6 can be carried out according to a method similar to the method applied in step B-2.

(Method F)

Method F is a method for producing compound (Ii) or compound (Ij) included in compound (I).

(Step F-1)

Step F-1 is a step of allowing compound (33) to react with compound (15) in the presence of a base. Compound (33) is publicly known or can be easily produced from a publicly known compound.

Step F-1 can be carried out according to a method similar to the method applied in step C-4.

(Step F-2)

Step F-2 is a step of allowing compound (34) to react with compound (7a) in the presence of a base.

Step F-2 can be carried out according to a method similar to the method applied in step A-5.

(Step F-3)

Step F-3 is a step of hydrolyzing compound (35) in the presence of a base.

Step F-3 can be carried out according to a method similar to the method applied in step A-6.

(Step F-4)

Step F-4 is a step of converting a methoxy group in compound (Ii) to a hydroxy group.

Step F-4 can be carried out according to a method similar to the method applied in step A-7.

Production of compound (Ij) from compound (34) in method F can also be carried out according to a method similar to method B using compound (9).

According to a method similar to method F, compound (I) can be produced by using compound (33) represented by the following formula

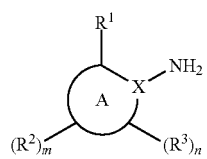

(33)

and compound (7) instead of compound (33a) and compound (7a), respectively.

(Method G)

Method G is a method for producing compound (Ij) included in compound (I).

(Step G-1)

Step G-1 is a step of allowing compound (33) to react with compound (36) in the presence of a base. Compound (36) is known or can be easily produced from a known compound.

Step G-1 can be carried out according to a method similar to the method applied in step C-4.

(Step G-2)

Step G-2 is a step of allowing compound (37) to react with compound (7a) in the presence of a base.

Step G-2 can be carried out according to a method similar to the method applied in step A-5.

(Step G-3)

Step G-3 is a step of removing a benzyl group in compound (38) in the presence of a palladium catalyst under a hydrogen atmosphere.

The palladium catalyst used is not limited as long as it can be used in a reaction of removing a benzyl group under a hydrogen atmosphere and is preferably a palladium compound such as palladium-carbon, palladium black, palladium hydroxide or palladium-barium sulfate, or a platinum compound such as platinum oxide or platinum black, and most preferably palladium hydroxide.

The solvent used is preferably acetic acid.

The reaction temperature is preferably between 0° C. and 100° C.

The reaction time is preferably between 30 minutes and 12 hours.

(Step G-4)

Step G-4 is a step of allowing compound (39) to react with compound (15) in the presence of a base.

Step G-4 can be carried out according to a method similar to the method applied in step C-4.

(Step G-5)

Step G-5 is a step of hydrolyzing compound (35) in the presence of a base.

Step G-5 can be carried out according to a method similar to the method applied in step A-6.

(Step G-6)

Step G-6 is a step of converting a methoxy group in the compound obtained in step G-5 to a hydroxy group.

Step G-6 can be carried out according to a method similar to the method applied in step A-7.

In step G-5 and step G-6, there may be a case in which compound (Ij) is obtained by reacting compound (35) according to a method similar to the method applied in step A-7.

(Method H)

Method H is a method for producing compound (Ik) included in compound (I).

(Step H-1)

Step H-1 is a step of esterifying compound (40) in the presence of an acid. Compound (40) is publicly known or can be easily produced from a publicly known compound.

The acid used is not limited as long as it can be used in a reaction of esterifying a carboxy group and is preferably an inorganic acid, and most preferably sulfuric acid.

The solvent used is preferably methanol.

The reaction temperature is preferably between 0° C. and 150° C.

The reaction time is preferably between 30 minutes and 12 hours.

(Step H-2)

Step H-2 is a step of allowing compound (41) to react with compound (15) in the presence of a base.

Step H-2 can be carried out according to a method similar to the method applied in step C-4.

(Step H-3)

Step H-3 is a step of reducing compound (42) in the presence of a palladium catalyst under a hydrogen atmosphere.

Step H-3 can be carried out according to a method similar to the method applied in step D-4.

In step H-3, compound (43) may be obtained in the form of free amine.

(Step H-4)

Step H-4 is a step of allowing compound (43) to react with compound (7a) in the presence of a base.

Step H-4 can be carried out according to a method similar to the method applied in step A-5.

(Step H-5)

Step H-5 is a step of converting the methoxycarbonyl group and the methoxy group in compound (44) to a carboxy group and a hydroxy group, respectively.

Step H-5 can be carried out according to a method similar to the method applied in step A-7.

Production of compound (Ik) from compound (43) in method H can also be carried out according to a method similar to method B using compound (9).

In method H, compound (Io) included in compound (I), which is represented by the following formula

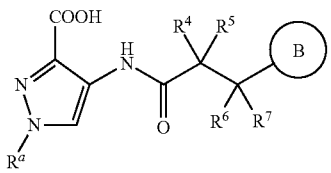

can be produced by using compound (7) instead of compound (7a).

(Method I)

Method I is a method for producing compound (7b) included in compound (7).

(Step I-1)

Step I-1 is a step of treating compound (45) with a halogenating reagent and then allowing the obtained acid halide compound to react with compound (46) in the presence of a base. Compound (45) and compound (46) are publicly known or can be easily produced from publicly known compounds.

The halogenating reagent used is not limited as long as it can convert a carboxylic acid to an acid halide and is preferably oxalyl chloride, or a thionyl halide such as thionyl chloride or thionyl bromide, and is most preferably oxalyl chloride. When oxalyl chloride is used as the halogenating reagent, a catalytic amount of dimethylformamide is preferably used.

The base used is preferably an organic amine, and most preferably triethylamine.

The solvent used is preferably a halogenated hydrocarbon, and most preferably methylene chloride.

The reaction temperature is preferably between −20° C. and 100° C.

The reaction time is preferably between 30 minutes and 12 hours.

(Step I-2)

Step I-2 is a step of treating compound (47) with Burgess Reagent in the presence of a base. Burgess Reagent indicates methyl N-(trimethylammoniumsulfonyl)carbamate (J. Am. Chem. Soc., 1968, Vol. 90, pp. 4744-4745).

The base used is preferably an organic amine, and most preferably triethylamine.

The solvent used is preferably a nitrile, and most preferably acetonitrile.

The reaction temperature is preferably between 0° C. and 150° C.

The reaction time is preferably between 30 minutes and 24 hours.

(Step I-3)

Step I-3 is a step of hydrolyzing compound (48) in the presence of a base.

Step I-3 can be carried out according to a method similar to the method applied in step A-6.

In method I, compound (7e) included in compound (7), which is represented by the following formula

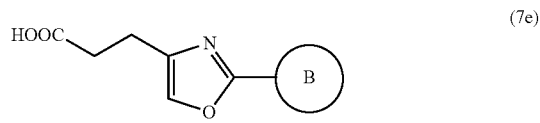

can be produced by using compound (46) represented by the following formula

instead of compound (46a).

(Method J)

Method J is a method for producing compound (7c) included in compound (7).

(Step J-1)

Step J-1 is a step of treating compound (47) with Lawesson Reagent in the presence of a base. The Lawesson Reagent indicates 2,4-bis(4-methoxyphenyl)-1,3-dithia-2,4-diphosphetan-2,4-disulfide.

The base used is preferably an organic amine, and most preferably pyridine.

The solvent used is preferably an aromatic hydrocarbon, and most preferably toluene.

The reaction temperature is preferably between 0° C. and 150° C.

The reaction time is preferably between 30 minutes and 24 hours.

(Step J-2)

Step J-2 is a step of hydrolyzing compound (49) in the presence of a base.

Step J-2 can be carried out according to a method similar to the method applied in step A-6.

In method J, compound (7f) included in compound (7), which is represented by the following formula

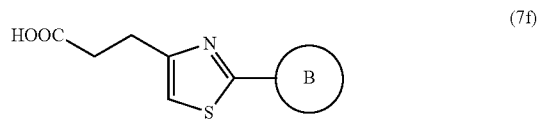

can be produced by using compound (47) represented by the following formula

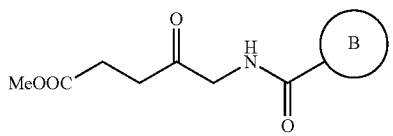

(47)

instead of compound (47a).

(Method K)

Method K is a method for producing compound (7d) included in compound (7).

(Step K-1)

Step K-1 is a step of allowing compound (50) to react with compound (51) in the presence of a palladium reagent and a base. Compound (50) and compound (51) are publicly known or can be easily produced from publicly known compounds.

The palladium reagent used is not limited as long as it can be used in a carbon-carbon bond forming reaction and may be for example, a palladium catalyst described in J. Tsuji, Palladium Reagents and Catalysis: New Perspectives for the 21$^{st}$ Century, 2004, John Wiley & Sons, Inc., etc. The palladium catalyst used is preferably tetrakis(triphenylphosphine)palladium(0), palladium(II) chloride, palladium(II) acetate or dichlorobis(triphenylphosphine)palladium(II), and most preferably tetrakis(triphenylphosphine)palladium(0).

The base used is preferably an alkali metal carbonate, and most preferably sodium carbonate.

The solvent used is preferably an amide, water or a mixture thereof, and most preferably a mixture of dimethylformamide and water.

The reaction temperature is preferably between 20° C. and 100° C.

The reaction time is preferably between 30 minutes and 24 hours.

When B$^1$ in compound (50) is a thiazolyl group, compound (50) may be treated with N-halogenosuccinimide (preferably N-chlorosuccinimide) so that a halogeno group (preferably a chloro group) can be introduced into the 4-position of the thiazolyl group.

(Step K-2)

Step K-2 is a step of hydrolyzing compound (52) in the presence of a base.

Step K-2 can be carried out according to a method similar to the method applied in step A-6.

In method K, compound (7 g) included in compound (7), which is represented by the following formula

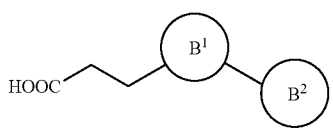

(7g)

can be produced by using compound (51) represented by the following formula

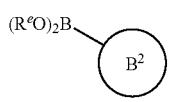

(51)

instead of compound (51a).

(Method L)

Method L is a method for producing compound (55) which is used in step M-1.

(Step L-1)

Step L-1 is a step of allowing compound (53) to react with diethyl oxalate in the presence of a base. Compound (53) is publicly known or can be easily produced from a publicly known compound.

The base used is preferably an alkali metal alkoxide, and most preferably sodium ethoxide.

The solvent used is preferably an alcohol, and most preferably ethanol.

The reaction temperature is preferably between 0° C. and 150° C.

The reaction time is preferably between 2 and 24 hours.

(Step L-2)

Step L-2 is a step of allowing the compound obtained in step L-2 to react with hydroxylamine.

The solvent used is preferably an alcohol, and most preferably ethanol.

The reaction temperature is preferably between 0° C. and 150° C.

The reaction time is preferably between 30 minutes and 12 hours.

(Step L-3)

Step L-3 is a step of reducing compound (54).

The reducing reagent used is not limited as long as it can be used in a reaction of reducing an ester group to a hydroxymethyl group and is preferably an aluminum hydride compound, and more preferably lithium aluminum hydride.

The solvent used is preferably an ether, and most preferably tetrahydrofuran.

The reaction temperature is preferably between −20° C. and 60° C.

The reaction time is preferably between 10 minutes and 24 hours.

(Step L-4)

Step L-4 is a step of oxidizing the compound obtained in step L-3.

The oxidizing reagent used is not limited as long as it can be used in a reaction of oxidizing a hydroxymethyl group to a formyl group and is preferably manganese dioxide.

The solvent used is preferably a halogenated hydrocarbon, and most preferably methylene chloride.

The reaction temperature is preferably between 0° C. and 50° C.

The reaction time is preferably between 30 minutes and 24 hours.

(Method M)

Method M is a method for producing compound (Ip) included in compound (I).

(Step M-1)

Step M-1 is a step of allowing compound (56) to react with compound (57) in the presence of zinc and 1,2-dibromoethane. Compound (56) can be produced by method L, for example. Compound (57) is publicly known or can be easily produced from a publicly known compound.

The solvent used is preferably an ether, and most preferably tetrahydrofuran.

The reaction temperature is preferably between 0° C. and 100° C.

The reaction time is preferably between 30 minutes and 12 hours.

(Step M-2)

Step M-2 is a step of allowing compound (58) to successively react with carbon disulfide and then with methyl iodide in the presence of a base.

The base used is preferably an organic amine, and most preferably DBU.

The solvent used is preferably an amide, and most preferably dimethylformamide.

The reaction temperature is preferably between 0° C. and 150° C.

The reaction time is preferably between 10 minutes and 12 hours.

(Step M-3)

Step M-3 is a step of reducing the compound obtained in step M-2 with a tin reagent in the presence of a radical initiator.

The tin reagent and radical initiator used are not limited as long as they can be used in the desired reduction reaction. A preferred combination of such tin reagent and radical initiator is a combination of tributyl tin hydride and 2,2'-azobisisobutyronitrile.

The solvent used is preferably an aromatic hydrocarbon, and most preferably benzene.

The reaction temperature is preferably between 0° C. and 150° C.

The reaction time is preferably between 30 minutes and 12 hours.

(Step M-4)

Step M-4 is a step of hydrolyzing compound (59) in the presence of a base.

Step M-4 can be carried out according to a method similar to the method applied in step A-6.

(Step M-5)

Step M-5 is a step of allowing compound (60) to react with compound (61) in the presence of a condensing reagent and a base. Compound (61) can be produced by a method similar to that in step A-4.

Step M-5 can be carried out according to a method similar to the method applied in step A-5.

(Step M-6)

Step M-6 is a step of removing two benzyl groups in compound (62) in the presence of a palladium catalyst under a hydrogen atmosphere.

Step M-6 can be carried out according to a method similar to the method applied in step G-3.

(Method N)

Method N is a method for producing compound (67) which can be used in step P-1, step Q-1, step R-1, or other steps.

(Step N-1)

Step N-1 is a step of allowing compound (63) to react with hydroxylamine. Compound (63) is publicly known or can be easily produced from a publicly known compound.

The solvent used is preferably an alcohol, water or a mixture thereof, and most preferably a mixture of ethanol and water.

The reaction temperature is preferably between 0° C. and 100° C.

The reaction time is preferably between 30 minutes and 12 hours.

(Step N-2)

Step N-2 is a step of treating the compound obtained in step N-1 with N-chlorosuccinimide.

The solvent used is preferably an amide, and most preferably dimethylformamide.

The reaction temperature is preferably between 0° C. and 100° C.

The reaction time is preferably between 30 minutes and 12 hours.

(Step N-3)

Step N-3 is a step of allowing compound (64) to react with compound (65) in the presence of a base. Compound (65) is publicly known or can be easily produced from a publicly known compound.

The base used is preferably an organic amine, and most preferably triethylamine.

The solvent used is preferably a halogenated hydrocarbon, and most preferably methylene chloride.

The reaction temperature is preferably between 0° C. and 100° C.

The reaction time is preferably between 30 minutes and 12 hours.

(Step N-4)

Step N-4 is a step of treating compound (66) with carbon tetrabromide in the presence of triphenylphosphine.

The solvent used is preferably a halogenated hydrocarbon, and most preferably methylene chloride.

The reaction temperature is preferably between 0° C. and 100° C.

The reaction time is preferably between 30 minutes and 24 hours.

(Method O)

Method O is a method for producing compound (70) which can be used in step P-1, step Q-1, step R-1, or other steps.

(Step O-1)

Step O-1 is a step of allowing compound (68) to react with diethyl oxalate in the presence of a base. Compound (68) is publicly known or can be easily produced from a publicly known compound.

Step O-1 can be carried out according to a method similar to the method applied in step L-1.

(Step O-2)

Step O-2 is a step of allowing the compound obtained in step 0-1 to react with hydroxylamine.

Step O-2 can be carried out according to a method similar to the method applied in step L-2.

(Step O-3)

Step O-3 is a step of reducing compound (69).

Step O-3 can be carried out according to a method similar to the method applied in step L-3.

(Step O-4)

Step O-4 is a step of treating the compound obtained in step 0-3 with carbon tetrabromide in the presence of triphenylphosphine.

Step O-4 can be carried out according to a method similar to the method applied in step N-4.

(Method P)

Method P is a method for producing compound (Ip) included in compound (I).

(Step P-1)

Step P-1 is a step of allowing compound (71) to react with compound (72) in the presence of copper. Compound (71) can be produced by method N or method O, for example. Compound (72) is publicly known or can be easily produced from a publicly known compound.

The solvent used is preferably a sulfoxide, and most preferably dimethyl sulfoxide.

The reaction temperature is preferably between 0° C. and 100° C.

The reaction time is preferably between 15 minutes and 12 hours.

(Step P-2)

Step P-2 is a step of hydrolyzing compound (73) in the presence of a base.

Step P-2 can be carried out according to a method similar to the method applied in step A-6.

(Step P-3)

Step P-3 is a step of allowing compound (74) to react with compound (75) in the presence of a condensing reagent and a base. Compound (75) can be produced by a method similar to that in step A-4.

Step P-3 can be carried out according to a method similar to the method applied in step A-5.

(Step P-4)

Step P-4 is a step of removing the allyl group in compound (76).

The reagent used is not limited as long as it can be used in a reaction of removing an allyl group and is preferably a combination of tetrakis(triphenylphosphine)palladium(0) and morpholine.

The solvent used is preferably a nitrile, and most preferably acetonitrile.

The reaction temperature is preferably between 0° C. and 100° C.

The reaction time is preferably between 30 minutes and 24 hours.

(Step P-5)

Step P-5 is a step of converting the methoxy group in the compound obtained in step P-4 to a hydroxy group.

Step P-5 can be carried out according to a method similar to the method applied in step A-7.

(Method Q)

Method Q is a method for producing compound (Iq) included in compound (I).

(Step Q-1)

Step Q-1 is a step of allowing compound (71) to react with compound (77) in the presence of a base. Compound (71) can be produced by method N or method O, for example. Compound (77) is publicly known or can be easily produced from a publicly known compound.

The base used is preferably an alkali metal alkoxide, and most preferably potassium tert-butoxide.

The solvent used is preferably an ether, and most preferably tetrahydrofuran.

The reaction temperature is preferably between −20° C. and 100° C.

The reaction time is preferably between 30 minutes and 12 hours.

(Step Q-2)

Step Q-2 is a step of hydrolyzing compound (78) in the presence of a base and then carrying out a decarboxylation reaction.

The base used in the hydrolysis is preferably an alkali metal hydroxide, and most preferably sodium hydroxide.

The solvent used is preferably a mixture of an alcohol and water, and most preferably a mixture of ethanol and water.

The reaction temperature is preferably between 0° C. and 100° C.

The reaction time is preferably between 30 minutes and 12 hours.

After the reaction solution obtained by the hydrolysis is acidified by addition of an acid such as acetic acid, the decarboxylation reaction is carried out by heating in a solvent. The solvent used is preferably a mixture of dioxane and xylene. The reaction temperature is preferably between 50° C. and 150° C. The reaction time is preferably between 1 and 48 hours.

(Step Q-3)

Step Q-3 is a step of allowing compound (79) to react with compound (75) in the presence of a condensing reagent and a base. Compound (75) can be produced by a method similar to that in step A-4.

Step Q-3 can be carried out according to a method similar to the method applied in step A-5.

(Step Q-4)

Step Q-4 is a step of removing the allyl group in compound (80).

Step Q-4 can be carried out according to a method similar to the method applied in step P-4.

(Step Q-5)

Step Q-5 is a step of converting the methoxy group in the compound obtained in step Q-4 to a hydroxy group.

Step Q-5 can be carried out according to a method similar to the method applied in step A-7.

(Method R)

Method R is a method for producing compound (Ir) included in compound (I).

(Step R-1)

Step R-1 is a step of allowing compound (71) to react with compound (81) in the presence of a base. Compound (71) can be produced by method N or method O, for example. Compound (81) is publicly known or can be easily produced from a publicly known compound.

The base used is preferably an alkali metal carbonate, and most preferably potassium carbonate.

The solvent used is preferably a nitrile, and most preferably acetonitrile.

The reaction temperature is preferably between 0° C. and 100° C. The reaction time is preferably between 1 and 48 hours.

(Step R-2)

Step R-2 is a step of hydrolyzing compound (82) in the presence of a base and then carrying out a decarboxylation reaction.

The base used in the hydrolysis is preferably an alkali metal hydroxide, and most preferably sodium hydroxide.

The solvent used is preferably a mixture of an alcohol and water, and most preferably a mixture of ethanol and water.

The reaction temperature is preferably between 0° C. and 100° C.

The reaction time is preferably between 30 minutes and 48 hours.

After the reaction solution obtained by the hydrolysis is acidified by addition of an acid such as acetic acid, the decarboxylation reaction is carried out by heating in a solvent. The solvent used is preferably the same solvent as used in the hydrolysis. The reaction temperature is preferably between 50° C. and 150° C. The reaction time is preferably between 1 and 24 hours.

(Step R-3)

Step R-3 is a step of allowing compound (7d) to react with compound (61) in the presence of a condensing reagent and a base. Compound (61) can be prepared by a method similar to that in step A-4.

Step R-3 can be carried out according to a method similar to the method applied in step A-5.

(Step R-4)

Step R-4 is the step of removing the benzyl group in compound (83) in the presence of a palladium catalyst under a hydrogen atmosphere.

Step R-4 can be carried out according to a method similar to the method applied in step G-3.

(Step R-5)

Step R-5 is a step of converting the methoxy group in the compound obtained in step R-4 to a hydroxy group.

Step R-5 can be carried out according to a method similar to the method applied in step A-7.

(Method S)

Method S is a method for producing compound (Is) included in compound (I).

(Step S-1)

Step S-1 is a step of treating compound (84) with a brominating reagent. Compound (84) can be produced, for example, by step M-3, step P-1, step Q-2, step R-2, or a method similar to the methods in these steps.

The brominating reagent used is not limited as long as it can be used in a bromination reaction at the 4-position of an isoxazole ring and is preferably N-bromosuccinimide.

The solvent used is preferably an amide, and most preferably dimethylformamide.

The reaction temperature is preferably between 0° C. and 100° C.

The reaction time is preferably between 30 minutes and 48 hours.

(Step S-2)

Step S-2 is a step of allowing compound (85) to react with a compound represented by the formula $R^j B(OR^j)_2$ [wherein each independently represents a $C_1$-$C_6$ alkyl group, or two $R^j$ taken together represent a $C_1$-$C_6$ alkylene group (preferably, a 1,2,3,4-tetramethylethylene group; —$CMe_2CMe_2$—)] in the presence of a palladium catalyst and a base.

The palladium catalyst and base used are not limited as long as they can be used in carbon-carbon bond forming reactions. The palladium catalyst used is preferably tetrakis(triphenylphosphine)palladium(0). The base used is preferably an alkali metal carbonate, and most preferably sodium carbonate.

The solvent used is preferably a mixture of an amide and water, and most preferably a mixture of dimethylacetamide and water.

The reaction temperature is preferably between 50° C. and 150° C.

The reaction time is preferably between 30 minutes and 12 hours.

There may be a case in which compound (87) is obtained in step S-2. In such case, the subsequent step S-3 may be omitted.

(Step S-3)

Step S-3 is a step of hydrolyzing compound (86) in the presence of a base.

Step S-3 can be carried out according to a method similar to the method applied in step A-6.

(Step S-4)

Step S-4 is a step of allowing compound (87) to react with compound (61) in the presence of a condensing reagent and a base. Compound (61) can be produced by a method similar to that in step A-4.

Step S-4 can be carried out according to a method similar to the method applied in step A-5.

(Step S-5)

Step S-5 is a step of removing the benzyl group in compound (88) in the presence of a palladium catalyst under a hydrogen atmosphere.

Step S-5 can be carried out according to a method similar to the method applied in step G-3.

(Step S-6)

Step S-6 is a step of converting the methoxy group in the compound obtained in step S-5 to a hydroxy group.

Step S-6 can be carried out according to a method similar to the method applied in step A-7.

(Method T)

Method T is a method for producing compound (It) included in compound (I).

(Step T-1)

Step T-1 is a step of allowing compound (89) to react with compound (90). Compound (89) and compound (90) are publicly known or can be easily produced from publicly known compounds.

Step T-1 is preferably carried out in the absence of a solvent.

The reaction temperature is preferably between 0° C. and 150° C.

The reaction time is preferably between 30 minutes and 24 hours.

(Step T-2)

Step T-2 is a step of allowing compound (91) to react with compound (92). Compound (92) is publicly known or can be easily produced from a publicly known compound.

The solvent used is preferably an alcohol, and most preferably ethanol.

The reaction temperature is preferably between 0° C. and 100° C.

The reaction time is preferably between 30 minutes and 24 hours.

(Step T-3)

Step T-3 is a step of reducing compound (93).

Step T-3 can be carried out according to a method similar to the method applied in step L-3.

(Step T-4)

Step T-4 is a step of oxidizing compound (94).

Step T-4 can be carried out according to a method similar to the method applied in step L-4.

(Step T-5)

Step T-5 is a step of subjecting the compound obtained in step T-4 to a Horner-Wadsworth-Emmons reaction (hereinafter referred to as a HWE reaction) in the presence of a base.

The HWE reaction reagent used is not limited as long as it can be used in such HWE reaction and is preferably a compound represented by the formula $(EtO)_2P(O)CH_2COOEt$ or $(EtO)_2P(O)CH(F)COOEt$.

The base used is preferably an alkali metal hydride, and most preferably sodium hydride.

The solvent used is preferably an ether, and most preferably tetrahydrofuran.

The reaction temperature is preferably between 0° C. and 100° C.

The reaction time is preferably between 30 minutes and 24 hours.

(Step T-6)

Step T-6 is a step of reducing compound (95) in the presence of a palladium catalyst under a hydrogen atmosphere.

The palladium catalyst used is not limited, as long as it can be used in a reduction reaction under a hydrogen atmosphere and is preferably a palladium compound such as palladium-carbon, palladium black, palladium hydroxide, or palladium-barium sulfate, or a platinum compound such as platinum oxide or platinum black, and most preferably palladium-carbon.

The solvent used is preferably an alcohol, acetic acid or a mixture thereof, and most preferably ethanol, acetic acid or a mixture thereof.

The reaction temperature is preferably between 0° C. and 100° C.

The reaction time is preferably between 30 minutes and 12 hours.

(Step T-7)

Step T-7 is a step of hydrolyzing the compound obtained in step T-6 in the presence of a base.

Step T-7 can be carried out according to a method similar to the method applied in step A-6.

(Step T-8)

Step T-8 is a step of allowing compound (96) to react with compound (6) in the presence of a condensing reagent and a base. Compound (6) can be produced by step A-4.

Step T-8 can be carried out according to a method similar to the method applied in step A-5.

(Step T-9)

Step T-9 is a step of hydrolyzing compound (97) in the presence of a base.

Step T-9 can be carried out according to a method similar to the method applied in step A-6.

When $R^h$ of compound (It) is a methoxy group, the methoxy group can be converted to a hydroxy group according to a method similar to the method applied in step A-7, as necessary.

When the compound represented by general formula (I) of the present invention or a pharmacologically acceptable salt thereof is used as a pharmaceutical agent, it can be directly administered as is. Otherwise, it can be mixed with pharmacologically acceptable additives, as appropriate, so that it can be orally administered in the form of a formulation such as a tablet, a capsule or a granule, or it can be parenterally administered in the form of a formulation such as an injection or a suppository.

The above-described formulations are produced by well known methods using additives such as an excipient, a binder, a disintegrator, a lubricant, an emulsifier, a stabilizer, a diluent, a solvent used for injection, and the like.

An excipient may be, for example, an organic excipient or an inorganic excipient. An organic excipient may be, for example, sugar derivatives such as lactose or saccharose; starch derivatives such as corn starch or potato starch; cellulose derivatives such as crystalline cellulose; or gum Arabic. An inorganic excipient may be, for example, sulfates such as calcium sulfate.

A binder may be, for example, the above-described excipients; gelatin; polyvinylpyrrolidone; or polyethylene glycol.

A disintegrator may be, for example, the above-described excipients; chemically modified starch or cellulose derivatives such as croscarmellose sodium or carboxymethyl starch sodium; or crosslinked polyvinylpyrrolidone.

A lubricant may be for example, talc; stearic acid; colloidal silica; waxes such as beeswax or spermaceti; sulfates such as sodium sulfate; lauryl sulfates such as sodium lauryl sulfate; or the starch derivatives described above as excipients.

An emulsifier may be, for example, colloidal clay such as bentonite or veegum; anionic surfactants such as sodium lauryl sulfate; cationic surfactants such as benzalkonium chloride; or nonionic surfactants such as polyoxyethylene alkyl ether.

A stabilizer may be, for example, parahydroxy benzoic acid esters such as methylparaben or propylparaben; alcohols such as chlorobutanol; or phenols such as phenol or cresol.

A diluent may be, for example, water, ethanol, or propylene glycol.

A solvent used for injection may be, for example, water, ethanol, or glycerin.

The compound represented by general formula (I) of the present invention or a pharmacologically acceptable salt thereof can be administered at a dosage of from 0.02 mg/kg as a lower limit (preferably, 0.1 mg/kg) to 100 mg/kg as an upper limit (preferably, 20 mg/kg) per adult human per administration in the case of oral administration, or at a dosage of from 0.002 mg/kg as a lower limit (preferably, 0.01 mg/kg) to 10 mg/kg as an upper limit (preferably, 2 mg/kg) per adult human per administration in the case of parenteral administration, one to six times per day, depending on the symptoms, age, and the like of a patient.

Effects of the Invention

The compound represented by general formula (I) of the present invention or a pharmacologically acceptable salt thereof has excellent properties such as lipolysis-suppressive activity, blood lipid level-regulating action (for example, reducing action on the level of NEFA or TG), in vivo activity, solubility, oral absorption property, metabolic stability, blood concentration, bioavailability (BA), tissue transitivity, physical stability, drug interaction, and safety [for example, flushing]; and it is useful as a pharmaceutical agent, preferably a pharmaceutical agent for the treatment or prophylaxis of dyslipidemia with low HDL cholesterol, hypercholesterolemia, dyslipidemia with high LDL cholesterol, dyslipidemia with high VLDL cholesterol, dyslipidemia with high triglyceride (hypertriglyceridemia), hyperlipidemia, dyslipidemia, lipid metabolism abnormality, arteriosclerosis, type I diabetes mellitus, type II diabetes mellitus, insulin resistance, cardiac failure, myocardial infarction, cardiovascular disease, apoplectic stroke, adiposity, angina, chronic renal failure, peripheral vascular disorder, non-alcoholic steatohepatitis, anorexia nervosa, metabolic syndrome, Alzheimer's disease, schizophrenia, or amyotrophic lateral sclerosis, or for reduction in event occurrence or mortality due to cardiovascular disease or coronary heart disease, more preferably a pharmaceutical agent for the treatment or prophylaxis of hyperlipidemia, dyslipidemia, lipid metabolism abnormality, arteriosclerosis, or type II diabetes mellitus, and even more preferably a pharmaceutical agent for the treatment or prophylaxis (preferably, treatment) of dyslipidemia or lipid metabolism abnormality.

MODE FOR CARRYING OUT THE INVENTION

Hereinafter, the present invention is explained in more detail, exemplifying Examples, Test Examples, and Formulation Examples. However, the scope of the present invention is not limited to these.

The following abbreviated symbols are used in the Examples.

Burgess reagent: methyl N-(trimethylammoniumsulfonyl)carbamate

DMF: dimethylformamide

DMSO: dimethyl sulfoxide

HATU: O-(7-azabenzotriazol-1-yl)-N,N,N',N'-tetramethyluronium hexafluorophosphate Lawesson reagent: 2,4-bis(4-methoxyphenyl)-1,3-dithia-2,4-diphosphetan-2,4-disulfide THF: tetrahydrofuran Boc$_2$O: di-t-butyl dicarbonate DBU: 1,8-diazabicyclo[5,4,0]undec-7-ene DMA: dimethylacetamide dppf: 1,1'-bis(diphenylphosphino)ferrocene HOBt: 1-hydroxybenzotriazole WSCI: 1-ethyl-3-(3-dimethylaminopropyl)carbodiimide

EXAMPLES

Example 1

4-{3-[4-(4-Hydroxyphenyl)phenyl]propanoyl}amino-1-methylpyrrole-3-carboxylic acid

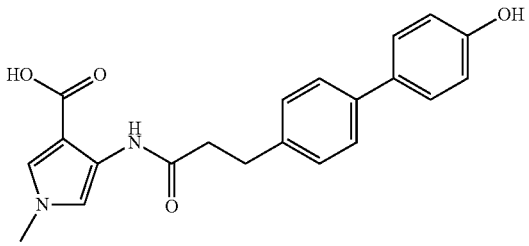 [SMILES: Cn1cc(NC(=O)CCc2ccc(-c3ccc(O)cc3)cc2)c(C(=O)O)c1]

(a) 4-Amino-1-methylpyrrole-3-carboxylic acid ethyl ester hydrochloride (a)-1

Sarcosine tert-butyl ester hydrochloride (7.19 g, 38.4 mmol) was added to a mixture of methylene chloride (50 mL) and a 2 N sodium hydroxide aqueous solution (20 mL), and the obtained mixture was stirred at room temperature for 1 hour. The reaction solution was extracted with methylene chloride (150 mL), and it was dried over sodium sulfate and was then concentrated.

The obtained residue was dissolved in THF (30 mL), and ethyl 2-(ethoxymethylene)-2-cyanoacetate (6.50 g, 38.4 mmol) was then added to the solution. The obtained mixture was stirred at room temperature for 18 hours, and then at 90° C. for 4 hours. The reaction solution was concentrated, and was then subjected to azeotropy with toluene. The residue was dissolved in THF (30 mL), and sodium hydride (1.46 g, 38.4 mmol) was then added to the solution at 0° C. The obtained mixture was stirred at room temperature for 1.5 hours. Thereafter, water (10 mL) was added to the reaction solution, and the solvent was distilled away. The residue was dissolved in ethyl acetate (100 mL) and water (30 mL) and the two layers were separated. The organic layer was washed with a saturated saline (30 mL), and it was dried over sodium sulfate and was then concentrated. The residue was purified by silica gel column chromatography (hexane/ethyl acetate) to obtain a pyrrole compound (6.78 g, yield: 66%).

(a)-2

The pyrrole compound (6.78 g, 25.3 mmol) obtained in Example 1(a)-1 was dissolved in 4N hydrochloric acid-dioxane (25 mL), and the obtained solution was then stirred at room temperature for 15 hours. The reaction solution was concentrated, so as to obtain the title compound (4.67 g, yield: 90%).

$^1$H NMR (500 MHz, DMSO-$d_6$): δ (ppm)=9.80 (2H, brs), 7.47 (1H, d, J=2.5 Hz), 6.99 (1H, brs), 4.22 (2H, q, J=7.1 Hz), 3.66 (3H, s), 1.28 (3H, t, J=7.1 Hz).

MS m/z: 169 (M+H)$^+$.

(b) 3-[4-(4-Methoxyphenyl)phenyl]propionic acid

A 2 M-sodium carbonate aqueous solution (3.4 mL, 6.75 mmol) and tetrakistriphenylphosphine palladium (130 mg, 0.113 mmol) were added to a solution of 4-methoxybromobenzene (421 mg, 2.25 mmol) and 4-(2-ethoxycarbonylethyl)phenylboronic acid (500 mg, 2.25 mmol) in DMF (10 mL). The obtained mixture was stirred at 80° C. for 8 hours. Thereafter, water was added to the reaction solution, and it was extracted with ethyl acetate. The organic layer was washed with 1 M-hydrochloric acid, a saturated sodium bicarbonate solution, and a saturated saline. The organic layer was dried over sodium sulfate, and the solvent was then distilled away. The obtained residue was purified by silica gel column chromatography to obtain an ester compound. A 1 M-sodium hydroxide aqueous solution (5 mL, 5.00 mmol) was added to a solution of the obtained ester compound in ethanol (20 mL), and the obtained mixture was then stirred at room temperature for 2 hours. Thereafter, 1 M-hydrochloric acid (10 mL, 10.0 mmol) was added to the reaction solution, and the precipitated crystals were then collected by filtration followed by being washed with water, so as to obtain the title compound (453 mg, yield in two steps: 79%).

$^1$H NMR (400 MHz, CDCl$_3$): δ (ppm)=7.53-7.47 (4H, m), 7.28 (2H, d, J=8.2 Hz), 6.98 (2H, d, J=9.0 Hz), 3.86 (3H, s), 3.01 (2H, t, J=7.6 Hz), 2.73 (2H, t, J=7.8 Hz).

(c) 4-{3-[4-(4-Hydroxyphenyl)phenyl]propanoyl}amino-1-methylpyrrole-3-carboxylic acid (c)-1

The compound (100 mg, 0.50 mmol) obtained in Example 1(a) and the compound (115 mg, 0.45 mmol) obtained in Example 1(b) were dissolved in dimethylformamide (3 mL), and HATU (240 mg, 0.59 mmol) was then added to the solution. The obtained mixture was cooled on ice under a nitrogen atmosphere. Triethylamine (0.2 mL, 0.90 mmol) was added to the reaction solution, and the obtained mixture was then stirred under ice cooling for 30 minutes. Thereafter, water (15 mL) was added to the reaction solution, and the generated precipitate was then collected by filtration, washed with water and then dried under reduced pressure, so as to obtain an ester compound (130 mg, yield: 71%) in the form of a colorless powder.

(c)-2

The compound (129 mg, 0.32 mmol) obtained in Example 1(c)-1 was dissolved in a mixture of THF (3 mL) and methanol (1 mL), and a 1 N lithium hydroxide aqueous solution (1 mL) was then added to the solution. The obtained mixture was stirred at 70° C. for 3 hours. The reaction solution was concentrated and was then neutralized with 2 N hydrochloric acid (0.6 mL). The generated precipitate was collected by filtration and was then washed with water. The obtained solid was dried under reduced pressure, so as to obtain the title compound (110 mg, yield: 91%).

(d) 4-{3-[4-(4-Hydroxyphenyl)phenyl]propanoyl}amino-1-methylpyrrole-3-carboxylic acid Methylene chloride (2 mL) was added to the compound (105 mg, 0.28 mmol) obtained in Example 1(c), and the obtained mixture was then cooled to −78° C. under a nitrogen atmosphere. Thereafter, a 1 N boron tribromide-methylene chloride solution (1.4 mL) was added to the reaction solution, and the obtained mixture was then stirred at room temperature for 1 hour. After completion of the reaction had been confirmed, the reaction solution was cooled to −78° C. Thereafter, water was added to the reaction solution, the temperature of the reaction mixture was raised to room temperature, and the obtained mixture was then stirred. The generated precipitate was collected by filtration and was then washed with water and methylene chloride and dried under reduced pressure, so as to obtain the title compound (94 mg, yield: 93%) in the form of a colorless powder.

¹H NMR (400 MHz, DMSO-d₆): δ (ppm)=12.2 (1H, brs), 9.50 (1H, brs), 9.34 (1H, brs), 7.46 (4H, dd, J=10.9 and 8.5 Hz), 7.28 (2H, d, J=8.3 Hz), 7.25 (1H, d, J=2.4 Hz), 7.21 (1H, d, J=2.5 Hz), 6.82 (2H, d, J=8.8 Hz), 3.60 (3H, s), 2.90 (2H, t, J=7.5 Hz), 2.68 (2H, t, J=7.6 Hz).

MS m/z: 363 (M−H)⁻.

Example 2

4-[3-(5-Chloro-6-hydroxy-2-naphthyl)propanoyl]amino-1-methylpyrrole-3-carboxylic acid

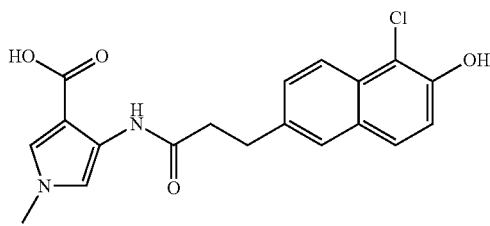 [SMILES: Cn1cc(NC(=O)CCc2ccc3c(Cl)c(O)ccc3c2)c(C(=O)O)c1]

Reactions were carried out in the same manner as in Examples 1(c) and 1(d) using the compound obtained in Example 1(a) and 3-(5-chloro-6-hydroxy-2-naphthyl)propionic acid synthesized by a method similar to the method described in WO2007/120575, so as to obtain the title compound in the form of a colorless powder.

¹H NMR (400 MHz, DMSO-d₆): δ (ppm)=12.2 (1H, brs), 10.3 (1H, s), 9.33 (1H, s), 7.93 (1H, d, J=8.6 Hz), 7.72-7.68 (2H, m), 7.52 (1H, dd, J=8.6, 1.5 Hz), 7.26-7.21 (3H, m), 3.60 (3H, s), 3.03 (2H, t, J=7.6 Hz), 2.76 (2H, t, J=7.6 Hz).

MS m/z: 371 (M−H)⁻.

Example 3

4-{3-[(5-Hydroxypyridin-2-yl)-1,2,4-oxadiazol-5-yl]propanoyl}amino-1-methylpyrrole-3-carboxylic acid

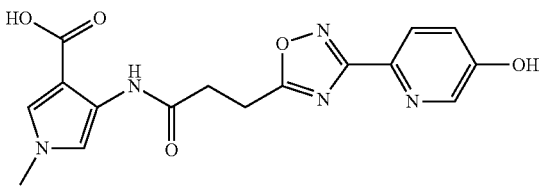 [SMILES: Cn1cc(NC(=O)CCc2nc(-c3ccc(O)cn3)no2)c(C(=O)O)c1]

(a) 2-Cyano-5-(4-methoxybenzyloxy)pyridine

Sodium hydride (1.44 g, 33 mmol) was dissolved in DMF (20 mL), and 4-methoxybenzyl alcohol (3.74 mL, 33 mmol) was then added to the solution under a nitrogen atmosphere and under ice cooling. The obtained mixture was stirred at room temperature for 30 minutes. Thereafter, 5-bromo-2-cyanopyridine (4.58 g, 25 mmol) was added to the reaction solution, and the obtained mixture was further stirred at room temperature for 30 minutes. Thereafter, water was added to the reaction solution, and it was then extracted with ethyl acetate and washed with water. The water layers were combined and extracted with methylene chloride. The organic layers were combined, were dried over sodium sulfate, and were then concentrated. The obtained residue was recrystallized from ethyl acetate, so as to obtain the title compound (3.57 g, yield: 60%) in the form of yellow crystals.

(b) 3-{[5-(4-Methoxybenzyloxy)pyridin-2-yl]-1,2,4-oxadiazol-5-yl}propionic acid

The compound (3.57 g, 15 mmol) obtained in Example 2(a) and hydroxylamine hydrochloride (1.24 g, 18 mmol) were dissolved in ethanol (70 mL), and a mixture of sodium hydroxide (0.7 g, 16 mmol) and water (7 mL) was then added to the solution at room temperature. The obtained mixture was left at room temperature overnight. The generated precipitate was collected by filtration, washed with ethanol and then dried under reduced pressure to obtain a desired compound (4.52 g, yield: 100%). The obtained compound was dissolved in pyridine (10 mL), and ethyl malonyl chloride (2.5 mL, 2.0 mmol) was then added to the solution. The obtained mixture was stirred at 130° C. for 4 hours. The reaction solution was concentrated under reduced pressure. Thereafter, water was added to the concentrate, and it was then extracted with methylene chloride. The organic layer was washed with water, and it was dried over sodium sulfate and was then concentrated. The generated precipitate was collected by filtration and was then washed with methanol to obtain a desired compound (2.89 g, yield: 51%) in the form of pale red crystals. The obtained compound (2.89 g, 7.5 mmol) was dissolved in a mixture of THF (50 mL) and methanol (20 mL), and a 1 N lithium hydroxide aqueous solution (30 mL) was then added to the solution. The obtained mixture was stirred at room temperature for 3 hours. The reaction solution was concentrated under reduced pressure, and 2 N hydrochloric acid (15 mL) was then added to the concentrate for neutralization. The generated precipitate was collected by filtration, washed with water and then dried under reduced pressure, so as to obtain the title compound (2.23 g, yield: 83%) in the form of pale yellow crystals.

¹H NMR (400 MHz, CDCl₃): δ (ppm)=8.54 (1H, d, J=2.7 Hz), 8.05 (1H, d, J=8.6 Hz), 7.39-7.35 (3H, m), 6.94 (2H, d, J=8.6 Hz), 5.11 (2H, s), 3.83 (3H, s), 3.29 (2H, t, J=7.2 Hz), 3.06 (2H, t, J=7.2 Hz).

(c) 4-{3-[(5-(4-Methoxybenzyloxy)pyridin-2-yl)-1,2,4-oxadiazol-5-yl]propanoyl}amino-1-methylpyrrole-3-carboxylic acid ethyl ester A reaction was carried out in the same manner as in Example 1(c)-1 using the compound obtained in Example 1(a) and the carboxylic acid obtained in Example 3(b), so as to obtain the title compound in the form of a colorless powder.

(d) 4-{3-[(5-Hydroxypyridin-2-yl)-1,2,4-oxadiazol-5-yl]propanoyl}amino-1-methylpyrrole-3-carboxylic acid The compound (126 mg, 0.25 mmol) obtained in Example 3(c) was dissolved in methylene chloride (2.0 mL), and tri-isopropylsilane (0.51 mL, 2.50 mmol) and trifluoroacetic acid (1.0 mL) were then added to the solution at 0° C. The reaction solution was stirred for 2 hours, and it was then concentrated. Ethanol (5.0 mL) and a 1 N lithium hydroxide aqueous solution (2.5 mL) were added to the residue, and the obtained mixture was then stirred at 100° C. for 3 hours. The reaction solution was concentrated, and 1 N hydrochloric acid (3 mL) and methylene chloride (3 mL) were then added thereto. The precipitated solid was collected by filtration and was then washed with water (10 mL). The obtained solid was purified by reverse-phase liquid chromatography (acetonitrile/water), so as to obtain the title compound (24 mg, yield: 27%) in the form of a white powder.

$^1$H NMR (500 MHz, MeOH-d4): δ (ppm)=8.21 (1H, d, J=2.4 Hz), 7.99 (1H, d, J=8.6 Hz), 7.31 (1H, dd, J=8.6, 2.4 Hz), 7.22 (1H, d, J=2.4 Hz), 7.16 (1H, d, J=2.4 Hz), 3.64 (3H, s), 3.33 (2H, t, J=7.1 Hz), 3.05 (2H, t, J=6.9 Hz).

MS m/z: 358 (M+H)$^+$.

Example 4

4-{3-[2-(4-Hydroxyphenyl)oxazol-5-yl]propanoyl}amino-1-methylpyrrole-3-carboxylic acid

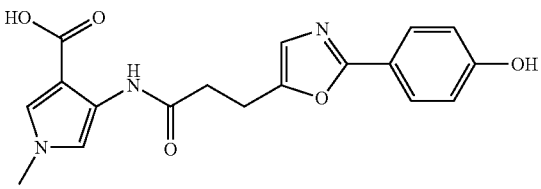 [SMILES: Cn1cc(NC(=O)CCc2cnc(-c3ccc(O)cc3)o2)c(C(=O)O)c1]

(a) 5-(4-Methoxybenzoyl)aminolevulinic acid methyl ester

Under a nitrogen atmosphere, a catalytic amount of dimethylformamide was added to a solution of p-methoxybenzoic acid (5 g, 33.0 mmol) in dichloromethane (50 mL), and the obtained mixture was then cooled to 0° C. Thereafter, oxalyl chloride (5.8 mL, 66.1 mmol) was added to the reaction solution, and the obtained mixture was then stirred at room temperature for 30 minutes. Thereafter, the solvent was distilled away, and the obtained residue was then added to a solution of 5-aminolevulinic acid methyl hydrochloride (1.0 g, 5.50 mmol) and triethylamine (2.3 mL, 16.5 mmol) in dichloromethane (80 mL) that had been cooled to 0° C. under a nitrogen atmosphere. The obtained mixture was stirred at room temperature for 3 hours. Thereafter, the solvent was distilled away, and the obtained residue was then purified by silica gel column chromatography (hexane/ethyl acetate), so as to obtain the title compound (6.46 g, yield: 84%).

(b) 3-[2-(4-Methoxyphenyl)oxazol-5-yl]propionic acid

Under a nitrogen atmosphere, a Burgess reagent (6.65 g, 27.9 mmol) was added to a solution of 5-(4-methoxybenzoyl)aminolevulinic acid methyl ester (4.46 g, 18.6 mmol) and triethylamine (3.41 mL, 24.2 mmol) in acetonitrile (50 mL). The obtained mixture was stirred at 80° C. for 5 hours. The solvent was distilled away, and the obtained residue was then purified by silica gel column chromatography (hexane/ethyl acetate) to obtain a cyclized compound (3.7 g, yield: 76%). A 1 M sodium hydroxide aqueous solution (50 mL, 50 mmol) was added to a solution of the obtained cyclized compound (3.7 g, 14.2 mmol) in methanol (100 mL), and the obtained mixture was then stirred at room temperature for 3 hours. Thereafter, 1 M hydrochloric acid (55 mL, 55 mmol) was added to the reaction solution, and the generated solid was then collected by filtration, washed with water and then washed with a mixture of n-hexane and dichloromethane, so as to obtain the title compound (3.5 mg, yield: 99%).

$^1$H NMR (400 MHz, CDCl$_3$): δ (ppm)=7.94 (2H, dt, J=9.4 and 2.5 Hz), 6.97 (2H, dt, J=9.4 and 2.4 Hz), 6.88 (1H, s), 3.86 (3H, s), 3.08 (2H, t, J=7.8 Hz), 2.79 (2H, t, J=7.4 Hz).

(c) 4-{3-[2-(4-Hydroxyphenyl)oxazol-5-yl]propanoyl}amino-1-methylpyrrole-3-carboxylic acid Reactions were carried out in the same manner as in Examples 1(c) and 1(d) using the compound obtained in Example 1(a) and the compound obtained in Example 4(b), so as to obtain the title compound in the form of a colorless powder.

$^1$H NMR (400 MHz, DMSO-d$_6$): δ (ppm)=12.2 (1H, brs), 10.0 (1H, s), 9.39 (1H, s), 7.74 (2H, d, J=8.6 Hz), 7.28 (1H, d, J=2.7 Hz), 7.24 (1H, d, J=2.7 Hz), 6.93 (1H, s), 6.85 (2H, d, J=8.6 Hz), 3.62 (3H, s), 3.01 (2H, t, J=7.4 Hz), 2.76 (2H, t, J=7.4 Hz).

MS m/z: 356 (M+H)$^+$.

Example 5

4-{3-(2-Phenylthiazol-5-yl)propanoyl}amino-1-methylpyrrole-3-carboxylic acid

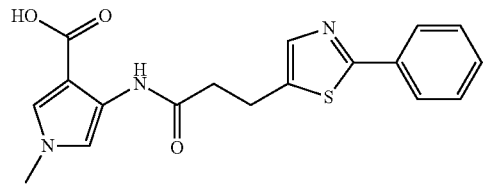 [SMILES: Cn1cc(NC(=O)CCc2cnc(-c3ccccc3)s2)c(C(=O)O)c1]

(a) 5-Benzoylaminolevulinic acid methyl ester

Under a nitrogen atmosphere, a solution of 5-aminolevulinic acid methyl hydrochloride (1.0 g, 5.5 mmol) and triethylamine (2.3 mL, 16.5 mmol) in dichloromethane (50 mL) was cooled to 0° C., and benzoyl chloride (0.7 mL, 6.1 mmol) was then added to the solution. The obtained mixture was stirred at room temperature for 3 hours. Thereafter, water was added to the reaction solution, and it was then extracted with ethyl acetate. The organic layer was washed with a saturated saline and was then dried over sodium sulfate. The solvent was distilled away, and the obtained residue was then purified by silica gel column chromatography (hexane/ethyl acetate), so as to obtain the title compound (1.29 g, yield: 94%).

(b) 3-(2-Phenylthiazol-5-yl)propionic acid

The compound (500 mg, 2.0 mmol) obtained in Example 5(a) was added to a solution of pyridine (0.3 mL, 4.012 mmol) in toluene (5 mL) under a nitrogen atmosphere, and a Lawesson reagent (1.1 g, 2.6 mmol) was then added to the solution. The reaction solution was stirred at 80° C. for 7 hours. Thereafter, water was added to the reaction solution, and it was extracted with ethyl acetate. The organic layer was washed with a saturated saline and was then dried over sodium sulfate. The solvent was distilled away, and the obtained residue was then purified by silica gel column chromatography (hexane/ethyl acetate) to obtain a desired compound (310 mg, yield: 62%). A 1 N sodium hydroxide aqueous solution (6.3 mL, 6.3 mmol) was added to a solution of the obtained compound (310 mg, 1.3 mmol) in methanol (15 mL), and the obtained mixture was then stirred at room temperature for 1 hour. Thereafter, 1 N hydrochloric acid (10 mL, 10 mmol) was added to the reaction solution, and the generated solid was collected by filtration, followed by being washed with water, so as to obtain the title compound (271 mg, yield: 93%).

$^1$H NMR (400 MHz, CDCl$_3$): δ (ppm)=7.90 (2H, dd, J=7.8 and 1.9 Hz), 7.61 (1H, s), 7.45-7.40 (3H, m), 3.22 (2H, t, J=7.1 Hz), 2.78 (2H, t, J=7.2 Hz).

(c) 4-[3-(2-Phenylthiazol-5-yl)propanoyl]amino-1-methylpyrrole-3-carboxylic acid A reaction was carried out in the same manner as in Example 1(c) using the compound obtained in Example 1(a) and the compound obtained in Example 5(b), so as to obtain the title compound in the form of a colorless powder.

$^1$H NMR (400 MHz, DMSO-d$_6$): δ (ppm)=9.42 (1H, brs), 7.87 (2H, dd, J=7.2 and 1.8 Hz), 7.68 (1H, d, J=0.8 Hz), 7.51-7.45 (3H, m), 7.28 (1H, d, J=2.0 Hz), 7.21 (1H, d, J=2.4 Hz), 3.61 (3H, s), 3.17 (2H, t, J=7.0 Hz), 2.78 (2H, t, J=7.0 Hz).

MS m/z: 356 (M+H)$^+$.

Example 6

4-{3-[2-(4-Hydroxyphenyl)thiazol-5-yl]propanoyl}amino-1-methylpyrrole-3-carboxylic acid

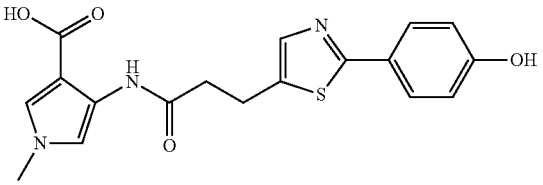

(a) 3-[2-(4-Methoxyphenyl)thiazol-5-yl]propionic acid

A reaction was carried out in the same manner as in Example 5(b) using the compound obtained in Example 4(a), so as to obtain the title compound in the form of a colorless powder.

$^1$H NMR (400 MHz, CDCl$_3$): δ (ppm)=7.70 (2H, dt, J=47.3 and 29.2 Hz), 7.54 (1H, s), 6.95 (2H, dt, J=9.3 and 2.5 Hz), 3.86 (3H, s), 3.20 (2H, t, J=7.5 Hz), 2.77 (2H, t, J=7.5 Hz).

(b) 4-{3-[2-(4-Hydroxyphenyl)thiazol-5-yl]propanoyl}amino-1-methylpyrrole-3-carboxylic acid Reactions were carried out in the same manner as in Examples 1(c) and 1(d) using the compound obtained in Example 1(a) and the compound obtained in Example 6(a), so as to obtain the title compound in the form of a colorless powder.

$^1$H NMR (400 MHz, DMSO-d$_6$): δ (ppm)=12.2 (1H, s), 9.94 (1H, s), 9.35 (1H, s), 7.68 (2H, d, J=8.6 Hz), 7.55 (1H, s), 7.28 (1H, d, J=2.3 Hz), 7.23 (1H, d, J=2.3 Hz), 6.84 (2H, d, J=8.6 Hz), 3.61 (3H, s), 3.13 (2H, t, J=7.0 Hz), 2.75 (2H, t, J=7.0 Hz).

MS m/z: 372 (M+H)$^+$.

Example 7

4-[3-(4-Chloro-2-phenylthiazol-5-yl)propanoyl]amino-1-methylpyrrole-3-carboxylic acid

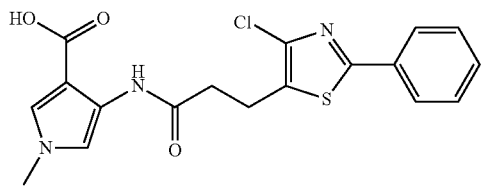 [SMILES: Cn1cc(NC(=O)CCc2sc(-c3ccccc3)nc2Cl)c(C(=O)O)c1]

(a) 3-(4-Chloro-2-bromothiazol-5-yl)propionic acid ethyl ester

N-Chlorosuccinimide (2.83 g, 21.3 mmol) was added to a solution of 3-(2-bromothiazol-5-yl)propionic acid ethyl ester synthesized by a method similar to the method described in J. Med. Chem., 2007, 50, p. 6303 in DMF (50 mL) under a nitrogen atmosphere. The obtained mixture was stirred at room temperature overnight, and then at 80° C. for 5 hours. Thereafter, the solvent was distilled away, and the obtained residue was then purified by silica gel column chromatography (hexane/ethyl acetate) to obtain a chloro compound (2.63 g, yield: 62%). N-bromosuccinimide (4.2 g, 23.7 mmol) was added to a DMF (30 mL) solution of the obtained chloro compound (2.6 g, 11.9 mmol) in DMF (30 mL) under a nitrogen atmosphere, and the obtained mixture was then stirred at 80° C. for 2 days. Thereafter, the solvent was distilled away, and the obtained residue was then purified by silica gel column chromatography (hexane/ethyl acetate), so as to obtain the title compound (886 mg, yield: 28%).

(b) 3-(4-Chloro-2-phenylthiazol-5-yl)propionic acid ethyl ester

A 2 M sodium carbonate aqueous solution (2.2 mL, 4.42 mmol) and tetrakistriphenylphosphine palladium (85 mg, 0.074 mmol) were added to a solution of the compound (440 mg, 1.47 mmol) obtained in Example 7(a) and phenylboronic acid (180 mg, 1.47 mmol) in DMF (7 mL). The obtained mixture was stirred at 80° C. for 3 hours. Thereafter, water was added to the reaction solution, and it was then extracted with ethyl acetate. The organic layer was washed with 1 N hydrochloric acid, a sodium bicarbonate aqueous solution, and a saturated saline. It was then dried over sodium sulfate. The solvent was distilled away, and the obtained residue was then purified by silica gel column chromatography (hexane/ethyl acetate), so as to obtain the title compound (224 mg, yield: 51%).

$^1$H NMR (400 MHz, CDCl$_3$): δ (ppm)=7.90-7.86 (2H, m), 7.44-7.41 (3H, m), 4.17 (2H, q, J=7.0 Hz), 3.16 (2H, t, J=7.3 Hz), 2.69 (2H, t, J=7.4 Hz), 1.27 (3H, t, J=7.4 Hz).

(c) 4-[3-(4-Chloro-2-phenylthiazol-5-yl)propanoyl]amino-1-methylpyrrole-3-carboxylic acid A 1 M sodium hydroxide aqueous solution (3.8 mL, 5.3 mmol) was added to a solution of the compound (344 mg, 1.06 mmol) obtained in Example 7(b) in ethanol (15 mL). The obtained mixture was stirred at room temperature overnight.

Thereafter, 1 M hydrochloric acid (5.0 mL, 7.0 mmol) was added to the reaction solution, and the generated solid was collected by filtration, followed by being washed with water, so as to obtain a carboxylic acid compound (178 mg, yield: 88%).

A reaction was carried out in the same manner as in Example 1(c) using the obtained carboxylic acid compound and the compound obtained in Example 1(a), so as to obtain the title compound in the form of a colorless powder.

$^1$H NMR (400 MHz, DMSO-d$_6$): δ (ppm)=9.36 (1H, s), 7.84 (2H, dd, J=6.5 and 3.0 Hz), 7.49 (3H, t, J=3.1 Hz), 7.25 (1H, d, J=2.3 Hz), 7.20 (1H, d, J=2.8 Hz), 3.59 (3H, s), 3.10 (2H, t, J=7.0 Hz), 2.76 (2H, t, J=7.0 Hz).

MS m/z: 390 (M+H)$^+$.

Example 8

4-{3-[4-Chloro-2-(4-hydroxyphenyl)thiazol-5-yl]propanoyl}amino-1-methylpyrrole-3-carboxylic acid

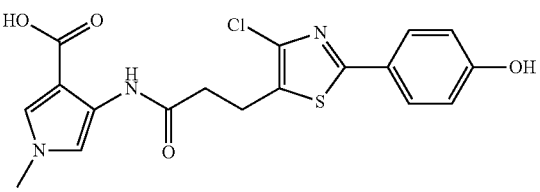 [SMILES: Cn1cc(NC(=O)CCc2sc(-c3ccc(O)cc3)nc2Cl)c(C(=O)O)c1]

(a) 3-[4-Chloro-2-(4-methoxyphenyl)thiazol-5-yl]propionic acid ethyl ester

A reaction was carried out in the same manner as in Example 7(b) using the compound obtained in Example 7(a) and p-methoxyphenylboronic acid, so as to obtain the title compound.

$^1$H NMR (400 MHz, CDCl$_3$): δ (ppm)=7.81 (2H, dt, J=9.5 and 2.5 Hz), 6.93 (2H, dt, J=9.4 and 2.4 Hz), 4.17 (2H, q, J=7.0 Hz), 3.85 (3H, s), 3.13 (2H, t, J=7.1 Hz), 2.67 (2H, t, J=7.4 Hz), 1.27 (3H, t, J=7.1 Hz).

(b) 4-{3-[4-Chloro-2-(4-hydroxyphenyl)thiazol-5-yl]propanoyl}amino-1-methylpyrrole-3-carboxylic acid Reactions were carried out in the same manner as in Examples 7(c) and 1(d) using the compound obtained in Example 8(a) and the compound obtained in Example 1(a), so as to obtain the title compound in the form of a colorless powder.

$^1$H NMR (400 MHz, DMSO-d$_6$): δ (ppm)=10.1 (1H, brs), 9.36 (1H, brs), 7.69 (2H, d, J=8.6 Hz), 7.27 (1H, d, J=2.4 Hz), 7.23 (1H, d, J=2.7 Hz), 6.86 (2H, dd, J=8.6 and 1.1 Hz), 3.61 (3H, s), 3.08 (2H, t, J=6.9 Hz), 2.75 (2H, t, J=7.0 Hz).

MS m/z: 404 (M−H)$^-$.

Example 9

4-{3-[2-(4-Hydroxy-3-fluorophenyl)thiazol-5-yl]propanoyl}amino-1-methylpyrrole-3-carboxylic acid

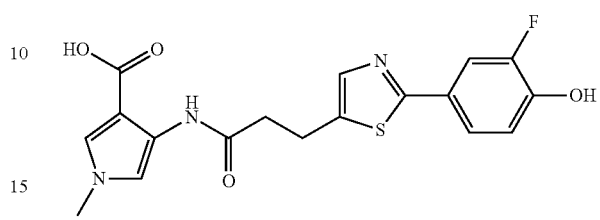

A reaction was carried out in the same manner as in Example 7(b) using the compound obtained in Example 7(a) and 3-fluoro-4-methoxyphenylboronic acid to obtain an ester compound. Thereafter, reactions were carried out in the same manner as in Examples 7(c) and 1(d) using the obtained ester compound and the compound obtained in Example 1(a), so as to obtain the title compound in the form of a colorless powder.

$^1$H NMR (400 MHz, DMSO-d$_6$): δ (ppm)=12.2 (1H, brs), 10.4 (1H, s), 9.34 (1H, s), 7.61 (1H, d, J=8.3 Hz), 7.59 (1H, s), 7.50 (1H, d, J=8.3 Hz), 7.28 (1H, d, J=2.3 Hz), 7.23 (1H, d, J=2.3 Hz), 7.03 (1H, t, J=8.8 Hz), 3.61 (3H, s), 3.14 (2H, t, J=7.0 Hz), 2.76 (2H, t, J=7.0 Hz).

MS m/z: 388 (M−H)$^-$.

Example 10

4-{3-[2-(3-Chloro-4-hydroxyphenyl)thiazol-5-yl]propanoyl}amino-1-methylpyrrole-3-carboxylic acid

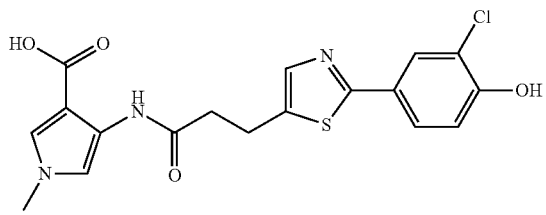 [SMILES: Cn1cc(NC(=O)CCc2cnc(-c3ccc(O)c(Cl)c3)s2)c(C(=O)O)c1]

A reaction was carried out in the same manner as in Example 7(b) using the compound obtained in Example 7(a) and 3-chloro-4-methoxyphenylboronic acid to obtain an ester compound. Thereafter, reactions were carried out in the same manner as in Examples 7(c) and 1(d) using the obtained ester compound and the compound obtained in Example 1(a), so as to obtain the title compound in the form of a colorless powder.

$^1$H NMR (400 MHz, DMSO-d$_6$): δ (ppm)=12.2 (1H, brs), 10.8 (1H, s), 9.34 (1H, s), 7.80 (1H, d, J=1.9 Hz), 7.64 (1H, dd, J=8.6, 1.9 Hz), 7.60 (1H, s), 7.28 (1H, d, J=2.3 Hz), 7.23 (1H, d, J=2.3 Hz), 7.05 (1H, d, J=8.6 Hz), 3.61 (3H, s), 3.14 (2H, t, J=7.0 Hz), 2.76 (2H, t, J=7.0 Hz).

MS m/z: 404 (M−H)$^-$.

Example 11

4-{3-[2-(5-Hydroxypyridin-2-yl)oxazol-5-yl]propanoyl}amino-1-butylpyrrole-3-carboxylic acid

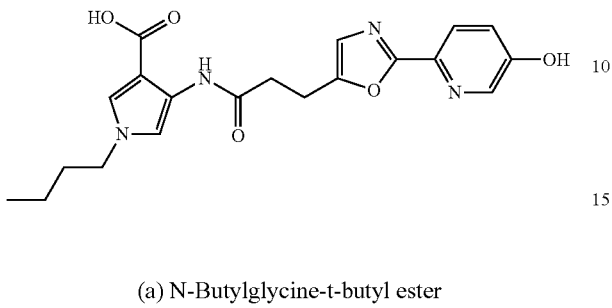

(a) N-Butylglycine-t-butyl ester

N-Butylamine (5 mL, 51 mmol) was dissolved in t-butyl methyl ether (100 mL), and bromoacetic acid t-butyl ester (3.7 mL, 25 mmol) was then added to the solution. The obtained mixture was stirred at room temperature overnight. The generated precipitate was filtered, and the filtrate was then concentrated under reduced pressure, so as to obtain the title compound (4.67 g, yield: 100%) in the form of a colorless oily substance.

(b) 4-Amino-1-butylpyrrole-3-carboxylic acid ethyl ester hydrochloride

A reaction was carried out in the same manner as in Example 1(a) using the compound obtained in Example 11(a), so as to obtain the title compound in the form of a yellow powder.

$^1$H NMR (400 MHz, DMSO-d$_6$): δ (ppm)=7.55 (1H, d, J=2.3 Hz), 7.04 (1H, d, J=2.3 Hz), 4.22 (2H, q, J=7.1 Hz), 3.95 (2H, t, J=7.3 Hz), 1.70-1.63 (2H, m), 1.29 (3H, t, J=7.1 Hz), 1.19 (2H, q, J=7.5 Hz), 0.88 (3H, t, J=7.5 Hz).

(c) 3-[2-(5-methoxypyridin-2-yl)oxazol-5-yl]propionic acid

Reactions were carried out in the same manner as in Examples 4(a) and 4(b) using 5-methoxypicolinic acid, so as to obtain the title compound.

$^1$H NMR (400 MHz, CDCl$_3$): δ (ppm)=8.42 (1H, d, J=2.3 Hz), 8.08 (1H, d, J=9.0 Hz), 7.33 (1H, t, J=4.1 Hz), 6.96 (1H, s), 3.93 (3H, s), 3.13 (2H, t, J=7.8 Hz), 2.88 (2H, t, J=7.6 Hz).

(d) 4-{3-[2-(5-Hydroxypyridin-2-yl)oxazol-5-yl]propanoyl}amino-1-butylpyrrole-3-carboxylic acid Reactions were carried out in the same manner as in Examples 1(c) and 1(d) using the compound obtained in Example 11(b) and the compound obtained in Example 11(c), so as to obtain the title compound in the form of a colorless powder.

$^1$H NMR (400 MHz, DMSO-d$_6$): δ (ppm)=10.5 (1H, brs), 9.41 (1H, s), 8.21 (1H, d, J=2.7 Hz), 7.89 (1H, d, J=8.9 Hz), 7.31-7.25 (3H, m), 7.03 (1H, s), 3.88 (2H, t, J=7.0 Hz), 3.03 (2H, t, J=7.6 Hz), 2.77 (2H, t, J=7.4 Hz), 1.65 (2H, t, J=7.2 Hz), 1.20 (2H, q, J=7.8 Hz), 0.87 (3H, t, J=7.4 Hz).

MS m/z: 397 (M−H)$^-$.

Example 12

4-{3-[3-(4-Hydroxyphenyl)-1,2,4-oxadiazol-5-yl]propanoyl}amino-1-ethylpyrrole-3-carboxylic acid

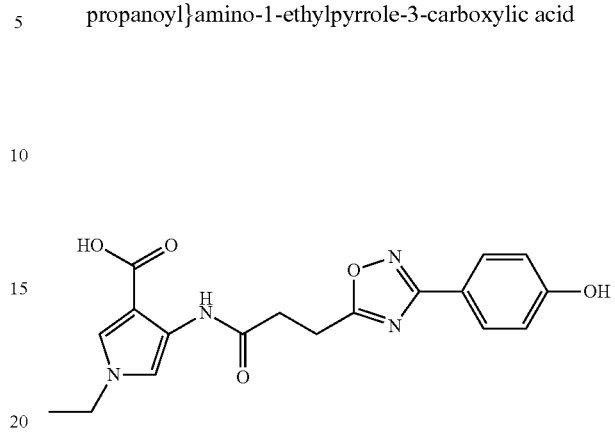

(a) 4-Amino-1-ethylpyrrole-3-carboxylic acid ethyl ester hydrochloride

Reactions were carried out in the same manner as in Examples 11(a) and 1(a) using a 2 N-THF solution of ethylamine, so as to obtain the title compound in the form of a pale yellow powder.

$^1$H NMR (400 MHz, DMSO-d$_6$): δ (ppm)=9.81 (2H, brs), 7.58 (1H, d, J=2.3 Hz), 7.05 (1H, s), 4.23 (2H, q, J=7.0 Hz), 3.98 (2H, q, J=7.0 Hz), 1.32 (3H, t, J=7.0 Hz), 1.28 (3H, t, J=7.0 Hz).

(b) 3-[3-(4-Methoxyphenyl)-1,2,4-oxadiazol-5-yl]propionic acid

A reaction was carried out in the same manner as in Example 3(b) using 4-ethoxybenzamidoxime, so as to obtain the title compound in the form of a colorless powder.

$^1$H NMR (500 MHz, CDCl$_3$): δ (ppm)=7.99 (2H, d, J=9.0 Hz), 6.98 (2H, d, J=9.0 Hz), 3.86 (3H, s), 3.24 (2H, t, J=7.4 Hz), 3.00 (2H, t, J=7.4 Hz).

(c) 4-{3-[3-(4-Hydroxyphenyl)-1,2,4-oxadiazol-5-yl]propanoyl}amino-1-ethylpyrrole-3-carboxylic acid Reactions were carried out in the same manner as in Examples 1(c) and 1(d) using the compound obtained in Example 12(a) and the compound obtained in Example 12(b), so as to obtain the title compound in the form of a colorless powder.

$^1$H NMR (400 MHz, DMSO-d$_6$): δ (ppm)=12.3 (1H, brs), 10.1 (1H, s), 9.50 (1H, s), 7.82 (2H, d, J=8.6 Hz), 7.28 (2H, s), 6.90 (2H, d, J=8.6 Hz), 3.89 (2H, q, J=7.2 Hz), 3.22 (2H, t, J=6.9 Hz), 2.97 (2H, t, J=6.9 Hz), 1.28 (3H, t, J=7.2 Hz).

MS m/z: 371 (M+H)$^+$.

Example 13

4-{3-[2-(4-Hydroxyphenyl)thiazol-5-yl]propanoyl}amino-1-ethylpyrrole-3-carboxylic acid

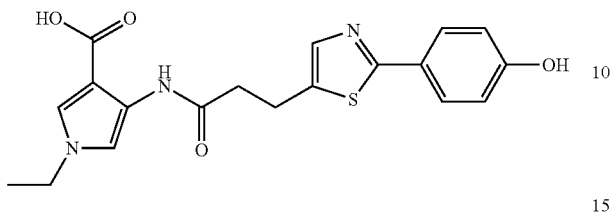

Reactions were carried out in the same manner as in Examples 1(c) and 1(d) using the compound obtained in Example 12(a) and the compound obtained in Example 6(a), so as to obtain the title compound in the form of a colorless powder.

$^1$H NMR (400 MHz, DMSO-$d_6$): δ (ppm)=9.36 (1H, s), 7.70 (2H, d, J=8.6 Hz), 7.58 (1H, s), 7.34 (1H, d, J=2.3 Hz), 7.30 (1H, d, J=2.3 Hz), 6.85 (2H, d, J=8.6 Hz), 3.92 (2H, q, J=7.0 Hz), 3.13 (2H, t, J=7.0 Hz), 2.76 (2H, t, J=7.0 Hz), 1.31 (3H, t, J=7.0 Hz).

MS m/z: 386 (M+H)$^+$.

Example 14

4-[3-(2-Phenylthiazol-5-yl)propanoyl]amino-1-(2-fluoroethyl)pyrrole-3-carboxylic acid

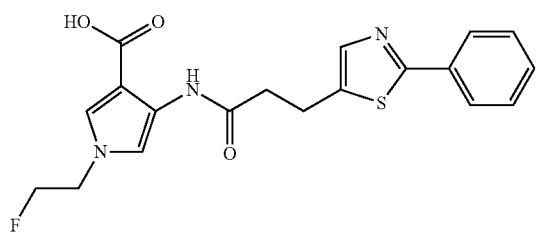 [SMILES: O=C(CCc1cnc(-c2ccccc2)s1)Nc1cn(CCF)cc1C(=O)O]

(a) 4-Amino-1-(2-fluoroethyl)pyrrole-3-carboxylic acid ethyl ester hydrochloride Reactions were carried out in the same manner as in Examples 11(a) and 1(a) using 2-fluoroethylamine, so as to obtain the title compound in the form of a pale yellow powder.

$^1$H NMR (400 MHz, DMSO-$d_6$): δ (ppm)=9.79 (2H, brs), 7.58 (1H, d, J=2.4 Hz), 7.08 (1H, s), 4.75 (1H, t, J=4.5 Hz), 4.63 (1H, t, J=4.5 Hz), 4.34 (1H, t, J=4.5 Hz), 4.27 (1H, t, J=4.5 Hz), 4.24 (2H, q, J=7.1 Hz), 1.29 (3H, t, J=7.1 Hz).

(b) 4-[3-(2-Phenylthiazol-5-yl)propanoyl]amino-1-(2-fluoroethyl)pyrrole-3-carboxylic acid A reaction was carried out in the same manner as in Example 1(c) using the compound obtained in Example 14(a) and the compound obtained in Example 5(a), so as to obtain the title compound in the form of a colorless powder.

$^1$H NMR (400 MHz, DMSO-$d_6$): δ (ppm)=12.3 (1H, brs), 9.37 (1H, s), 7.87 (2H, dd, J=7.8, 1.6 Hz), 7.69 (1H, s), 7.51-7.46 (3H, m), 7.40 (1H, d, J=2.3 Hz), 7.32 (1H, d, J=2.4 Hz), 4.72 (1H, t, J=4.5 Hz), 4.61 (1H, t, J=4.7 Hz), 4.26 (1H, t, J=4.5 Hz), 4.19 (1H, t, J=4.7 Hz), 3.17 (2H, t, J=7.1 Hz), 2.80 (2H, t, J=7.1 Hz).

MS m/z: 388 (M+H)$^+$.

Example 15

4-{3-[(5-Hydroxypyridin-2-yl)-1,2,4-oxadiazol-5-yl]propanoyl}amino-1-(3,5-difluorobenzyl)pyrrole-3-carboxylic acid

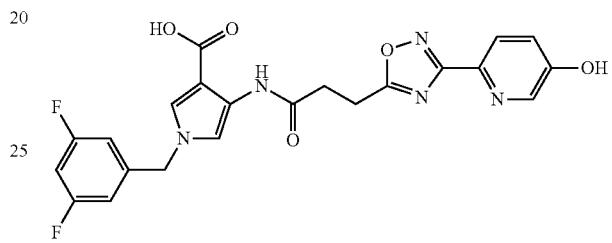

(a) 4-Amino-1-(3,5-difluorobenzyl)pyrrole-3-carboxylic acid ethyl ester hydrochloride Reactions were carried out in the same manner as in Examples 11(a) and (1a) using 3,5-difluorobenzylamine, so as to obtain the title compound in the form of a pale yellow powder.

$^1$H NMR (400 MHz, DMSO-$d_6$): δ (ppm)=9.86 (2H, brs), 7.74 (1H, d, J=2.4 Hz), 7.27-7.21 (1H, m), 7.18 (1H, d, J=2.4 Hz), 7.11-7.07 (2H, m), 5.20 (2H, s), 4.23 (2H, q, J=7.1 Hz), 1.29 (3H, t, J=7.1 Hz).

(b) 4-{3-[(5-Hydroxypyridin-2-yl)-1,2,4-oxadiazol-5-yl]propanoyl}amino-1-(3,5-difluorobenzyl)pyrrole-3-carboxylic acid Reactions were carried out in the same manner as in Examples 1(c) and 3(d) using the compound obtained in Example 15(a) and the compound obtained in Example 3(b), so as to obtain the title compound in the form of a colorless powder.

$^1$H NMR (400 MHz, DMSO-$d_6$): δ (ppm)=12.4 (1H, brs), 10.6 (1H, s), 9.45 (1H, s), 8.27 (1H, d, J=2.8 Hz), 7.90 (1H, d, J=8.6 Hz), 7.48 (1H, d, J=2.3 Hz), 7.36 (1H, d, J=2.3 Hz), 7.31 (1H, dd, J=8.7, 2.8 Hz), 7.20-7.15 (1H, m), 7.01 (2H, d, J=6.7 Hz), 5.11 (2H, s), 3.23 (2H, t, J=6.9 Hz), 2.99 (2H, t, J=6.9 Hz).

MS m/z: 470 (M+H)$^+$.

Example 16

4-{3-[(4-Hydroxyphenyl)-1,2,4-oxadiazol-5-yl]propanoyl}amino-1-(3,5-difluorobenzyl)pyrrole-3-carboxylic acid

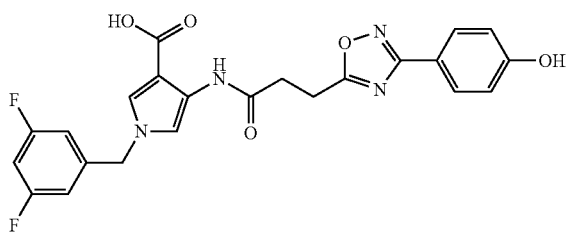 [SMILES: O=C(CCc1nc(-c2ccc(O)cc2)no1)Nc1cn(Cc2cc(F)cc(F)c2)cc1C(=O)O]

Reactions were carried out in the same manner as in Examples 1(c) and 1(d) using the compound obtained in Example 15(a) and the compound obtained in Example 12(b), so as to obtain the title compound in the form of a colorless powder.

$^1$H NMR (400 MHz, DMSO-d$_6$): δ (ppm)=12.4 (1H, s), 10.1 (1H, s), 9.45 (1H, s), 7.81 (2H, d, J=8.6 Hz), 7.48 (1H, d, J=2.4 Hz), 7.36 (1H, d, J=2.4 Hz), 7.21-7.16 (1H, m), 7.02 (2H, d, J=6.2 Hz), 6.90 (2H, d, J=8.6 Hz), 5.12 (2H, s), 3.21 (2H, t, J=7.0 Hz), 2.97 (2H, t, J=7.0 Hz).

MS m/z: 469 (M+H)$^+$.

Example 17

5-{3-[(5-Hydroxypyridin-2-yl)-1,2,4-oxadiazol-5-yl]propanoyl}amino-2-butylpyrazol-4-carboxylic acid

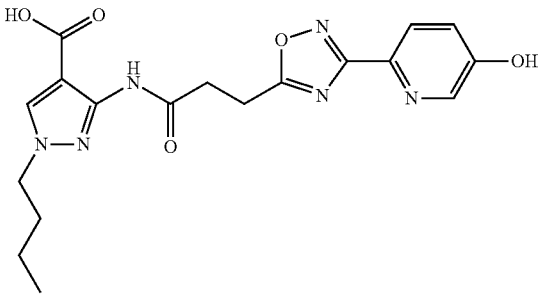 [SMILES: CCCCn1cc(C(=O)O)c(NC(=O)CCc2nc(-c3ccc(O)cn3)no2)n1]

(a) 5-Amino-2-butylpyrazol-3-carboxylic acid ethyl ester

Sodium hydride (920 mg, 21 mmol) was added to a solution of 5-aminopyrazol-3-carboxylic acid ethyl ester (3.10 g, 20 mmol) in acetonitrile (100 mL) under a nitrogen atmosphere, and the obtained mixture was then stirred at room temperature for 30 minutes. The reaction solution was cooled on ice, and butyl iodide (2.3 mL, 20 mmol) was then added thereto. The obtained mixture was stirred at room temperature for 1 hour, and then at 60° C. for 1 hour. The reaction solution was left at room temperature overnight. Thereafter, the solvent was distilled away, and water was then added to the residue, followed by extraction with ethyl acetate. The organic layer was washed with water and a saturated saline, and it was dried over sodium sulfate and was then concentrated. The residue was purified by silica gel column chromatography (hexane/ethyl acetate), so as to obtain the title compound (1.60 g, yield: 38%) in the form of a pale yellow oily substance.

$^1$H NMR (400 MHz, CDCl$_3$): δ (ppm)=7.58 (1H, s), 4.66 (2H, brs), 4.27 (2H, q, J=7.1 Hz), 3.90 (2H, t, J=7.1 Hz), 1.84-1.76 (2H, m), 1.37-1.24 (5H, m), 0.94 (3H, t, J=7.4 Hz).

(b) 5-{3-[(5-Hydroxypyridin-2-yl)-1,2,4-oxadiazol-5-yl]propanoyl}amino-2-butylpyrazol-3-carboxylic acid Reactions were carried out in the same manner as in Examples 1(c) and 3(d) using the compound obtained in Example 17(a) and the compound obtained in Example 3(b), so as to obtain the title compound in the form of a colorless powder.

$^1$H NMR (400 MHz, DMSO-d$_6$): δ (ppm)=10.6 (1H, s), 8.28 (1H, d, J=2.8 Hz), 8.19 (1H, s), 7.92 (1H, d, J=8.6 Hz), 7.32 (1H, dd, J=8.4 and 3.0 Hz), 4.04 (2H, t, J=7.0 Hz), 3.45-3.34 (2H, m), 3.22 (2H, t, J=6.9 Hz), 1.74-1.71 (2H, m), 1.24-1.17 (2H, m), 0.87 (3H, t, J=7.4 Hz).

Example 18

4-{3-[2-(4-Hydroxyphenyl)thiazol-5-yl]propanoyl}amino-1-(3-methoxypropyl)pyrrole-3-carboxylic acid

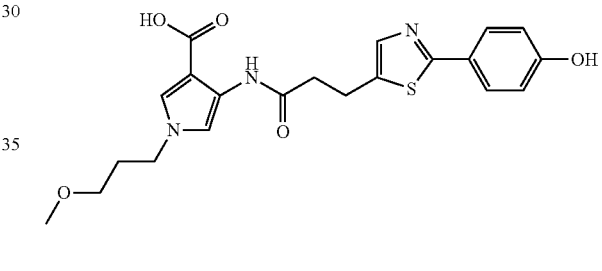

(a) 4-Amino-1-(3-methoxypropyl)pyrrole-3-carboxylic acid ethyl ester hydrochloride Reactions were carried out in the same manner as in Examples 11(a) and 11(b) using 3-methoxypropylamine, so as to obtain the title compound.

$^1$H NMR (500 MHz, DMSO-d$_6$): δ (ppm)=9.95 (2H, brs), 7.51 (1H, s), 7.07 (1H, s), 4.21 (2H, q, J=7.1 Hz), 3.99 (2H, t, J=7.1 Hz), 3.24 (2H, t, J=6.3 Hz), 3.22 (3H, s), 1.95-1.90 (2H, m), 1.28 (3H, t, J=7.1 Hz).

(b) 4-{3-[2-(4-Hydroxyphenyl)thiazol-5-yl]propanoyl}amino-1-(3-methoxypropyl)pyrrole-3-carboxylic acid Reactions were carried out in the same manner as in Examples 1(c) and 1(d) using the compound obtained in Example 18(a) and the compound obtained in Example 6(a), so as to obtain the title compound in the form of a colorless powder.

$^1$H NMR (500 MHz, DMSO-d$_6$): δ (ppm)=9.35 (1H, s), 7.68 (2H, d, J=8.7 Hz), 7.55 (1H, s), 7.30 (1H, d, J=2.4 Hz), 7.25 (1H, d, J=2.4 Hz), 6.84 (2H, d, J=8.7 Hz), 3.92 (2H, t, J=6.8 Hz), 3.23 (2H, t, J=6.1 Hz), 3.22 (3H, s), 3.12 (2H, t, J=7.1 Hz), 2.75 (2H, t, J=7.1 Hz), 1.93-1.88 (2H, m).

MS m/z: 430 (M+H)$^+$.

Example 19

4-{3-[2-(4-Hydroxy-2-methylphenyl)thiazol-5-yl]propanoyl}amino-1-ethylpyrrole-3-carboxylic acid

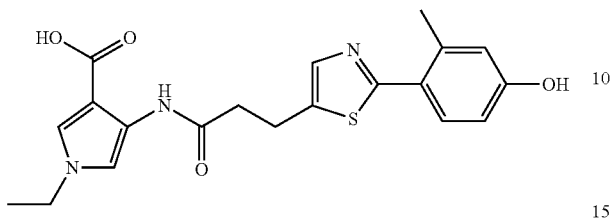

Using 3-(2-bromothiazol-5-yl)propionic acid ethyl ester synthesized by a method similar to the method described in J. Med. Chem., 2007, 50, p. 6303 and the compound obtained in Example 12(b), a reaction was carried out in the same manner as in Example 1(c)-1 to obtain an amide compound. Using the obtained amide compound and 2-methyl-4-methoxyphenylboronic acid, a reaction was carried out in the same manner as in Example 7(b). Using the obtained compound, reactions were carried out in the same manner as in Examples 1(c)-2 and 1(d), so as to obtain the title compound in the form of a powder.

$^1$H NMR (400 MHz, DMSO-$d_6$): δ (ppm)=12.2 (1H, brs), 9.79 (1H, s), 9.36 (1H, s), 7.61 (1H, s), 7.50 (1H, d, J=8.6 Hz), 7.34 (1H, d, J=2.4 Hz), 7.30 (1H, d, J=2.4 Hz), 6.71 (1H, d, J=2.7 Hz), 6.68 (1H, dd, J=8.6, 2.7 Hz), 3.92 (2H, q, J=7.2 Hz), 3.15 (2H, t, J=7.2 Hz), 2.76 (2H, t, J=7.3 Hz), 2.44 (3H, s), 1.31 (3H, t, J=7.2 Hz).

MS m/z: 398 (M–H)$^-$.

Example 20

4-{3-[4-Chloro-2-(4-hydroxy-2,5-difluorophenyl)thiazol-5-yl]propanoyl}amino-1-ethylpyrrole-3-carboxylic acid

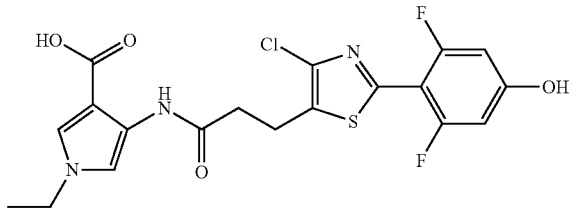 [SMILES: CCn1cc(NC(=O)CCc2sc(-c3c(F)cc(O)cc3F)nc2Cl)c(C(=O)O)c1]

Using the compound obtained in Example 7(a) and the compound obtained in Example 12(b), a reaction was carried out in the same manner as in Example 1(c)-1 to obtain an amide compound. Using the obtained amide compound and 2,5-difluoro-4-methoxyphenylboronic acid, a reaction was carried out in the same manner as in Example 7(b). Using the obtained compound, reactions were carried out in the same manner as in Examples 1(c)-2 and 1(d), so as to obtain the title compound in the form of a colorless powder.

$^1$H NMR (400 MHz, DMSO-$d_6$): δ (ppm)=12.2 (1H, brs), 11.0 (1H, s), 9.37 (1H, s), 7.33 (1H, d, J=2.4 Hz), 7.30 (1H, d, J=2.4 Hz), 6.64 (2H, d, J=10.6 Hz), 3.92 (2H, q, J=7.2 Hz), 3.12 (2H, t, J=7.0 Hz), 2.78 (2H, t, J=7.0 Hz), 1.30 (3H, t, J=7.2 Hz).

MS m/z: 456 (M+H)$^+$.

Example 21

4-{3-[4-Chloro-2-(2,4-dihydroxyphenyl)thiazol-5-yl]propanoyl}amino-1-ethylpyrrole-3-carboxylic acid

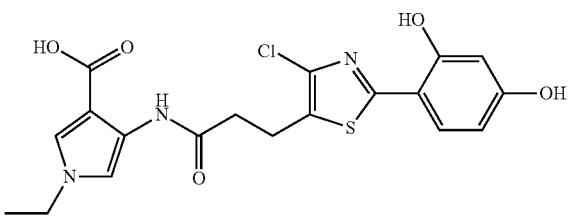 [SMILES: CCn1cc(NC(=O)CCc2sc(-c3ccc(O)cc3O)nc2Cl)c(C(=O)O)c1]

(a) 2,4-Bis(methoxymethyleneoxy)phenylboronic acid

Sodium hydride (10.64 g, 279 mmol) was added to DMF (200 mL), and to the reaction mixture above a suspension of 4-bromoresorcinol (24.74 g, 127 mmol) in DMF (50 mL) was then added dropwise under ice cooling. The obtained mixture was stirred for 1 hour, and chloromethyl methyl ether (22.2 mL, 292 mmol) was then added to the reaction solution. The obtained mixture was stirred at room temperature for 13 hours. Thereafter, water was added to the reaction solution, and it was then extracted with ethyl acetate. The organic layer was washed with water and a saturated saline, and it was then dried over anhydrous sodium sulfate. Thereafter, the solvent was distilled away. The obtained residue was purified by column chromatography (hexane/ethyl acetate) to obtain a colorless oily substance (33.5 g, yield: 95%). The obtained compound (33.5 g, 121 mmol) was dissolved in 1,4-dioxane (450 mL), and bis(pinacolato)diboron (61.4 g, 242 mmol), potassium acetate (35.6 g, 367 mmol) and PdCl$_2$(dppf).CH$_2$Cl$_2$ (14.8 g, 18.13 mmol) were then added to the solution. The obtained mixture was stirred at 95° C. for 4 days. Thereafter, the reaction solution was concentrated, and water was then added thereto, followed by extraction with ethyl acetate. The organic layer was washed with a saturated saline, and it was then dried over anhydrous sodium sulfate. Thereafter, the solvent was distilled away. The obtained residue was purified by column chromatography (hexane/ethyl acetate), so as to obtain the title compound (26.3 g, yield: 67%) in the form of a yellow oily substance.

$^1$H NMR (400 MHz, CDCl$_3$): δ (ppm)=7.65 (1H, d, J=7.8 Hz), 6.72 (1H, dd, J=7.8, 2.3 Hz), 6.70 (1H, d, J=2.3 Hz), 5.19 (2H, s), 5.18 (2H, s), 3.52 (3H, s), 3.47 (3H, s), 1.33 (12H, s).

(b) 4-{3-[4-Chloro-2-(2,4-bis(methoxymethyleneoxy)phenyl)thiazol-5-yl]propanoyl}amino-1-ethylpyrrole-3-carboxylic acid Using the compound obtained in Example 7(a) and the compound obtained in Example 12(b), a reaction was carried out in the same manner as in Example 1(c)-1 to obtain an amide compound. Using the obtained amide compound and the compound obtained in Example 21(a), a reaction was carried out in the same manner as in Example 7(b), so as to obtain the title compound in the form of powder.

$^1$H NMR (400 MHz, CDCl$_3$): δ (ppm)=9.34 (1H, brs), 8.25 (1H, d, J=8.6 Hz), 7.44 (1H, d, J=2.4 Hz), 7.09 (1H, d, J=2.4 Hz), 6.89 (1H, d, J=2.4 Hz), 6.79 (1H, dd, J=8.6, 2.4 Hz), 5.34

(2H, s), 5.21 (2H, s), 4.27 (2H, q, J=7.0 Hz), 3.90 (2H, q, J=7.5 Hz), 3.50 (6H, s), 3.24 (2H, t, J=7.6 Hz), 2.75 (2H, t, J=7.6 Hz), 1.44 (3H, t, J=7.4 Hz), 1.34 (3H, t, J=7.1 Hz).

(c) 4-{3-[4-Chloro-2-(2,4-dihydroxyphenyl)thiazol-5-yl]propanoyl}amino-1-ethylpyrrole-3-carboxylic acid Using the compound obtained in Example 22(b), a reaction was carried out in the same manner as in Example 1(c)-1. The obtained carboxylic acid compound (1.06 g, 2.03 mmol) was dissolved in methanol (15 mL), and a 4 N hydrochloric acid-dioxane solution (4.5 mL) was then added to the solution. The obtained mixture was stirred at room temperature for 2 hours, and the reaction solution was then concentrated. The residue was purified by silica gel column chromatography (dichloromethane/methanol), so as to obtain the title compound (490 mg, yield: 55%) in the form of a white solid.

$^1$H NMR (400 MHz, DMSO-$d_6$): δ (ppm)=12.2 (1H, brs), 10.9 (1H, brs), 9.93 (1H, s), 9.37 (1H, s), 7.85 (1H, d, J=8.6 Hz), 7.33 (1H, d, J=2.3 Hz), 7.30 (1H, d, J=2.3 Hz), 6.43 (1H, d, J=2.4 Hz), 6.37 (1H, dd, J=8.6, 2.4 Hz), 3.92 (2H, q, J=7.0 Hz), 3.06 (2H, t, J=7.2 Hz), 2.73 (2H, t, J=7.2 Hz), 1.31 (3H, t, J=7.2 Hz).

MS m/z: 436 (M+H)$^+$.

Example 22

4-{3-[2-(4-Hydroxyphenyl)thiazol-5-yl]-2-fluoropropanoyl}amino-1-ethylpyrrole-3-carboxylic acid

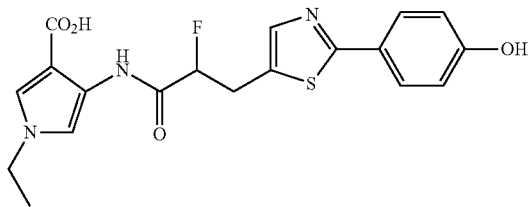 [SMILES: CCn1cc(NC(=O)C(F)Cc2cnc(-c3ccc(O)cc3)s2)c(C(=O)O)c1]

(a) 4-Amino-1-ethylpyrrole-3-carboxylic acid allyl ester hydrochloride

Using the compound obtained in Example 12(a) and allyl 2-(ethoxymethylene)-2-cyanoacetate synthesized from allyl cyanoacetate and triethyl orthoformate according to a method similar to the method described in J. Chem. Soc. section C, 1971, 1501, a reaction was carried out in the same manner as in Example 12(b), so as to obtain the title compound in the form of a pale yellow powder.

$^1$H NMR (400 MHz, MeOH-d4): δ (ppm)=7.51 (1H, d, J=2.4 Hz), 7.02 (1H, d, J=2.4 Hz), 6.09-6.01 (1H, m), 5.41-5.36 (1H, m), 5.28-5.25 (1H, m), 4.78-4.76 (2H, m), 4.03 (2H, q, J=7.2 Hz), 1.43 (3H, t, J=7.4 Hz).

(b) 5-Hydroxymethyl-2-(4-methoxyphenyl)thiazole (b)-1
Palladium acetate (0.82 g, 3.66 mmol), triphenylphosphine (4.80 g, 18.29 mmol), and a 2 M-sodium carbonate aqueous solution (183.0 mL, 366.0 mmol) were added to a solution of 2-bromothiazole (20.00 g, 121.94 mmol) and 4-methoxyphenylboric acid (25.94 g, 170.71 mmol) in DMF (400 mL). The obtained mixture was stirred at 100° C. for 3 hours. Thereafter, water was added to the reaction solution, and it was then extracted with a mixture of ethyl acetate and toluene (1:1). The extract was washed with water and a saturated saline, and it was then dried over anhydrous sodium sulfate, followed by concentration. The residue was purified by silica gel column chromatography (hexane/ethyl acetate) to obtain a thiazole compound (20.40 g, yield: 88%) in the form of a yellow oily substance.

Thereafter, n-butyl lithium (2.64 M hexane solution, 52.5 mL, 138.67 mmol) was added dropwise to a solution of the obtained thiazole compound (20.40 g, 106.67 mmol) in THF (500 mL) at −78° C. After stirring for 2 hours, DMF (16.4 mL, 213.33 mmol) was added dropwise to the reaction solution, and the reaction temperature was then raised to 0° C. The solution was stirred for 2 hours. Thereafter, acetic acid (7.9 mL, 138.67 mmol) was added dropwise to the reaction solution, and the solvent was then distilled away. The residue was dissolved in ethyl acetate, and water was then added to the solution and the two layers were separated. The water layer was extracted with ethyl acetate. The combined organic layer was washed with water and a saturated saline, and it was then dried over anhydrous sodium sulfate, followed by concentration. The residue was recrystallized from diisopropyl ether to obtain an aldehyde compound (18.31 g, yield: 78%) in the form of a yellow powder.

(b)-2
The aldehyde compound (18.31 g, 83.51 mmol) obtained in Example 22(b)-1 was dissolved in a mixture of THF (150 mL) and methanol (100 mL), and sodium borohydride (3.16 g, 83.51 mmol) was then added to the solution at 0° C. The obtained mixture was stirred for 15 minutes. Thereafter, a 10% citric acid aqueous solution was added to the reaction solution, and the solvent was then distilled away, followed by extraction twice with ethyl acetate. The combined organic layer was washed with water and a saturated saline, and it was then dried over anhydrous sodium sulfate, followed by concentration, so as to obtain the title compound (18.2 g, yield: 99%) in the form of a white solid.

$^1$H NMR (400 MHz, CDCl$_3$): δ (ppm)=7.87 (2H, d, J=9.0 Hz), 7.65 (1H, s), 6.96 (2H, d, 9.0 Hz), 4.88 (2H, s), 3.86 (3H, s).

(c) 5-Bromomethyl-2-(4-methoxyphenyl)thiazole

Carbon tetrabromide (21.86 g, 83.35 mmol) and triphenylphosphine (27.64 g, 83.53 mmol) were added to a solution of the compound (18.20 g, 82.25 mmol) obtained in Example 22(b) in dichloromethane (500 mL) at room temperature. The obtained mixture was stirred for 15 minutes. Thereafter, the solvent was distilled away, and the residue was then purified by silica gel column chromatography (hexane/ethyl acetate), so as to obtain the title compound (21.53 g, yield: 100%) in the form of a pale yellow solid.

$^1$H NMR (400 MHz, CDCl$_3$): δ (ppm)=7.86 (2H, d, J=9.0 Hz), 7.73 (1H, s), 6.95 (2H, d, J=9.0 Hz), 4.75 (2H, s), 3.86 (3H, s).

(d) 3-[2-(4-Methoxyphenyl)thiazol-5-yl]-2-fluoropropionic acid

Potassium t-butoxide was added to a solution of fluoromalonic acid diethyl ester (14.18 g, 79.57 mmol) in THF (250 mL) at room temperature, and the obtained mixture was then stirred for 10 minutes. The reaction solution was cooled to 0° C. A solution of the compound (21.53 g, 75.78 mmol) obtained in Example 22(c) in THF (50 mL) was added thereto, and the reaction temperature was then raised to room temperature. The reaction mixture was stirred at room temperature for 2 hours, and acetic acid (0.87 mL, 15.16 mmol) was then added to the reaction solution. Thereafter, the solvent was distilled away, and water was then added to the residue, followed by extraction twice with ethyl acetate. The combined organic layer was washed with a saturated saline, and it was then dried over anhydrous sodium sulfate, followed by concentration. The residue was purified by silica gel column chromatography (hexane/ethyl acetate) to obtain a diester compound (21.50 g, yield: 74%) in the form of a yellow oily substance.

1 M-Sodium hydroxide aqueous solution (140 mL, 140 mmol) was added to a solution of the obtained diester compound (21.50 g, 56.37 mmol) in ethanol (400 mL), and the obtained mixture was then stirred at room temperature for 1 hour. Thereafter, 5 M-hydrochloric acid was added to the reaction solution to make it acidic, and the solvent was then distilled away until the volume of the reaction solution became half of the original volume. The generated precipitate was collected by filtration. The filtrate was extracted with ethyl acetate twice. The combined organic layer was washed with a saturated saline, and it was then dried over anhydrous sodium sulfate, followed by concentration. The residue was combined with the precipitate collected by filtration, and the obtained product was then dissolved in a mixture of 1,4-dioxane (250 mL) and xylene (250 mL). The obtained mixture was stirred at 130° C. for 20 hours. Thereafter, the solvent was distilled away, and the residue was then washed with acetonitrile, so as to obtain the title compound (14.18 g, yield: 89%) in the form of a colorless powder.

$^1$H NMR (400 MHz, CD$_3$OD): δ (ppm)=7.82 (2H, d, J=9.0 Hz), 7.59 (1H, s), 7.01 (2H, d, J=9.0 Hz), 5.23 (1H, ddd, 3.9, 6.3 and 48.1 Hz), 3.85 (3H, s), 3.60-3.40 (2H, m).

(e) 4-{3-[2-(4-Methoxyphenyl)thiazol-5-yl]-2-fluoropropanoyl}amino-1-ethylpyrrole-3-carboxylic acid HATU (23.00 g, 60.49 mmol) and triethylamine (21.1 mL, 151.23 mmol) were added at 0° C. to a solution of the compound (14.18 g, 50.41 mmol) obtained in Example 22(d) and the compound (11.62 g, 50.41 mmol) obtained in Example 22(a) in DMF (300 mL). The temperature of the obtained mixture was raised to room temperature, and the mixture was then stirred for 1 hour. Thereafter, water was added to the reaction solution, followed by extraction twice with ethyl acetate. The combined organic layer was washed with a saturated saline, and it was then dried over anhydrous sodium sulfate, followed by concentration. The residue was purified by silica gel column chromatography (hexane/ethyl acetate) to obtain an amide compound (19.91 g, yield: 86%) in the form of a yellow syrupy substance.

Morpholine (7.9 mL, 90.97 mmol) and tetrakistriphenylphosphine palladium (2.50 g, 2.17 mmol) were added to a solution of the obtained amide compound (19.82 g, 43.32 mmol) in acetonitrile (250 mL) at room temperature, and the obtained mixture was then stirred for 6.5 hours. Thereafter, 5 M-hydrochloric acid was added to the reaction solution to make it acidic, and the generated precipitate was then collected by filtration. The precipitate was washed with dichloromethane, so as to obtain the title compound (17.43 g, yield: 96%) in the form of a pale yellow powder.

$^1$H NMR (400 MHz, DMSO-d$_6$): δ (ppm)=10.0 (1H, brs), 7.81 (2H, d, J=9.0 Hz), 7.65 (1H, s) 7.38 (1H, d, J=2.4 Hz), 7.34 (1H, d, J=2.4 Hz), 7.03 (2H, d, J=9.0 Hz), 5.49 (1H, ddd, J=3.9, 6.7 and 48.5 Hz), 3.94 (2H, q, 7.0 Hz), 3.81 (3H, s), 3.63-3.42 (2H, m), 1.32 (3H, t, J=7.0 Hz).

(f) 4-{3-[2-(4-hydroxyphenyl)thiazol-5-yl]-2-fluoropropanoyl}amino-1-ethylpyrrole-3-carboxylic acid The compound obtained in Example 22(d) was treated in the same manner as in Example 1(d), so as to obtain the title compound in the form of a pale yellow powder.

$^1$H NMR (400 MHz, DMSO-d$_6$): δ (ppm)=10.0 (1H, brs), 7.70 (2H, d, J=8.6 Hz), 7.60 (1H, s) 7.37 (1H, d, J=2.7 Hz), 7.33 (1H, d, J=2.7 Hz), 6.84 (2H, d, J=8.6 Hz), 5.48 (1H, ddd, J=3.1, 6.3 and 47.3 Hz), 3.94 (2H, q, 7.0 Hz), 3.61-3.40 (2H, m), 1.31 (3H, t, J=7.0 Hz).

MS m/z: 403 (M+H)$^+$.

Example 23

(−)-4-{3-[2-(4-Hydroxyphenyl)thiazol-5-yl]-2-fluoropropanoyl}amino-1-ethylpyrrole-3-carboxylic acid and

(+)-4-{3-[2-(4-hydroxyphenyl)thiazol-5-yl]-2-fluoropropanoyl}amino-1-ethylpyrrole-3-carboxylic acid The (±)-4-{3-[2-(4-hydroxyphenyl)thiazol-5-yl]-2-fluoropropanoyl}amino-1-ethylpyrrole-3-carboxylic acid obtained in Example 22 was subjected to high performance liquid chromatography (HPLC), so as to obtain the title compound.

HPLC conditions for fractionation and analysis were as described below.
Conditions (1) (For Fractionation)
  Column: CHIRALPAK IC, 2.5 cmφ×25 cm
  Mobile phase: hexane/ethanol/trifluoroacetic acid (70/30/0.1) (V/V/V)
  Flow rate: 15 mL/min
  Detector: UV (254 nm)
  Column temperature: 25° C.
  Sample concentration: 100 mg of racemic form/10 mL of a mixture of (hexane:ethanol (1:1) (V/V))
  Amount of sample poured: 1 mL
Conditions (2) (For Analysis)
  Column: CHIRALPAK IC, 0.46 cmφ×25 cm
  Mobile phase: hexane/ethanol/trifluoroacetic acid (70/30/0.1) (V/V/V)
  Flow rate: 1.0 mL/min
  Detector: UV (254 nm)
  Column temperature: 25° C.

(a) (−)-4-{3-[2-(4-Hydroxyphenyl)thiazol-5-yl]-2-fluoropropanoyl}amino-1-ethylpyrrole-3-carboxylic acid Property: pale yellow solid
Retention time under conditions (2): 6.1 min
$[α]^D_{20}$: −135.6° (c=1.00, ethanol)
$^1$H NMR: It is identical to the (±)-4-[3-{2-(4-hydroxyphenyl)thiazol-5-yl}-2-fluoropropanoyl]amino-1-ethylpyrrole-3-carboxylic acid in Example 22.

(b) (+)-4-{3-[2-(4-Hydroxyphenyl)thiazol-5-yl]-2-fluoropropanoyl}amino-1-ethylpyrrole-3-carboxylic acid Property: pale yellow solid
Retention time under conditions (2): 7.2 min
$[α]^D_{20}$: +140.6° (c=1.00, ethanol)

¹H NMR: It is identical to the (±)-4-[3-{2-(4-hydroxyphenyl)thiazol-5-yl}-2-fluoropropanoyl]amino-1-ethylpyrrole-3-carboxylic acid in Example 22.

Example 24

4-{3-(4-Phenyl-5-methylimidazol-1-yl)propanoyl}amino-1-ethylpyrrole-3-carboxylic acid

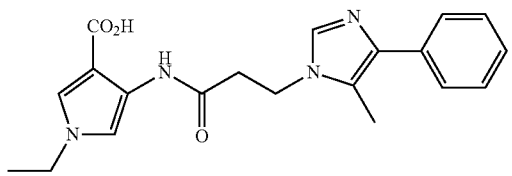 [SMILES: CCn1cc(NC(=O)CCn2cnc(-c3ccccc3)c2C)c(C(=O)O)c1]

(a) 4-[3-(4-Phenyl-5-methylimidazol-1-yl)propanoyl]amino-1-ethylpyrrole-3-carboxylic acid ethyl ester Ethyl acrylate (242 μL, 2.24 mmol) and polystyrene-1,5,7-triazabicyclo[4,4,0]dec-5-ene (72 mg, 0.19 mmol) were added to a solution of 4-bromo-5-methylimidazole (300 mg, 1.86 mmol) in acetonitrile (3 mL). The obtained mixture was stirred at room temperature for 16 hours, and then at 60° C. for 8 hours. The reaction solution was filtered and was then concentrated so as to obtain an adduct as an isometric mixture (6:1).

Tetrakistriphenylphosphine palladium (56.0 mg, 0.05 mmol) and a 2 M-sodium carbonate aqueous solution (1.5 mL, 3.0 mmol) were added to a solution of the obtained adduct (253.2 mg, 0.97 mmol) and phenylboric acid (141.9 mg, 1.16 mmol) in 1,4-dioxane (4 mL), and then a reaction was carried out using a microwave reactor (140° C., 30 minutes). Thereafter, 5 M hydrochloric acid was added to the reaction solution to make it acidic, and it was then concentrated.

HATU (479.5 mg, 1.26 mmol) and triethylamine (540 μL, 3.88 mmol) were added at 0° C. to a solution of the obtained residue and the compound (212.1 mg, 0.97 mmol) obtained in Example 12(b) in DMF (6 mL). The temperature of the obtained mixture was raised to room temperature, and the mixture was then stirred for 1 hour. Thereafter, water was added to the reaction solution, and it was then extracted with ethyl acetate twice. The combined organic layer was washed with a saturated saline, and it was then dried over anhydrous sodium sulfate, followed by concentration. The obtained residue was purified by silica gel column chromatography (NH, hexane/ethyl acetate), so as to obtain the title compound (140.0 mg, yield in three steps: 37%) in the form of a yellow syrupy substance.

¹H NMR (400 MHz, CDCl₃): δ (ppm)=9.35 (1H, brs), 7.63 (2H, dd, J=1, 2 and 8.2 Hz), 7.56 (1H, s), 7.39 (2H, dd, J=7.4 and 8.2 Hz), 7.38 (1H, d, J=2.4 Hz), 7.24 (1H, tt, J=1.2 and 7.4 Hz), 7.08 (1H, d, J=2.4 Hz), 4.33 (2H, t, J=7.0 Hz), 4.25 (2H, q, J=7.4 Hz), 3.90 (2H, q, J=7.4 Hz), 2.82 (2H, t, J=7.0 Hz), 2.43 (3H, s), 1.44 (3H, t, J=7.4 Hz), 1.32 (3H, t, J=7.4 Hz).

(b) 4-[3-(4-Phenyl-5-methylimidazol-1-yl)propanoyl]amino-1-ethylpyrrole-3-carboxylic acid 1 M-Lithium hydroxide aqueous solution (1.14 mL, 1.14 mmol) was added to a solution of the compound (140.0 mg, 0.38 mmol) obtained in Example 24(a) in ethanol (2.0 mL), and the obtained mixture was then stirred at 70° C. for 3 hours. Thereafter, the reaction solution was neutralized with 5 M-hydrochloric acid, and the solvent was then distilled away. The residue was purified by reverse-phase liquid chromatography (acetonitrile/water), so as to obtain the title compound (68.2 mg, yield: 45%) in the form of a colorless powder.

¹H NMR (400 MHz, DMSO-d₆): δ (ppm)=9.35 (1H, brs), 7.61 (1H, s), 7.58 (2H, dd, J=1, 2 and 8.6 Hz), 7.36 (1H, dd, J=7.4 and 8.6 Hz), 7.33 (1H, d, J=2.4 Hz), 7.29 (1H, d, J=2.4 Hz), 7.20 (1H, tt, J=1.2 and 7.4 Hz), 4.22 (2H, t, J=6.7 Hz), 3.91 (2H, q, J=7.0 Hz), 2.90 (2H, t, J=6.7 Hz), 2.39 (3H, s), 1.30 (3H, t, J=7.0 Hz).

MS m/z: 367 (M+H)⁺.

Example 25

4-{3-[3-(4-Hydroxyphenyl)-4-ethylisoxazol-5-yl]propanoyl}amino-1-ethylpyrrole-3-carboxylic acid

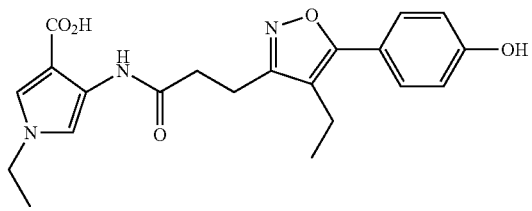 [SMILES: CCc1c(CCC(=O)Nc2cn(CC)cc2C(=O)O)noc1-c1ccc(O)cc1]

(a) 4-Amino-1-ethylpyrrole-3-carboxylic acid benzyl ester hydrochloride

Using the compound obtained in Example 11(a) and benzyl 2-(ethoxymethylene)-2-cyanoacetate synthesized from benzyl cyanoacetate and triethyl orthoformate according to a method similar to the method described in J. Chem. Soc. section C, 1971, 1501, a reaction was carried out in the same manner as in Example 11(b), so as to obtain the title compound in the form of a pale yellow powder.

¹H NMR (500 MHz, MeOH-d4): δ (ppm)=7.51 (1H, d, J=2.4 Hz), 7.44 (1H, d, J=6.9 Hz), 7.38-7.31 (3H, m), 7.02 (1H, d, J=2.4 Hz), 5.31 (2H, s), 4.02 (2H, t, J=7.4 Hz), 1.42 (3H, t, J=7.4 Hz).

(b) 3-[3-(4-Benzyloxyphenyl)-4-bromoisoxazol-5-yl]propionic acid 1,4-Phenylenediisocyanate (19.95 g, 124.56 mmol) and triethylamine (26.0 mL, 186.73 mmol) were added to a solution of 1-(benzyloxy)-4-ethynylbenzene (12.97 g, 62.28 mmol) and 4-nitrobutanoic acid methyl ester (13.74 g, 93.42 mmol) in toluene (700 mL). The obtained mixture was stirred at 110° C. for 6 hours. The reaction solution was filtered with celite, and the solvent was then distilled away. The residue was washed with diisopropyl ether to obtain an isoxazole compound (14.50 g, yield: 69%) in the form of a colorless powder.

N-Bromosuccinimide (15.37 g, 86.33 mmol) was added to a solution of the obtained isoxazole compound (27.73 g, 82.22 mmol) in DMF (220 mL) at room temperature, and the obtained mixture was then stirred for 5.5 hours. Thereafter, water (70 mL) was added to the reaction solution, and the precipitated crude crystals were collected by filtration, so as to obtain a bromo compound in the form of a grayish powder.

The obtained bromo compound was dissolved in a mixture of methanol (400 mL) and THF (100 mL), and a 3 M-sodium hydroxide aqueous solution (55 mL, 165 mmol) was then added to the solution. The obtained mixture was stirred at 60° C. for 1.5 hours. Thereafter, 5 M hydrochloric acid was added to the reaction solution to make it acidic, and the precipitated crude crystals were collected by filtration, so as to obtain the title compound (32.20 g, yield in two steps: 97%) in the form of a colorless powder.

$^1$H NMR (400 MHz, CDCl$_3$): δ (ppm)=7.97 (2H, d, J=8.8 Hz), 7.45-7.33 (5H, m), 7.08 (2H, d, J=8.8 Hz), 5.13 (2H, s), 3.03 (2H, t, J=8.3 Hz), 2.91 (2H, t, J=8.3 Hz).

(c) 4-{3-[3-(4-Benzyloxyphenyl)-4-vinylisoxazol-5-yl]propanoyl}amino-1-ethylpyrrole-3-carboxylic acid benzyl ester HATU (23.00 g, 60.49 mmol) and triethylamine (21.1 mL, 151.23 mmol) were added at 0° C. to a solution of the compound (19.06 g, 47.37 mmol) obtained in Example 25(b) and the compound (13.30 g, 47.37 mmol) obtained in Example 25(a) in DMF (250 mL). The temperature of the obtained mixture was raised to room temperature, and the mixture was then stirred for 2 hours. Thereafter, water and ethyl acetate were added to the reaction solution, and the precipitated crude crystals were then collected by filtration followed by being washed with water and acetonitrile, so as to obtain an amide compound (27.34 g, yield: 92%) in the form of a grayish powder.

Tetrakistriphenylphosphine palladium (0.99 g, 0.86 mmol) and a 2 M-sodium carbonate aqueous solution (64 mL, 128 mmol) were added to a solution of the obtained amide compound (27.00 g, 42.96 mmol) and vinyl boric acid pinacol ester (9.92 g, 64.44 mmol) in DMA (270 mL). The obtained mixture was stirred at 130° C. for 1 hour. Thereafter, water was added to the reaction solution, and it was then extracted with ethyl acetate twice. The combined organic layer was washed with water and a saturated saline, and it was then dried over anhydrous sodium sulfate, followed by concentration. The residue was purified by silica gel column chromatography (hexane/ethyl acetate), so as to obtain the title compound (20.43 g, yield: 83%) in the form of a colorless solid.

$^1$H NMR (400 MHz, CDCl$_3$): δ (ppm)=9.33 (1H, brs), 7.65 (2H, d, J=8.8 Hz), 7.45-7.31 (6H, m), 7.12 (1H, d, J=2.9 Hz), 7.06 (2H, d, J=8.8 Hz), 6.60 (1H, dd, J=11.7 and 18.1 Hz), 5.58 (1H, d, J=18.1 Hz), 5.41 (1H, d, J=11.7 Hz), 5.27 (2H, s), 5.12 (2H, s), 3.88 (2H, q, J=7.3 Hz), 3.19 (2H, t, J=7.8 Hz), 2.90 (2H, t, J=7.8 Hz), 1.42 (3H, t, J=7.3 Hz).

(d) 4-{3-[3-(4-Hydroxyphenyl)-4-ethylisoxazol-5-yl]propanoyl}amino-1-ethylpyrrole-3-carboxylic acid The compound (18.52 g, 32.17 mmol) obtained in Example 25(c) was dissolved in a mixture of ethanol (145 mL) and THF (145 mL), and 20% palladium hydroxide-carbon (1.85 g) was then added to the solution. The obtained mixture was stirred at room temperature under a hydrogen atmosphere for 5 hours. Thereafter, the reaction solution was filtered with celite and Empore (registered trademark) and was then concentrated. The obtained crude crystals were washed with acetonitrile, so as to obtain the title compound (11.51 g, yield: 90%) in the form of a colorless powder.

$^1$H NMR (400 MHz, DMSO-d$_6$): δ (ppm)=12.23 (1H, s), 9.98 (1H, s), 9.39 (1H, s), 7.50 (2H, d, J=9.0 Hz), 7.30 (1H, d, J=2.4 Hz), 7.29 (1H, d, J=2.4 Hz), 6.91 (2H, d, J=9.0 Hz), 3.91 (2H, q, J=7.4 Hz), 2.93 (2H, t, J=7.4 Hz), 2.79 (2H, t, J=7.4 Hz), 2.56 (2H, q, J=7.4 Hz), 1.30 (3H, t, J=7.4 Hz), 1.14 (3H, t, J=7.4 Hz).

MS m/z: 398 (M+H)$^+$.

Example 26

4-[2-Fluoro-3-(5-methyl-1-phenylpyrazol-5-yl)propanoyl]amino-1-ethylpyrrole-3-carboxylic acid

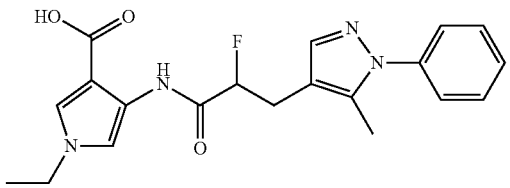 [SMILES: CCn1cc(NC(=O)C(F)Cc2cnn(-c3ccccc3)c2C)c(C(=O)O)c1]

(a) Ethyl 5-methyl-1-phenylpyrazol-4-carboxylate

A mixture of ethyl acetoacetate (1.5 g, 11.5 mmol) and dimethylformamide dimethyl acetal (1.68 mL, 12.7 mmol) was stirred at 120° C. for 2 hours. The reaction solution was cooled to room temperature, and a solution of phenyl hydrazine hydrochloride (1.67 g, 11.5 mmol) in ethanol (30 mL) was then added thereto. The obtained mixture was stirred at 80° C. for 2.5 hours. The reaction solution was cooled to room temperature, and it was then concentrated under reduced pressure. The residue was purified with a fractionation purification apparatus (Biotage, ethyl acetate:hexane=1:19-3:7), so as to obtain the title compound (2.32 g, 87%) in the form of a yellow oily product.

$^1$H NMR (400 MHz, CDCl$_3$): δ (ppm)=8.06 (1H, s), 7.57-7.42 (5H, m), 4.36 (2H, q, J=7.3 Hz), 2.60 (3H, s), 1.41 (3H, t, J=7.3 Hz).

(b) (5-Methyl-1-phenylpyrazol-4-yl)methanol

The compound (2.32 g, 10 mmol) obtained in Example 26(a) was dissolved in THF (25 mL), and the obtained mixture was then stirred under ice cooling. Lithium aluminum hydride (0.38 g, 10 mmol) was gradually added to the reaction solution, and the obtained mixture was then stirred for 1.5 hours, while raising the temperature of the reaction mixture to room temperature. Thereafter, water was added to the reaction solution, and insoluble materials were then removed by filtration with celite. The filtrate was extracted with ethyl acetate three times. The organic layer was washed with a saturated saline, and it was then dried over anhydrous sodium sulfate, followed by concentration under reduced pressure. The residue was purified with a fractionation purification apparatus (Biotage, ethyl acetate:hexane=1:1-4:1), so as to obtain the title compound (1.46 g, 77%) in the form of a colorless solid.

$^1$H NMR (400 MHz, CDCl$_3$): δ (ppm)=7.62 (1H, s), 7.50-7.34 (5H, m), 4.59 (2H, s), 2.33 (3H, s), 1.45 (1H, brs).

MS m/z: 189 (M+H)$^+$.

(c) 5-Methyl-1-phenylpyrazol-4-carbaldehyde

The compound (700 mg, 3.7 mmol) obtained in Example 26(b) was dissolved in THF (15 mL), and manganese dioxide (1102 mg, 11.2 mmol) was then added to the solution. The obtained mixture was stirred at 70° C. for 3 hours. Thereafter, insoluble materials were removed by filtration, and the filtrate was then concentrated under reduced pressure. The residue was purified with a fractionation purification apparatus (Biotage, ethyl acetate:hexane=1:9-3:7), so as to obtain the title compound (575 mg, 83%) in the form of a colorless oily product.

$^1$H NMR (400 MHz, CDCl$_3$): δ (ppm)=9.97 (1H, s), 8.04 (1H, s), 7.55-7.40 (5H, m), 2.58 (3H, s).

(d) Ethyl 2-fluoro-3-(5-methyl-1-phenylpyrazol-4-yl)acrylate

Sodium hydride (32 mg, 0.83 mmol) was suspended in THF (3 mL), and under ice cooling, triethyl 2-fluoro-2-phosphonoacetate (0.17 mL, 0.83 mmol) was added dropwise to the suspension. Fifteen minutes later, a solution of the compound (140 mg, 0.75 mmol) obtained in Example 26(c) in THF (3 mL) was added dropwise to the reaction solution, and the obtained mixture was then stirred for 2 hours, while raising the temperature of the reaction solution to room temperature. Thereafter, a sodium bicarbonate aqueous solution was added to the reaction solution, followed by extraction three times with ethyl acetate. The organic layer was washed with a saturated saline, and it was then dried over anhydrous sodium sulfate, followed by concentration under reduced pressure. The residue was purified with a fractionation purification apparatus (Biotage, ethyl acetate:hexane=1:9-3:7), so as to obtain the title compound (123 mg, 60%, E/Z mixture) in the form of a colorless solid.

MS m/z: 275 (M+H)$^+$.

(e) Ethyl 2-fluoro-3-(5-methyl-1-phenylpyrazol-4-yl)propionate

The compound (120 mg, 0.44 mmol) obtained in Example 26(d) was dissolved in a mixture of ethanol (5 mL) and THF (5 mL), and 10% palladium-carbon (24 mg) was then added to the solution. The obtained mixture was stirred under a hydrogen atmosphere at room temperature for 10 hours. Thereafter, 10% palladium-carbon (24 mg) was added to the reaction solution, and the obtained mixture was further stirred for 10 hours. Thereafter, the catalyst was removed by filtration, and the filtrate was then concentrated under reduced pressure. The residue was purified with a fractionation purification apparatus (Biotage, ethyl acetate:hexane=1:9-3:7), so as to obtain the title compound (67 mg, 55%) in the form of a colorless oily product.

$^1$H NMR (400 MHz, CDCl$_3$): δ (ppm)=7.51 (1H, s), 7.48-7.33 (5H, m), 5.04 (1H, ddd, J=49, 6.7, 4.7 Hz), 4.29-4.20 (2H, m), 3.10 (1H, t, J=5.9 Hz), 3.04 (1H, t, J=5.9 Hz), 2.26 (3H, s), 1.28 (3H, t, J=7.0 Hz).

MS m/z: 277 (M+H)$^+$.

(f) 4-[2-Fluoro-3-(5-methyl-1-phenylpyrazol-5-yl)propanoyl]amino-1-ethylpyrrole-3-carboxylic acid Using a 5 N-sodium hydroxide aqueous solution, the compound obtained in Example 26(e) was converted to a carboxylic acid compound. The reaction was carried out in the same manner as in Example 1(c) using the obtained carboxylic acid compound and the compound obtained in Example 12(b), so as to obtain the title compound in the form of a colorless powder.

$^1$H NMR (400 MHz, DMSO-d$_6$): δ (ppm)=12.3 (1H, brs), 9.92 (1H, brs), 7.52-7.31 (8H, m), 5.36 (1H, ddd, J=48, 6.7, 3.9 Hz), 3.93 (2H, q, J=7.4 Hz), 3.19-2.93 (2H, m), 2.21 (3H, s), 1.30 (3H, t, J=7.4 Hz).

MS m/z: 383 (M−H)$^−$.

Example 27

4-[3-(5-Ethyl-1-phenylpyrazol-5-yl)-2-fluoropropanoyl]amino-1-ethylpyrrole-3-carboxylic acid

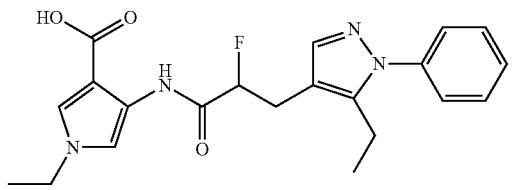 [SMILES: CCc1c(CC(F)C(=O)Nc2cn(CC)cc2C(=O)O)cnn1-c1ccccc1]

Using methylpropanoyl acetate instead of methyl acetoacetate, a reaction was carried out in the same manner as in Example 26 to obtain the title compound.

$^1$H NMR (400 MHz, DMSO-d$_6$): δ (ppm)=12.3 (1H, brs), 9.94 (1H, brs), 7.52-7.31 (8H, m), 5.35 (1H, ddd, J=48, 7.0, 3.9 Hz), 3.91 (2H, q, J=7.0 Hz), 3.19-2.93 (2H, m), 2.63 (2H, dq J=7.4, 3.1 Hz), 1.28 (3H, t, J=7.4 Hz), 0.89 (3H, t, J=7.4 Hz).

MS m/z: 397 (M−H)$^−$.

Example 28

4-{3-(4-Phenyl-5-ethylimidazol-1-yl)propanoyl}amino-1-ethylpyrrole-3-carboxylic acid

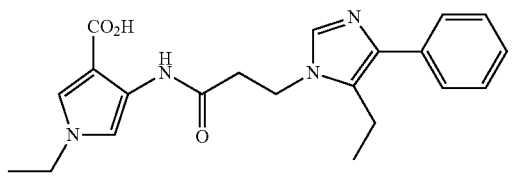 [SMILES: CCc1c(-c2ccccc2)ncn1CCC(=O)Nc1cn(CC)cc1C(=O)O]

(a) 5-Ethyl-4-phenylimidazole

An aqueous solution (5 mL) of concentrated hydrochloric acid (0.6 mL) and sodium thiocyanate (1.62 g, 20.03 mmol) was added to a solution of 2-aminopropiophenone hydrochloride (2.00 g, 10.02 mmol) in ethanol (20 mL). The obtained mixture was stirred at 70° C. for 1 hour. The solvent was distilled away, and acetic acid (20 mL) was then added to the residue. The obtained mixture was stirred at 100° C. for 3 hours. Thereafter, water was added to the reaction solution, and the precipitated crude crystals were collected by filtration. Raney Ni was added to a solution of the obtained crude crystals in ethanol (40 mL), and the obtained mixture was then stirred at 70° C. for 2 hours. The reaction solution was filtered with celite, and the filtrate was then concentrated. The residue was washed with acetonitrile, so as to obtain the title compound (0.88 g, yield in two steps: 45%).

(b) 4-{3-(4-Phenyl-5-ethylimidazol-1-yl)propanoyl}amino-1-ethylpyrrole-3-carboxylic acid benzyl ester The compound (774.2 mg, 3.83 mmol) obtained in Example 28(a) was suspended in acetonitrile (15 mL), and potassium carbonate (1058.1 mg, 7.66 mmol), ethyl 3-bromopropionate (736 μL, 5.74 mmol) and tetrabutylammonium iodide (28.3 mg, 0.08 mmol) were then added to the suspension. The obtained mixture was stirred at 70° C. for 5.5 hours. Thereafter, potassium carbonate (525.0 mg, 3.80 mmol) and ethyl 3-bromopropionate (370 μL, 2.81 mmol) were further added to the reaction solution, and the obtained mixture was then stirred for 2.5 hours. Thereafter, the reaction solution was filtered with celite, and the filtrate was then concentrated. The residue was purified by silica gel column chromatography (hexane/ethyl acetate) to obtain an ester compound in the form of a yellow syrupy substance.

A 1 M-sodium hydroxide aqueous solution (5.2 mL, 5.2 mmol) was added to a solution of the obtained ester compound in ethanol (10 mL), and the obtained mixture was then stirred for 1 hour. The reaction solution was neutralized with 5 M-hydrochloric acid and was then concentrated.

HATU (988.6 mg, 2.60 mmol) and triethylamine (557 μL, 4.00 mmol) were added at 0° C. to a solution of the obtained residue and the compound (437.4 mg, 2.00 mmol) obtained in Example 25(a) in DMF (10 mL). The temperature of the obtained mixture was raised to room temperature, and the mixture was then stirred for 1 hour. Thereafter, water was added to the reaction solution, and it was then extracted with ethyl acetate twice. The combined organic layer was washed with a saturated saline, and it was then dried over anhydrous sodium sulfate, followed by concentration. The obtained residue was purified by silica gel column chromatography (NH, hexane/ethyl acetate), so as to obtain the title compound (654.4 mg, yield in three steps: 56%) in the form of a yellow syrupy substance.

$^1$H NMR (400 MHz, CDCl$_3$): δ (ppm)=9.28 (1H, br.s), 7.65 (2H, dd, J=8.2 and 1.2 Hz), 7.54 (1H, s), 7.41-7.32 (9H, m), 7.25 (1H, m), 7.13 (1H, d, J=2.4 Hz), 5.25 (2H, s), 4.32 (2H, t, J=7.0 Hz), 3.89 (2H, q, J=7.4 Hz), 2.84 (2H, q, J=7.4 Hz), 2.81 (2H, t, J=7. Hz), 1.44 (3H, t, J=7.4 Hz), 1.26 (3H, t, J=7.4 Hz).

(c) 4-{3-(4-Phenyl-5-ethylimidazol-1-yl)propanoyl}amino-1-ethylpyrrole-3-carboxylic acid 10% Palladium-carbon (59.0 mg) was added to a solution of the compound (590.0 mg, 1.25 mmol) obtained in Example 28(b) in ethanol (10 mL), and the obtained mixture was then stirred under a hydrogen atmosphere at room temperature for 5 hours. Thereafter, methanol was added to the reaction solution, and the mixture was then heated. The reaction solution was filtered with celite, and the filtrate was then concentrated. The residue was washed with methanol, so as to obtain the title compound (380.2 mg, yield: 80%) in the form of a colorless powder.

$^1$H NMR (400 MHz, DMSO-d$_6$): δ (ppm)=12.21 (1H, br.s), 9.39 (1H, s), 7.64 (1H, s), 7.59 (2H, dd, J=1.2 and 7.8 Hz), 7.37 (2H, t, J=7.8 Hz), 7.33 (1H, d, J=2.4 Hz), 7.29 (1H, d, J=2.4 Hz), 7.21 (1H, tt, 1.2 and 7.8 Hz), 4.21 (2H, t, J=7.0 Hz), 3.91 (2H, q, J=7.0 Hz), 2.94 (2H, t, J=7.0 Hz), 2.82 (2H, q, J=7.4 Hz), 1.30 (3H, t, J=7.0 Hz), 1.21 (3H, t, J=7.4 Hz).

MS m/z: 381 (M+H)$^+$.

Example 29

4-[3-(5-Cyclopropyl-1-phenylpyrazol-5-yl)propanoylamino]-1-ethylpyrrole-3-carboxylic acid

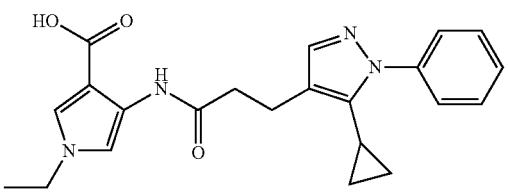 [SMILES: CCn1cc(NC(=O)CCc2cnn(-c3ccccc3)c2C2CC2)c(C(=O)O)c1]

(a) 5-Cyclopropyl-1-phenylpyrazol-4-carbaldehyde

Reactions were carried out in the same manner as in Examples 26(a) to (c) using methyl 3-cyclopropyl-3-oxopropionate, so as to obtain the title compound in the form of a colorless solid.

$^1$H NMR (400 MHz, CDCl$_3$): δ (ppm)=10.0 (1H, s), 8.04 (1H, s), 7.55-7.41 (5H, m), 2.03-1.95 (1H, m), 1.03-0.97 (2H, m), 0.81-0.76 (2H, m).

(b) Ethyl (5-cyclopropyl-1-phenylpyrazol-4-yl)acrylate

Reactions were carried out in the same manner as in Examples 26(d) and 26(e) using the compound obtained in Example 29(a) and triethyl phosphonoacetate, so as to obtain the title compound in the form of a colorless oily product.

$^1$H NMR (400 MHz, CDCl$_3$): δ (ppm)=7.54-7.49 (2H, m), 7.45-7.39 (3H, m), 7.35-7.30 (1H, m), 4.15 (2H, q, J=7.0 Hz), 2.86 (2H, t, J=7.4 Hz), 2.62 (2H, t, J=7.4 Hz), 1.82-1.73 (1H, m), 1.25 (3H, t, J=7.0 Hz), 0.86-0.80 (2H, m), 0.45-0.39 (2H, m).

MS m/z: 285 (M+H)$^+$.

(c) 4-[3-(5-Cyclopropyl-1-phenylpyrazol-5-yl)propanoyl]amino-1-ethylpyrrole-3-carboxylic acid A reaction was carried out in the same manner as in Examples 26(f) using the compound obtained in Example 29(b), so as to obtain the title compound in the form of a colorless oily product.

$^1$H NMR (400 MHz, DMSO-d$_6$): δ (ppm)=12.2 (1H, brs), 9.34 (1H, brs), 7.57-7.52 (2H, m), 7.49-7.44 (3H, m), 7.38-7.33 (1H, m), 7.31 (1H, d, J=2.4 Hz), 7.27 (1H, d, J=2.4 Hz), 3.90 (2H, q, J=7.4 Hz), 2.79 (2H, t J=7.8 Hz), 2.65 (2H, t, J=7.8 Hz), 1.99-1.90 (1H, m), 1.29 (3H, t, J=7.4 Hz), 0.83-0.76 (2H, m), 0.36-0.30 (2H, m).

MS m/z: 391 (M−H)$^-$.

Example 30

4-[3-(5-Cyclopropyl-1-phenylpyrazol-5-yl)-2-fluoropropanoylamino]-1-ethylpyrrole-3-carboxylic acid

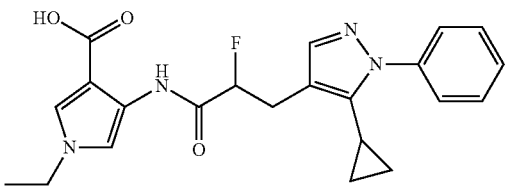 [SMILES: CCn1cc(NC(=O)C(F)Cc2cnn(-c3ccccc3)c2C2CC2)c(C(=O)O)c1]

Reactions were carried out in the same manner as in Examples 26(d) to (f) using the compound obtained in Example 29(a), so as to obtain the title compound in the form of a colorless solid.

$^1$H NMR (400 MHz, DMSO-d$_6$): δ (ppm)=12.4 (1H, brs), 9.99 (1H, brs), 7.58-7.51 (2H, m), 7.50-7.44 (3H, m), 7.40-7.32 (3H, m), 5.40 (1H, ddd, J=48, 7.4, 3.1 Hz), 3.93 (2H, q, J=7.4 Hz), 3.22 (1H, ddd, J=27, 16, 3.1 Hz), 3.06 (1H, ddd J=27, 16, 7.4 Hz), 1.98-1.89 (1H, m), 1.31 (3H, t, J=7.4 Hz), 0.82-0.75 (2H, m), 0.37-0.26 (2H, m).

MS m/z: 409 (M−H)$^-$.

Example 31

4-{3-[3-(4-Hydroxyphenyl)-4-cyclopropylisoxazol-5-yl]propanoyl}amino-1-ethylpyrrole-3-carboxylic acid

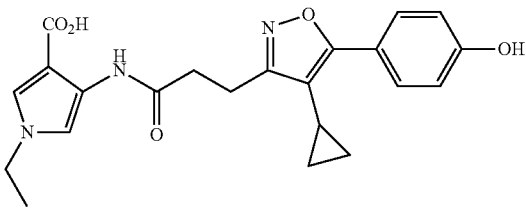 [SMILES: CCn1cc(NC(=O)CCc2noc(-c3ccc(O)cc3)c2C2CC2)c(C(=O)O)c1]

(a) 4-{3-[3-(4-Methoxyphenyl)-4-cyclopropylisoxazol-5-yl]propanoyl}amino-1-ethylpyrrole-3-carboxylic acid ethyl ester A reaction was carried out in the same manner as in Example 25(b) using 1-methoxy-4-propanoylbenzene. Using the compound obtained from the above-described reaction, the compound obtained in Example 12(b) and cyclopropylboric acid, a reaction was carried out in the same manner as in Example 25(c), so as to obtain the title compound.

$^1$H NMR (400 MHz, CDCl$_3$): δ (ppm)=9.38 (1H, br.s), 7.80 (2H, d, J=9.0 Hz), 7.43 (1H, d, J=2.4 Hz), 7.09 (1H, d, J=2.4 Hz), 6.98 (2H, d, J=9.0 Hz), 4.28 (2H, q, J=7.0 Hz), 3.89 (2H, q, J=7.0 Hz), 3.87 (3H, s), 3.17 (2H, dd, J=7.4 and 8.2 Hz), 2.93 (2H, dd, J=7.4 and 8.2 Hz), 1.66 (1H, m), 1.43 (3H, t, J=7.0 Hz), 1.35 (3H, t, J=7.0 Hz), 0.97 (2H, m), 0.43 (2H, m).

(b) 4-{3-[3-(4-Hydroxyphenyl)-4-cyclopropylisoxazol-5-yl]propanoyl}amino-1-ethylpyrrole-3-carboxylic acid Reactions were carried out in the same manner as in Examples 1(c)-2 and 1(d) using the compound obtained in Example 31(a), so as to obtain the title compound in the form of a pale yellow powder.

$^1$H NMR (400 MHz, DMSO-d$_6$): δ (ppm)=12.21 (1H, br.s), 9.97 (1H, s), 9.30 (1H, br.s), 7.66 (2H, d, J=8.8 Hz), 7.30 (1H, d, J=2.4 Hz), 7.29 (1H, d, J=2.4 Hz), 6.90 (2H, d, J=8.8 Hz), 3.91 (2H, q, J=7.3 Hz), 3.00 (2H, t, J=7.3 Hz), 2.83 (2H, t, J=7.3 Hz), 1.74 (1H, m), 1.30 (3H, t, J=7.3 Hz), 0.94 (2H, m), 0.35 (2H, m).

MS m/z: 410 (M+H)$^+$.

Example 32

4-{3-[3-(4-Hydroxyphenyl)-4-ethylisoxazol-5-yl]-2-fluoropropanoyl}amino-1-ethylpyrrole-3-carboxylic acid

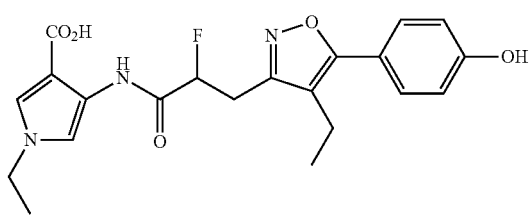

(a) 3-(4-Methoxyphenyl)-5-hydroxymethylisoxazole (a)-1

20% Sodium ethoxide (28.3 mL, 73.3 mmol) was added to a solution of 4-methoxyacetophenone (10.0 g, 66.6 mmol) and diethyl oxalate (10.0 mL, 73.6 mmol) in ethanol (125 mL), and the obtained mixture was then stirred at 80° C. for 6 hours. Thereafter, diethyl oxalate (4.0 mL, 29.4 mmol) and 20% sodium ethoxide (10.0 mL, 25.9 mmol) were further added to the reaction solution, and the obtained mixture was then stirred at 80° C. for 2 hours. Thereafter, the precipitated crude crystals were collected by filtration and were then washed with ethanol to obtain a yellowish brown powder.

The obtained yellowish brown powder was suspended in ethanol, and hydroxylamine hydrochloride (4.63 g, 66.6 mmol) was then added to the suspension. The obtained mixture was stirred at 80° C. for 1.5 hours. Thereafter, the solvent was distilled away, and water was then added to the residue, followed by extraction twice with ethyl acetate. The combined organic layer was washed with a saturated saline, and it was then dried over anhydrous sodium sulfate, followed by concentration. The residue was purified by silica gel column chromatography (hexane/ethyl acetate) to obtain an isoxazole compound (8.4 g, yield in two steps: 51%) in the form of a colorless powder.

(a)-2

Lithium aluminum hydride (1.29 g, 33.97 mmol) was added at 0° C. to a solution of the isoxazole compound (8.40 g, 33.97 mmol) obtained in Example 32(a)-1 in THF (170 mL). The temperature of the obtained mixture was raised to room temperature, and the mixture was then stirred for 2 hours. Thereafter, water (1.3 mL), a 3 M-sodium hydroxide aqueous solution (1.3 mL) and water (3.6 mL) were successively added to the reaction solution, and the obtained mixture was then stirred. The reaction mixture was filtered with celite, and the filtrate was then concentrated, so as to obtain the title compound (6.09 g, yield: 87%) in the form of a colorless solid.

$^1$H NMR (400 MHz, CDCl$_3$): δ (ppm)=7.72 (2H, d, J=8.8 Hz), 6.98 (2H, d, J=8.8 Hz), 6.46 (1H, s), 4.79 (2H, s), 3.86 (3H, s).

(b) 3-(4-Methoxyphenyl)-5-bromomethylisoxazole

A reaction was carried out in the same manner as in Example 22(c) using the compound obtained in Example 32(a) to obtain the title compound.

$^1$H NMR (400 MHz, CDCl$_3$): δ (ppm)=7.72 (2H, d, J=9.0 Hz), 6.99 (2H, d, J=9.0 Hz), 6.50 (1H, s), 4.46 (2H, s), 3.87 (3H, s).

(c) 3-[3-(4-Methoxyphenyl)-4-bromoisoxazol-5-yl]-2-fluoropropionic acid

Potassium t-butoxide (3.62 g, 32.23 mmol) was added to a solution of fluoromalonic acid diethyl ester (5.02 g, 28.20 mmol) in DMF (70 mL) at room temperature, and the obtained mixture was then stirred for 10 minutes. Thereafter, a solution of the compound obtained in Example 32(b) (7.20 g, 26.85 mmol) in DMF solution (10 mL) was added to the reaction solution, and the temperature of the obtained mixture was then raised to room temperature. The mixture was stirred at room temperature for 1 hour. Thereafter, ethyl acetate (80 mL), toluene (80 mL) and water (80 mL) were added to the reaction solution and the two layers were separated. The obtained organic layer was washed with water and a saturated saline, and it was then dried over anhydrous sodium sulfate, followed by concentration. The residue was purified by silica gel column chromatography (hexane/ethyl acetate) to obtain a diester compound (9.48 g, yield: 97%) in the form of a colorless oily substance.

N-Bromosuccinimide (5.08 g, 28.54 mmol) was added to a solution of the obtained diester compound (9.48 g, 25.95 mmol) in DMF (80 mL), and the obtained mixture was then stirred at room temperature for 13 hours. Thereafter, ethyl acetate (80 mL), toluene (80 mL) and water (80 mL) were added to the reaction solution and the two layers were separated. The obtained organic layer was washed with water and a saturated saline, and it was then dried over anhydrous sodium sulfate, followed by concentration. The residue was purified by silica gel column chromatography (hexane/ethyl acetate) to obtain a bromo compound (11.53 g, yield: 100%) in the form of a colorless oily substance.

A 1 M-sodium hydroxide aqueous solution (80 mL, 80 mmol) was added to a solution of the obtained bromo compound (11.53 g, 25.95 mmol) in ethanol (120 mL), and the obtained mixture was then stirred at room temperature for 1 hour. Thereafter, 5 M-hydrochloric acid was added to the reaction solution to make it acidic, and it was then extracted with ethyl acetate twice. The combined organic layer was washed with a saturated saline, and it was then dried over anhydrous sodium sulfate, followed by concentration. The obtained residue was dissolved in 1,4-dioxane (100 mL) and xylene (100 mL), and the obtained mixture was then stirred at 130° C. for 8 hours. Thereafter, the reaction solution was concentrated, so as to obtain the title compound (8.68 g, yield: 99%) in the form of a colorless powder.

$^1$H NMR (400 MHz, CDCl$_3$): δ (ppm)=7.98 (2H, d, J=9.0 Hz), 7.01 (2H, d, J=9.0 Hz), 6.07 (1H, br.s), 5.45 (1H, ddd, J=5.1, 7.8 and 48.1 Hz), 3.88 (3H, s), 3.50-3.33 (2H, m).

(d) 4-[3-{3-(4-Hydroxyphenyl)-4-ethylisoxazol-5-yl}-2-fluoropropanoyl]amino-1-ethylpyrrole-3-carboxylic acid HATU (2.65 g, 6.97 mmol) and triethylamine (2.43 mL, 17.44 mmol) were added at 0° C. to a solution of the compound (2.00 g, 5.81 mmol) obtained in Example 32(c) and the compound (1.63 g, 5.81 mmol) obtained in Example 25(a) in DMF (25 mL). The temperature of the obtained mixture was raised to room temperature, and the mixture was then stirred for 1 hour. Thereafter, water was added to the reaction solution, and it was then extracted with ethyl acetate twice. The combined organic layer was washed with a saturated saline, and it was then dried over anhydrous sodium sulfate, followed by concentration. The obtained residue was purified by silica gel column chromatography (NH, hexane/ethyl acetate) to obtain an amide compound (3.18 g, yield: 96%) in the form of a yellow syrupy substance.

Tributyl(vinyl)tin (1.45 mL, 4.96 mmol) and tetrakistriphenylphosphine palladium (0.14 g, 0.12 mmol) were added to a solution of the obtained amide compound (2.36 g, 4.14 mmol) in toluene (25 mL). The obtained mixture was stirred at 110° C. for 3 hours. Thereafter, an aqueous solution (10 mL) of potassium fluoride dihydrate (1.87 g, 19.86 mmol) was added to the reaction solution, and the obtained mixture was then stirred at room temperature for 1 hour, and then the two layers were separated. The organic layer was washed with water, and it was then filtered with celite, followed by concentration. The residue was purified by silica gel column chromatography (hexane/ethyl acetate) to obtain a vinyl isoxazole compound (1.80 g, yield: 84%).

The obtained vinyl isoxazole compound (1.25 g, 2.43 mmol) was dissolved in a mixture of ethanol (20 mL) and ethyl acetate (20 mL), and 20% palladium hydroxide-carbon (125 mg) was then added to the solution. The obtained mixture was stirred under a hydrogen atmosphere at room temperature for 3 hours. The reaction solution was filtered with celite, and the filtrate was then concentrated. The residue was washed with ethyl acetate, so as to obtain the title compound (1.00 g, yield: 94%) in the form of a colorless powder.

$^1$H NMR (400 MHz, DMSO-d$_6$): δ (ppm)=12.39 (1H, s), 10.06 (1H, d, J=3.5 Hz), 9.99 (1H, s), 7.64 (2H, d, J=9.0 Hz), 7.39 (1H, d, J=2.7 Hz), 7.36 (1H, d, J=2.7 Hz), 6.92 (2H, d, J=9.0 Hz), 5.55 (1H, ddd, J=3.5, 7.8 and 48.1 Hz), 3.95 (2H, q, J=7.4 Hz), 3.43-3.21 (2H, m), 2.57 (2H, q, J=7.4 Hz), 1.32 (3H, t, J=7.4 Hz), 1.12 (3H, t, J=7.4 Hz).

MS m/z: 430 (M+H)$^+$.

Example 33

4-{3-[4-Chloro-(4-hydroxyphenyl)isoxazol-5-yl]propanoyl}amino-1-ethylpyrrole-3-carboxylic acid

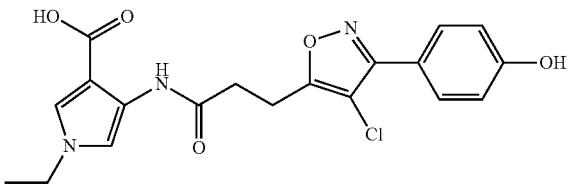

(a) [3-(4-Methoxyphenyl)isoxazol-5-yl]methanol p-Anisaldehyde (3.0 g, 22 mol) was dissolved in ethanol (30 mL), and sodium bicarbonate (2.2 g, 26 mmol) was then added to the solution. The obtained mixture was stirred at room temperature, and an aqueous solution (15 mL) of hydroxylamine hydrochloride (1.7 g, 24 mmol) was then added to the reaction solution. The obtained mixture was stirred at room temperature for 1 hour. Thereafter, the reaction solution was concentrated under reduced pressure, and a sodium bicarbonate aqueous solution was then added to the residue, followed by extraction three times with ethyl acetate. The organic layer was washed with a saturated saline, and it was then dried over anhydrous sodium sulfate, followed by concentration under reduced pressure. The residue was dissolved in dimethylformamide (40 mL), and the mixture was then stirred under ice cooling. Subsequently, N-chlorosuccinimide (2.9 g, 22 mmol) was added to the reaction solution. The obtained mixture was stirred for 2.5 hours, while raising the temperature of the reaction mixture to room temperature. Thereafter, water was added to the reaction solution, and it was then extracted with ethyl acetate three times. The organic layer was washed with a saturated saline, and it was then dried over anhydrous sodium sulfate, followed by concentration under reduced pressure. The residue was purified with a fractionation purification apparatus (Biotage, ethyl acetate:hexane=2:98-2:3). The obtained chloro compound (2.5 g, 13.5 mmol) was dissolved in dichloromethane (30 mL), and propargyl alcohol (1.2 mL, 20.2 mmol) and triethylamine (2.3 mL, 16.2 mmol) were then added to the solution. The obtained mixture was stirred at room temperature for 2 hours. The reaction solution was concentrated under reduced pressure, and the residue was purified with a fractionation purification apparatus (Biotage, ethyl acetate:hexane=1:3-3:1), so as to obtain the title compound (1.8 g, 65%) in the form of a yellow solid.

$^1$H NMR (400 MHz, CDCl$_3$): δ (ppm)=7.71 (2H, d, J=8.6 Hz), 6.95 (2H, d, J=8.6 Hz), 6.49 (1H, s), 4.79 (2H, d, J=5.1 Hz), 3.84 (3H, s), 2.23 (1H, t. J=5.1 Hz).

MS m/z: 206 (M+H)$^+$.

(b) 5-Bromomethyl-3-(4-methoxyphenyl)isoxazole

The compound (1.4 g, 6.8 mmol) obtained in Example 33(a) was dissolved in dichloromethane (30 mL), and triphenylphosphine (2.0 g, 7.5 mmol) and carbon tetrabromide (2.5 g, 7.5 mmol) were added to the solution under ice cooling. The obtained mixture was stirred for 1 hour. The reaction solution was concentrated under reduced pressure, and the residue was then purified with a fractionation purification apparatus (Biotage, ethyl acetate:hexane=2:98-1:3), so as to obtain the title compound (1.66 g, 97%) in the form of a colorless solid.

$^1$H NMR (400 MHz, CDCl$_3$): δ (ppm)=7.71 (2H, d, J=8.6 Hz), 6.96 (2H, d, J=8.6 Hz), 6.56 (1H, s), 4.48 (2H, s), 3.84 (3H, s).

(c) Methyl 3-[3-(4-methoxyphenyl)isoxazol-5-yl]propionate

The compound (0.80 g, 2.98 mmol) obtained in Example 33(b) was dissolved in acetonitrile (12 mL), and triethyl methanetricarboxylate (0.70 mL, 3.3 mmol) and potassium carbonate (0.49 g, 3.6 mmol) were then added to the solution. The obtained mixture was stirred at room temperature overnight. Thereafter, insoluble materials were removed by filtration, and the filtrate was then concentrated under reduced pressure. The residue was purified with a fractionation purification apparatus (Biotage, ethyl acetate:hexane=1:9-3:7) to obtain a triester compound (1.25 g, quantitative) in the form of a colorless oily product. The obtained triester compound was dissolved in a mixture of ethanol (10 mL) and THF (10 mL), and a 5 N-sodium hydroxide aqueous solution (4.5 mL, 22 mmol) was then added to the solution. The obtained mixture was stirred at room temperature for 3 days. Thereafter, the reaction solution was concentrated under reduced pressure, and acetic acid (30 mL) was then added to the residue. The obtained mixture was stirred at 120° C. for 6.5 hours. The reaction solution was cooled to room temperature, and it was then concentrated under reduced pressure. Thereafter, water was added to the residue, and insoluble materials were then collected by filtration. These were then dissolved in a mixture of methanol (6 mL) and THF (6 mL), and a 2 N-trimethylsilyldiazomethane solution (3 mL) was then added to the solution. The obtained mixture was stirred at room temperature for 2 days. Thereafter, the reaction solution was concentrated under reduced pressure, and the residue was then purified with a fractionation purification apparatus (Biotage, ethyl acetate:hexane=1:19-2:3), so as to obtain the title compound (0.71 g, 91%) in the form of a colorless solid.

$^1$H NMR (400 MHz, CDCl$_3$): δ (ppm)=7.70 (2H, d, J=9.0 Hz), 6.94 (2H, d, J=9.0 Hz), 6.27 (1H, s), 3.83 (3H, s), 3.70 (3H, s), 3.11 (2H, t. J=7.4 Hz), 2.76 (2H, t, J=7.4 Hz).

MS m/z: 262 (M+H)$^+$.

(d) Methyl 3-[4-chloro-3-(4-methoxyphenyl)isoxazol-5-yl]propionate

The compound (0.68 g, 2.6 mmol) obtained in Example 33(c) was dissolved in acetic acid (10 mL), and N-chlorosuccinimide (0.38 g, 2.9 mmol) was then added to the solution. The obtained mixture was stirred at 70° C. for 2 hours. The reaction solution was concentrated under reduced pressure, and a 1 N-sodium hydroxide aqueous solution was then added to the residue, followed by extraction three times with ethyl acetate. The organic layer was successively washed with a 10% citric acid aqueous solution and a saturated saline, and it was then dried over anhydrous sodium sulfate, followed by concentration under reduced pressure. The residue was purified with a fractionation purification apparatus (ethyl acetate:hexane=1:19-1:3), so as to obtain the title compound (0.23 g, 29%) in the form of a colorless solid.

$^1$H NMR (400 MHz, CDCl$_3$): δ (ppm)=7.80 (2H, d, J=8.6 Hz), 6.98 (2H, d, J=8.6 Hz), 3.85 (3H, s), 3.71 (3H, s), 3.14 (2H, t. J=7.4 Hz), 2.79 (2H, t, J=7.4 Hz).

(e) 4-{3-[-4-Chloro-(4-hydroxyphenyl)isoxazol-5-yl]propanoyl}amino-1-ethylpyrrole-3-carboxylic acid Reactions were carried out in the same manner as in Examples 26(f) and 1(d) using the compound obtained in Example 33(d), so as to obtain the title compound in the form of a pale yellow solid.

$^1$H NMR (400 MHz, DMSO-d$_6$): δ (ppm)=12.2 (1H, brs), 9.99 (1H, brs), 9.36 (1H, brs), 7.62 (2H, d, J=8.6 Hz), 7.29 (1H, d, J=2.4 Hz), 7.27 (1H, d, J=2.4 Hz), 6.90 (2H, d, J=8.6 Hz), 3.89 (2H, q, J=7.4 Hz), 3.10 (2H, t, J=7.4 Hz), 2.84 (2H, t, J=7.4 Hz), 1.28 (3H, t, J=7.4 Hz).

MS m/z: 402 (M−H)$^−$.

Example 34

4-{3-[5-(4-Hydroxyphenyl)-4-chloroisoxazol-3-yl]propanoyl}amino-1-ethylpyrrole-3-carboxylic acid

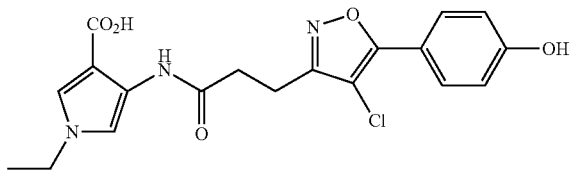 [SMILES: CCn1cc(NC(=O)CCc2noc(-c3ccc(O)cc3)c2Cl)c(C(=O)O)c1]

A reaction was carried out in the same manner as in Example 25(b) using 1-methoxy-4-propanoylbenzene and N-chlorosuccinimide to obtain a carboxylic acid compound. Using the obtained carboxylic acid compound and the compound obtained in Example 12(b), reactions were carried out in the same manner as in Examples 1(c) and 1(d), so as to obtain the title compound.

$^1$H NMR (400 MHz, DMSO-d$_6$): δ (ppm)=12.21 (1H, br.s), 10.23 (1H, br.s), 9.41 (1H, s), 7.79 (2H, d, J=9.0 Hz), 7.30 (1H, d, J=2.7 Hz), 7.29 (1H, d, J=2.7 Hz), 6.96 (2H, d, J=9.0 Hz), 3.91 (2H, q, J=7.4 Hz), 2.97 (2H, t, J=7.0 Hz), 2.83 (2H, t, J=7.0 Hz), 1.30 (3H, t, J=7.4 Hz).

MS m/z: 404 (M+H)$^+$.

Example 35

4-{3-[4-Ethyl-(4-hydroxyphenyl)isoxazol-5-yl]propanoyl}amino-1-ethylpyrrole-3-carboxylic acid

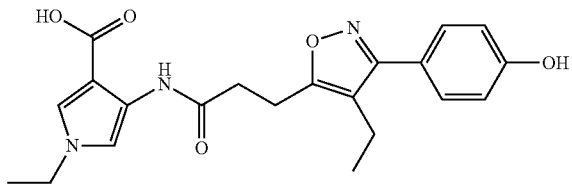 [SMILES: CCc1c(-c2ccc(O)cc2)noc1CCC(=O)Nc1cn(CC)cc1C(=O)O]

(a) Methyl 3-[4-bromo-3-(4-methoxyphenyl)isoxazol-5-yl]propionate

The compound (0.71 g, 2.7 mmol) obtained in Example 33(c) was dissolved in acetic acid (14 mL), and N-bromosuccinimide (0.53 g, 3.0 mmol) was then added to the solution. The obtained mixture was stirred at 70° C. for 4 hours. Thereafter, the reaction solution was concentrated under reduced pressure, and a 1 N-sodium hydroxide aqueous solution was then added to the residue, followed by extraction three times with ethyl acetate. The organic layer was washed with a saturated saline, and it was then dried over anhydrous sodium sulfate, followed by concentration under reduced pressure. The residue was purified with a fractionation purification apparatus (ethyl acetate:hexane=1:19-3:7), so as to obtain the title compound (0.65 g, 70%) in the form of a colorless oily product.

$^1$H NMR (400 MHz, CDCl$_3$): δ (ppm)=7.79 (2H, d, J=9.0 Hz), 6.98 (2H, d, J=9.0 Hz), 3.85 (3H, s), 3.71 (3H, s), 3.15 (2H, t. J=7.4 Hz), 2.79 (2H, t, J=7.4 Hz).

MS m/z: 340 (M+H)$^+$.

(b) Ethyl 4-{3-[4-bromo-3-(4-methoxyphenyl)isoxazol-5-yl]propanoylamino}-1-ethylpyrrole-3-carboxylate The compound (0.65 g, 1.9 mmol) obtained in Example 35(a) was dissolved in a mixture of methanol (6 mL) and THF (6 mL), and a 5 N-sodium hydroxide aqueous solution (1.1 mL, 5.6 mmol) was then added to the solution. The obtained mixture was stirred at room temperature for 1 hour. Thereafter, concentrated hydrochloric acid (0.47 mL) was added to the reaction solution, and the mixture was then concentrated under reduced pressure. The residue was dissolved in dimethylformamide (12 mL). To this solution, ethyl 4-amino-1-ethylpyrrole-3-carboxylate hydrochloride (0.42 g, 1.9 mmol), HATU (0.79 g, 2.1 mmol), and diisopropylethylamine (0.66 mL, 3.8 mmol) were added, and the obtained mixture was then stirred at room temperature overnight. Thereafter, a sodium bicarbonate aqueous solution was added to the reaction solution, and it was then extracted with ethyl acetate three times. The organic layer was washed with a saturated saline, and it was then dried over anhydrous sodium sulfate, followed by concentration under reduced pressure. The residue was purified with a fractionation purification apparatus (Biotage, ethyl acetate:hexane=3:7-3:2), so as to obtain the title compound (0.93 g, quantitative) in the form of a yellow solid.

$^1$H NMR (400 MHz, CDCl$_3$): δ (ppm)=9.35 (1H, brs), 7.85 (2H, d, J=8.8 Hz), 7.44 (1H, d, J=2.4 Hz), 7.11 (1H, d, J=2.4 Hz), 7.02 (2H, d, J=8.8 Hz), 4.31 (2H, q, J=7.3 Hz), 3.92 (2H, q, J=7.3 Hz), 3.89 (3H, s), 3.28 (2H, t. J=7.8 Hz), 2.89 (2H, t, J=7.8 Hz), 1.47 (3H, t, J=7.3 Hz), 1.37 (3H, t, J=7.3 Hz).

MS m/z: 446 (M+H)$^+$.

(c) Ethyl 4-{3-[4-ethyl-3-(4-methoxyphenyl)isoxazol-5-yl]propanoylamino}-1-ethylpyrrole-3-carboxylate The compound (150 mg, 0.31 mmol) obtained in Example 35(b) was dissolved in dioxane (3 mL). Thereafter, vinyl boronic acid pinacol ester (0.10 mL, 0.61 mmol), tetrakistriphenylphosphine palladium (35 mg, 0.03 mmol), and a 2 N sodium carbonate aqueous solution (0.93 mL) were added to the solution, and the obtained mixture was then stirred at 110° C. for 4 hours. Thereafter, vinyl boronic acid pinacol ester (0.11 mL) and tetrakistriphenylphosphine palladium (35 mg) were added to the reaction solution, and the obtained mixture was further stirred for 3 hours. The reaction solution was cooled to room temperature, and a sodium bicarbonate aqueous solution was then added thereto, followed by extraction three times with ethyl acetate. The organic layer was washed with a saturated saline, and it was then dried over anhydrous sodium sulfate, followed by concentration under reduced pressure. The residue was purified with a fractionation purification apparatus (Biotage, ethyl acetate:hexane=1:9-2:3) to obtain a vinyl compound (87 mg, 65%). The obtained vinyl compound was dissolved in a mixture of ethanol (5 mL) and THF (5 mL), and 20% palladium hydroxide (17 mg) was then added to the solution. The obtained mixture was stirred under a hydrogen atmosphere at room temperature for 2 hours. Thereafter, the catalyst was removed by filtration, and the filtrate was then concentrated under reduced pressure. The residue was purified with a fractionation purification apparatus (ethyl acetate:hexane=1:4-1:1), so as to obtain the title compound (75 mg, 86%) in the form of a colorless oily product.

$^1$H NMR (400 MHz, CDCl$_3$): δ (ppm)=9.31 (1H, brs), 7.54 (2H, d, J=8.6 Hz), 7.39 (1H, d, J=2.4 Hz), 7.07 (1H, d, J=2.4

Hz), 6.96 (2H, d, J=8.6 Hz), 4.26 (2H, q, J=7.4 Hz), 3.87 (2H, q, J=7.4 Hz), 3.84 (3H, s), 3.15 (2H, t. J=7.4 Hz), 2.81 (2H, t, J=7.4 Hz), 2.51 (2H, q, J=7.4 Hz), 1.42 (3H, t, J=7.4 Hz), 1.33 (3H, t, J=7.4 Hz), 1.05 (3H, t, J=7.4 Hz).

MS m/z: 440 (M+H)+.

(d) 4-{3-[4-Ethyl-(4-hydroxyphenyl)isoxazol-5-yl]propanoylamino}-1-ethylpyrrole-3-carboxylic acid The compound (125 mg, 0.28 mmol) obtained in Example 35(c) was dissolved in a mixture of ethanol (5 mL) and THF (5 mL), and a 1 N-lithium hydroxide aqueous solution (1.14 mL) was then added to the solution. The obtained mixture was stirred at 85° C. for 7 hours. Thereafter, concentrated hydrochloric acid (0.095 mL) was added to the reaction solution, and the mixture was then concentrated under reduced pressure. The residue was purified with a fractionation purification apparatus (dichloromethane, and then, dichloromethane:methanol=85:15) to obtain a carboxylic acid compound (77 mg, 66%) in the form of a colorless solid. The obtained carboxylic acid compound (134 mg, 0.33 mmol) was suspended in dichloromethane (4 mL), and 1 N-boron tribromide (1.3 mL) was added to the suspension under ice cooling. While gradually raising the temperature of the obtained mixture to room temperature, the mixture was stirred overnight. Thereafter, water was added to the reaction solution, and it was then extracted with a mixture of ethyl acetate and THF three times. The organic layer was washed with a saturated saline, and it was then dried over anhydrous sodium sulfate, followed by concentration under reduced pressure. The residue was purified with a fractionation purification apparatus (Biotage, dichloromethane, and then, dichloromethane:methanol=80:20), so as to obtain the title compound (80 mg, 53%) in the form of a pale yellow solid.

1H NMR (400 MHz, DMSO-d6): δ (ppm)=9.50 (1H, brs), 7.40 (2H, d, J=8.6 Hz), 7.27 (1H, d, J=2.4 Hz), 7.24 (1H, d, J=2.4 Hz), 6.86 (2H, d, J=8.6 Hz), 3.88 (2H, q, J=7.4 Hz), 3.03 (2H, t, J=7.0 Hz), 2.74 (2H, t, J=7.0 Hz), 1.28 (3H, t, J=7.4 Hz), 0.97 (3H, t, J=7.4 Hz).

Example 36

4-{3-[3-(4-Hydroxyphenyl)-4-ethylisoxazol-5-yl]propanoyl}amino-1-methylpyrrole-3-carboxylic acid

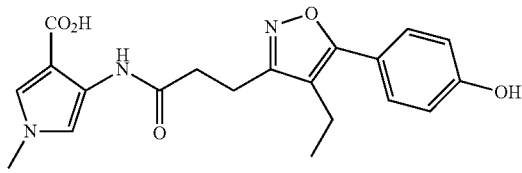 [SMILES: CCc1c(CCC(=O)Nc2cn(C)cc2C(=O)O)noc1-c1ccc(O)cc1]

Using the compound obtained in Example 1(a) and the carboxylic acid compound obtained in Example 25(b), a reaction was carried out in the same manner as in Example 25(c). The obtained vinyl isoxazole compound (363.5 mg, 0.65 mmol) was dissolved in a mixture of ethanol (7 mL) and dichloromethane (3 mL), and 20% palladium hydroxide-carbon (36.0 mg) was then added to the solution. The obtained mixture was stirred under a hydrogen atmosphere at room temperature for 2 hours. The reaction solution was filtered with celite and Empore (registered trademark), and was then concentrated.

A 1 M-lithium hydroxide aqueous solution (2 mL, 2.0 mmol) was added to a solution of the obtained crude crystals in ethanol (5 mL), and the obtained mixture was then stirred at 70° C. for 7 hours. The reaction solution was made acidic by addition of 5 M-hydrochloric acid. The precipitated crude crystals were collected by filtration and were then washed with acetonitrile, so as to obtain the title compound (235.8 mg, yield in two steps: 83%) in the form of a colorless powder.

1H NMR (400 MHz, DMSO-d6): δ (ppm)=12.22 (1H, s), 9.96 (1H, s), 9.37 (1H, s), 7.49 (2H, d, J=8.8 Hz), 7.24 (1H, d, J=2.4 Hz), 7.22 (1H, d, J=2.4 Hz), 6.91 (2H, d, J=8.8 Hz), 3.60 (3H, s), 2.93 (2H, t, J=7.3 Hz), 2.79 (2H, t, J=7.3 Hz), 2.56 (2H, q, J=7.3 Hz), 1.14 (3H, t, J=7.3 Hz).

MS m/z: 384 (M+H)+.

Example 37

4-{3-[4-Chloro-2-(4-hydroxyphenyl)thiazol-5-yl]-2-fluoropropanoyl}amino-1-ethylpyrrole-3-carboxylic acid

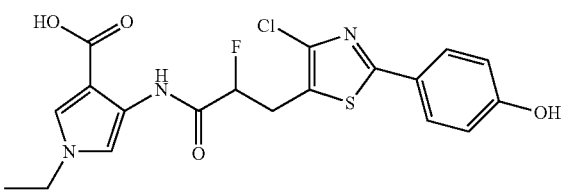 [SMILES: CCn1cc(NC(=O)C(F)Cc2sc(-c3ccc(O)cc3)nc2Cl)c(C(=O)O)c1]

(a) 3-[4-Chloro-2-(4-hydroxyphenyl)thiazol-5-yl]-2-fluoropropionic acid

Using 4-chlorothiazol-5-carbaldehyde synthesized by a method similar to the method described in J. C. S. Perkin Trans. 1, 1992, 8, p. 973, a reaction was carried out in the same manner as in Example 22(c) to obtain a bromo compound. Using the obtained bromo compound, a reaction was carried out in the same manner as in Example 22(d), so as to obtain the title compound.

1H NMR (400 MHz, CDCl3): δ (ppm)=5.18 (1H, ddd, J=48.1, 7.0 and 4.3 Hz), 3.55-3.36 (2H, m).

(b) 4-{3-[4-Chloro-2-(4-hydroxyphenyl)thiazol-5-yl]-2-fluoropropanoyl}amino-1-ethylpyrrole-3-carboxylic acid Using the compound obtained in Example 37(a) and the compound obtained in Example 22(a), a reaction was carried out in the same manner as in Example 1(c)-1. The obtained amide compound was reacted with 4-methoxyboronic acid in the same manner as in Example 1(b) to obtain an ester compound. Using the obtained ester compound, reactions were carried out in the same manner as in Examples 1(c)-2 and 1(d), so as to obtain the title compound in the form of a solid.

1H NMR (400 MHz, DMSO-d6): δ (ppm)=10.1 (1H, brs), 7.71 (2H, d, J=8.6 Hz), 7.37 (1H, d, J=2.0 Hz), 7.33 (1H, brs), 6.86 (2H, d, J=8.6 Hz), 5.57-5.44 (1H, m), 4.03 (2H, q, J=7.0 Hz), 3.94 (2H, q, J=7.2 Hz), 3.55-3.43 (2H, m), 1.31 (3H, t, J=7.2 Hz), 1.18 (3H, t, J=7.2 Hz).

MS 438 (M+H)+.

Example 38

4-{3-[(4-Hydroxyphenyl)-4-methylisoxazol-5-yl]propanoyl}amino-1-ethylpyrrole-3-carboxylic acid

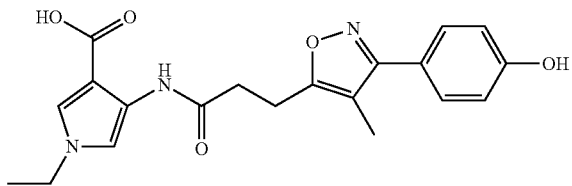 [SMILES: CCn1cc(NC(=O)CCc2onc(-c3ccc(O)cc3)c2C)c(C(=O)O)c1]

(a) [3-(4-Benzyloxyphenyl)-4-methylisoxazol-5-yl]methanol

4-Benzyloxybenzaldehyde (5.0 g, 23.6 mmol) was dissolved in a mixture of ethanol (40 mL) and THF (10 mL), and sodium bicarbonate (2.4 g, 28.3 mmol) was then added to the solution. While stirring the mixture at room temperature, an aqueous solution (25 mL) of hydroxylamine hydrochloride (1.86 g, 25.9 mmol) was added thereto. The obtained mixture was stirred for 1.5 hours. The reaction solution was concentrated under reduced pressure, and water was then added to the residue, followed by extraction three times with ethyl acetate. The organic layer was washed with a saturated saline, and it was then dried over anhydrous sodium sulfate, followed by concentration under reduced pressure. The residue was dissolved in dimethylformamide (40 mL), and N-chlorosuccinimide (3.15 g, 23.6 mmol) was then added to the solution. The obtained mixture was stirred at room temperature overnight. Thereafter, water was added to the reaction solution, and it was then extracted with ethyl acetate three times. The organic layer was washed with a saturated saline, and it was then dried over anhydrous sodium sulfate, followed by concentration under reduced pressure. The residue was purified with a fractionation purification apparatus (Biotage, ethyl acetate:hexane=2:98-3:7). The obtained compound (3.0 g, 11.5 mmol) was dissolved in dichloroethane (30 mL), and 2-butyn-1-ol (2.6 mL, 34.4 mmol) and triethylamine (1.9 mL, 13.8 mmol) were then added to the solution. The obtained mixture was stirred at 90° C. for 4 hours. Thereafter, the reaction solution was concentrated under reduced pressure, and the residue was then purified with a fractionation purification apparatus (Biotage, ethyl acetate:hexane=1:4-4:1), so as to obtain the title compound (0.88 g, 26%) in the form of an isometric mixture.

MS m/z: 296 (M+H)$^+$.

(b) 3-(4-Benzyloxyphenyl)-5-bromomethyl-4-methylisoxazole

A reaction was carried out in the same manner as in Example 22(c) using the compound obtained in Example 38(a), so as to obtain an isometric mixture of the title compound in the form of a colorless solid.

(c) Methyl 3-[3-(4-benzyloxyphenyl)-4-methylisoxazol-5-yl]propionate

A reaction was carried out in the same manner as in Example 33(b) using the compound obtained in Example 38(b), so as to obtain the title compound in the form of a colorless oily product.

(d) 1-Ethyl-4-{3-[3-(4-hydroxyphenyl)-4-methylisoxazol-5-yl]propanoyl}aminopyrrole-3-carboxylic acid ethyl ester The compound (200 mg, 0.57 mmol) obtained in Example 38(c) was dissolved in a mixture of methanol (3 mL) and THF (3 mL), and a 5 N-sodium hydroxide aqueous solution (0.34 mL) was then added to the solution. The obtained mixture was stirred at room temperature for 1.5 hours. Thereafter, concentrated hydrochloric acid (0.14 mL) was added to the reaction solution, and the mixture was then concentrated under reduced pressure. The residue was suspended in dimethylformamide (3 mL), and the compound (124 mg, 0.57 mmol)) obtained in Example 12(b), HATU (238 mg, 0.63 mmol) and diisopropylethylamine (0.20 mL, 1.14 mmol) were then added to the suspension. The obtained mixture was stirred at room temperature overnight. Thereafter, sodium bicarbonate aqueous solution was added to the reaction solution, and the mixture was then extracted with ethyl acetate three times. The organic layer was washed with a saturated saline, and it was then dried over anhydrous sodium sulfate, followed by concentration under reduced pressure. The residue was purified with a fractionation purification apparatus (ethyl acetate:hexane=1:4-1:1). The obtained compound was dissolved in a mixture of ethanol (5 mL) and THF (5 mL), and 20% palladium hydroxide (53 mg) was then added to the solution. The obtained mixture was stirred under a hydrogen atmosphere at room temperature for 2 hours. Thereafter, the catalyst was removed by filtration, and the filtrate was then concentrated under reduced pressure. The residue was purified with a fractionation purification apparatus (Biotage, ethyl acetate:hexane=3:7-7:3), and was then purified by thin-layer chromatography for separation (diisopropyl ether:ethyl acetate=1:4), so as to obtain the title compound (52 mg, 24%) in the form of a colorless oily product.

$^1$H NMR (400 MHz, CDCl$_3$): δ (ppm)=9.38 (1H, brs), 7.54 (2H, d, J=8.8 Hz), 7.43 (1H, d, J=2.4 Hz), 7.11 (1H, d, J=2.4 Hz), 6.92 (2H, d, J=8.8 Hz), 4.31 (2H, q, J=7.3 Hz), 3.91 (2H, q, J=7.4 Hz), 3.18 (2H, t. J=7.3 Hz), 2.85 (2H, t, J=7.3 Hz), 2.09 (3H, s), 1.46 (3H, t, J=7.3 Hz), 1.37 (3H, t, J=7.3 Hz).

(e) 4-{3-[(4-Hydroxyphenyl)-4-methylisoxazol-5-yl]propanoyl}amino-1-ethylpyrrole-3-carboxylic acid A reaction was carried out in the same manner as in Example 1(c)-2 using the compound obtained in Example 38(d), so as to obtain the title compound in the form of a colorless solid.

$^1$H NMR (400 MHz, DMSO-d$_6$): δ (ppm)=12.2 (1H, brs), 9.79 (1H, brs), 9.34 (1H, brs), 7.44 (2H, d, J=8.6 Hz), 7.29 (1H, d, J=2.4 Hz), 7.27 (1H, d, J=2.4 Hz), 6.85 (2H, d, J=8.6 Hz), 3.89 (2H, q, J=7.0 Hz), 3.02 (2H, t, J=7.4 Hz), 2.74 (2H, t, J=7.4 Hz), 2.02 (3H, s), 1.28 (3H, t, J=7.0 Hz).

MS m/z: 382 (M−H)$^-$.

Example 39

4-{3-[2-(4-Hydroxyphenyl)thiazol-5-yl]-2,2-difluoropropanoyl}amino-1-ethylpyrrole-3-carboxylic acid

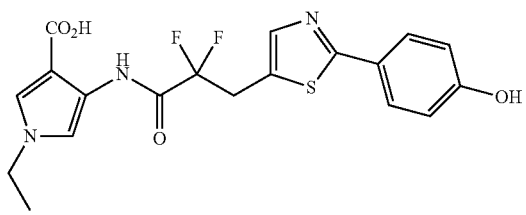 [SMILES: CCn1cc(NC(=O)C(F)(F)Cc2cnc(-c3ccc(O)cc3)s2)c(C(=O)O)c1]

(a) 3-[2-(4-Methoxyphenyl)thiazol-5-yl]-2,2-difluoropropionic acid

Copper powder (447 mg, 7.04 mmol) was suspended in DMSO (8 mL), and a solution of ethyl iododifluoroacetate in DMSO (2 mL) was then added to the suspension. The obtained mixture was stirred at room temperature for 30 minutes. Thereafter, the bromo compound (500.0 mg, 1.76 mmol) obtained in Example 22(c) was further added to the reaction solution, and the obtained mixture was stirred for 15 minutes. Thereafter, water was added to the reaction solution, and it was then extracted with ethyl acetate. The resultant was washed with a saturated saline, and it was then dried over anhydrous sodium sulfate, followed by concentration. The obtained residue was purified by silica gel column chromatography (hexane/ethyl acetate) to obtain a difluoroester compound (339.3 mg, yield: 59%) in the form of a yellow oily substance.

A 1 M-sodium hydroxide aqueous solution was added to a solution of the obtained difluoroester compound (339.3 mg, 1.04 mmol) in ethanol (6 mL), and the obtained mixture was then stirred at room temperature for 15 minutes. Thereafter, the reaction solution was made acidic by addition of 5 M-hydrochloric acid, and it was then extracted with ethyl acetate twice. The combined organic layer was washed with a saturated saline, and it was then dried over anhydrous sodium sulfate, followed by concentration, so as to obtain the title compound (310.2 mg, yield: 100%) in the form of a pale yellow solid.

$^1$H NMR (400 MHz, CDCl$_3$): δ (ppm)=7.78 (2H, d, J=9.0 Hz), 7.64 (1H, s), 6.97 (2H, d, J=9.0 Hz), 3.86 (3H, s), 3.65 (2H, t, J=13.3 Hz).

(b) 4-{3-[2-(4-Hydroxyphenyl)thiazol-5-yl]-2,2-difluoropropanoyl}amino-1-ethylpyrrole-3-carboxylic acid Reactions were carried out in the same manner as in Examples 22(e) and 22(f) using the compound obtained in Example 30(a), so as to obtain the title compound in the form of a pale yellow powder.

$^1$H NMR (400 MHz, DMSO-d$_6$): δ (ppm)=10.32 (1H, br.s), 7.72 (2H, d, J=8.6 Hz), 7.68 (1H, s), 7.40 (2H, s), 6.85 (2H, d, J=8.6 Hz), 3.96 (2H, q, J=7.0 Hz), 3.89 (2H, t, J=17.2 Hz), 1.32 (3H, t, J=7.0 Hz).

MS m/z: 422 (M+H)$^+$.

Example 40

4-{3-[4-Ethyl-3-(4-hydroxyphenyl)isoxazol-5-yl]-2,2-difluoropropanoyl}amino-1-ethylpyrrole-3-carboxylic acid

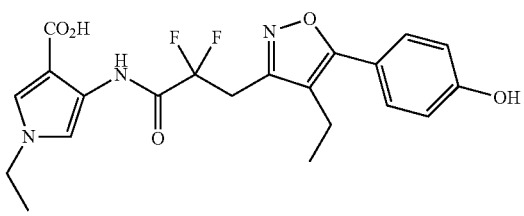 [SMILES: CCc1c(CC(F)(F)C(=O)Nc2cn(CC)cc2C(=O)O)noc1-c1ccc(O)cc1]

(a) 4-Vinyl-3-(4-benzyloxyphenyl)isoxazol-5-carbaldehyde

N-Bromosuccinimide (1.99 g, 11.20 mmol) was added to a solution of the compound (3.00 g, 8.61 mmol) obtained in Example 32(a)-1 in DMF (30 mL), and the obtained mixture was then stirred at room temperature for 8 hours. Thereafter, water (30 mL) was added to the reaction solution, and the precipitated crude crystals were collected by filtration to obtain a bromo isoxazole compound (3.46 g, yield: 100%) in the form of a colorless powder.

Tributyl(vinyl)tin (2.66 mL, 9.10 mmol) and tetrakistriphenylphosphine palladium (0.26 g, 0.23 mmol) were added to a solution of the obtained bromo isoxazole compound (3.05 g, 7.58 mmol) in toluene (40 mL). The obtained mixture was stirred at 110° C. for 5.5 hours. Thereafter, an aqueous solution (20 mL) of potassium fluoride dihydrate (3.43 g, 36.40 mmol) was added to the reaction solution, and the obtained mixture was then stirred at room temperature for 1 hour, and then the two layers were separated. The organic layer was washed with water, and it was filtered with celite, followed by concentration. The residue was purified by silica gel column chromatography (hexane/ethyl acetate) to obtain a vinyl isoxazole compound (1.75 g, yield: 45%).

10% Palladium hydroxide-carbon (200.0 mg) was added to a solution of the obtained vinyl isoxazole compound (1.75 g, 5.01 mmol) in ethanol (35 mL), and the obtained mixture was then stirred under a hydrogen atmosphere at room temperature for 2 hours. The reaction solution was filtered with celite, and it was then concentrated. Potassium carbonate (415.4 mg, 3.01 mmol) and benzyl bromide (238 μL, 2.00 mmol) were added to a solution of the residue in acetone (35 mL), and the obtained mixture was then stirred at 60° C. for 3.5 hours. The reaction solution was filtered with celite, and it was then concentrated. The residue was purified by silica gel column chromatography (hexane/ethyl acetate) to obtain an ethyl isoxazole compound (1.27 g, yield: 72%).

Lithium aluminum hydride (137.6 mg, 3.61 mmol) was added at 0° C. to a solution of the obtained ethyl isoxazole compound (1.27 g, 3.61 mmol) in THF (25 mL). The temperature of the obtained mixture was raised to room temperature, and the mixture was then stirred for 15 minutes. Thereafter, water (0.14 mL), a 3 M-sodium hydroxide aqueous solution (0.14 mL), and water (0.42 mL) were successively added to the reaction solution at 0° C., and the obtained mixture was then stirred for 30 minutes. Thereafter, the reaction mixture was filtered with celite, and the filtrate was then concentrated. The residue was purified by silica gel column chromatography (hexane/ethyl acetate) to obtain an alcohol compound (1.05 g, yield: 94%).

Manganese dioxide (843.1 mg, 9.70 mmol) was added to a solution of the obtained alcohol compound (500 mg, 1.62 mmol) in dichloromethane (10 mL), and the obtained mixture was then stirred at room temperature for 18 hours. The reaction solution was filtered with celite, followed by concentration, so as to obtain the title compound (475.3 mg, yield: 96%).

$^1$H NMR (400 MHz, CDCl$_3$): δ (ppm)=10.24 (1H, s), 7.65 (2H, d, J=9.0 Hz), 7.46-7.54 (5H, m), 7.10 (2H, d, J=9.0 Hz), 5.15 (2H, s), 2.85 (2H, q, J=7.4 Hz), 1.25 (3h, t, J=7.4 Hz).

(b) 3-[4-Vinyl-3-(4-benzyloxyphenyl)isoxazol-5-yl]-2,2-difluoropropionic acid

Zinc powder (225.2 mg, 3.44 mmol) was suspended in THF (7 mL), and 1,2-dibromoethane (10 μL) and ethyl bromodifluoroacetate were then added to the suspension. The obtained mixture was stirred at 60° C. for 15 minutes. A solution of the compound obtained in Example 40(a) in THF (5 mL) was added to the reaction solution, and the obtained mixture was then stirred at 60° C. for 1.5 hours. The reaction solution was poured into a potassium hydrogensulfate aqueous solution, and it was then extracted with ethyl acetate twice. The combined organic layer was washed with a saturated saline, and it was dried over anhydrous sodium sulfate, followed by concentration. The residue was purified by silica gel column chromatography (hexane/ethyl acetate) to obtain an alcohol compound (244.2 mg, yield: 49%) in the form of a colorless oily substance.

Carbon disulfide (292.1 μL, 5.66 mmol) and DBU (338 μL, 2.26 mmol) were added to a solution of the obtained alcohol compound (244.0 mg, 0.57 mmol) in DMF (4 mL), and the obtained mixture was then stirred at room temperature for 30 minutes. Subsequently, methyl iodide (352 μL, 5.66 mmol) was added to the reaction solution, and the obtained mixture was then stirred for 15 minutes. Thereafter, the reaction solution was poured into water, and it was then extracted with ethyl acetate twice. The combined organic layer was washed with a saturated saline, and it was then dried over anhydrous sodium sulfate, followed by concentration. The residue was purified by silica gel column chromatography (hexane/ethyl acetate) to obtain a xanthate compound (244.2 mg, yield: 83%) in the form of a yellow oily substance.

Tributyl(vinyl)tin hydride (138 μL, 0.51 mmol) and azobisisobutyronitrile (7.7 mg, 0.05 mmol) were added to a solution of the obtained xanthate compound (244.2 mg, 0.47 mmol) in benzene (2.5 mL), and the obtained mixture was then stirred at 70° C. for 2 hours. The reaction solution was concentrated, and the residue was then purified by silica gel column chromatography (hexane/ethyl acetate) to obtain a difluoroester compound (140.0 mg, yield: 72%) in the form of a colorless solid.

The obtained difluoroester compound (156.0 mg, 0.38 mmol) was dissolved in a mixture of ethanol (2 mL) and THF (0.5 mL), and a 1 M-sodium hydroxide aqueous solution (570 μL, 0.57 mmol) was then added to the solution at 0° C. The obtained mixture was stirred for 5 minutes. Thereafter, the reaction solution was made acidic by addition of 5 M-hydrochloric acid, and it was then extracted with ethyl acetate, washed with a saturated saline, and then dried over anhydrous sodium sulfate, followed by concentration, so as to obtain the title compound (142.1 mg, 98%) in the form of a colorless solid.

$^1$H NMR (400 MHz, CDCl$_3$): δ (ppm)=7.65 (2H, d, J=9.0 Hz), 7.46-7.36 (5H, m), 7.08 (2H, d, J=8.6 Hz), 5.13 (2H, s), 3.61 (2H, t, J=14.2 Hz), 2.67 (2H, q, J=7.4 Hz), 1.22 (3H, t, J=7.6 Hz).

(c) 4-{3-[4-Ethyl-3-(4-hydroxyphenyl)isoxazol-5-yl]-2,2-difluoropropanoyl}amino-1-ethylpyrrole-3-carboxylic acid HATU (179.6 mg, 0.47 mmol) and triethylamine (152 μL, 1.09 mmol) were added at 0° C. to a solution of the compound (140.7 mg, 0.36 mmol) obtained in Example 40(b) and the compound (102.0 mg, 0.36 mmol) obtained in Example 25(a) in DMF (3 mL). The temperature of the obtained mixture was raised to room temperature, and the mixture was then stirred for 1 hour. Thereafter, water was added to the reaction solution, and it was then extracted with ethyl acetate twice. The combined organic layer was washed with a saturated saline, and it was then dried over anhydrous sodium sulfate, followed by concentration. The obtained residue was purified by silica gel column chromatography (hexane/ethyl acetate) to obtain an amide compound (141.1 mg, yield: 63%) in the form of a pale yellow syrupy substance.

The obtained amide compound (141.1 mg, 0.23 mmol) was dissolved in a mixture of ethanol (2 mL) and THF (1 mL), and 20% palladium hydroxide-carbon (14.0 mg) was then added to the solution. The obtained mixture was stirred under a hydrogen atmosphere at room temperature for 3 hours. Thereafter, the reaction solution was filtered with celite and Empore (registered trademark), and it was then concentrated. The obtained crude crystals were washed with acetonitrile, so as to obtain the title compound (68.5 mg, yield: 69%) in the form of a colorless powder.

$^1$H NMR (400 MHz, DMSO-d$_6$): δ (ppm)=12.6 (1H, brs), 10.4 (1H, brs), 10.0 (1H, s), 7.53 (2H, d, J=8.6 Hz), 7.42 (1H, d, J=2.3 Hz), 7.40 (1H, d, J=2.4 Hz), 6.93 (2H, d, J=8.6 Hz), 3.97 (2H, q, J=7.4 Hz), 3.71 (2H, t, J=17.0 Hz), 2.60 (2H, q, J=7.9 Hz), 1.32 (3H, t, J=7.2 Hz), 1.11 (3H, t, J=7.2 Hz).

MS m/z: 432 (M+H)$^+$.

Example 41

4-{3-[4-Ethyl-5-(4-hydroxyphenyl)isoxazol-3-yl]-2,2-difluoropropanoyl}amino-1-ethylpyrrole-3-carboxylic acid

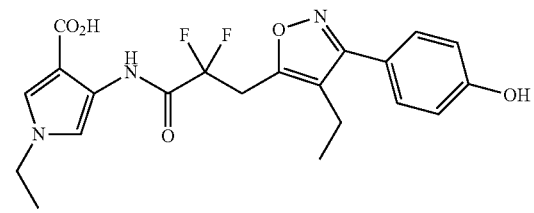 [SMILES: CCc1c(-c2ccc(O)cc2)noc1CC(F)(F)C(=O)Nc1cn(CC)cc1C(=O)O]

(a) 3-Hydroxymethyl-5-(4-benzyloxyphenyl)isoxazole

An aqueous solution (50 mL) of sodium carbonate (4.75 g, 56.54 mmol) and hydroxylamine hydrochloride (3.71 g, 51.83 mmol) was added to a solution of p-benzyloxy benzaldehyde (10.00 g, 41.12 mmol) in ethanol (100 mL). The obtained mixture was stirred at room temperature for 1 hour.

Thereafter, the solvent was distilled away, water was then added to the residue, and crude crystals were then collected by filtration.

A 10% sodium hypochlorite aqueous solution (56 mL, 75.4 mmol) was added at 0° C. to a solution of the obtained crude crystals in dichloromethane (120 mL), and the obtained mixture was then stirred for 1 hour. Thereafter, propargyl alcohol (3.96 g, 50.68 mmol) was added to the reaction solution, and the obtained mixture was then stirred at 55° C. for 2 hours. Thereafter, the solvent was distilled away, water was then added to the residue, and crude crystals were then collected by filtration. The obtained crude crystals were dissolved in ethyl acetate, and insoluble materials were removed by filtration. The obtained filtrate was concentrated to obtain crude crystals. The obtained crude crystals were recrystallized with ethyl acetate to obtain an isoxazole compound (6.43 g, yield in two steps: 49%) in the form of a colorless powder.

$^1$H NMR (400 MHz, CDCl$_3$): δ (ppm)=7.75 (2H, d, J=9.0 Hz), 7.47-7.33 (5H, m), 7.06 (2H, d, J=9.0 Hz), 6.52 (1H, s), 5.13 (2H, s), 4.82 (2H, d, J=5.8 Hz), 1.97 (1H, t, J=5.8 Hz).

(b) 4-Ethyl-5-(4-benzyloxyphenyl)isoxazol-3-carbaldehyde (b)-1

N-Bromosuccinimide (2.82 g, 15.84 mmol) was added to a solution of the isoxazole compound (3.00 g, 13.20 mmol) obtained in Example 40(a) in DMF (30 mL), and the obtained mixture was then stirred at 60° C. for 2 hours. Thereafter, water was added to the reaction solution, and it was then extracted with a mixture of ethyl acetate and toluene twice, washed with water and a saturated saline, and then dried over anhydrous sodium sulfate, followed by concentration. The residue was purified by silica gel column chromatography (hexane/ethyl acetate) to obtain a bromo compound (3.02 g, yield: 81%) in the form of a pale yellow oily substance.

Vinyl boronic acid pinacol ester (1.90 g, 12.37 mmol), tetrakistriphenylphosphine palladium (0.19 g, 0.16 mmol), and a 2 M-sodium carbonate aqueous solution (12 mL, 24.0 mmol) were added a solution of the obtained bromo compound (2.97 g, 8.25 mmol) in DMA (40 mL). The obtained mixture was stirred at 130° C. for 2 hours. Thereafter, water was added to the reaction solution, and it was then extracted with a mixture of ethyl acetate and toluene twice, washed with water and a saturated saline, and then dried over anhydrous sodium sulfate, followed by concentration. The residue was purified by silica gel column chromatography (hexane/ethyl acetate) to obtain a vinyl isoxazole compound (1.93 g, yield: 76%) in the form of a colorless solid.

10% Palladium-carbon (0.13 g) was added to a solution of the obtained vinyl isoxazole compound (1.80 g, 5.86 mmol) in ethyl acetate (40 mL), and the obtained mixture was then stirred under a hydrogen atmosphere at room temperature for 30 minutes. The reaction solution was filtered with celite, and the filtrate was then concentrated. The residue was purified by silica gel column chromatography (hexane/ethyl acetate) to obtain an ethyl isoxazole compound (1.59 g, yield: 82%) in the form of a colorless solid.

(b)-2

Manganese dioxide (1.29 g, 14.84 mmol) was added to a solution of the ethyl isoxazole compound (570.0 mg, 1.85 mmol) obtained in Example 41(b)-1 in dichloromethane (12 mL), and the obtained mixture was then stirred at room temperature for 4.5 hours. The reaction solution was filtered with celite, and the filtrate was then concentrated. The residue was purified by silica gel column chromatography (hexane/ethyl acetate) to obtain an aldehyde compound (387.0 mg, yield: 68%) in the form of a colorless solid.

$^1$H NMR (400 MHz, CDCl$_3$): δ (ppm)=10.1 (1H, s), 7.59 (2H, d, J=9.0 Hz), 7.47-7.34 (5H, m), 7.11 (2H, d, J=9.0 Hz), 5.14 (2H, s), 2.88 (2H, q, J=7.6 Hz), 1.20 (3H, t, J=7.6 Hz).

(c) 3-[4-Ethyl-5-(4-hydroxyphenyl)isoxazol-3-yl]-2,2-difluoropropionic acid

A reaction was carried out in the same manner as in Example 40(b) using the compound obtained in Example 41(b) to obtain a carboxylic acid compound in the form of a colorless solid.

$^1$H NMR (500 MHz, CDCl$_3$): δ (ppm)=7.58 (2H, d, J=8.8 Hz), 7.46-7.33 (5H, m), 7.08 (2H, d, J=8.8 Hz), 5.12 (2H, s), 4.12 (2H, q, J=7.4 Hz), 3.64 (2H, t, J=14.2 Hz), 2.58 (2H, q, J=7.4 Hz), 1.26 (3H, t, J=7.4 Hz), 1.09 (3H, t, J=7.4 Hz).

(d) 4-{3-[4-ethyl-5-(4-hydroxyphenyl)isoxazol-3-yl]-2,2-difluoropropanoyl}amino-1-ethylpyrrole-3-carboxylic acid A reaction was carried out in the same manner as in Example 40(c) using the compound obtained in Example 41(c) to obtain the title compound in the form of a colorless powder.

$^1$H NMR (400 MHz, DMSO-d$_6$): δ (ppm)=12.6 (1H, brs), 10.3 (1H, brs), 9.86 (1H, s), 7.45 (2H, d, J=8.7 Hz), 7.42 (1H, d, J=2.3 Hz), 7.41 (1H, d, J=2.3 Hz), 6.89 (2H, d, J=8.7 Hz), 3.97 (2H, q, J=7.4 Hz), 3.88 (2H, t, J=17.4 Hz), 2.55 (2H, q, J=7.4 Hz), 1.32 (3H, t, J=7.4 Hz), 0.95 (3H, t, J=7.4 Hz).

MS m/z: 432 (M+H)$^+$.

Example 42

4-{3-[4-Chloro-5-(4-hydroxyphenyl)isoxazol-3-yl]-2,2-difluoropropanoyl}amino-1-ethylpyrrole-3-carboxylic acid

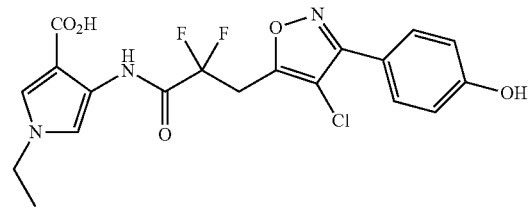 [SMILES: CCn1cc(NC(=O)C(F)(F)Cc2onc(-c3ccc(O)cc3)c2Cl)c(C(=O)O)c1]

(a) 4-Chloro-3-bromomethyl-5-(4-methoxyphenyl)isoxazole

A reaction was carried out in the same manner as in Example 41(a) using p-anisaldehyde to obtain an isoxazole compound (2.50 g, 8.89 mmol). To a solution of the thus obtained isoxazole compound in DMF (25 mL), N-chlorosuccinimide was added, and the obtained mixture was then stirred at 60° C. for 2 hours. Thereafter, water was added to the reaction solution, and it was then extracted with a mixture of ethyl acetate and toluene twice, washed with water and a saturated saline, and then dried over anhydrous sodium sulfate, followed by concentration. The residue was purified by silica gel column chromatography (hexane/ethyl acetate) to obtain a chloroisoxazole compound (1.44 g, yield: 51%) in the form of a pale yellow syrupy substance.

Carbon tetrabromide (2.39 g, 7.21 mmol) and triphenylphosphine (1.73 g, 6.61 mmol) were added to a solution of the obtained chloroisoxazole compound (1.44 g, 6.01 mmol) in dichloromethane (20 mL) at room temperature. The obtained mixture was stirred for 30 minutes. Thereafter, the solvent was distilled away, and the residue was then purified by silica gel column chromatography (hexane/ethyl acetate), so as to obtain the title compound (0.75 g, yield: 41%) in the form of a colorless solid.
$^1$H NMR (400 MHz, CDCl$_3$): δ (ppm)=7.85 (2H, d, J=9.0 Hz), 7.02 (2H, d, J=9.0 Hz), 4.53 (2H, s), 3.88 (3H, s).

(b) 3-[4-Chloro-5-(4-methoxyphenyl)isoxazol-3-yl]-2,2-difluoropropionic acid

A reaction was carried out in the same manner as in Example 39(a) using the compound obtained in Example 42(a) to obtain the title compound in the form of a colorless syrupy substance.
$^1$H NMR (400 MHz, CDCl$_3$): δ (ppm)=7.84 (2H, d, J=9.0 Hz), 7.02 (2H, d, J=9.0 Hz), 3.88 (3H, s), 3.73 (2H, t, J=14.6 Hz).

(c) 4-{3-[4-Chloro-5-(4-hydroxyphenyl)isoxazol-3-yl]-2,2-difluoropropanoyl}amino-1-ethylpyrrole-3-carboxylic acid Reactions were carried out in the same manner as in Examples 22(e) and 22(f) using the compound obtained in Example 42(b), so as to obtain the title compound in the form of a pale yellow powder.
$^1$H NMR (400 MHz, CDCl$_3$): δ (ppm)=12.6 (1H, brs), 10.4 (1H, brs), 10.1 (1H, s), 7.67 (2H, d, J=8.6 Hz), 7.43 (1H, d, J=2.3 Hz), 7.41 (1H, d, J=2.3 Hz), 6.94 (2H, d, J=8.6 Hz), 4.00 (2H, t, J=17.4 Hz), 3.97 (2H, q, J=7.2 Hz), 1.33 (3H, t, J=7.2 Hz).
MS m/z: 432 (M+H)$^+$.

Example 43

4-{3-[4-Chloro-3-(4-hydroxy-2-fluorophenyl)isoxazol-5-yl]propanoyl}amino-1-ethylpyrrole-3-carboxylic acid

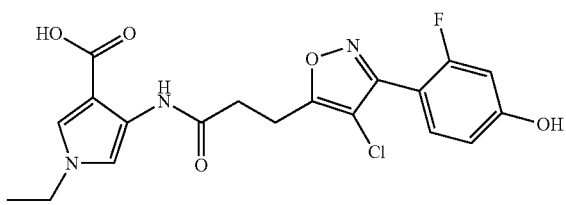 [SMILES: CCn1cc(NC(=O)CCc2onc(-c3ccc(O)cc3F)c2Cl)c(C(=O)O)c1]

(a) 3-[4-Chloro-3-(4-methoxy-2-fluorophenyl)isoxazol-5-yl]propionic acid

Reactions were carried out in the same manner as in Examples 33(a) to (d) and 33(e)-1 using 4-methoxy-2-fluorobenzaldehyde, so as to obtain the title compound.
$^1$H NMR (400 MHz, CDCl$_3$): δ (ppm)=7.49 (1H, t, J=8.2 Hz), 6.82 (1H, dd, J=8.6, 2.8 Hz), 6.77 (1H, dd, J=12.0, 2.5 Hz), 3.87 (3H, s), 3.19 (2H, t, J=7.6 Hz), 2.89 (2H, t, J=7.6 Hz).

(b) 4-{3-[4-Chloro-3-(4-hydroxy-2-fluorophenyl)isoxazol-5-yl]propanoyl}amino-1-ethylpyrrole-3-carboxylic acid Reactions were carried out in the same manner as in Examples 33(e)-2 and 33(f) using the compound obtained in Example 43(a), so as to obtain the title compound in the form of a powder.
$^1$H NMR (400 MHz, DMSO-d$_6$): δ (ppm)=12.2 (1H, brs), 10.5 (1H, s), 9.40 (1H, s), 7.39 (1H, t, J=8.6 Hz), 7.32 (1H, d, J=2.3 Hz), 7.30 (1H, d, J=2.3 Hz), 6.79-6.75 (2H, m), 3.91 (2H, q, J=7.3 Hz), 3.14 (2H, t, J=7.2 Hz), 2.88 (2H, t, J=7.2 Hz), 1.30 (3H, t, J=7.2 Hz).
MS m/z: 422 (M+H)$^+$.

Example 44

4-{3-[3-(4-Hydroxyphenyl)isoxazol-5-yl]propanoyl}amino-1-ethylpyrrole-3-carboxylic acid

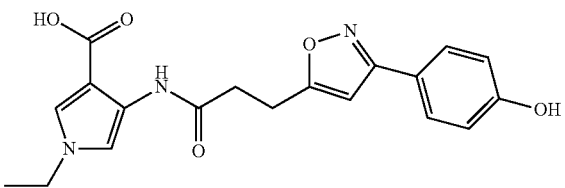 [SMILES: CCn1cc(NC(=O)CCc2cc(-c3ccc(O)cc3)no2)c(C(=O)O)c1]

Reactions were carried out in the same manner as in Examples 33(e) and 33(f) using the compound obtained in Example 33(c), so as to obtain the title compound in the form of a powder.
$^1$H NMR (400 MHz, DMSO-d$_6$): δ (ppm)=12.2 (1H, brs), 9.87 (1H, s), 9.40 (1H, s), 7.64 (2H, d, J=8.6 Hz), 7.32 (1H, d, J=2.4 Hz), 7.30 (1H, d, J=2.4 Hz), 6.86 (2H, d, J=8.6 Hz), 6.71 (1H, s), 3.91 (2H, q, J=7.3 Hz), 3.06 (2H, t, J=7.2 Hz), 2.83 (2H, t, J=7.2 Hz), 1.30 (3H, t, J=7.2 Hz).
MS m/z: 370 (M+H)$^+$.

Example 45

4-{3-[4-Ethyl-3-(4-hydroxy-2-fluorophenyl)isoxazol-5-yl]propanoyl}amino-1-ethylpyrrole-3-carboxylic acid

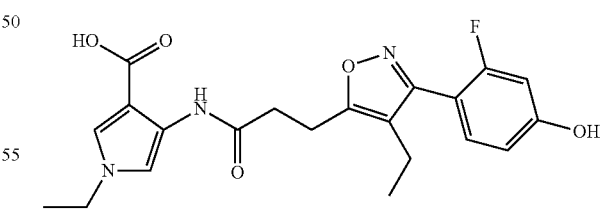

(a) 3-[4-Ethyl-3-(4-methoxy-2-fluorophenyl)isoxazol-5-yl]propionic acid

Reactions were carried out in the same manner as in Examples 33(a) to (c) and 8(a) using 4-methoxy-2-fluorobenzaldehyde. Using the obtained compound, a reaction was carried out in the same manner as in Example 33(e)-1, so as to obtain the title compound.

¹H NMR (400 MHz, CDCl₃): δ (ppm)=7.40 (1H, t, J=8.4 Hz), 6.80 (1H, dd, J=8.6, 2.3 Hz), 6.73 (1H, dd, J=11.8, 2.3 Hz), 6.40-6.33 (1H, m), 5.28 (1H, d, J=5.5 Hz), 5.27 (1H, d, J=12.5 Hz), 3.86 (3H, s), 3.21 (2H, t, J=7.6 Hz), 2.86 (2H, t, J=7.6 Hz).

(b) 4-{3-[4-Ethyl-3-(4-hydroxy-2-fluorophenyl)isoxazol-5-yl]propanoyl}amino-1-ethylpyrrole-3-carboxylic acid Reactions were carried out in the same manner as in Examples 33(e)-2 and 33(f) using the compound obtained in Example 45(a), so as to obtain the title compound in the form of a powder.

¹H NMR (400 MHz, DMSO-d₆): δ (ppm)=12.2 (1H, brs), 10.3 (1H, s), 9.37 (1H, s), 7.32 (1H, d, J=2.3 Hz), 7.30 (1H, d, J=2.3 Hz), 7.27 (1H, t, J=8.8 Hz), 6.75-6.71 (2H, m), 3.92 (2H, q, J=7.3 Hz), 3.07 (2H, t, J=7.4 Hz), 2.78 (2H, t, J=7.4 Hz), 2.35 (2H, q, J=7.6 Hz), 1.30 (3H, t, J=7.2 Hz), 0.91 (3H, t, J=7.6 Hz).

MS m/z: 416 (M+H)⁺.

Example 46

4-{3-[4-Chloro-5-(4-hydroxyphenyl)isoxazol-3-yl]-2-fluoropropanoyl}amino-1-ethylpyrrole-3-carboxylic acid

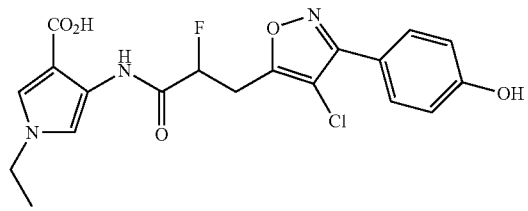 [SMILES: CCn1cc(NC(=O)C(F)Cc2onc(-c3ccc(O)cc3)c2Cl)c(C(=O)O)c1]

(a) 3-[4-Chloro-5-(4-methoxyphenyl)isoxazol-3-yl]-2-fluoropropionic acid

A reaction was carried out in the same manner as in Example 22(d) using the compound obtained in Example 42(a), so as to obtain the title compound.

¹H NMR (500 MHz, CDCl₃): δ (ppm)=7.83 (2H, d, J=8.3 Hz), 7.01 (2H, d, J=8.8 Hz), 5.38 (1H, ddd, J=4.4, 7.3 and 47.9 Hz), 3.87 (3H, s), 3.59-3.46 (2H, m).

(b) 4-{3-[4-Chloro-5-(4-hydroxyphenyl)isoxazol-3-yl]-2-fluoropropanoyl}amino-1-ethylpyrrole-3-carboxylic acid Reactions were carried out in the same manner as in Examples 22(e) and 22(f) using the compound obtained in Example 46(a), so as to obtain the title compound in the form of a pale yellow powder.

¹H NMR (400 MHz, DMSO-d₆): δ (ppm)=12.4 (1H, brs), 10.1 (1H, s), 7.65 (2H, d, J=9.0 Hz), 7.40 (1H, d, J=2.4 Hz), 7.37 (1H, d, J=2.4 Hz), 6.93 (2H, d, J=9.0 Hz), 5.64 (1H, ddd, J=4.3, 7.4 and 47.7 Hz), 3.95 (2H, q, J=7.4 Hz), 3.66-3.47 (2H, m), 1.32 (3H, t, J=7.4 Hz).

MS m/z: 421 (M+H)⁺.

Example 47

4-{3-[3-(4-Hydroxyphenyl)isoxazol-5-yl]propanoyl}amino-1-butylpyrrole-3-carboxylic acid

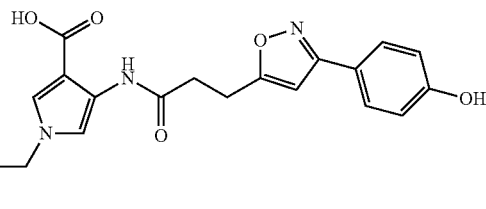

Reactions were carried out in the same manner as in Examples 1(c) and 1(d) using the compound obtained in Example 33(c) and the compound obtained in Example 11(b), so as to obtain the title compound in the form of a powder.

¹H NMR (500 MHz, DMSO-d₆): δ (ppm)=12.2 (1H, brs), 9.85 (1H, s), 9.38 (1H, s), 7.63 (2H, d, J=8.3 Hz), 7.29 (1H, d, J=2.4 Hz), 7.27 (1H, d, J=2.4 Hz), 6.85 (2H, d, J=8.3 Hz), 6.70 (1H, s), 3.87 (2H, t, J=7.1 Hz), 3.06 (2H, t, J=7.4 Hz), 2.83 (2H, t, J=7.4 Hz), 1.68-1.62 (2H, m), 1.23-1.16 (2H, m), 0.87 (3H, t, J=7.3 Hz).

MS m/z: 398 (M+H)⁺.

Example 48

4-{3-[3-(5-Hydroxypyridin-2-yl)-1,2,4-oxadiazol-5-yl]propanoyl}amino-1-isopropylpyrrole-3-carboxylic acid

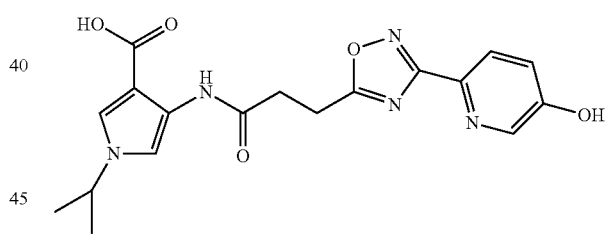

(a) 4-Amino-1-isopropylpyrrole-3-carboxylic acid ethyl ester hydrochloride

Reactions were carried out in the same manner as in Examples 11(a) and 11(b) using isopropylamine, so as to obtain the title compound.

¹H NMR (400 MHz, DMSO-d₆): δ (ppm)=9.90 (2H, brs), 7.61 (1H, d, J=2.4 Hz), 7.10 (1H, s), 4.43-4.36 (1H, m), 4.23 (2H, q, J=7.2 Hz), 1.38 (6H, d, J=6.7 Hz), 1.29 (3H, t, J=7.2 Hz).

(b) 4-{3-[3-(5-Hydroxypyridin-2-yl)-1,2,4-oxadiazol-5-yl]propanoyl}amino-1-isopropylpyrrole-3-carboxylic acid Reactions were carried out in the same manner as in Examples 3(c) and 3(d) using the compound obtained in Example 48(a) and the compound obtained in Example 3(b), so as to obtain the title compound in the form of a powder.

¹H NMR (400 MHz, DMSO-d₆): δ (ppm)=12.3 (1H, brs), 10.6 (1H, s), 9.45 (1H, s), 8.27 (1H, d, J=2.7 Hz), 7.91 (1H, d, J=8.6 Hz), 7.35-7.32 (2H, m), 7.30 (1H, d, J=2.7 Hz), 4.31-4.25 (1H, m), 3.24 (2H, t, J=6.9 Hz), 3.00 (2H, t, J=6.9 Hz), 1.34 (6H, d, J=6.6 Hz).

MS m/z: 384 (M−H)⁻.

Example 49

4-{3-[3-(4-Hydroxyphenyl)-1,2,4-oxadiazol-5-yl]propanoyl}amino-1-benzylpyrrole-3-carboxylic acid

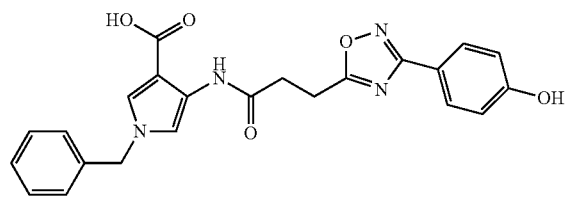 [SMILES: O=C(CCc1nc(-c2ccc(O)cc2)no1)Nc1cn(Cc2ccccc2)cc1C(=O)O]

(a) 4-Amino-1-benzylpyrrole-3-carboxylic acid ethyl ester hydrochloride

Reactions were carried out in the same manner as in Examples 11(a) and 11(b) using benzylamine, so as to obtain the title compound.

¹H NMR (400 MHz, DMSO-d₆): δ (ppm)=9.91 (2H, brs), 7.67 (1H, d, J=2.4 Hz), 7.41-7.30 (5H, m), 7.12 (1H, s), 5.19 (2H, s), 4.22 (2H, q, J=7.0 Hz), 1.28 (3H, t, J=7.0 Hz).

(b) 4-{3-[3-(4-Hydroxyphenyl)-1,2,4-oxadiazol-5-yl]propanoyl}amino-1-benzylpyrrole-3-carboxylic acid A reaction was carried out in the same manner as in Example 12(c) using the compound obtained in Example 49(a) and the compound obtained in Example 12(b), so as to obtain the title compound in the form of a powder.

¹H NMR (400 MHz, DMSO-d₆): δ (ppm)=12.3 (1H, brs), 10.1 (1H, s), 9.44 (1H, s), 7.81 (2H, d, J=9.0 Hz), 7.42 (1H, s), 7.41-7.25 (6H, m), 6.90 (2H, d, J=9.0 Hz), 5.09 (2H, s), 3.20 (2H, t, J=7.0 Hz), 2.96 (2H, t, J=7.0 Hz).

MS m/z: 433 (M+H)⁺.

Example 50

4-{3-[3-(4-Hydroxyphenyl)-1,2,4-oxadiazol-5-yl]propanoyl}amino-1-butyl-2-methylpyrrole-3-carboxylic acid

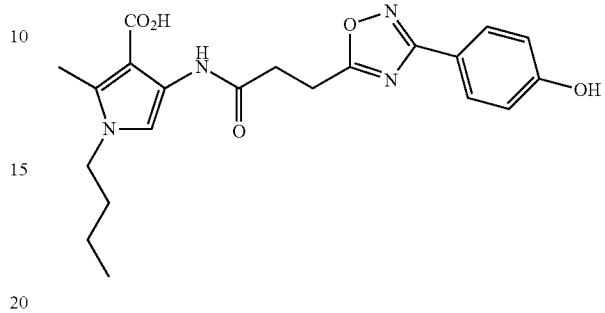

(a) 4-t-Butoxycarbonylamino-2-methylpyrrole-3-carboxylic acid ethyl ester

Triethylamine (8.25 mL, 59.17 mmol) was added to a solution of amino acetonitrile hydrochloride (7.00 g, 53.79 mmol) in ethanol (23 mL), and the obtained mixture was then stirred at room temperature for 10 minutes. Thereafter, ethyl acetoacetate (5.47 g, 59.17 mmol) was added to the reaction solution, and the obtained mixture was then stirred at 70° C. for 1 hour. Thereafter, the solvent was distilled away, and ice water (50 mL) was then added to the reaction solution, followed by stirring at 0° C. The generated precipitate was collected by filtration to obtain an enamine compound (7.35 g, yield: 81%) in the form of a colorless powder.

The obtained enamine compound (7.35 g, 43.7 mmol) was added to a solution of sodium ethoxide in ethanol prepared from sodium metal (1.11 g, 48.1 mmol), and the obtained mixture was then stirred at room temperature for 18 hours. Thereafter, a 4 M-hydrochloric acid-ethyl acetate solution was added to the reaction solution to neutralize it (pH=6), and the solvent was then distilled away. The generated precipitate was collected by filtration to obtain an aminopyrrole compound in the form of a brown solid.

Triethylamine (4.74 mL, 34.0 mmol), Boc2O (7.42 g, 34.0 mmol), and DMAP (3.12 g, 25.5 mmol) were added to a solution of the obtained aminopyrrole compound in dichloromethane (150 mL). The obtained mixture was stirred at room temperature for 4 hours. Thereafter, water was added to the reaction solution, and it was then extracted with ethyl acetate twice, washed with a saturated saline, and then dried over anhydrous sodium sulfate, followed by concentration. The obtained residue was purified by silica gel column chromatography (hexane/ethyl acetate), so as to obtain the title compound (1.84 g, yield in two steps: 20%) in the form of a colorless oily substance.

¹H NMR (400 MHz, CDCl₃): δ (ppm)=8.49 (1H, brs), 7.90 (1H, brs), 7.01 (1H, d, J=1.9 Hz), 4.31 (2H, q, J=7.2 Hz), 2.45 (3H, s), 1.49 (9H, s), 1.37 (3H, t, J=7.2 Hz).

(b) 4-Amino-1-butyl-2-methylpyrrole-3-carboxylic acid ethyl ester hydrochloride

60% Sodium hydride (178.9 mg, 4.47 mmol) was added to a solution of the compound (1.00 g, 3.73 mmol) obtained in Example 50(a) in DMF (10 mL), and the obtained mixture was then stirred at room temperature for 20 minutes. Thereafter, n-butyl iodide (470 μL, 4.10 mmol) was added at 0° C. to the reaction solution, and the temperature of the obtained mixture was raised to room temperature, followed by stirring for 1 hour. Thereafter, water was added to the reaction solution, and it was then extracted with ethyl acetate twice, washed with a saturated saline, and then dried over anhydrous sodium sulfate, followed by concentration. The obtained residue was purified by silica gel column chromatography (hexane/ethyl acetate) to obtain a butylpyrrole compound (0.78 g, yield: 64%) in the form of a colorless oily substance.

A 4 M-hydrochloric acid-ethyl acetate solution was added to the obtained butylpyrrole compound (0.78 g, 2.4 mmol) at room temperature, and the obtained mixture was then left to rest for 6 hours. Thereafter, the solvent was distilled away, so as to obtain the title compound (0.62 g, yield: 100%) in the form of a pale yellow brown powder.

$^1$H NMR (400 MHz, DMSO-$d_6$): δ (ppm)=7.05 (1H, brs), 5.24 (2H, brs), 4.34 (2H, q, J=7.4 Hz), 3.69 (2H, t, J=7.5 Hz), 2.63 (3H, s), 1.71 (2H, m), 1.39-1.32 (5H, m), 0.98 (3H, t, J=7.4 Hz).

(c) 4-{3-[3-(4-Hydroxyphenyl)-1,2,4-oxadiazol-5-yl]propanoyl}amino-1-butyl-2-methylpyrrole-3-carboxylic acid Reactions were carried out in the same manner as in Examples 3(c) and 3(d) using the compound obtained in Example 50(c) and the compound obtained in Example 3(b) to obtain the title compound.

$^1$H NMR (500 MHz, DMSO-$d_6$): δ (ppm)=12.4 (1H, brs), 10.6 (1H, s), 9.61 (1H, s), 8.26 (1H, d, J=3.0 Hz), 7.90 (1H, d, J=8.8 Hz), 7.30 (1H, dd, J=8.8 and 3.0 Hz), 7.18 (1H, s), 3.81 (2H, t, J=7.0 Hz), 3.23 (2H, t, J=7.0 Hz), 2.96 (2H, t, J=7.0 Hz), 1.56 (2H, m), 1.23 (2H, m), 0.86 (3H, t, J=7.3 Hz).

MS m/z: 414 (M+H)$^+$.

Example 51

4-{3-[3-(4-Hydroxyphenyl)-1,2,4-oxadiazol-5-yl]propanoyl}amino-5-cyano-1-butylpyrrole-3-carboxylic acid

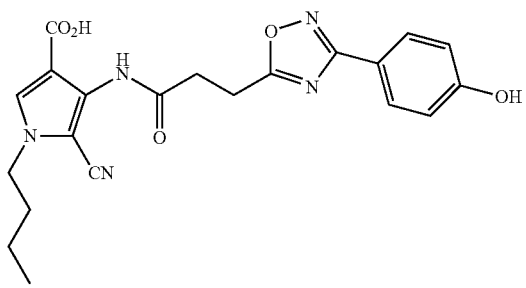 [SMILES: CCCCn1cc(C(=O)O)c(NC(=O)CCc2nc(-c3ccc(O)cc3)no2)c1C#N]

(a) 4-Amino-5-cyano-1-butylpyrrole-3-carboxylic acid ethyl ester hydrochloride

Boc$_2$O (8.84 g, 40.6 mmol) and pyridine (2.46 mL, 30.4 mmol) were added to a solution of the compound (5.00 g, 20.3 mmol) obtained in Example 11(b) in dichloromethane (100 mL), and the obtained mixture was then stirred at room temperature for 1 hour. Thereafter, water was added to the reaction solution, and the mixture was then extracted with dichloromethane twice, washed with a saturated saline, and then dried over anhydrous sodium sulfate, followed by concentration. The obtained residue was purified by silica gel column chromatography (hexane/ethyl acetate) to obtain a Boc-aminopyrrole compound (6.29 g, yield: 100%) in the form of a colorless oily substance.

Chlorosulfonyl isocyanate (28 μL, 0.32 mmol) was added at 0° C. to a solution of the obtained Boc-aminopyrrole compound (100 mg, 0.32 mmol) in acetonitrile (1 mL), and the obtained mixture was then stirred for 2 hours. Thereafter, DMF (51 μL, 0.64 mmol) and triethylamine (90 μL, 0.64 mmol) were added to the reaction solution, and the obtained mixture was then stirred at room temperature for 1 hour. The reaction solution was filtered, and the filtrate was then diluted with ethyl acetate, washed with water, and then concentrated. The residue was purified by silica gel column chromatography (hexane/ethyl acetate) to obtain a cyanoaminopyrrole compound (67.9 mg, yield: 63%) in the form of a pale yellow oily substance.

A 4 M-hydrochloric acid-dioxane solution was added to the obtained cyanoaminopyrrole compound (67.9 mg, 0.20 mmol), and the obtained mixture was left at rest at room temperature for 24 hours. Thereafter, the reaction solution was concentrated, so as to obtain the title compound (54.3 mg, yield: 100%).

$^1$H NMR (400 MHz, CDCl$_3$): δ (ppm)=7.09 (1H, s), 4.85 (2H, brs), 4.28 (2H, q, J=7.1 Hz), 3.87 (2H, t, J=7.0 Hz), 1.79 (2H, m), 1.38-1.28 (5H, m), 0.95 (2H, t, J=7.4 Hz).

(b) 4-{3-[3-(4-Hydroxyphenyl)-1,2,4-oxadiazol-5-yl]propanoyl}amino-5-cyano-1-butylpyrrole-3-carboxylic acid Reactions were carried out in the same manner as in Examples 3-(c) and 3(d) using the compound obtained in Example 51(a) and the carboxylic acid compound obtained in Example 3(b) to obtain the title compound.

$^1$H NMR (400 MHz, DMSO-$d_6$): δ (ppm)=12.7 (1H, brs), 10.6 (1H, brs), 9.97 (1H, brs), 8.28 (1H, d, J=3.0 Hz), 7.92 (1H, d, J=8.6 Hz), 7.75 (1H, s), 7.31 (1H, dd, J=8.6 and 3.0 Hz), 4.03 (2H, t, J=6.8 Hz), 3.25 (2H, t, J=6.9 Hz), 3.00 (2H, t, J=6.9 Hz), 1.70 (2H, m), 1.23 (2H, m), 0.88 (3H, t, J=7.4 Hz).

MS m/z: 425 (M+H)$^+$.

Example 52

4-{3-[3-(4-Hydroxyphenyl)-1,2,4-oxadiazol-5-yl]propanoyl}amino-2-chloro-1-butylpyrrole-3-carboxylic acid

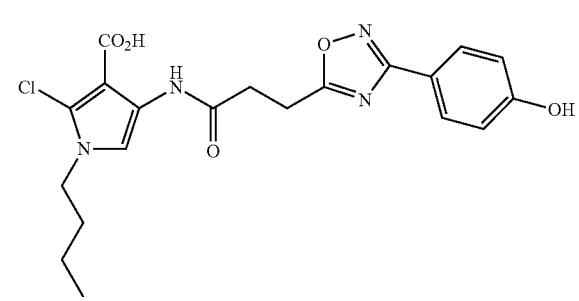 [SMILES: CCCCn1cc(NC(=O)CCc2nc(-c3ccc(O)cc3)no2)c(C(=O)O)c1Cl]

(a) 4-Amino-2-chloro-1-butylpyrrole-3-carboxylic acid ethyl ester hydrochloride N-Chlorosuccinimide (0.47 g, 3.54 mmol) was added at 0° C. to a solution of the compound (1.00 g, 3.22 mmol) obtained in Example 11(b) in carbon tetrachloride (10 mL). The temperature of the obtained mixture was raised to room temperature, and the mixture was then stirred for 1.5 hours. Thereafter, the solvent was distilled away, and the residue was purified by silica gel column chromatography (hexane/ethyl acetate) to obtain a chloroaminopyrrole compound (0.24 g, yield: 22%) in the form of a pale yellow oily substance.

A 4 M-hydrochloric acid-dioxane solution was added to the obtained chloroaminopyrrole compound (190 mg, 0.61 mmol), and the obtained mixture was then left to rest at room temperature for 8 hours. Thereafter, the reaction solution was concentrated to obtain the title compound (172.1 mg, yield: 100%) in the form of a pale violet solid.

$^1$H NMR (400 MHz, MeOH-d4): δ (ppm)=9.79 (2H, brs), 7.15 (1H, s), 4.26 (2H, q, J=7.0 Hz), 4.02 (2H, t, J=7.2 Hz), 1.64 (2H, m), 1.31 (3H, t, J=7.0 Hz), 1.25 (2H, m), 0.89 (3H, t, J=7.4 Hz).

(b) 4-{3-[3-(4-Hydroxyphenyl)-1,2,4-oxadiazol-5-yl]propanoyl}amino-2-chloro-1-butylpyrrole-3-carboxylic acid Reactions were carried out in the same manner as in Examples 3(c) and 3(d) using the compound obtained in Example 51(a) and the compound obtained in Example 3(b) to obtain the title compound.

$^1$H NMR (400 MHz, DMSO-d$_6$): δ (ppm)=10.7 (1H, brs), 9.64 (1H, brs), 8.27 (1H, d, J=3.0 Hz), 7.90 (1H, d, J=8.6 Hz), 7.38 (1H, s), 7.31 (1H, dd, J=8.6 and 3.0 Hz), 3.93 (2H, t, J=7.2 Hz), 3.24 (2H, t, J=7.0 Hz), 2.99 (2H, t, J=7.0 Hz), 1.61 (2H, m), 1.23 (2H, m), 0.86 (3H, t, J=7.5 Hz).

MS m/z: 434 (M+H)$^+$.

Example 53

4-{3-[4-Trifluoromethyl-5-(4-hydroxyphenyl)isoxazol-3-yl]propanoyl}amino-1-ethylpyrrole-3-carboxylic acid

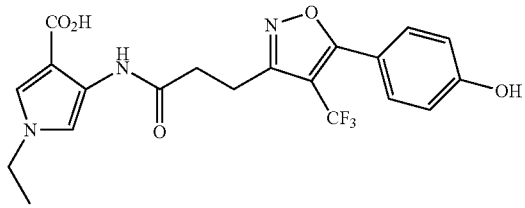 [SMILES: CCn1cc(NC(=O)CCc2noc(-c3ccc(O)cc3)c2C(F)(F)F)c(C(=O)O)c1]

(a) 3-[4-Trifluoromethyl-5-(4-hydroxyphenyl)isoxazol-3-yl]propionic acid 1,4-Phenylene diisocyanate (597.1 mg, 3.73 mol) and triethylamine (780 μL, 5.60 mmol) were added to a solution of 1-methoxy-4-trifluoropropynylbenzene (373.2 mg, 1.86 mmol) and 4-nitrobutanoic acid methyl ester (441.5 mg, 2.80 mmol) in toluene (10 mL). Using a microwave reactor, the obtained mixture was stirred at 150° C. for 2 hours. The reaction solution was filtered with celite, and the solvent was then distilled away. The residue was purified by silica gel column chromatography (hexane/ethyl acetate) to obtain a trifluoromethyl isoxazole compound (144.0 mg, yield: 25%).

A 1M-sodium hydroxide aqueous solution (880 μL, 0.88 mmol) was added to a solution of the obtained trifluoromethyl isoxazole compound (144.0 mg, 0.44 mmol) in ethanol (3 mL), and the obtained mixture was then stirred at room temperature for 1 hour. Thereafter, 5 M-hydrochloric acid was added to the reaction solution, and the generated precipitate was then collected by filtration, so as to obtain the title compound (129.7 mg, yield: 94%) in the form of a colorless powder.

$^1$H NMR (500 MHz, CDCl$_3$): δ (ppm)=7.66 (2H, d, J=8.8 Hz), 7.01 (2H, d, J=8.8 Hz), 3.88 (3H, s), 3.15 (2H, t, J=7.3 Hz), 2.92 (2H, t, J=7.3 Hz).

(b) 4-{3-[4-Trifluoromethyl-5-(4-hydroxyphenyl)isoxazol-3-yl]propanoyl}amino-1-ethylpyrrole-3-carboxylic acid Reactions were carried out in the same manner as in Examples 1(c) and 1(d) using the compound obtained in Example 53(a) to obtain the title compound in the form of a colorless powder.

$^1$H NMR (400 MHz, DMSO-d$_6$): δ (ppm)=12.2 (1H, s), 10.4 (1H, s), 9.41 (1H, s), 7.55 (2H, d, J=8.6 Hz), 7.31 (1H, d, J=2.3 Hz), 7.30 (1H, d, J=2.3 Hz), 6.97 (2H, d, J=8.6 Hz), 3.91 (2H, q, J=7.1 Hz), 3.09 (2H, t, J=7.1 Hz), 2.85 (2H, t, J=7.1 Hz), 1.30 (3H, t, J=7.1 Hz).

MS m/z: 438 (M+H)$^+$.

Example 54

4-{3-[2-(4-Hydroxyphenyl)thiazol-5-yl]-2-methylpropanoyl}amino-1-ethylpyrrole-3-carboxylic acid

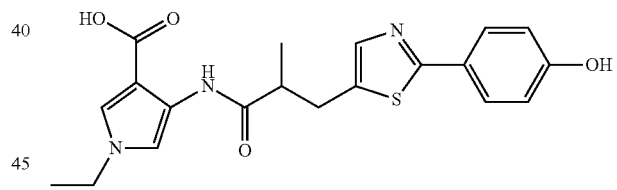

A solution of sodium hydride (450 mg, 11.7 mmol) in THF (100 mL) was cooled on ice under a nitrogen atmosphere, and methyl malonic acid diethyl ester (2 mL, 11.7 mmol) was then added dropwise to the reaction solution. The temperature of the reaction solution was raised to room temperature, and it was then stirred for 1 hour. Thereafter, 2-chloro-5-chloromethylthiazole (2.0 g, 13 mmol) was added to the reaction solution, and the obtained mixture was then stirred at room temperature for 1 day. Subsequently, water was added to the reaction solution, and it was then extracted with ethyl acetate. The organic layer was washed with water and a saturated saline. The organic layer was dried over anhydrous sodium sulfate, and the solvent was then distilled away. The obtained residue was purified by silica gel column chromatography (hexane/ethyl acetate) to obtain an oily substance (1.7 g, yield: 48%).

The obtained compound was dissolved in ethanol (15 mL), and a 2 N-sodium hydroxide aqueous solution (15 mL) was then added to the solution. The obtained mixture was stirred at room temperature for 1 day. Thereafter, the reaction solution was neutralized with 2 N-hydrochloric acid, sodium chloride was then added to the reaction solution, and the organic layer was then extracted with ethyl acetate. The organic layer was washed with water and a saturated saline, and it was then dried over anhydrous sodium sulfate. The solvent was distilled away to obtain a colorless solid (0.98 g, yield: 71%). The obtained solid was dissolved in xylene (70 mL), and the obtained mixture was then heated to reflux for 4 hours. Thereafter, the solvent was distilled away to obtain an oily substance (860 mg, yield: 99%).

A reaction was carried out in the same manner as in Example 1(c)-1 using the above-obtained compound (205 mg, 1.0 mmol) and the compound obtained in Example 12(a). Subsequently, a reaction was carried out in the same manner as in Example 7(b) using 4-methoxyphenylboronic acid. Using the obtained ester compound, reactions were carried out in the same manner as in Example 1(c)-2 and 1(d), so as to obtain the title compound (85.5 mg) in the form of a yellow solid.

$^1$H NMR (500 MHz, CD$_3$OD): δ (ppm)=9.49 (1H, brs), 7.68 (2H, d, J=8.3 Hz), 7.46 (1H, s), 7.14 (1H, d, J=2.4 Hz), 6.86 (2H, d, J=8.8 Hz), 3.92 (2H, q, J=7.0 Hz), 3.28 (1H, dd, J=14.6 and 7.8 Hz), 3.00 (1H, dd, J=14.8 and 6.5 Hz), 2.76-2.75 (1H, m), 1.45 (3H, t, J=7.3 Hz), 1.32 (3H, d, J=7.0 Hz), 1.27 (3H, t, J=7.1 Hz).

Example 55

4-{3-[5-(4-Hydroxyphenyl)[1,3,4]thiadiazole-2-yl]propanoyl}amino-1-ethylpyrrole-3-carboxylic acid

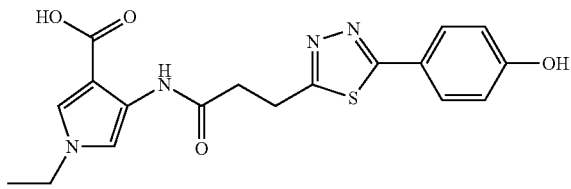 [SMILES: CCn1cc(NC(=O)CCc2nnc(-c3ccc(O)cc3)s2)c(C(=O)O)c1]

(a) Ethyl 3-[5-(4-methoxyphenyl)-[1,3,4]thiadiazol-2-yl]propionate

4-Methoxybenzoyl hydrazide (1.0 g, 6.02 mmol) was suspended in dichloromethane (18 mL), and succinic acid chloride monoethyl ester (0.86 mL, 6.02 mmol) and pyridine (0.54 mL, 6.62 mmol) were then added to the suspension under ice cooling. While gradually raising the temperature of the obtained mixture to room temperature, the mixture was stirred overnight. Thereafter, 1 N-hydrochloric acid was added to the reaction solution, and the obtained mixture was then extracted with dichloromethane three times. The organic layer was washed with a saturated sodium bicarbonate aqueous solution, and it was then dried over anhydrous sodium sulfate, followed by concentration under reduced pressure.

The obtained residue was suspended in toluene (25 mL), and a Lawesson reagent (1.95 g, 4.81 mmol) and pyridine (0.97 mL) were then added to the suspension. The obtained mixture was stirred at 100° C. for 1 hour. Thereafter, the reaction solution was concentrated, and the residue was then purified with a fractionation purification apparatus (Biotage, ethyl acetate:hexane=1:19-2:3), so as to obtain the title compound (1.76 g, quantitative) in the form of a colorless solid.

$^1$H NMR (400 MHz, CDCl$_3$): δ (ppm)=7.85 (2H, d, J=9.3 Hz), 6.95 (2H, d, J=9.3 Hz), 4.16 (2H, q, J=7.4 Hz), 3.85 (3H, s), 3.41 (2H, t, J=7.0 Hz), 2.89 (2H, t, J=7.0 Hz), 1.26 (3H, t, J=7.4 Hz).
MS m/z: 293 (M+H)$^+$.

(b) 3-[5-(4-Methoxyphenyl)-[1,3,4]thiadiazol-2-yl]propionic acid

The compound (1.76 g, 6.02 mmol) obtained in Example 55(a) was dissolved in a mixture of ethanol (15 mL) and THF (15 mL), and a 5 N-sodium hydroxide aqueous solution (3.60 mL) was then added to the solution. The obtained mixture was stirred at room temperature for 2 hours. Thereafter, 1 N-hydrochloric acid was added to the reaction solution, and the obtained mixture was then extracted with a mixed solvent of ethyl acetate and THF three times. The organic layer was washed with a saturated saline, and it was then dried over anhydrous sodium sulfate, followed by concentration under reduced pressure. The residue was purified with a fractionation purification apparatus (Biotage, dichloromethane:methanol=98:2-80:20), so as to obtain the title compound (1.25 g, 79%) in the form of a colorless solid.

(c) 4-{3-[5-(4-Methoxyphenyl)[1,3,4]thiadiazol-2-yl]propanoylamino}-1-methylpyrrole-3-carboxylic acid ethyl ester The compound (80 mg, 0.30 mmol) obtained in Example 55(b) and ethyl 4-amino-1-methylpyrrole-3-carboxylate hydrochloride (103 mg, 0.39 mmol) were dissolved in dimethylformamide (3 mL). Thereafter, HATU (163 mg, 0.43 mmol) and diisopropylethylamine (0.089 mL, 0.51 mmol) were added to the solution, and the obtained mixture was then stirred at room temperature for 5 hours. A sodium bicarbonate aqueous solution was added to the reaction solution, and the obtained mixture was then extracted with a mixture of ethyl acetate and THF three times. The organic layer was washed with a saturated saline, and it was then dried over anhydrous sodium sulfate, followed by concentration under reduced pressure. The residue was purified with a fractionation purification apparatus (Biotage, ethyl acetate:hexane=3:7, and then ethyl acetate), so as to obtain the title compound (162 mg, quantitative) in the form of a colorless solid.

$^1$H NMR (400 MHz, CDCl$_3$): δ (ppm)=9.36 (1H, brs), 7.84 (2H, d, J=8.6 Hz), 7.39 (1H, d, J=2.4 Hz), 7.07 (1H, d, J=2.4 Hz), 6.94 (2H, d, J=8.6 Hz), 4.26 (2H, q, J=7.4 Hz), 3.87 (2H, q, J=7.0 Hz), 3.81 (3H, s), 3.51 (2H, t, J=7.0 Hz), 2.96 (2H, t, J=7.0 Hz), 1.42 (3H, t, J=7.4 Hz), 1.32 (3H, t, J=7.0 Hz).
MS m/z: 429 (M+H)$^+$.

(d) 4-{3-[5-(4-Methoxyphenyl)[1,3,4]thiadiazol-2-yl]propanoylamino}-1-methylpyrrole-3-carboxylic acid The compound (162 mg, 0.39 mmol) obtained in Example 55(c) was dissolved in ethanol (6 mL)-THF (6 mL), and a 1 N-lithium hydroxide aqueous solution (1.56 mL) was then added to the solution. The obtained mixture was stirred at 75° C. for 6.5 hours. Thereafter, concentrated hydrochloric acid (0.13 mL) was added to the reaction solution, and the obtained mixture was then concentrated under reduced pressure. The residue was purified with a fractionation purification apparatus (Biotage, dichloromethane:methanol=98:2-75:25), so as to obtain the title compound (93 mg) in the form of a colorless solid. The obtained compound was suspended in dichloromethane (5 mL), and it was then cooled in a dry ice/acetone bath. A 1 N-boron tribromide-dichloromethane solution (1.68 mL) was added to the reaction solution. While gradually raising the temperature of the reaction mixture to room temperature, the mixture was stirred overnight. Thereafter, water was added to the reaction solution, and the mixture was then extracted with a mixture of ethyl acetate-THF three times. The organic layer was washed with a saturated saline, and it was then dried over anhydrous sodium sulfate, followed by concentration under reduced pressure. The residue was purified with a fractionation purification apparatus (Biotage, dichloromethane:methanol=97:3-60:40), so as to obtain the title compound (65 mg, 73%).

$^1$H NMR (400 MHz, DMSO-$d_6$): δ (ppm)=12.3 (1H, brs), 10.2 (1H, brs), 9.47 (1H, brs), 7.78 (2H, d, J=8.8 Hz), 7.34 (1H, d, J=2.4 Hz), 7.32 (1H, d, J=2.4 Hz), 6.92 (2H, d, J=8.8 Hz), 3.93 (2H, q, J=7.3 Hz), 3.40 (2H, t, J=7.3 Hz), 2.95 (2H, t, J=7.3 Hz), 1.33 (2H, t, J=7.3 Hz).

MS m/z: 385 (M−H)$^−$.

Example 56

4-{3-[1-(4-Hydroxyphenyl)-5-isopropylpyrazol-4-yl] propanoylamino}-1-ethylpyrrole-3-carboxylic acid

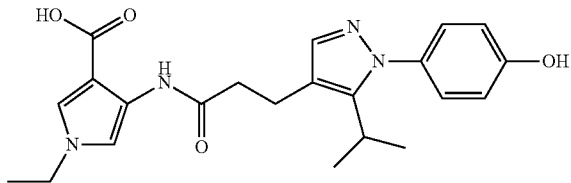 [SMILES: CCn1cc(NC(=O)CCc2cnn(-c3ccc(O)cc3)c2C(C)C)c(C(=O)O)c1]

(a) 5-Isopropyl-1-(4-methoxyphenyl)pyrazol-4-carboxylic acid ethyl ester

A mixture of ethyl isobutyryl acetate (500 mg, 3.16 mmol) and dimethylformamide dimethylacetal (414 mg, 3.48 mmol) was stirred at 120° C. for 2 hours. The reaction solution was cooled to room temperature, and 4-methoxyphenyl hydrazine hydrochloride (552 mg, 3.16 mmol) and ethanol (8 mL) were then added thereto. The obtained mixture was stirred at 80° C. for 1.5 hours. The reaction solution was cooled to room temperature, and it was then concentrated under reduced pressure. The residue was purified with a fractionation purification apparatus (Biotage, ethyl acetate:hexane=1:19-1:4), so as to obtain the title compound (682 mg, 75%) in the form of a yellow solid.

$^1$H NMR (400 MHz, CDCl$_3$): δ (ppm)=7.98 (1H, s), 7.25 (2H, d, J=8.6 Hz), 6.97 (2H, d, J=8.6 Hz), 4.30 (2H, q, J=7.4 Hz), 3.85 (3H, s), 3.24 (1H, sept, J=7.0 Hz), 1.36 (3H, t, J=7.4 Hz), 1.31 (6H, d, J=7.0 Hz).

MS m/z: 289 (M+H)$^+$.

(b) [5-Isopropyl-1-(4-methoxyphenyl)pyrazol-4-yl] methanol

The compound (680 mg, 2.36 mmol) obtained in Example 56(a) was dissolved in THF (10 mL). While stirring the solution under ice cooling, lithium aluminum hydride (98 mg, 2.59 mmol) was gradually added to the reaction solution, and the obtained mixture was stirred at the same temperature for 1 hour. Thereafter, water was added to the reaction solution, and insoluble materials were removed by filtration with celite, and the filtrate was then extracted with ethyl acetate three times. The organic layer was washed with a saturated saline, and it was then dried over anhydrous sodium sulfate, followed by concentration under reduced pressure. The residue was purified with a fractionation purification apparatus (Biotage, ethyl acetate:hexane=1:1, and then ethyl acetate), so as to obtain the title compound (490 mg, 84%) in the form of a colorless solid.

$^1$H NMR (400 MHz, CDCl$_3$): δ (ppm)=7.55 (1H, s), 7.25 (2H, d, J=8.6 Hz), 6.95 (2H, d, J=8.6 Hz), 4.67 (2H, s), 3.84 (3H, s), 3.04 (1H, sept, J=7.0 Hz), 1.56 (1H, brs), 1.27 (6H, d, J=7.0 Hz).

MS m/z: 247 (M+H)$^+$.

(c) 5-Isopropyl-1-(4-methoxyphenyl)pyrazol-4-carbaldehyde

The compound (490 mg, 1.99 mmol) obtained in Example 56(b) was dissolved in THF (10 mL), and manganese dioxide (590 mg, 5.97 mmol) was then added to the solution. The obtained mixture was stirred at room temperature for 42 hours. Thereafter, manganese dioxide (295 mg, 2.98 mmol) was added to the reaction mixture, and the obtained mixture was further stirred for 24 hours. Thereafter, insoluble materials were removed by filtration, and the filtrate was then concentrated under reduced pressure. The residue was purified with a fractionation purification apparatus (Biotage, ethyl acetate:hexane=1:9-2:3), so as to obtain the title compound (486 mg, quantitative) in the form of a colorless solid.

$^1$H NMR (400 MHz, CDCl$_3$): δ (ppm)=10.04 (1H, s), 8.03 (1H, s), 7.27 (2H, d, J=9.0 Hz), 6.99 (2H, d, J=9.0 Hz), 3.86 (3H, s), 3.16 (1H, sept, J=7.0 Hz), 1.35 (6H, d, J=7.0 Hz).

(d) Ethyl 3-[5-isopropyl-1-(4-methoxyphenyl)pyrazol-4-yl]acrylate

Sodium hydride (37 mg, 0.98 mmol) was suspended in THF (4 mL), and triethyl phosphonoacetate (220 mg, 0.98 mmol) was then added dropwise to the suspension under ice cooling. The obtained mixture was stirred at the same temperature for 30 minutes. Thereafter, a solution of the compound (200 mg, 0.82 mmol) obtained in Example 56(c) in THF (3 mL) was added to the reaction solution. While gradually raising the temperature of the reaction mixture to room temperature, the reaction solution was stirred for 2.5 hours. Thereafter, a saturated saline was added to the reaction solution, and the mixture was extracted with ethyl acetate three times. The organic layer was washed with a saturated saline, and it was then dried over anhydrous sodium sulfate, followed by concentration under reduced pressure. The residue was purified with a fractionation purification apparatus (Biotage, ethyl acetate:hexane=1:9-2:3), so as to obtain the title compound (256 mg, quantitative) in the form of a colorless solid.

$^1$H NMR (400 MHz, CDCl$_3$): δ (ppm)=7.86 (1H, s), 7.85 (1H, d, J=16.1 Hz), 7.30 (2H, d, J=8.8 Hz), 7.01 (2H, d, J=8.8 Hz), 6.23 (1H, d, J=16.1 Hz), 4.28 (2H, q, J=7.3 Hz), 3.89 (3H, s), 3.14 (1H, sept, J=6.8 Hz), 1.36 (3H, t, J=7.3 Hz), 1.34 (6H, d, J=6.8 Hz).

MS m/z: 315 (M+H)$^+$.

(e) Ethyl 3-[5-isopropyl-1-(4-methoxyphenyl)pyrazol-4-yl]propionate

The compound (254 mg, 0.81 mmol) obtained in Example 56(d) was dissolved in a mixture of ethanol (5 mL) and THF (5 mL), and 10% palladium-carbon (50 mg) was then added to the solution. The obtained mixture was stirred under a hydrogen atmosphere at room temperature for 2 hours. Thereafter, the catalyst was removed by filtration, and the reaction solution was then concentrated under reduced pressure. The residue was purified with a fractionation purification apparatus (Biotage, ethyl acetate:hexane=1:4-2:3), so as to obtain the title compound (243 mg, 95%) in the form of a colorless oily product.

¹H NMR (400 MHz, CDCl₃): δ (ppm)=7.39 (1H, s), 7.24 (2H, d, J=9.0 Hz), 6.94 (2H, d, J=9.0 Hz), 4.15 (2H, q, J=7.4 Hz), 3.83 (3H, s), 3.01 (1H, sept, J=6.7 Hz), 2.89 (2H, t, J=7.4 Hz), 2.62 (2H, t, J=7.4 Hz), 1.26 (3H, t, J=7.4 Hz), 1.34 (6H, d, J=6.7 Hz).

MS m/z: 317 (M+H)⁺.

(f) 4-{3-[5-Isopropyl-1-(4-methoxyphenyl)pyrazol-4-yl]propionate

The compound (120 mg, 0.38 mmol) obtained in Example 56(e) was dissolved in a mixture of ethanol (2 mL) and THF (2 mL), and a 5 N-sodium hydroxide aqueous solution (228 μl) was then added to the solution. Thereafter, the obtained mixture was stirred at room temperature for 4 hours. Thereafter, concentrated hydrochloric acid (95 μl) was added to the reaction solution, and the reaction solution was then concentrated under reduced pressure, so as to obtain a crude product of the title compound.

(g) Ethyl 4-{3-[5-isopropyl-1-(4-methoxyphenyl)pyrazol-4-yl]propanoylamino}-1-ethylpyrrolecarboxylate A reaction was carried out in the same manner as in Example 1(c)-1 using the compound (0.38 mmol) obtained in Example 56(f), ethyl 4-amino-1-methylpyrrole-3-carboxylate hydrochloride (83 mg, 0.38 mmol), HATU (159 mg, 0.42 mmol), and diisopropylethylamine (132 μl, 0.76 mmol), so as to obtain the title compound (172 mg, quantitative) in the form of a colorless oily product.

¹H NMR (400 MHz, CDCl₃): δ (ppm)=9.32 (1H, brs), 7.43 (1H, d, J=2.4 Hz), 7.41 (1H, s), 7.24 (1H, d<J=9.0 Hz), 7.07 (1H, d, J=2.4 Hz), 6.93 (2H, d, J=9.0 Hz), 4.27 (2H, q, J=7.0 Hz), 3.88 (2H, q, J=7.4 Hz), 3.83 (3H, s), 3.06-2.96 (3H, m), 2.68 (2H, t, J=7.4 Hz), 1.42 (3H, t, J=7.4 Hz), 1.33 (3H, t, J=7.0 Hz), 1.24 (6H, d, J=6.7 Hz).

MS m/z: 453 (M+H)⁺.

(h) 4-{3-[5-Isopropyl-1-(4-hydroxyphenyl)pyrazol-4-yl]propanoylamino}-1-ethylpyrrolecarboxylic acid Reactions were carried out in the same manner as in Examples 1(c)-2 and 1(d) using the compound obtained in Example 56(g), so as to obtain the title compound in the form of a colorless solid.

¹H NMR (400 MHz, DMSO-d₆): δ (ppm)=12.2 (1H, brs), 9.77 (1H, brs), 9.37 (1H, brs), 7.35 (1H, s), 7.31 (1H, d, J=2.7 Hz), 7.27 (1H, d, J=2.7 Hz), 7.11 (2H, d, J=8.2 Hz), 6.83 (2H, d, J=8.2 Hz), 3.90 (2H, q, J=7.4 Hz), 2.93 (1H, sept, J=7.4 Hz), 2.82 (2H, t, J=7.4 Hz), 2.63 (2H, t, J=7.4 Hz), 1.29 (2H, t, J=7.4 Hz), 1.17 (6H, d, J=7.4 Hz).

MS m/z: 409 (M–H)⁻.

Example 57

4-{3-[4-Chloro-3-(4-hydroxyphenyl)isothiazol-5-yl]propanoylamino}-1-ethylpyrrole-3-carboxylic acid

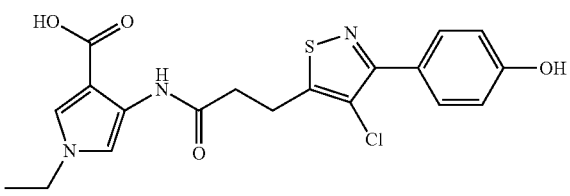

(a) 5-(4-Methoxyphenyl)-[1,3,4]oxathiazol-2-one

4-Methoxybenzamide (3.0 g, 19.9 mmol) was suspended in a mixture of toluene (30 mL) and THF (15 mL), and chlorosulfenyl chloride (3.35 mL, 39.7 mmol) was then added to the suspension. The obtained mixture was stirred at 80° C. for 2.5 hours. The reaction solution was cooled to room temperature, and it was then concentrated under reduced pressure. Thereafter, diethyl ether was added to the residue, and insoluble materials were then removed by filtration, so as to obtain the title compound (3.64 g, 88%) in the form of a colorless solid.

¹H NMR (400 MHz, CDCl₃): δ (ppm)=7.94 (2H, d, J=8.8 Hz), 7.00 (2H, d, J=8.8 Hz), 3.91 (3H, s).

(b) Ethyl 3-(4-methoxyphenyl)isothiazol-5-carboxylate

The compound (1.8 g, 8.6 mmol) obtained in Example 57(a) was dissolved in xylene (10 mL), and ethyl propynoate (2.2 mL, 21.5 mmol) was then added to the solution. Using a microwave reactor, the obtained mixture was stirred at 170° C. for 30 minutes. The reaction solution was cooled to room temperature, and it was then concentrated under reduced pressure. The residue was purified with a fractionation purification apparatus (Biotage, ethyl acetate:hexane=2:98-1:4), so as to obtain the title compound (1.25 g, 55%) in the form of a yellow oily product.

¹H NMR (400 MHz, CDCl₃): δ (ppm)=8.03 (1H, s), 7.89 (2H, d, J=8.6 Hz), 6.96 (2H, d, J=8.6 Hz), 4.40 (2H, q, J=7.4 Hz), 3.85 (3H, s), 1.40 (3H, t, J=7.4 Hz).

MS m/z: 264 (M+H)⁺.

(c) [3-(4-Methoxyphenyl)isothiazol-5-yl]methanol

The compound (1.1 g, 4.18 mmol) obtained in Example 57(b) was dissolved in a mixture of ethanol (5 mL) and THF (5 mL), and a 5 N-sodium hydroxide aqueous solution (0.84 mL, 16.7 mmol) was then added to the solution. The obtained mixture was stirred at room temperature for 4 hours. Thereafter, 1 N-hydrochloric acid was added to the reaction solution, and the mixture was then extracted with ethyl acetate three times. The organic layer was washed with a saturated saline, and it was then dried over anhydrous sodium sulfate, followed by concentration under reduced pressure. The residue was dissolved in THF (5 mL), and a borane-dimethyl sulfide complex (0.51 mL, 5.42 mmol) was added to the solution. The obtained mixture was stirred at 60° C. for 1.5 hours. Thereafter, water was added to the reaction solution, and the obtained mixture was then stirred for 10 minutes. Thereafter, a saturated saline was added to the reaction solution, and the mixture was then extracted with ethyl acetate three times. The organic layer was washed with a saturated saline, and it was then dried over anhydrous sodium sulfate, followed by concentration under reduced pressure. The residue was purified with a fractionation purification apparatus (Biotage, ethyl acetate:hexane=1:4-4:1), so as to obtain the title compound (0.67 g, 72%) in the form of a pale yellow solid.

$^1$H NMR (400 MHz, CDCl$_3$): δ (ppm)=7.90 (2H, d, J=8.8 Hz), 7.44 (1H, s), 6.99 (2H, d, J=8.8 Hz), 5.05 (2H, s), 3.88 (3H, s).

MS m/z: 222 (M+H)$^+$.

(d) [4-Chloro-3-(4-methoxyphenyl)isothiazol-5-yl]methanol

The compound (332 mg, 1.5 mmol) obtained in Example 57(c) was dissolved in dimethylformamide (5 mL), and N-chlorosuccinimide (220 mg, 1.65 mmol) was then added to the solution. The obtained mixture was stirred at room temperature overnight. Thereafter, a saturated saline was added to the reaction solution, and the mixture was then extracted with ethyl acetate three times. The organic layer was washed with a saturated saline, and it was then dried over anhydrous sodium sulfate, followed by concentration under reduced pressure. The residue was purified with a fractionation purification apparatus (Biotage, ethyl acetate:hexane=1:4-1:1), so as to obtain the title compound (210 mg, 55%) in the form of a colorless solid.

$^1$H NMR (400 MHz, CDCl$_3$): δ (ppm)=7.82 (2H, d, J=8.6 Hz), 6.97 (2H, d, J=8.6 Hz), 4.98 (2H, s), 3.85 (3H, s).

(e) 3-[4-Chloro-3-(4-methoxyphenyl)isothiazol-5-yl]propionic acid (e)-1

The compound (206 mg, 0.81 mmol) obtained in Example 57(d) was dissolved in dichloromethane (5 mL), and phosphorous tribromide (0.03 mL, 0.32 mmol) was then added to the solution. The obtained mixture was stirred at room temperature for 30 minutes. The reaction solution was concentrated under reduced pressure, and the residue was then dissolved in a mixture of acetonitrile (3 mL) and dimethylformamide (1 mL). Triethyl methanetricarboxylate (0.26 mL, 1.22 mmol) and potassium carbonate (390 mg, 2.82 mmol) were added to the obtained solution, and the obtained mixture was then stirred at 60° C. for 3 hours. Thereafter, a saturated saline was added to the reaction solution, and the mixture was then extracted with ethyl acetate three times. The organic layer was washed with a saturated saline, and it was then dried over anhydrous sodium sulfate, followed by concentration under reduced pressure. The residue was purified with a fractionation purification apparatus (Biotage, ethyl acetate:hexane=2:98-1:3) to obtain a triester compound (320 mg, 72%) in the form of a yellow oily product.

(e)-2

The triester compound obtained in Example 57(e)-1 was dissolved in a mixture of ethanol (5 mL) and THF (5 mL), and 5 N-sodium hydroxide (1.23 mL, 6.13 mmol) was then added to the solution. The obtained mixture was stirred at room temperature overnight. The reaction solution was concentrated under reduced pressure, and acetic acid (5 mL) was then added to the residue. The obtained mixture was stirred at 120° C. for 4 hours. The reaction solution was concentrated under reduced pressure, and 1 N-hydrochloric acid was then added to the residue, followed by extraction three times with ethyl acetate. The organic layer was washed with a saturated saline, and it was then dried over anhydrous sodium sulfate, followed by concentration under reduced pressure, to obtain a crude product of the title compound.

(f) Allyl 4-{3-[4-chloro-3-(4-methoxyphenyl)isothiazole-5-yl]propanoylamino}-1-ethylpyrrole-3-carboxylate Using the compound (195 mg, 0.65 mmol) obtained in Example 57(e), allyl 4-amino-1-ethylpyrrole-3-carboxylate (151 mg, 0.65 mmol), HATU (274 mg, 0.72 mmol), and diisopropylethylamine (0.14 mL, 0.79 mmol), a reaction was carried out in the same manner as in Example 1(c)-1, so as to obtain the title compound (171 mg, 55%) in the form of a yellow oily product.

$^1$H NMR (400 MHz, CDCl$_3$): δ (ppm)=9.32 (1H, brs), 7.86 (2H, d, J=8.8 Hz), 7.47 (1H, d, J=2.4 Hz), 7.15 (1H, d, J=2.4 Hz), 7.01 (2H, d, J=8.8 Hz), 6.08-5.96 (1H, m), 5.39 (1H, dd, J=18, 1.5 Hz), 5.29 (1H, dd, J=10, 1.5 Hz), 4.75 (2H, d, J=5.9 Hz), 3.94 (2H, q, J=7.3 Hz), 3.89 (3H, s), 3.38 (2H, t. J=7.3 Hz), 2.83 (2H, t, J=7.3 Hz), 1.48 (3H, t, J=7.3 Hz).

(g) 4-{3-[4-Chloro-3-(hydroxyphenyl)isothiazol-5-yl]propanoylamino}-1-ethylpyrrole-3-carboxylic acid The compound (170 mg, 0.36 mmol) obtained in Example 57(f) was dissolved in THF (4 mL), and tetrakistriphenylphosphine palladium (17 mg, 0.01 mmol) and pyrrolidine (0.060 mL, 0.72 mmol) were then added to the solution. The obtained mixture was stirred at room temperature for 6 hours. The reaction solution was concentrated under reduced pressure. The residue was purified with a fractionation purification apparatus (Biotage, dichloromethane, and then dichloromethane:methanol=85:15) to obtain a carboxylic acid compound (155 mg, quantitative) in the form of a yellow amorphous solid. The obtained carboxylic acid compound was suspended in dichloromethane (5 mL), and it was then cooled in a dry ice-acetone bath. Thereafter, 1 N-boron tribromide (1.8 mL) was added to the reaction solution. While gradually raising the temperature of the reaction mixture to room temperature, the mixture was stirred overnight. Thereafter, water was added to the reaction solution, and the mixture was then extracted with a mixture of ethyl acetate and THF three times. The organic layer was washed with a saturated saline, and it was then dried over anhydrous sodium sulfate, followed by concentration under reduced pressure. The residue was purified with a fractionation purification apparatus (Biotage, dichloromethane, and then, dichloromethane:methanol=4:1), and was then purified by thin-layer chromatography for separation (dichloromethane:methanol=92:8), so as to obtain the title compound (50 mg, 33%) in the form of a yellow solid.

$^1$H NMR (400 MHz, DMSO-d$_6$): δ (ppm)=9.49 (1H, brs), 7.64 (2H, d, J=8.6 Hz), 7.30 (1H, d, J=2.4 Hz), 7.25 (1H, d, J=2.4 Hz), 6.86 (2H, d, J=8.6 Hz), 3.90 (2H, q, J=7.0 Hz), 3.20 (2H, t, J=7.0 Hz), 2.81 (2H, t, J=7.0 Hz), 1.29 (3H, t, J=7.0 Hz).

MS m/z: 418 (M−H)$^-$.

Example 58

4-{3-[4-Ethyl-3-(4-hydroxyphenyl)isothiazol-5-yl]propanoylamino}-1-ethylpyrrole-3-carboxylic acid

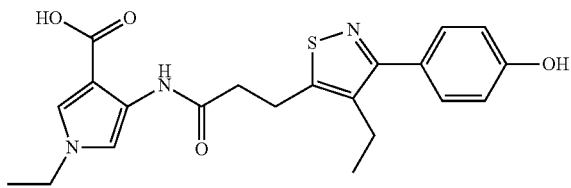

(a) [4-Bromo-3-(4-methoxyphenyl)isothiazol-5-yl]methanol

The compound (410 mg, 1.85 mmol) obtained in Example 57(c) was dissolved in dimethylformamide (5 mL), and N-bromosuccinimide (363 mg, 2.04 mmol) was then added to the solution. The obtained mixture was stirred at room temperature overnight. Thereafter, a saturated saline was added to the reaction solution, and the mixture was then extracted with ethyl acetate three times. The organic layer was washed with a saturated saline, and it was then dried over anhydrous sodium sulfate, followed by concentration under reduced pressure. The residue was purified with a fractionation purification apparatus (Biotage, ethyl acetate:hexane=1:4-2:3), so as to obtain the title compound (190 mg, 34%) in the form of a yellow solid.

$^1$H NMR (400 MHz, CDCl$_3$): δ (ppm)=7.78 (2H, d, J=8.6 Hz), 6.97 (2H, d, J=8.6 Hz), 4.96 (2H, s), 3.85 (3H, s), 2.19 (1H, brs).

(b) Triethyl 2-[4-bromo-3-(4-methoxyphenyl)isothiazol-5-yl]ethanetricarboxylate The compound (190 mg, 0.63 mmol) obtained in Example 58(a) was suspended in toluene (3 mL), and thionyl chloride (0.055 mL, 0.76 mmol) and pyridine (1 drop) were then added to the suspension. The obtained mixture was stirred at 120° C. for 10 minutes. The reaction solution was cooled to room temperature, and it was then concentrated under reduced pressure. The residue was dissolved in acetonitrile (3 mL), and triethyl methanetricarboxylate (0.17 mL, 0.82 mmol), potassium carbonate (218 mg, 1.58 mmol) and sodium iodide (9 mg, 0.06 mmol) were then added to the solution. The obtained mixture was stirred at 100° C. for 1.5 hours. The reaction solution was concentrated under reduced pressure, and a sodium bicarbonate aqueous solution was then added to the residue, followed by extraction three times with ethyl acetate. The organic layer was washed with a saturated saline, and it was then dried over anhydrous sodium sulfate, followed by concentration under reduced pressure. The residue was purified with a fractionation purification apparatus (Biotage, ethyl acetate:hexane=1:9-2:3), so as to obtain the title compound (324 mg, quantitative) in the form of a yellow oily product.

$^1$H NMR (400 MHz, CDCl$_3$): δ (ppm)=7.78 (2H, d, J=8.8 Hz), 7.00 (2H, d, J=8.8 Hz), 4.31 (6H, q, J=7.3 Hz), 3.89 (3H, s), 1.29 (9H, t, J=7.3 Hz).

MS m/z: 514 (M+H)$^+$.

(c) 1-Ethyl-4-{3-[4-ethyl-3-(4-hydroxyphenyl)isothiazol-5-yl]propanoylamino}pyrrole-3-carboxylic acid A reaction was carried out in the same manner as in Example 57(e)-2 using the compound obtained in Example 58(b) to obtain a carboxylic acid compound in the form of colorless solid. Using the obtained carboxylic acid compound, reactions were carried out in the same manner as in Examples 25(c) and 25(d). Using the obtained amide compound, a reaction was carried out in the same manner as in Example 1(d), so as to obtain the title compound in the form of a colorless solid.

$^1$H NMR (400 MHz, DMSO-d$_6$): δ (ppm)=12.2 (1H, brs), 9.67 (1H, brs), 9.36 (1H, brs), 7.36 (2H, d, J=8.6 Hz), 7.32 (1H, d, J=2.4 Hz), 7.28 (1H, d, J=2.4 Hz), 6.82 (2H, d, J=8.6 Hz), 3.90 (2H, q, J=7.4 Hz), 3.16 (2H, t, J=7.0 Hz), 2.76 (2H, t, J=7.0 Hz), 2.64 (2H, q, J=7.4 Hz), 1.29 (3H, t, J=7.0 Hz), 1.01 (3H, t, J=7.4 Hz).

MS m/z: 412 (M−H)$^-$.

Example 59

4-{3-[4-Acetyl-5-(4-hydroxyphenyl)isoxazol-3-yl]propanoyl}amino-1-ethylpyrrole-3-carboxylic acid

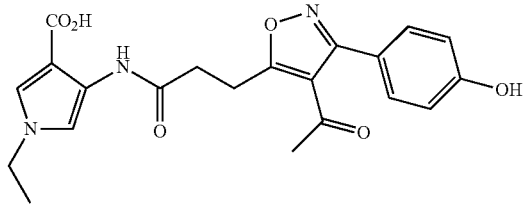 [SMILES: CCn1cc(NC(=O)CCc2onc(-c3ccc(O)cc3)c2C(C)=O)c(C(=O)O)c1]

(a) 4-Acetyl-3-tetrahydropyranyloxymethyl-5-(4-benzyloxyphenyl)isoxazole n-Butyl lithium (2.64 M-hexane solution, 17.70 mL) was added dropwise to a solution of 2-propy-2-yloxytetrahydropyran (5.48 g, 39.09 mmol) in THF (60 mL) at −78° C. The obtained mixture was stirred for 1 hour. A solution of N-acetylmorpholine (6.06 g, 46.91 mmol) in THF (10 mL) was added dropwise to the reaction solution. The temperature of the obtained mixture was raised to 0° C., and the mixture was then stirred for 1.5 hours. The reaction solution was poured into a saturated ammonium chloride aqueous solution, and the obtained mixture was then extracted with a mixture of hexane and ethyl acetate twice. The combined organic layer was washed with a saturated saline, and it was then dried over anhydrous sodium sulfate, followed by concentration. The residue was purified by silica gel column chromatography (hexane/ethyl acetate) to obtain an acetyl compound (2.43 g, yield: 34%) in the form of a pale yellow oily substance.

A 10% sodium hypochlorite aqueous solution (15.7 mL, 21.07 mmol) was added at 0° C. to a solution of the obtained acetyl compound (2.40 g, 13.17 mmol) and 4-benzyloxybenzaldehyde oxime (2.99 g, 13.17 mmol) in THF (40 mL). The temperature of the obtained mixture was raised to room temperature, and the mixture was then stirred for 18 hours. Thereafter, the solvent was distilled away, and the residue was then extracted with ethyl acetate twice, washed with a saturated saline, and then dried over anhydrous sodium sulfate, followed by concentration. The residue was purified by silica gel column chromatography (hexane/ethyl acetate), so as to obtain the title compound (2.70 g, yield: 50%) in the form of a yellow oily substance.

¹H NMR (500 MHz, CDCl₃): δ (ppm)=7.47 (2H, d, J=8.8 Hz), 7.47-7.33 (5H, m), 7.08 (2H, d, J=8.8 Hz), 5.12 (2H, s), 5.04 (1H, d, J=14.2 Hz), 4.88 (1H, d, J=14.2 Hz), 4.83 (1H, t, J=3.4 Hz), 3.89 (1H, m), 3.57 (1H, m), 2.17 (3H, s), 1.88-1.55 (6H, m).

(b) 4-Acetyl-3-bromomethyl-5-(4-benzyloxyphenyl)isoxazole

A 10% hydrochloric acid-methanol solution (1 mL) was added at 0° C. to a solution of the compound (2.62 g, 6.43 mmol) obtained in Example 59(a) in methanol (50 mL), and the obtained mixture was then stirred for 1 hour. The reaction solution was concentrated to obtain an alcohol compound (2.08 g, yield: 100%) in the form of a yellowish brown solid.

Carbon tetrabromide (3.20 g, 9.65 mmol) and triphenylphosphine (2.36 g, 9.01 mmol) were added to a solution of the obtained alcohol compound (2.08 g, 6.43 mmol) in dichloromethane (40 mL) at room temperature, and the obtained mixture was then stirred for 1 hour. The solvent was distilled away, and the residue was then purified by silica gel column chromatography (hexane/ethyl acetate), so as to obtain the title compound (2.48 g, yield: 100%) in the form of a pale yellow oily substance.

¹H NMR (500 MHz, CDCl₃): δ (ppm)=7.46-7.34 (5H, m), 7.45 (2H, d, J=8.8 Hz), 7.10 (2H, d, J=8.8 Hz), 5.13 (2H, s), 4.74 (2H, s), 2.16 (3H, s).

(c) 3-[4-Acetyl-5-(4-benzyloxyphenyl)isoxazol-3-yl]propionic acid

Triethyl methanetricarboxylate (1.64 g, 7.06 mmol) and potassium carbonate (1.15 g, 8.35 mmol) were added to a solution of the compound (2.48 g, 6.42 mmol) obtained in Example 59(b) in acetonitrile (40 mL). The obtained mixture was stirred at 60° C. for 1.5 hours. The reaction mixture was filtered with celite, and the filtrate was then concentrated. The residue was purified by silica gel column chromatography (hexane/ethyl acetate) to obtain a triester compound (2.91 g, yield: 87%) in the form of a colorless solid.

A 1 M-sodium hydroxide aqueous solution (11.2 mL, 11.2 mmol) was added to a solution of the obtained triester compound (1.50 g, 2.79 mmol) in ethanol (15 mL), and the obtained mixture was then stirred at room temperature for 3 hours. The reaction solution was concentrated, and acetic acid (10 mL) was then added thereto, followed by stirring at 110° C. for 5 hours. Thereafter, water was added to the reaction solution, and it was then extracted with ethyl acetate twice. The combined organic layer was washed with water and a saturated saline, and it was then dried over anhydrous sodium sulfate, followed by concentration, so as to obtain the title compound in the form of a yellow syrupy substance.

¹H NMR (500 MHz, CDCl₃): δ (ppm)=7.47-7.33 (7H, m), 7.08 (2H, d, J=8.8 Hz), 5.12 (2H, s), 3.38 (2H, t, J=7.4 Hz), 2.90 (2H, t, J=7.4 Hz), 2.11 (3H, s).

(d) 4-{3-[4-Acetyl-5-(4-hydroxyphenyl)isoxazol-3-yl]propanoyl}amino-1-ethylpyrrole-3-carboxylic acid Reactions were carried out in the same manner as in Examples 22(e) and 22(f) using the compound obtained in Example 59(c), so as to obtain the title compound in the form of a colorless powder.

¹H NMR (400 MHz, DMSO-d₆): δ (ppm)=12.2 (1H, brs), 9.92 (1H, s), 9.38 (1H, s), 7.37 (2H, d, J=9.0 Hz), 7.31 (2H, s), 6.88 (2H, d, J=9.0 Hz), 3.91 (2H, q, J=7.4 Hz), 3.32 (2H, t, J=7.3 Hz), 2.88 (2H, t, J=7.2 Hz), 2.16 (3H, s), 1.30 (3H, t, J=7.4 Hz).

MS m/z: 412 (M+H)⁺.

Example 60

4-{3-[4-Cyano-5-(4-hydroxyphenyl)isoxazol-3-yl]propanoyl}amino-1-ethylpyrrole-3-carboxylic acid

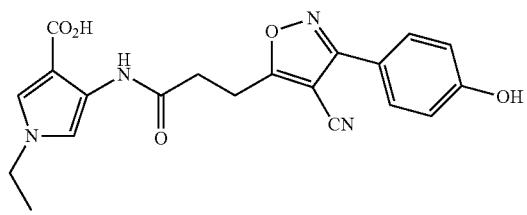 [SMILES: CCn1cc(NC(=O)CCc2onc(-c3ccc(O)cc3)c2C#N)c(C(=O)O)c1]

(a) 3-Tetrahydropyranyloxymethyl-5-(4-benzyloxyphenyl)isoxazol-4-carboxylic acid methyl ester n-Butyl lithium (2.64 M-hexane solution, 11.9 mL) was added dropwise to a solution of 2-propy-2-yloxytetrahydropyran (4.00 g, 28.53 mmol) in THF (40 mL) at −78° C. The obtained mixture was stirred for 1 hour. A solution of methyl chloroformate (2.97 g, 31.39 mmol) in THF (10 mL) was added dropwise to the reaction solution. The temperature of the obtained mixture was raised to 0° C., and the mixture was then stirred for 1.5 hours. The reaction solution was poured into a saturated ammonium chloride aqueous solution, and the obtained mixture was then extracted with a mixture of hexane and ethyl acetate twice. The combined organic layer was washed with a saturated saline, and it was then dried over anhydrous sodium sulfate, followed by concentration. The residue was purified by silica gel column chromatography (hexane/ethyl acetate) to obtain a methyl ester compound (4.66 g, yield: 90%) in the form of a pale yellow oily substance.

A 10% sodium hypochlorite aqueous solution (52.4 mL, 70.38 mmol) was added at 0° C. to a solution of the obtained methyl ester compound (4.65 g, 23.46 mmol) in THF (80 mL) and 4-methoxybenzaldehyde oxime (3.55 g, 23.46 mmol). The temperature of the obtained mixture was raised to room temperature, and the mixture was then stirred for 19 hours. Thereafter, the solvent was distilled away, and the residue was then extracted with ethyl acetate twice, washed with a saturated saline, and then dried over anhydrous sodium sulfate, followed by concentration. The residue was purified by silica gel column chromatography (hexane/ethyl acetate), so as to obtain the title compound (6.60 g, yield: 81%) in the form of a yellow oily substance.

¹H NMR (400 MHz, CDCl₃): δ (ppm)=7.62 (2H, d, J=9.0 Hz), 6.98 (2H, d, J=9.0 Hz), 5.10 (1H, d, J=13.7 Hz), 4.97 (1H, d, J=13.7 Hz), 4.86 (1H, t, J=3.5 Hz), 3.92 (1H, m), 3.87 (3H, s), 3.82 (3H, s), 3.59 (1H, m), 1.88-1.55 (6H, m).

(b) 4-Cyano-3-tetrahydropyranyloxymethyl-5-(4-benzyloxyphenyl)isoxazole

The compound (6.60 g, 19.00 mmol) obtained in Example 60(a) was dissolved in a mixture of methanol (30 mL) and THF (30 mL), and a 5 M-sodium hydroxide aqueous solution (7.6 mL, 38.0 mmol) was then added to the solution. The obtained mixture was stirred at room temperature for 6 hours. The reaction solution was made weakly acidic (pH 5 to 6) by addition of a citric acid aqueous solution, and it was then extracted with ethyl acetate twice. The combined organic layer was washed with a saturated saline, and it was then dried over anhydrous sodium sulfate to obtain a carboxylic acid compound in the form of a yellow syrupy substance. To a solution of the obtained carboxylic acid compound in DMF (70 mL), ammonium chloride (4.07 g, 76.0 mmol), WSCI (4.37 g, 22.8 mmol), HOBt (3.49 g, 22.8 mmol) and diisopropylethylamine (13.2 mL, 76.0 mmol) were added. The obtained mixture was stirred at room temperature for 15 hours. Thereafter, water was added to the reaction solution, and it was then extracted with a mixture of toluene and ethyl acetate twice. The combined organic layer was washed with water and a saturated saline, and it was then dried over anhydrous sodium sulfate, followed by concentration. The obtained residue was purified by silica gel column chromatography (hexane/ethyl acetate) to obtain an amide compound (3.29 g, yield in two steps: 52%) in the form of a colorless solid.

Triethylamine (3.45 mL, 14.85 mmol) and trifluoroacetic anhydride (2.08 mL, 14.85 mmol) were added at 0° C. to a solution of the obtained amide compound (3.29 g, 9.90 mmol) in dichloromethane (60 mL), and the obtained mixture was then stirred for 1 hour. Thereafter, water was added to the reaction solution, and the mixture was then extracted with dichloromethane, washed with a saturated saline, and then dried over anhydrous sodium sulfate, followed by concentration. The obtained residue was purified by silica gel column chromatography (hexane/ethyl acetate), so as to obtain the title compound (2.28 g, yield: 100%) in the form of a colorless oily substance.

$^1$H NMR (500 MHz, CDCl$_3$): δ (ppm)=7.92 (2H, d, J=8.8 Hz), 7.03 (2H, d, J=8.8 Hz), 4.97 (1H, d, J=14.6 Hz), 4.85 (1H, t, J=3.2 Hz), 4.81 (1H, d, J=14.6 Hz), 3.89 (1H, m), 3.88 (3H, s), 3.61 (1H, m), 1.90 (1H, m), 1.79 (2H, m), 1.65 (1H, m), 1.62-1.55 (2H, m).

(c) 4-Cyano-3-bromomethyl-5-(4-benzyloxyphenyl) isoxazole

A reaction was carried out in the same manner as in Example 59(b) using the compound obtained in Example 60(b), so as to obtain the title compound in the form of a colorless oily substance.

$^1$H NMR (400 MHz, CDCl$_3$): δ (ppm)=7.92 (2H, d, J=9.0 Hz), 7.04 (2H, d, J=9.0 Hz), 4.60 (2H, s), 3.89 (3H, s).

(d) 3-[4-Cyano-5-(4-hydroxyphenyl)isoxazol-3-yl] propionic acid

A reaction was carried out in the same manner as in Example 59(c) using the compound obtained in Example 60(c), so as to obtain the title compound in the form of a yellowish brown powder.

$^1$H NMR (500 MHz, CDCl$_3$): δ (ppm)=7.89 (2H, d, J=8.8 Hz), 7.02 (2H, d, J=8.8 Hz), 3.87 (3H, s), 3.32 (2H, t, J=7.4 Hz), 2.95 (2H, t, J=7.4 Hz).

(e) 4-{3-[4-Cyano-5-(4-hydroxyphenyl)isoxazol-3-yl]propanoyl}amino-1-ethylpyrrole-3-carboxylic acid Reactions were carried out in the same manner as in Examples 22(e) and 1(d) using the compound obtained in Example 60(d), so as to obtain the title compound in the form of a colorless powder.

$^1$H NMR (500 MHz, DMSO-d$_6$): δ (ppm)=12.2 (1H, brs), 10.2 (1H, s), 9.40 (1H, s), 7.70 (2H, d, J=8.8 Hz), 7.30 (1H, d, J=2.4 Hz), 7.29 (1H, d, J=2.4 Hz), 6.96 (2H, d, J=8.8 Hz), 3.90 (2H, q, J=7.3 Hz), 3.29 (2H, t, J=7.1 Hz), 2.98 (2H, t, J=7.1 Hz), 1.29 (3H, t, J=7.3 Hz).

MS m/z: 395 (M+H)$^+$.

Example 61

4-{3-[3-(4-Hydroxyphenyl)isoxazol-5-yl] propanoyl}amino-1-propylpyrrole-3-carboxylic acid

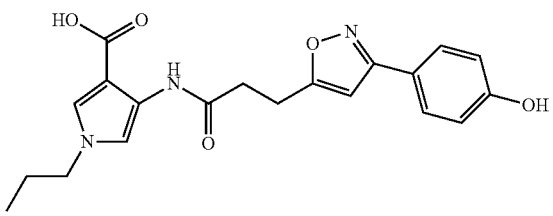 [SMILES: CCCn1cc(NC(=O)CCc2cc(-c3ccc(O)cc3)no2)c(C(=O)O)c1]

Reactions were carried out in the same manner as in Examples 12(a) and 12(b) using propylamine. Using the thus obtained compound and the compound obtained in Example 33(c), a reaction was carried out in the same manner as in Example (47), so as to obtain the title compound.

$^1$H NMR (400 MHz, DMSO-d$_6$): δ (ppm)=12.3 (1H, brs), 9.88 (1H, s), 9.40 (1H, s), 7.64 (2H, d, J=8.6 Hz), 7.30 (1H, d, J=2.4 Hz), 7.28 (1H, d, J=2.4 Hz), 6.86 (2H, d, J=8.6 Hz), 6.71 (1H, s), 3.84 (2H, t, J=7.0 Hz), 3.06 (2H, t, J=7.4 Hz), 2.83 (2H, t, J=7.4 Hz), 1.71-1.64 (2H, m), 0.79 (3H, t, J=7.2 Hz).

MS m/z: 384 (M+H)$^+$.

Example 62

4-{3-[3-(4-Hydroxyphenyl)isoxazol-5-yl]-2-fluoropropanoyl}amino-1-ethylpyrrole-3-carboxylic acid

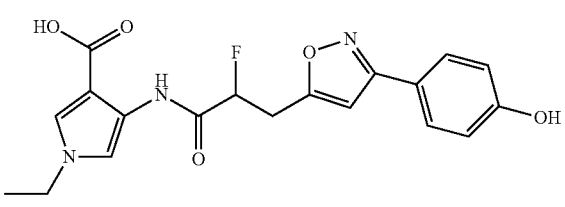 [SMILES: CCn1cc(NC(=O)C(F)Cc2cc(-c3ccc(O)cc3)no2)c(C(=O)O)c1]

(a) 3-[3-(4-Benzyloxyphenyl)isoxazol-5-yl]-2-fluoropropionic acid

Reactions were carried out in the same manner as in Examples 7(b) and 22(c) using the compound obtained in Example 41(a), so as to obtain the title compound.

$^1$H NMR (500 MHz, DMSO-d$_6$): δ (ppm)=7.78 (2H, d, J=8.8 Hz), 7.47 (2H, d, J=7.4 Hz), 7.40 (2H, dd, J=7.4, 7.4 Hz), 7.35 (1H, d, J=7.4 Hz), 7.14 (2H, d, J=8.8 Hz), 6.84 (1H, s), 5.43-5.31 (1H, m), 5.17 (2H, s), 3.51-3.31 (2H, m).

(b) 4-{3-[3-(4-Hydroxyphenyl)isoxazol-5-yl]-2-fluoropropanoyl}amino-1-ethylpyrrole-3-carboxylic acid Reactions were carried out in the same manner as in Examples 1(c) and 1(d) using the compound obtained in Example 62(a) and the compound obtained in Example 22(a), so as to obtain the title compound in the form of a powder.

$^1$H NMR (400 MHz, DMSO-$d_6$): δ (ppm)=12.4 (1H, brs), 10.1 (1H, brs), 9.91 (1H, s), 7.65 (2H, d, J=8.6 Hz), 7.40 (1H, d, J=2.3 Hz), 7.37 (1H, d, J=2.3 Hz), 6.86 (2H, d, J=8.6 Hz), 6.81 (1H, s), 5.68-5.54 (1H, m), 3.95 (2H, q, J=7.1 Hz), 3.60-3.40 (2H, m), 1.32 (3H, t, J=7.1 Hz).

MS m/z: 388 (M+H)$^+$.

Example 63

4-{3-[3-(4-Hydroxyphenyl)isoxazol-5-yl]-2,2-difluoropropanoyl}amino-1-ethylpyrrole-3-carboxylic acid

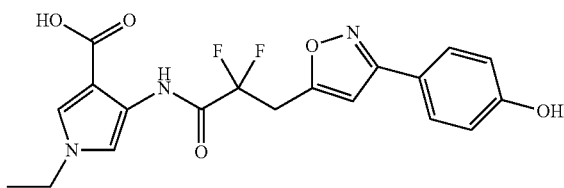 [SMILES: CCn1cc(NC(=O)C(F)(F)Cc2cc(-c3ccc(O)cc3)no2)c(C(=O)O)c1]

(a) 3-[3-(4-Benzyloxyphenyl)isoxazol-5-yl]-2,2-difluoropropionic acid

Reactions were carried out in the same manner as in Examples 41(b)-2 and 40(b) using the compound obtained in Example 41(a), so as to obtain the title compound.

$^1$H NMR (400 MHz, DMSO-$d_6$): δ (ppm)=7.80 (2H, d, J=8.6 Hz), 7.48 (2H, d, J=7.0 Hz), 7.42-7.39 (2H, m), 7.36 (1H, d, J=7.1 Hz), 7.14 (2H, d, J=8.6 Hz), 6.80 (1H, s), 5.18 (2H, s), 3.49 (2H, t, J=16.4 Hz).

(b) 4-{3-[3-(4-Hydroxyphenyl)isoxazol-5-yl]-2,2-difluoropropanoyl}amino-1-ethylpyrrole-3-carboxylic acid A reaction was carried out in the same manner as in Example 40(c) using the compound obtained in Example 63(a), so as to obtain the title compound in the form of a powder.

$^1$H NMR (400 MHz, DMSO-$d_6$): δ (ppm)=12.6 (1H, brs), 10.4 (1H, s), 9.93 (1H, s), 7.68 (2H, d, J=8.6 Hz), 7.43 (1H, d, J=2.4 Hz), 7.41 (1H, d, J=2.4 Hz), 6.92 (1H, s), 6.87 (2H, d, J=8.6 Hz), 3.97 (2H, q, J=7.3 Hz), 3.93 (2H, t, J=18.0 Hz), 1.32 (3H, t, J=7.2 Hz).

MS m/z: 406 (M+H)$^+$.

Example 64

4-{3-[5-(4-Hydroxyphenyl)isoxazol-3-yl]-2,2-difluoropropanoyl}amino-1-ethylpyrrole-3-carboxylic acid

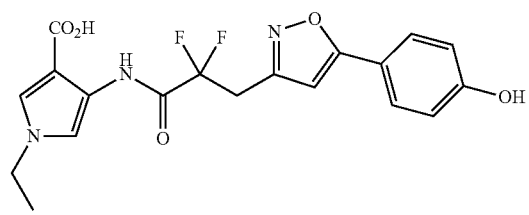 [SMILES: CCn1cc(NC(=O)C(F)(F)Cc2cc(-c3ccc(O)cc3)on2)c(C(=O)O)c1]

(a) 3-[5-(4-Hydroxyphenyl)isoxazol-3-yl]-2,2-difluoropropionic acid

Reactions were carried out in the same manner as in Examples 32(a) and 32(b) using 4-benzyloxyacetophenone to obtain bromomethylisoxazole. Using the thus obtained compound, a reaction was carried out in the same manner as in Example 39(a), so as to obtain the title compound in the form of a colorless powder.

$^1$H NMR (400 MHz, CDCl$_3$): δ (ppm)=7.71 (2H, d, J=9.0 Hz), 7.46-7.34 (5H, m), 7.05 (2H, d, J=9.0 Hz), 5.13 (1H, s), 3.59 (2H, t, J=15.6 Hz).

(b) 4-{3-[5-(4-Hydroxyphenyl)isoxazol-3-yl]-2,2-difluoropropanoyl}amino-1-ethylpyrrole-3-carboxylic acid A reaction was carried out in the same manner as in Example 40(c) using the compound obtained in Example 64(a), so as to obtain the title compound.

$^1$H NMR (400 MHz, DMSO-$d_6$): δ (ppm)=10.2 (1H, brs), 7.69 (2H, d, J=8.6 Hz), 7.34 (1H, brs), 7.27 (1H, brs), 6.89 (2H, d, J=9.0 Hz), 6.77 (1H, s), 3.93 (2H, q, J=5.5 Hz), 3.69 (2H, t, J=17.6 Hz), 1.32 (3H, t, J=7.2 Hz).

MS m/z: 406 (M+H)$^+$.

Example 65

4-{3-[4-Difluoromethyl-3-(4-hydroxyphenyl)isoxazol-5-yl]propanoyl}amino-1-ethylpyrrole-3-carboxylic acid

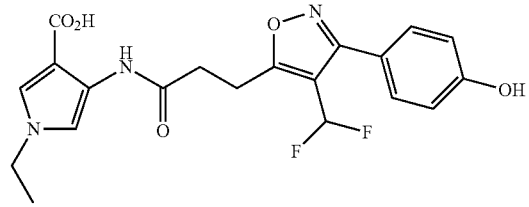 [SMILES: CCn1cc(NC(=O)CCc2onc(-c3ccc(O)cc3)c2C(F)F)c(C(=O)O)c1]

(a) 3-Tetrahydropyranyloxymethyl-5-(4-benzyloxyphenyl)isoxazol-4-carbaldehyde

Lithium aluminum hydride (0.66 g, 17.42 mmol) was added at 0° C. to a solution of the compound (6.05 g, 17.42 mmol) obtained in Example 60(a) in THF (90 mL). The temperature of the obtained mixture was raised to room temperature, and the mixture was then stirred for 15 minutes. Thereafter, water (0.66 mL), a 3 M-sodium hydroxide aqueous solution (0.66 mL), and water (1.98 mL) were successively added to the reaction solution at 0° C., and the obtained mixture was then stirred for 30 minutes. Thereafter, the reaction mixture was filtered with celite, and the filtrate was then concentrated. The residue was purified by silica gel column chromatography (hexane/ethyl acetate), so as to obtain an alcohol compound (4.04 g, yield: 73%) in the form of a colorless oily substance.

Thereafter, 1,1,1-tris(acetyloxy)-1,1-dihydro-1,2-benziodoxol-3-(1H)-one (Dess-Martin reagent; 1.64 g, 3.76 mmol) was added at 0° C. to a solution of the obtained alcohol compound (1.00 g, 3.13 mmol) in dichloromethane (20 mL). The temperature of the obtained mixture was raised to room temperature, and the mixture was then stirred for 4 hours. Thereafter, a 5% sodium thiosulfate aqueous solution was added to the reaction solution, and the mixture was then extracted with dichloromethane. The organic layer was washed with a saturated saline, and it was then dried over anhydrous sodium sulfate, followed by concentration. The obtained residue was purified by silica gel column chromatography (hexane/ethyl acetate), so as to obtain the title compound (0.84 g, 85%) in the form of a pale yellow oily substance.

$^1$H NMR (400 MHz, CDCl$_3$): δ (ppm)=10.1 (1H, s), 7.70 (2H, d, J=9.0 Hz), 7.04 (2H, d, J=9.0 Hz), 5.14 (1H, d, J=14.5 Hz), 4.98 (1H, d, J=14.4 Hz), 4.86 (1H, t, J=3.1 Hz), 3.93-3.87 (1H, m), 3.88 (3H, s), 3.62-3.57 (1H, m), 1.90-1.57 (8H, m).

(b) 4-Difluoromethyl-3-tetrahydropyranyloxymethyl-5-(4-benzyloxyphenyl)isoxazole Bis(methoxyethyl)aminosulfur trifluoride (Deoxofluor; 976 μL, 5.29 mmol) was added at 0° C. to a solution of the compound (840 mg, 2.65 mmol) obtained in Example 65(a) in dichloromethane (20 mL). The temperature of the obtained mixture was raised to room temperature, and the mixture was then stirred for 5 hours. Thereafter, the reaction solution was concentrated, and the residue was then purified by silica gel column chromatography (hexane/ethyl acetate), so as to obtain the title compound (701.3 mg, 78%) in the form of a yellow oily substance.

$^1$H NMR (400 MHz, CDCl$_3$): δ (ppm)=7.68 (2H, d, J=8.7 Hz), 7.01 (2H, d, J=8.7 Hz), 6.87 (1H, t, J=54.2 Hz), 4.96 (1H, d, J=13.7 Hz), 4.80 (1H, d, J=13.7 Hz), 4.80 (1H, t, J=3.1 Hz), 3.91-3.85 (1H, m), 3.87 (3H, s), 3.62-3.57 (1H, m), 1.88-1.55 (8H, m).

(c) 3-[4-Difluoromethyl-3-(4-hydroxyphenyl)isoxazol-5-yl]propionic acid

Reactions were carried out in the same manner as in Examples 59(b) and 59(c) using the compound obtained in Example 65(b), so as to obtain a carboxylic acid compound in the form of a colorless powder.

$^1$H NMR (400 MHz, CDCl$_3$): δ (ppm)=7.61 (2H, d, J=9.0 Hz), 7.01 (2H, d, J=9.0 Hz), 6.67 (1H, t, J=54.0 Hz), 3.87 (3H, s), 3.29 (2H, t, J=7.4 Hz), 2.90 (2H, t, J=7.4 Hz).

(d) 4-{3-[4-Difluoromethyl-3-(4-hydroxyphenyl)isoxazol-5-yl]propanoyl}amino-1-ethylpyrrole-3-carboxylic acid Reactions were carried out in the same manner as in Examples 22(e) and 22(f) using the compound obtained in Example 65(c), so as to obtain the title compound in the form of a colorless powder.

$^1$H NMR (400 MHz, DMSO-d$_6$): δ (ppm)=9.96 (1H, s), 9.38 (1H, brs), 7.52 (2H, d, J=8.6 Hz), 7.30 (2H, brs), 7.22 (1H, t, J=53.2 Hz), 3.91 (2H, q, J=7.3 Hz), 3.25 (2H, t, J=7.0 Hz), 2.86 (2H, t, J=7.0 Hz), 1.30 (3H, t, J=7.2 Hz).

MS m/z: 420 (M+H)$^+$.

Example 66

4-{3-[4-Ethyl-3-(5-hydroxypyridin-2-yl)isoxazol-5-yl]-2,2-difluoropropanoyl}amino-1-ethylpyrrole-3-carboxylic acid

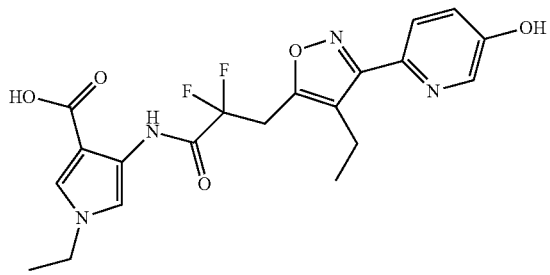 [SMILES: CCc1c(-c2ccc(O)cn2)noc1CC(F)(F)C(=O)Nc1cn(CC)cc1C(=O)O]

(a) 5-Benzyloxypyridin-2-carbaldehyde

5-Hydroxy-2-methylpyridine (10.20 g, 91.60 mmol) was dissolved in a mixture of acetone (160 mL) and water (60 mL). Sodium hydroxide (4.20 g, 100.76 mmol) and benzyl bromide (11.97 mL, 100.76 mmol) were added to the solution, and the obtained mixture was then stirred at 85° C. for 8 hours. Thereafter, the reaction solution was concentrated, and methylene chloride and water were added to the residue and the two layers were separated. The organic layer was dried over anhydrous sodium sulfate, and the solvent was then distilled away. The obtained residue was purified by silica gel column chromatography (hexane/ethyl acetate), so as to obtain a benzyl compound (14.80 g, yield: 81%) in the form of a yellow oily substance.

The obtained benzyl compound (14.80 g, 74.28 mmol) was dissolved in chloroform (150 mL), and 3-chloroperbenzoic acid (19.23 g, 111.42 mmol) was then added thereto under ice cooling. The reaction solution was stirred at room temperature for 2 hours. Thereafter, a 20% sodium sulfite aqueous solution (60 mL) was added to the reaction solution, and the obtained mixture was further stirred at room temperature for 20 minutes. The reaction solution was extracted with methylene chloride. The organic layer was dried over anhydrous sodium sulfate, and the solvent was then distilled away. The obtained residue was purified by NH column chromatography (methylene chloride/methanol). The obtained oxidized compound was dissolved in methylene chloride (200 mL), and trifluoroacetic anhydride (42 mL, 297.12 mmol) was then added to the solution under ice cooling. The obtained mixture was stirred at room temperature for 16 hours. Thereafter, methanol (100 mL) was added to the reaction solution, and the obtained mixture was then stirred at room temperature for 20 minutes, followed by concentration. Methylene chloride and a 5 N sodium hydroxide aqueous solution were added to the residue and the two layers were separated. The organic layer was dried over anhydrous sodium sulfate, and the solvent was then distilled away. The obtained residue was purified by NH column chromatography (methylene chloride/ methanol), so as to obtain an alcohol compound (10.80 g, yield in two steps: 68%) in the form of a pale brown solid.

The obtained alcohol compound (4.86 g, 22.58 mmol) was dissolved in chloroform (100 mL), and manganese dioxide (24 g) was then added to the solution. The obtained mixture was stirred at room temperature for 23 hours. Thereafter, the reaction solution was filtered with celite, and the solvent was then distilled away. The obtained residue was purified by silica gel column chromatography (hexane/ethyl acetate), so as to obtain the title compound (3.83 g, yield: 80%) in the form of a pale yellow solid.

$^1$H NMR (400 MHz, CDCl$_3$): δ (ppm)=10.0 (1H, s), 8.52 (1H, d, J=2.7 Hz), 7.97 (1H, d, J=8.6 Hz), 7.46-7.36 (6H, m), 5.22 (2H, s).

(b) 4-{3-[4-Ethyl-3-(5-hydroxypyridin-2-yl)isoxazol-5-yl]-2,2-difluoropropanoyl}amino-1-ethylpyrrole-3-carboxylic acid Reactions were carried out in the same manner as in Examples 22(b)-2 and 22(c) using the compound obtained in Example 66(a), so as to obtain a bromo compound. Using the obtained bromo compound, a reaction was carried out in the same manner as in Example 39, so as to obtain the title compound in the form of a pale yellow solid.

$^1$H NMR (400 MHz, MeOH-d$_4$): δ (ppm)=8.23 (1H, d, J=2.7 Hz), 7.70 (1H, d, J=8.6 Hz), 7.36 (1H, d, J=2.3 Hz), 7.27 (1H, dd, J=8.6, 2.7 Hz), 7.19 (1H, d, J=2.3 Hz), 3.95 (2H, q, J=7.4 Hz), 3.78 (2H, t, J=16.2 Hz), 2.75 (2H, q, J=7.6 Hz), 2.76 (3H, t, J=7.6 Hz), 1.02 (3H, t, J=7.4 Hz).

MS m/z: 435 (M+H)$^+$.

Example 67

Production of Potassium Salt

One equivalent amount of potassium t-butoxide was added to a solution of a carboxylic acid compound in methanol, and the obtained mixture was then stirred at room temperature for 30 minutes. Thereafter, the solvent was distilled away, and the residue was then washed with acetonitrile to obtain a potassium salt in the form of a solid.

(1) 4-{3-[(5-Hydroxypyridin-2-yl)-1,2,4-oxadiazol-5-yl]propanoyl}amino-1-methylpyrrole-3-carboxylic acid potassium salt (the potassium salt of the compound of Example 3)

$^1$H NMR (500 MHz, DMSO-d$_6$): δ (ppm)=11.6 (1H, brs), 8.14 (1H, s), 7.81 (1H, d, J=8.8 Hz), 7.24 (1H, brs), 6.95 (1H, d, J=2.4 Hz), 6.71 (1H, d, J=2.5 Hz), 3.50 (3H, s), 3.20 (2H, t, J=7.1 Hz), 2.86 (2H, t, J=7.1 Hz).

(2) 4-{3-[3-(4-Hydroxyphenyl)-1,2,4-oxadiazol-5-yl]propanoyl}amino-1-ethylpyrrole-3-carboxylic acid potassium salt (the potassium salt of the compound of Example 12)

$^1$H NMR (400 MHz, DMSO-d$_6$): δ (ppm)=11.9 (1H, brs), 7.82 (2H, d, J=8.6 Hz), 6.97 (1H, s), 6.91 (2H, d, J=8.6 Hz), 6.92 (1H, s), 3.77 (2H, q, J=7.2 Hz), 3.20 (2H, t, J=7.0 Hz), 2.84 (2H, t, J=7.0 Hz), 1.25 (3H, t, J=7.2 Hz).

(3) 4-{3-[2-(4-Hydroxyphenyl)thiazol-5-yl]propanoyl}amino-1-ethylpyrrole-3-carboxylic acid potassium salt (the potassium salt of the compound of Example 13)

$^1$H NMR (400 MHz, DMSO-d$_6$): δ (ppm)=11.8 (1H, brs), 10.9 (1H, brs), 7.67 (2H, d, J=8.6 Hz), 7.54 (1H, s), 7.04 (1H, d, J=2.7 Hz), 6.86 (2H, d, J=8.6 Hz), 6.74 (1H, d, J=2.7 Hz), 3.80 (2H, q, J=7.2 Hz), 3.13 (2H, t, J=7.4 Hz), 2.60 (2H, t, J=7.4 Hz), 1.27 (3H, t, J=7.2 Hz).

(4) 4-{3-[(5-Hydroxypyridin-2-yl)-1,2,4-oxadiazol-5-yl]propanoyl}amino-1-(3,5-difluorobenzyl)pyrrole-3-carboxylic acid potassium salt (the potassium salt of the compound of Example 15)

$^1$H NMR (400 MHz, DMSO-d$_6$): δ (ppm)=11.8 (1H, brs), 8.22 (1H, s), 7.88 (1H, d, J=9.0 Hz), 7.32 (1H, brs), 7.13 (1H, t, J=2.5 Hz), 7.06 (1H, s), 6.88 (3H, m), 5.01 (2H, s), 3.21 (2H, t, J=6.9 Hz), 2.87 (2H, t, J=6.9 Hz).

(5) 4-{3-[4-Chloro-2-(4-hydroxy-2,5-difluorophenyl)thiazol-5-yl]propanoyl}amino-1-ethylpyrrole-3-carboxylic acid potassium salt (the potassium salt of the compound of Example 20)

$^1$H NMR (400 MHz, DMSO-d$_6$): δ (ppm)=11.0 (1H, brs), 7.14 (1H, d, J=2.4 Hz), 6.93 (1H, d, J=2.8 Hz), 6.52 (2H, d, J=12.5 Hz), 3.84 (2H, q, J=7.3 Hz), 3.09 (2H, t, J=7.4 Hz), 2.66 (2H, t, J=7.4 Hz), 1.29 (3H, t, J=7.2 Hz).

(6) 4-{3-[4-Chloro-2-(2,4-dihydroxyphenyl)thiazol-5-yl]propanoyl}amino-1-ethylpyrrole-3-carboxylic acid potassium salt (the potassium salt of the compound of Example 21)

$^1$H NMR (400 MHz, DMSO-d$_6$): δ (ppm)=7.79 (1H, d, J=8.6 Hz), 7.10 (1H, brs), 6.86 (1H, brs), 6.48 (1H, brs), 6.23 (1H, d, J=8.6 Hz), 3.82 (2H, q, J=7.2 Hz), 3.04 (2H, t, J=7.4 Hz), 2.61 (2H, t, J=7.4 Hz), 1.28 (3H, t, J=7.2 Hz).

(7) 4-{3-[2-(4-Hydroxyphenyl)thiazol-5-yl]-2-fluoropropanoyl}amino-1-ethylpyrrole-3-carboxylic acid potassium salt (the potassium salt of the compound of Example 22)

$^1$H NMR (400 MHz, DMSO-d$_6$): δ (ppm)=7.69 (2H, d, J=8.0 Hz), 7.60 (1H, s), 7.12 (1H, s), 6.87 (2H, d, J=8.0 Hz), 6.78 (1H, brs), 5.37-5.25 (1H, m), 3.82 (2H, q, J=7.3 Hz), 3.59-3.39 (2H, m), 1.28 (3H, t, J=7.3 Hz).

(8) (−)-4-{3-[2-(4-Hydroxyphenyl)thiazol-5-yl]-2-fluoropropanoyl}amino-1-ethylpyrrole-3-carboxylic acid potassium salt (the potassium salt of the compound of Example 23(a))

$^1$H NMR (400 MHz, DMSO-d$_6$): it is identical to that of the compound of Example 64(7).

(9) (+)-4-{3-[2-(4-Hydroxyphenyl)thiazol-5-yl]-2-fluoropropanoyl}amino-1-ethylpyrrole-3-carboxylic acid potassium salt (the potassium salt of the compound of Example 23(b))

$^1$H NMR (400 MHz, DMSO-d$_6$): it is identical to that of the compound of Example 64(7).

(10) 4-{3-[3-(4-Hydroxyphenyl)-4-ethylisoxazol-5-yl]propanoyl}amino-1-ethylpyrrole-3-carboxylic acid potassium salt (the potassium salt of the compound of Example 25)

$^1$H NMR (400 MHz, DMSO-d$_6$): δ (ppm)=7.50 (2H, d, J=8.8 Hz), 7.04 (1H, br.s), 6.92 (2H, d, J=8.8 Hz), 6.79 (1H, br.s), 3.80 (2H, q, J=7.3 Hz), 2.92 (2H, t, J=7.3 Hz), 2.68 (2H, t, J=7.3 Hz), 2.56 (2H, q, J=7.3 Hz), 1.27 (3H, t, J=7.3 Hz), 1.14 (3H, t, J=7.3 Hz).

(11) 4-{3-[3-(4-Hydroxyphenyl)-4-cyclopropylisoxazol-5-yl]propanoyl}amino-1-ethylpyrrole-3-carboxylic acid potassium salt (the potassium salt of the compound of Example 31)

$^1$H NMR (400 MHz, DMSO-d$_6$): δ (ppm)=7.66 (2H, d, J=9.0 Hz), 7.03 (1H, br.s), 6.92 (2H, d, J=9.0 Hz), 6.75 (1H, br.s), 3.79 (2H, q, J=7.4 Hz), 2.99 (2H, t, J=7.4 Hz), 2.70 (2H, t, J=7.4 Hz), 1.73 (1H, m), 1.27 (3H, t, J=7.4 Hz), 0.93 (2H, m), 0.35 (2H, m).

(12) 4-{3-[3-(4-Hydroxyphenyl)-4-ethylisoxazol-5-yl]-2-fluoropropanoyl}amino-1-ethylpyrrole-3-carboxylic acid potassium salt (the potassium salt of the compound of Example 32)

¹H NMR (400 MHz, DMSO-d₆): δ (ppm)=12.31 (1H, br.s), 11.25 (1H, br.s), 7.50 (2H, d, J=9.0 Hz), 7.13 (1H, d, J=2.4 Hz), 6.95 (2H, d, J=9.0 Hz), 6.81 (1H, d, J=2.4 Hz), 5.36 (1H, ddd, J=3.1, 9.0 and 48.9 Hz), 3.84 (2H, q, J=7.4 Hz), 3.35 (1H, ddd, J=3.1, 16.0 and 34.4 Hz), 3.15 (1H, ddd, J=9.0, 16.0 and 19.2 Hz), 2.57 (2H, q, J=7.4 Hz), 1.29 (3H, t, J=7.4 Hz), 1.10 (3H, t, J=7.4 Hz).

(13) 4-{3-[4-Chloro-(4-hydroxyphenyl)isoxazol-5-yl]propanoyl}amino-1-ethylpyrrole-3-carboxylic acid potassium salt (the potassium salt of the compound of Example 33)

¹H NMR (400 MHz, DMSO-d₆): δ (ppm)=11.8 (1H, brs), 7.61 (2H, d, J=8.2 Hz), 6.99 (1H, s), 6.91 (2H, d, J=8.2 Hz), 6.71 (1H, s), 3.77 (2H, q, J=7.4 Hz), 3.10 (2H, t, J=7.4 Hz), 2.69 (2H, t, J=7.4 Hz), 1.25 (3H, t, J=7.4 Hz).

(14) 4-{5-[3-(4-Hydroxyphenyl)-4-chloroisoxazol-3-yl]propanoyl}amino-1-ethylpyrrole-3-carboxylic acid potassium salt (the potassium salt of the compound of Example 34)

¹H NMR (400 MHz, DMSO-d₆): δ (ppm)=11.97 (1H, br.s), 11.53 (1H, br.s), 7.79 (2H, d, J=8.8 Hz), 7.05 (1H, d, J=2.7 Hz), 7.00 (2H, d, J=8.8 Hz), 6.81 (1H, d, J=2.7 Hz), 3.81 (2H, q, J=7.3 Hz), 2.96 (2H, t, J=7.3 Hz), 2.72 (2H, t, J=7.3 Hz), 1.28 (3H, t, J=7.3 Hz).

(15) 4-{3-[4-Ethyl-(4-hydroxyphenyl)isoxazol-5-yl]propanoyl}amino-1-ethylpyrrole-3-carboxylic acid potassium salt (the potassium salt of the compound of Example 35)

¹H NMR (400 MHz, DMSO-d₆): δ (ppm)=11.9 (1H, brs), 7.38 (2H, d, J=8.2 Hz), 6.98 (1H, s), 6.82 (2H, d, J=8.2 Hz), 6.67 (1H, s), 3.76 (2H, q, J=7.4 Hz), 3.02 (2H, t, J=7.4 Hz), 2.59 (2H, t, J=7.4 Hz), 2.50-2.46 (2H, m), 1.24 (3H, t, J=7.4 Hz), 0.97 (3H, t, J=7.4 Hz).

(16) 4-{3-[3-(4-Hydroxyphenyl)-4-ethylisoxazol-5-yl]propanoyl}amino-1-methylpyrrole-3-carboxylic acid potassium salt (the potassium salt of the compound of Example 36)

¹H NMR (400 MHz, DMSO-d₆): δ (ppm)=11.68 (1H, br.s), 11.16 (1H, br.s), 7.50 (2H, d, J=9.0 Hz), 6.97 (1H, d, J=2.4 Hz), 6.95 (2H, d, J=9.0 Hz), 6.68 (1H, d, J=2.4 Hz), 3.51 (3H, s), 2.92 (2H, t, J=7.3 Hz), 2.68 (2H, t, J=7.3 Hz), 2.55 (2H, q, J=7.4 Hz), 1.13 (3H, t, J=7.4 Hz).

(17) 4-[3-{(4-Hydroxyphenyl)-4-methylisoxazol-5-yl}propanoyl]amino-1-ethylpyrrole-3-carboxylic acid potassium salt (the potassium salt of the compound of Example 38)

¹H NMR (400 MHz, DMSO-d₆): δ (ppm)=11.8 (1H, brs), 7.41 (2H, d, J=8.6 Hz), 6.99 (1H, d, J=2.4 Hz), 6.89 (2H, d, J=8.6 Hz), 6.69 (1H, d, J=2.4 Hz), 3.77 (2H, q, J=7.4 Hz), 3.01 (2H, t, J=7.4 Hz), 2.58 (2H, t, J=7.4 Hz), 2.01 (3H, s), 1.25 (3H, t, J=7.4 Hz).

(18) 4-{3-[2-(4-Hydroxyphenyl)thiazol-5-yl]-2,2-difluoropropanoyl}amino-1-ethylpyrrole-3-carboxylic acid potassium salt (the potassium salt of the compound of Example 39)

¹H NMR (400 MHz, DMSO-d₆): δ (ppm)=13.33 (1H, br.s), 10.46 (1H, br.s), 7.72 (2H, d, J=8.6 Hz), 7.66 (1H, s), 7.09 (1H, d, J=2.4 Hz), 6.85 (2H, d, J=8.6 Hz), 6.78 (1H, d, J=2.4 Hz), 3.83 (2H, q, J=7.0 Hz), 3.79 (2H, t, J=16.8 Hz), 1.29 (3H, t, J=7.0 Hz).

(19) 4-{3-[4-Ethyl-3-(4-hydroxyphenyl)isoxazol-5-yl]-2,2-difluoropropanoyl}amino-1-ethylpyrrole-3-carboxylic acid potassium salt (the potassium salt of the compound of Example 40)

¹H NMR (400 MHz, DMSO-d₆): δ (ppm)=10.3 (1H, brs), 7.54 (2H, d, J=8.6 Hz), 7.11 (1H, brs), 6.93 (2H, d, J=8.6 Hz), 6.83 (1H, brs), 3.85 (2H, q, J=7.2 Hz), 3.62 (2H, t, J=18.2 Hz), 2.60 (2H, q, J=7.2 Hz), 1.29 (3H, t, J=7.2 Hz), 1.11 (3H, t, J=7.2 Hz).

(20) 4-{3-[4-Ethyl-5-(4-hydroxyphenyl)isoxazol-3-yl]-2,2-difluoropropanoyl}amino-1-ethylpyrrole-3-carboxylic acid potassium salt (the potassium salt of the compound of Example 41)

¹H NMR (400 MHz, DMSO-d₆): δ (ppm)=13.4 (1H, brs), 10.2 (1H, brs), 7.47 (2H, d, J=8.6 Hz), 7.11 (1H, d, J=2.3 Hz), 6.90 (2H, d, J=8.6 Hz), 6.81 (1H, d, J=2.3 Hz), 3.85 (2H, q, J=7.4 Hz), 3.78 (2H, t, J=17.0 Hz), 2.55 (2H, q, J=7.4 Hz), 1.29 (3H, t, J=7.4 Hz), 0.95 (3H, t, J=7.4 Hz).

(21) 4-{3-[4-Chloro-5-(4-hydroxyphenyl)isoxazol-3-yl]-2,2-difluoropropanoyl}amino-1-ethylpyrrole-3-carboxylic acid potassium salt (the potassium salt of the compound of Example 42)

¹H NMR (500 MHz, CDCl₃): δ (ppm)=13.4 (1H, brs), 10.5 (1H, brs), 7.66 (2H, d, J=8.8 Hz), 7.11 (1H, d, J=2.4 Hz), 6.94 (2H, d, J=8.8 Hz), 6.83 (1H, d, J=2.4 Hz), 3.88 (2H, t, J=17.4 Hz), 3.85 (2H, q, J=7.3 Hz), 1.29 (3H, t, J=7.3 Hz).

(22) 4-{3-[4-Chloro-3-(4-hydroxy-2-fluorophenyl)isoxazol-5-yl]propanoyl}amino-1-ethylpyrrole-3-carboxylic acid potassium salt (the potassium salt of the compound of Example 43)

¹H NMR (400 MHz, DMSO-d₆): δ (ppm)=11.6 (1H, brs), 7.32 (1H, t, J=8.8 Hz), 7.05 (1H, d, J=2.0 Hz), 6.80-6.75 (3H, m), 3.81 (2H, q, J=7.3 Hz), 3.14 (2H, t, J=7.4 Hz), 2.72 (2H, t, J=7.4 Hz), 1.28 (3H, t, J=7.2 Hz).

(23) 4-[3-{3-(4-Hydroxyphenyl)isoxazol-5-yl}propanoyl]amino-1-ethylpyrrole-3-carboxylic acid potassium salt (the potassium salt of the compound of Example 44)

¹H NMR (400 MHz, DMSO-d₆): δ (ppm)=11.8 (1H, brs), 7.62 (2H, d, J=8.6 Hz), 7.02 (1H, s), 6.88 (2H, d, J=8.6 Hz), 6.73 (1H, d, J=2.3 Hz), 6.70 (1H, s), 3.79 (2H, q, J=7.4 Hz), 3.05 (2H, t, J=7.4 Hz), 2.68 (2H, t, J=7.4 Hz), 1.27 (3H, t, J=7.4 Hz).

(24) 4-{3-[4-Ethyl-3-(4-hydroxy-2-fluorophenyl)isoxazol-5-yl]propanoyl}amino-1-ethylpyrrole-3-carboxylic acid potassium salt (the potassium salt of the compound of Example 45)

¹H NMR (400 MHz, DMSO-d₆): δ (ppm)=11.8 (1H, brs), 7.19 (1H, t, J=8.8 Hz), 7.04 (1H, s), 6.76 (1H, s), 6.68 (2H, d, J=8.6 Hz), 3.80 (2H, q, J=7.4 Hz), 3.06 (2H, t, J=7.4 Hz), 2.62 (2H, t, J=7.4 Hz), 2.33 (2H, q, J=7.6 Hz), 1.27 (3H, t, J=7.4 Hz), 0.90 (3H, t, J=7.6 Hz).

(25) 4-{3-[4-Chloro-5-(4-hydroxyphenyl)isoxazol-3-yl]-2-fluoropropanoyl}amino-1-ethylpyrrole-3-carboxylic acid potassium salt (the potassium salt of the compound of Example 46)

¹H NMR (500 MHz, DMSO-d₆): δ (ppm)=12.4 (1H, brs), 11.2 (1H, brs), 7.64 (2H, d, J=8.8 Hz), 7.12 (1H, d, J=2.4 Hz), 6.94 (2H, d, J=8.8 Hz), 6.80 (1H, d, J=2.4 Hz), 5.46 (1H, ddd, 3.6, 8.6 and 48.3 Hz), 3.83 (2H, q, J=7.4 Hz), 3.56 (1H, ddd, J=3.6, 15.9 and 30.3 Hz), 3.43 (1H, ddd, 8.6, 15.9 and 20.5 Hz), 1.29 (3H, t, J=7.4 Hz).

(26) 4-{3-[3-(4-Hydroxyphenyl)isoxazol-5-yl]propanoyl}amino-1-butylpyrrole-3-carboxylic acid potassium salt (the potassium salt of the compound of Example 47)

¹H NMR (400 MHz, DMSO-d₆): δ (ppm)=11.9 (1H, brs), 7.62 (2H, d, J=8.2 Hz), 6.98 (1H, d, J=2.3 Hz), 6.85 (2H, d, J=8.2 Hz), 6.69 (1H, s), 6.68 (1H, d, J=2.3 Hz), 3.74 (2H, t, J=6.9 Hz), 3.05 (2H, t, J=7.6 Hz), 2.68 (2H, t, J=7.6 Hz), 1.64-1.57 (2H, m), 1.22-1.17 (2H, m), 0.86 (3H, t, J=7.4 Hz).

(27) 4-{3-[4-Trifluoromethyl-5-(4-hydroxyphenyl)isoxazol-3-yl]propanoyl}amino-1-ethylpyrrole-3-carboxylic acid potassium salt (the potassium salt of the compound of Example 53)

$^1$H NMR (500 MHz, DMSO-d$_6$): δ (ppm)=11.6 (1H, brs), 7.55 (2H, d, J=8.8 Hz), 7.04 (1H, d, J=2.4 Hz), 6.99 (2H, d, J=8.8 Hz), 6.79 (1H, d, J=2.4 Hz), 3.81 (2H, q, J=7.3 Hz), 3.08 (2H, t, J=7.6 Hz), 2.75 (2H, t, J=7.6 Hz), 1.28 (3H, t, J=7.3 Hz).

(28) 4-{3-[4-Acetyl-5-(4-hydroxyphenyl)isoxazol-3-yl]propanoyl}amino-1-ethylpyrrole-3-carboxylic acid potassium salt (the potassium salt of the compound of Example 59)

$^1$H NMR (500 MHz, DMSO-d$_6$): δ (ppm)=11.9 (1H, s), 7.32 (2H, d, J=8.3 Hz), 6.99 (1H, d, J=2.5 Hz), 6.84 (2H, d, J=8.3 Hz), 6.70 (1H, d, J=2.5 Hz), 3.78 (2H, q, J=7.1 Hz), 3.31 (2H, t, J=7.6 Hz), 2.71 (2H, t, J=7.6 Hz), 2.16 (3H, s), 1.26 (3H, t, J=7.1 Hz).

(29) 4-{3-[4-Cyano-5-(4-hydroxyphenyl)isoxazol-3-yl]propanoyl}amino-1-ethylpyrrole-3-carboxylic acid potassium salt (the potassium salt of the compound of Example 60)

$^1$H NMR (400 MHz, DMSO-d$_6$): δ (ppm)=11.8 (1H, brs), 11.0 (1H, brs), 7.70 (2H, d, J=9.0 Hz), 7.01 (1H, d, J=2.4 Hz), 6.98 (2H, d, J=9.0 Hz), 6.75 (1H, d, J=2.4 Hz), 3.79 (2H, q, J=7.3 Hz), 3.29 (2H, t, J=7.2 Hz), 3.29 (2H, t, J=7.2 Hz), 3.29 (3H, t, J=7.2 Hz).

(30) 4-{3-[3-(4-Hydroxyphenyl)isoxazol-5-yl]propanoyl}amino-1-propylpyrrole-3-carboxylic acid potassium salt (the potassium salt of the compound of Example 61)

$^1$H NMR (400 MHz, DMSO-d$_6$): δ (ppm)=11.9 (1H, brs), 7.61 (2H, d, J=8.6 Hz), 6.99 (1H, d, J=2.3 Hz), 6.84 (2H, d, J=8.6 Hz), 6.69 (2H, s), 3.71 (2H, t, J=6.9 Hz), 3.05 (2H, t, J=7.6 Hz), 2.68 (2H, t, J=7.6 Hz), 1.69-1.60 (2H, m), 0.79 (3H, t, J=7.4 Hz).

(31) 4-{3-[3-(4-Hydroxyphenyl)isoxazol-5-yl]-2-fluoropropanoyl}amino-1-ethylpyrrole-3-carboxylic acid potassium salt (the potassium salt of the compound of Example 62)

$^1$H NMR (400 MHz, DMSO-d$_6$): δ (ppm)=12.5 (1H, brs), 7.63 (2H, d, J=8.6 Hz), 7.11 (1H, s), 6.86 (2H, d, J=8.6 Hz), 6.81 (1H, s), 6.77 (1H, s), 5.50-5.35 (1H, m), 3.82 (2H, q, J=7.2 Hz), 3.55-3.34 (2H, m), 1.29 (3H, t, J=7.2 Hz).

(32) 4-{3-[3-(4-Hydroxyphenyl)isoxazol-5-yl]-2,2-difluoropropanoyl}amino-1-ethylpyrrole-3-carboxylic acid potassium salt (the potassium salt of the compound of Example 63)

$^1$H NMR (400 MHz, DMSO-d$_6$): δ (ppm)=13.5 (1H, brs), 7.67 (2H, d, J=7.9 Hz), 7.10 (1H, s), 6.89 (1H, s), 6.88 (1H, s), 6.87 (2H, d, J=7.9 Hz), 6.79 (1H, s), 3.84 (2H, q, J=7.4 Hz), 3.82 (2H, t, J=13.3 Hz), 1.29 (3H, t, J=7.4 Hz).

(33) 4-{3-[5-(4-Hydroxyphenyl)isoxazol-3-yl]-2,2-difluoropropanoyl}amino-1-ethylpyrrole-3-carboxylic acid potassium salt (the potassium salt of the compound of Example 64)

$^1$H NMR (400 MHz, DMSO-d$_6$): δ (ppm)=13.4 (1H, brs), 7.56 (2H, d, J=8.6 Hz), 7.11 (1H, d, J=2.7 Hz), 6.80 (1H, d, J=2.7 Hz), 6.71 (2H, d, J=8.6 Hz), 3.84 (2H, q, J=7.5 Hz), 3.58 (2H, t, J=17.6 Hz), 1.29 (3H, t, J=7.5 Hz).

(34) 4-{3-[4-Difluoromethyl-3-(4-hydroxyphenyl)isoxazol-5-yl]propanoyl}amino-1-ethylpyrrole-3-carboxylic acid potassium salt (the potassium salt of the compound of Example 65)

$^1$H NMR (400 MHz, DMSO-d$_6$): δ (ppm)=11.8 (1H, brs), 10.7 (1H, brs), 7.51 (2H, d, J=8.6 Hz), 7.22 (1H, t, J=53.4 Hz), 7.02 (1H, d, J=2.3 Hz), 6.91 (2H, d, J=8.6 Hz), 6.75 (1H, d, J=2.3 Hz), 3.80 (2H, q, J=7.1 Hz), 3.25 (2H, t, J=7.2 Hz), 2.71 (2H, t, J=7.4 Hz), 1.27 (3H, t, J=7.2 Hz).

(35) 4-{3-[4-Ethyl-3-(5-hydroxypyridin-2-yl)isoxazol-5-yl]-2,2-difluoropropanoyl}amino-1-ethylpyrrole-3-carboxylic acid potassium salt (the potassium salt of the compound of Example 66)

$^1$H NMR (400 MHz, MeOH-d$_4$): δ (ppm)=8.07 (1H, s), 7.52 (1H, d, J=8.6 Hz), 7.30 (1H, d, J=2.3 Hz), 7.09 (1H, d, J=2.3 Hz), 7.08 (1H, d, J=8.6 Hz), 3.93 (2H, q, J=7.5 Hz), 3.75 (2H, t, J=16.4 Hz), 2.72 (2H, q, J=7.5 Hz), 1.40 (3H, t, J=7.5 Hz), 0.98 (3H, t, J=7.5 Hz).

Test Example 1

Adipocyte Lipolysis Assay

The suppressive or promoting activity of a test compound on the lipolysis of neutral fat can be assayed according to an adipocyte lipolysis assay as a cell line assay. If a beta adrenoceptor is stimulated with isoproterenol or the like in adipocytes, lipolysis action in which neutral fat accumulated in the cells is decomposed into fatty acid and glycerol can be promoted, and as a result, the amount of such fatty acid or glycerol released out of the cells can be increased. When a test compound that suppresses lipolysis is added to adipocytes, lipolysis-promoting action by isoproterenol stimulation is reduced, and the concentration of fatty acid or glycerol in a medium is decreased. Accordingly, the suppressive activity of a test compound on lipolysis can be assayed by measuring the reduction percentage of the fatty acid concentration or glycerol concentration in a culture supernatant. Likewise, the promoting activity of a test compound on lipolysis can be assayed by measuring the increase percentage of the fatty acid concentration or glycerol concentration in a medium.

[1] Substances Used (1) Human subcutaneous adipocytes disseminated onto a 96 well (Dainippon Sumitomo Pharma Co., Ltd.: F-SA-1096)
(2) Adipocyte Maintenance Medium (Dainippon Sumitomo Pharma Co., Ltd.: AM 1)
(3) Lipolysis assay buffer [137 mM NaCl, 5 mM KCl, 4.2 mM NaHCO$_3$, 1.3 mM CaCl$_2$, 0.5 mM KH$_2$PO$_4$, 0.5 mM MgCl$_2$, 0.5 mM MgSO$_4$, 5 mM Glucose, 20 mM Hepes (pH 7.4), 1% BSA, 1 μM Isoproterenol]
(4) NEFA-C Test Wako (Wako Pure Chemical Industries, Ltd.)

[2] Preparation of Screening Materials

1 μL each of a test compound prepared with DMSO was added to a lipolysis assay buffer that had previously been heated to 37° C., so that it resulted in a concentration of 100 mM, 10 mM, 1 mM, 0.1 mM, 0.01 mM, or 0 mM. In this operation, the actual concentration of the test compound in the buffer was 1/1000 of the above-described concentration.

The above-described subcutaneous adipocytes were cultured in 200 μL of an Adipocyte Maintenance Medium in each well for 7 days. During this culturing operation, the medium was exchanged with a fresh one every 3 days. The medium was exchanged by discarding 100 μL of the medium in each well and then adding 100 μL of a fresh Adipocyte Maintenance Medium to the well. Thereafter, the adipocytes were washed with a Lipolysis assay buffer. Subsequently, 50 μL of a Lipolysis assay buffer that contained the above-described test compound was added to each well, and it was then incubated for 5 hours. In order to obtain the measurement value of the test compound in each concentration, 5 wells on a 96-well plate were used with respect to each concentration. As a positive control of a compound having lipolysis suppressive activity, nicotinic acid was used with reference to a previous report [Green A et. al., J. Biol. Chem., 1992, 267(5), 3223-9].

[3] Measurement Procedures

40 µL of a culture supernatant was extracted from each well, and the fatty acid concentration in the supernatant was then measured. Such fatty acid concentration was measured as follows, using the above-described NEFA-C Test Wako. 80 µL of liquid A included in the kit was added to 40 µL of the culture supernatant extracted from each well, and the obtained mixture was then incubated at 37° C. for 10 minutes. Thereafter, 160 µL of liquid B was added, and the obtained mixture was further incubated at 37° C. for 10 minutes. Thereafter, the absorbance at a wavelength of 550 nM was measured. At the same time, a standard fatty acid solution included in the kit was diluted to prepare a dilution series having a volume of 40 µL. According to the same operations as described above, liquid A and liquid B were added, and the absorbance was then measured. In accordance with instructions included with the kit, a calibration curve was prepared. Based on the thus prepared calibration curve, the fatty acid concentration in the culture supernatant was calculated. The reduction percentage of the fatty acid concentration was calculated with the following formula, setting the reduction percentage obtained by addition of 100 µM (final concentration) of nicotinic acid at 100%.

Fatty acid concentration reduction percentage (%)= [(Fatty acid concentration of test compound addition group−fatty acid concentration of nicotinic acid addition group)/(fatty acid concentration of control group−fatty acid concentration of nicotinic acid addition group)]×100

The obtained fatty acid concentration reduction percentage was fitted to a four-parameter logistic model (referring to XLfit 4.1: CTC Laboratories Systems) as shown in the following formula. Based on the obtained fitting formula, an $IC_{50}$ value was calculated as a test compound concentration that gives 50% of fatty acid concentration reduction percentage.

$$Y=((A-D)/(1+(x/c)^B))+D$$

[4] Results

The test results of the Example compounds are shown in Table 1.

TABLE 1

| Example No. | $IC_{50}$ (nM) |
|---|---|
| 1 | 1100 |
| 2 | 535 |
| 3 | 7 |
| 4 | 232 |
| 5 | 663 |
| 6 | 24 |
| 7 | 1500 |
| 8 | 76 |
| 9 | 125 |
| 10 | 151 |
| 11 | 88 |
| 12 | 29 |
| 13 | 40 |
| 14 | 255 |
| 15 | 2 |
| 16 | 29 |
| 17 | 49 |
| 18 | 9 |
| 19 | 93 |
| 20 | 30 |
| 21 | 41 |
| 22 | 29 |
| 23a | 15 |

TABLE 1-continued

| Example No. | $IC_{50}$ (nM) |
|---|---|
| 23b | 103 |
| 24 | 20 |
| 25 | 31 |
| 26 | 10 |
| 27 | 36 |
| 28 | 19 |
| 29 | 42 |
| 30 | 42 |
| 31 | 50 |
| 32 | 41 |
| 33 | 7 |
| 34 | 20 |
| 35 | 8 |
| 36 | 12 |
| 37 | 13 |
| 38 | 4 |
| 39 | 40 |
| 40 | 9 |
| 41 | 9 |
| 42 | 13 |
| 43 | 7 |
| 44 | 8 |
| 45 | 9 |
| 46 | 9 |
| 47 | 8 |
| 48 | 1000 |
| 49 | 135 |
| 50 | 823 |
| 51 | 264 |
| 52 | 771 |
| 53 | 138 |
| 54 | 228 |
| 55 | 10 |
| 56 | 101 |
| 57 | 161 |
| 58 | 72 |
| 59 | 5 |
| 60 | 9 |
| 61 | 22 |
| 62 | 28 |
| 63 | 13 |
| 64 | 29 |
| 65 | 18 |
| 66 | 10 |

The compound of the present invention has excellent lipolysis-suppressive activity, and it is useful as a pharmaceutical agent for the treatment or prophylaxis of hyperlipidemia, dyslipidemia, lipid metabolism abnormality, arteriosclerosis, type II diabetes mellitus, and the like.

Formulation Example 1

A tablet was produced according to a well known method using the compound of each example (10 mg), colloidal silica dioxide (0.2 mg), magnesium stearate (5 mg), microcrystalline cellulose (175 mg), starch (10 mg), and lactose (98.8 mg). The obtained tablet may be coated, as necessary.

INDUSTRIAL APPLICABILITY

The compound represented by general formula (I) of the present invention or a pharmacologically acceptable salt thereof has excellent properties such as lipolysis-suppressive activity, blood lipid level-regulating action (for example, reducing action on the level of NEFA or TG), in vivo activity, solubility, oral absorption property, metabolic stability, blood concentration, bioavailability (BA), tissue transitivity, physical stability, drug interaction, and safety [for example, flushing]; and it is useful as a pharmaceutical agent, preferably a pharmaceutical agent for treatment and prophylaxis of dyslipidemia with low HDL cholesterol, hypercholesterolemia, dyslipidemia with high LDL cholesterol, dyslipidemia with high VLDL cholesterol, dyslipidemia with high triglyceride (hypertriglyceridemia), hyperlipidemia, dyslipidemia, lipid metabolism abnormality, arteriosclerosis, type I diabetes mellitus, type II diabetes mellitus, insulin resistance, cardiac failure, myocardial infarction, cardiovascular disease, apoplectic stroke, adiposity, angina, chronic renal failure, peripheral vascular disorder, non-alcoholic steatohepatitis, anorexia nervosa, metabolic syndrome, Alzheimer's disease, schizophrenia, or amyotrophic lateral sclerosis or for reduction in event occurrence or mortality due to cardiovascular disease or coronary heart disease, more preferably a pharmaceutical agent for the treatment and prophylaxis of hyperlipidemia, dyslipidemia, lipid metabolism abnormality, arteriosclerosis, or type II diabetes mellitus, and even more preferably a pharmaceutical agent for the treatment and prophylaxis of (preferably, treatment) of dyslipidemia or lipid metabolism abnormality.

The invention claimed is:

1. A compound represented by the following general formula (I) or a pharmacologically acceptable salt thereof

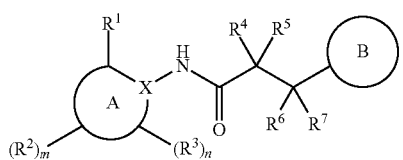

(I)

wherein A including X represents a pyrrolyl group, and X represents a carbon atom; or A including X represents a pyrazolyl group,
$R^1$ represents a carboxy group, a carboxymethyl group, or a tetrazolyl group,
each $R^2$ independently represents a group selected from substituent group α,
each $R^3$ independently represents a phenyl group, a substituted phenyl group (wherein the substituent(s) represent 1 to 4 groups independently selected from substituent group α), a 5- or 6-membered aromatic heterocyclyl group, a substituted 5- or 6-membered aromatic heterocyclyl group (wherein the substituent (s) represent 1 to 4 groups independently selected from substituent group α), a phenyl($C_1$-$C_6$ alkyl) group, a substituted phenyl($C_1$-$C_6$ alkyl) group (wherein the substituent(s) represent 1 to 4 groups independently selected from substituent group α), a 5- or 6-membered aromatic heterocyclyl($C_1$-$C_6$ alkyl) group, or a substituted 5- or 6-membered aromatic heterocyclyl($C_1$-$C_6$ alkyl) group (wherein the substituent(s) represent 1 to 4 groups independently selected from substituent group α),
m represents 0, 1, 2, or 3,
n represents 0 or 1, provided that when m is 3, n is 0,
each of $R^4$, $R^5$, $R^6$, and $R^7$ independently represents a hydrogen atom, a $C_1$-$C_6$ alkyl group, a halogeno($C_1$-$C_6$ alkyl) group, a hydroxy group, a $C_1$-$C_6$ alkoxy group, or a halogeno group,
B represents a naphthyl group, a substituted naphthyl group (wherein the substituent(s) represent 1 to 4 groups independently selected from substituent group α), a 9- or 10-membered aromatic heterocyclyl group, a substituted 9- or 10-membered aromatic heterocyclyl group (wherein the substituent(s) represent 1 to 4 groups independently selected from substituent group α), or a group represented by the following formula (II)

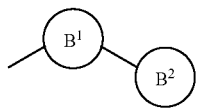

(II)

wherein each of $B^1$ and $B^2$ independently represents a phenyl group, a substituted phenyl group (wherein the substituent(s) represent 1 to 4 groups independently selected from substituent group α), a 5- or 6-membered aromatic heterocyclyl group, or a substituted 5- or 6-membered aromatic heterocyclyl group (wherein the substituent(s) represent 1 to 4 groups independently selected from substituent group α),
and
substituent group α represents the group consisting of a $C_1$-$C_6$ alkyl group, a hydroxy($C_1$-$C_6$ alkyl) group, a ($C_1$-$C_6$ alkoxy)-($C_1$-$C_6$ alkyl) group, a halogeno($C_1$-$C_6$ alkyl) group, a ($C_3$-$C_8$ cycloalkyl)-($C_1$-$C_6$ alkyl) group, a $C_3$-$C_8$ cycloalkyl group, a $C_2$-$C_6$ alkenyl group, a $C_2$-$C_6$ alkynyl group, a hydroxy group, a $C_1$-$C_6$ alkoxy group, a halogeno($C_1$-$C_6$ alkoxy) group, a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group, a formylamino group, a ($C_1$-$C_6$ alkyl)carbonylamino group, a ($C_1$-$C_6$ alkoxy)carbonylamino group, a ($C_1$-$C_6$ alkyl)sulfonylamino group, a formyl group, a ($C_1$-$C_6$ alkyl)carbonyl group, a carboxy group, a ($C_1$-$C_6$ alkoxy)carbonyl group, a carbamoyl group, a ($C_1$-$C_6$ alkylamino)carbonyl group, a di($C_1$-$C_6$ alkyl)aminocarbonyl group, an aminosulfonyl group, a ($C_1$-$C_6$ alkylamino)sulfonyl group, a di($C_1$-$C_6$ alkyl)aminosulfonyl group, a cyano group, a nitro group, and a halogeno group.

2. The compound according to claim 1 or a pharmacologically acceptable salt thereof, wherein A is a pyrrolyl group and X is a carbon atom.

3. The compound according to claim 1 or a pharmacologically acceptable salt thereof, which is represented by the following general formula (I-1)

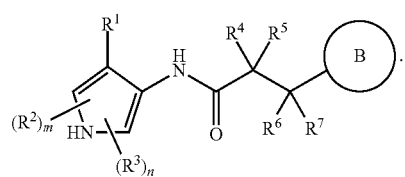

(I-1)

4. The compound according to claim 1 or a pharmacologically acceptable salt thereof, which is represented by the following general formula (I-3):

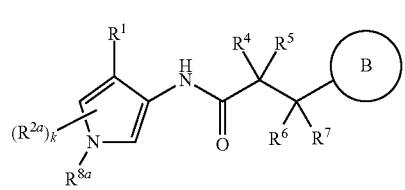

(I-3)

wherein $R^{8a}$ represents a hydrogen atom, a $C_1$-$C_6$ alkyl group, a hydroxy($C_1$-$C_6$ alkyl) group, a ($C_1$-$C_6$ alkoxy)-($C_1$-$C_6$ alkyl) group, a halogeno($C_1$-$C_6$ alkyl) group, a ($C_3$-$C_8$ cycloalkyl)-($C_1$-$C_6$ alkyl) group, a $C_3$-$C_8$ cycloalkyl group, a $C_2$-$C_6$ alkenyl group, a $C_2$-$C_6$ alkynyl group, a $C_1$-$C_6$ alkylsulfonyl group, a formyl group, a ($C_1$-$C_6$ alkyl)carbonyl group, a ($C_1$-$C_6$ alkoxy)carbonyl group, a carbamoyl group, a ($C_1$-$C_6$ alkylamino)carbonyl group, a di($C_1$-$C_6$ alkyl)aminocarbonyl group, an aminosulfonyl group, a ($C_1$-$C_6$ alkylamino)sulfonyl group, or a di($C_1$-$C_6$ alkyl)aminosulfonyl group, each $R^{2a}$ independently represents a $C_1$-$C_4$ alkyl group, a halogeno($C_1$-$C_4$ alkyl) group, a ($C_3$-$C_6$ cycloalkyl)-($C_1$-$C_4$ alkyl) group, a $C_3$-$C_6$ cycloalkyl group, a $C_2$-$C_4$ alkenyl group, a $C_2$-$C_4$ alkynyl group, a hydroxy group, a $C_1$-$C_4$ alkoxy group, a formyl group, a ($C_1$-$C_4$ alkyl)carbonyl group, a cyano group, or a halogeno group, and k represents 0, 1, or 2.

5. The compound according to claim 4 or a pharmacologically acceptable salt thereof, wherein $R^{8a}$ represents a hydrogen atom, a $C_1$-$C_4$ alkyl group, a ($C_1$-$C_2$ alkoxy)-($C_1$-$C_4$ alkyl) group, a ($C_3$-$C_6$ cycloalkyl)-($C_1$-$C_4$ alkyl) group, a halogeno($C_1$-$C_4$ alkyl) group, a $C_3$-$C_6$ cycloalkyl group, a $C_2$-$C_4$ alkenyl group, or a $C_2$-$C_4$ alkynyl group, each $R^{2a}$ represents a $C_1$-$C_2$ alkyl group, a halogeno($C_1$-$C_2$ alkyl) group (wherein the halogeno group represent 1 to 5 groups selected from the group consisting of a fluoro group and a chloro group), a $C_3$-$C_4$ cycloalkyl group, a cyano group, a fluoro group, or a chloro group, and k represents 0 or 1.

6. The compound according to claim 4 or a pharmacologically acceptable salt thereof, wherein $R^{8a}$ represents a $C_1$-$C_4$ alkyl group, and k represents 0.

7. The compound according to claim 4 or a pharmacologically acceptable salt thereof, wherein $R^{8a}$ represents an ethyl group, and k represents 0.

8. The compound according to claim 1 or a pharmacologically acceptable salt thereof, which is represented by the following general formula (I-4)

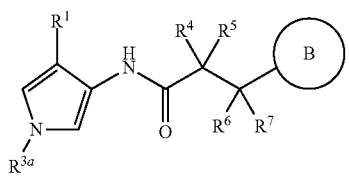

(I-4)

wherein $R^{3a}$ represents a phenyl($C_1$-$C_2$ alkyl) group or a substituted phenyl($C_1$-$C_2$ alkyl) group (wherein the substituent(s) represent 1 to 3 groups independently selected from substituent group α1), and substituent group α1 represents the group consisting of a $C_1$-$C_2$ alkyl group, a halogeno($C_1$-$C_2$ alkyl) group (wherein the halogeno group(s) represent 1 to 5 groups selected from the group consisting of a fluoro group and a chloro group), a fluoro group, and a chloro group.

9. The compound according to claim 8 or a pharmacologically acceptable salt thereof, wherein $R^{3a}$ represents a phenylmethyl group or a substituted phenylmethyl group (wherein the substituent(s) represent 1 to 3 groups independently selected from substituent group α2), and substituent group α2 represents the group consisting of a methyl group, a trifluoromethyl group, and a fluoro group.

10. The compound according to claim 1 or a pharmacologically acceptable salt thereof, which is represented by the following general formula (I-2)

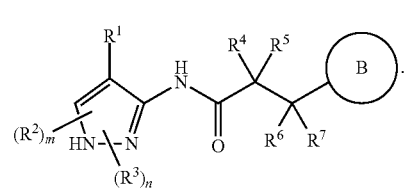

(I-2)

11. The compound according to claim 1 or a pharmacologically acceptable salt thereof, which is represented by the following general formula (I-5)

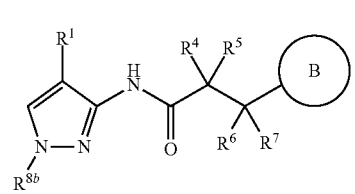

(I-5)

wherein $R^{8b}$ represents a hydrogen atom, a $C_1$-$C_4$ alkyl group, a ($C_1$-$C_2$ alkoxy)-($C_1$-$C_4$ alkyl) group, a halogeno ($C_1$-$C_4$ alkyl) group, a $C_3$-$C_6$ cycloalkyl group, a $C_2$-$C_4$ alkenyl group, or a $C_2$-$C_4$ alkynyl group.

12. The compound according to claim 11 or a pharmacologically acceptable salt thereof, wherein $R^{8b}$ represents a $C_1$-$C_4$ alkyl group.

13. The compound according to claim 1 or a pharmacologically acceptable salt thereof, wherein $R^1$ represents a carboxy group.

14. The compound according to claim 1 or a pharmacologically acceptable salt thereof, wherein each of $R^4$, $R^5$, $R^6$, and $R^7$ independently represents a hydrogen atom, a $C_1$-$C_2$ alkyl group, a halogeno($C_1$-$C_2$ alkyl) group (wherein the halogeno group(s) represent 1 to 5 groups selected from the group consisting of a fluoro group and a chloro group), a fluoro group, or a chloro group.

15. The compound according to claim 1 or a pharmacologically acceptable salt thereof, wherein each of $R^4$, $R^5$, $R^6$, and $R^7$ independently represents a hydrogen atom or a fluoro group.

16. The compound according to claim 1 or a pharmacologically acceptable salt thereof, wherein each of $R^4$ and $R^5$ independently represents a hydrogen atom or a fluoro group, and $R^6$ and $R^7$ each represent a hydrogen atom.

17. The compound according to claim 1 or a pharmacologically acceptable salt thereof, wherein B represents a naphthyl group or a substituted naphthyl group (wherein the substituent(s) represent 1 to 3 groups independently selected from substituent group α3), and substituent group α3 represents the group consisting of a $C_1$-$C_2$ alkyl group, a halogeno($C_1$-$C_2$ alkyl) group (wherein the halogeno group(s) represent 1 to 5 groups selected from the group consisting of a fluoro group and a chloro group), a hydroxy group, a $C_1$-$C_2$ alkoxy group, a fluoro group, and a chloro group.

18. The compound according to claim 1 or a pharmacologically acceptable salt thereof, wherein B represents a group represented by the following formula (IIa)

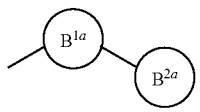

(IIa)

wherein $B^{1a}$ represents a phenyl group, a substituted phenyl group (wherein the substituent(s) represent 1 to 3 groups independently selected from substituent group α4), a 5-membered aromatic heterocyclyl group, or a substituted 5-membered aromatic heterocyclyl group (wherein the substituent(s) represent 1 to 3 groups independently selected from substituent group α4), $B^{2a}$ represents a phenyl group, a substituted phenyl group (wherein the substituent(s) represent 1 to 3 groups independently selected from substituent group α5), a pyridyl group, or a substituted pyridyl group (wherein the substituent(s) represent 1 to 3 groups independently selected from substituent group α5), substituent group α4 represents the group consisting of a $C_1$-$C_4$ alkyl group, a halogeno($C_1$-$C_4$ alkyl) group, a ($C_3$-$C_6$ cycloalkyl)-($C_1$-$C_4$ alkyl) group, a $C_3$-$C_6$ cycloalkyl group, a $C_1$-$C_4$ alkoxy group, a formyl group, a ($C_1$-$C_4$ alkyl)carbonyl group, a cyano group, a fluoro group, a chloro group, and a bromo group, and substituent group α5 represents the group consisting of a $C_1$-$C_4$ alkyl group, a halogeno($C_1$-$C_4$ alkyl) group, a hydroxy group, a $C_1$-$C_4$ alkoxy group, a fluoro group, a chloro group, and a bromo group.

19. The compound according to claim 1 or a pharmacologically acceptable salt thereof, wherein B represents a group represented by the following formula (IIb)

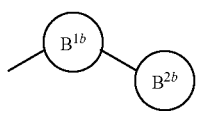

(IIb)

wherein $B^{1b}$ represents a nitrogen-containing 5-membered aromatic heterocyclyl group or a substituted nitrogen-containing 5-membered aromatic heterocyclyl group (wherein the substituent(s) represent 1 or 2 groups independently selected from substituent group α6), $B^{2b}$ represents a phenyl group, a substituted phenyl group (wherein the substituent(s) represent 1 or 2 groups independently selected from substituent group α7), a pyridyl group, or a substituted pyridyl group (wherein the substituent(s) represent 1 or 2 groups independently selected from substituent group α7), substituent group α6 represents the group consisting of a $C_1$-$C_4$ alkyl group, a halogeno($C_1$-$C_2$ alkyl) group (wherein the halogeno group(s) represent 1 to 5 groups selected from the group consisting of a fluoro group and a chloro group), a ($C_3$-$C_4$ cycloalkyl)-($C_1$-$C_2$ alkyl) group, a $C_3$-$C_4$ cycloalkyl group, a ($C_1$-$C_2$ alkyl)carbonyl group, a cyano group, a fluoro group, and a chloro group, and substituent group α7 represents the group consisting of a $C_1$-$C_2$ alkyl group, a hydroxy group, a fluoro group, and a chloro group.

20. The compound according to claim 1 or a pharmacologically acceptable salt thereof, wherein B represents a group represented by the following formula (IIc)

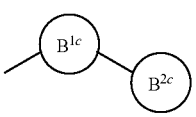

(IIc)

wherein $B^{1c}$ represents a group selected from the following groups or a group which is selected from the following groups and substituted (wherein the substituent represents one group independently selected from substituent group α8)

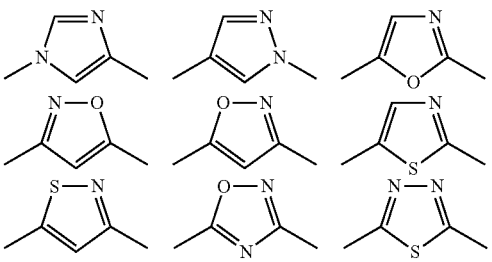

$B^{2c}$ represents a phenyl group or a 4-hydroxyphenyl group, and substituent group α8 represents the group consisting of a $C_1$-$C_4$ alkyl group, a halogeno($C_1$-$C_2$ alkyl) group (wherein the halogeno group(s) represent 1 to 5 groups selected from the group consisting of a fluoro group and a chloro group), a cyclopropyl group, a methylcarbonyl group, a cyano group, a fluoro group, and a chloro group.

21. The compound according to claim 1 or a pharmacologically acceptable salt thereof, wherein B represents a group represented by the following formula (IId)

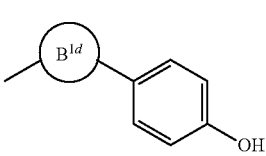

(IId)

wherein $B^{1d}$ represents a group selected from the following groups or a group which is selected from the following groups and substituted (wherein the substituent represents one group selected from substituent group α9)

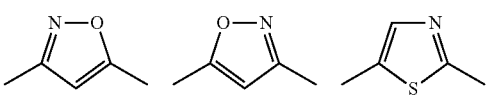

and substituent group α9 represents the group consisting of a methyl group, an ethyl group, and a chloro group.

22. The compound according to claim 1 or a pharmacologically acceptable salt thereof, which is selected from the group consisting of 4-{3-[2-(4-hydroxyphenyl)thiazol-5-yl]
propanoyl}amino-1-ethylpyrrole-3-carboxylic acid;
4-{3-[2-(4-hydroxyphenyl)thiazol-5-yl]-2-
fluoropropanoyl}amino-1-ethylpyrrole-3-carboxylic
acid;
4-{3-[3-(4-hydroxyphenyl)-4-ethylisoxazol-5-yl]
propanoyl}amino-1-ethylpyrrole-3-carboxylic acid;
4-{3-[4-chloro-(4-hydroxyphenyl)isoxazol-5-yl]
propanoyl}amino-1-ethylpyrrole-3-carboxylic acid;
4-{3-[4-ethyl-(4-hydroxyphenyl)isoxazol-5-yl]
propanoyl}amino-1-ethylpyrrole-3-carboxylic acid;
4-{3-[(4-hydroxyphenyl)-4-methylisoxazol-5-yl]
propanoyl}amino-1-ethylpyrrole-3-carboxylic acid;
4-{3-[2-(4-hydroxyphenyl)thiazol-5-yl]-2,2-
difluoropropanoyl}amino-1-ethylpyrrole-3-carboxylic
acid;
4-{3-[4-ethyl-3-(4-hydroxyphenyl)isoxazol-5-yl]-2,2-
difluoropropanoyl}amino-1-ethylpyrrole-3-carboxylic
acid;
4-{3-[4-ethyl-5-(4-hydroxyphenyl)isoxazol-3-yl]-2,2-
difluoropropanoyl}amino-1-ethylpyrrole-3-carboxylic
acid;
4-{3-[4-chloro-5-(4-hydroxyphenyl)isoxazol-3-yl]-2,2-
fluoropropanoyl}amino-1-ethylpyrrole-3-carboxylic
acid;
4-{3-[3-(4-hydroxyphenyl)isoxazol-5-yl]-2-
fluoropropanoyl}amino-1-ethylpyrrole-3-carboxylic
acid; and
4-{3-[3-(4-hydroxyphenyl)isoxazol-5-yl]-2,2-
difluoropropanoyl}amino-1-ethylpyrrole-3-carboxylic
acid.

23. A pharmaceutical composition comprising, as an active ingredient, the compound according to claim 1 or a pharmacologically acceptable salt thereof.

24. A method for the treatment of hyperlipidemia, dyslipidemia, lipid metabolism abnormality, arteriosclerosis, or type II diabetes mellitus, which comprises administering a pharmaceutically effective amount of the compound according to claim 1 or a pharmacologically acceptable salt thereof to a warm-blooded animal.

25. The method according to claim 24, wherein the disease is dyslipidemia.

26. The method according to claim 24, wherein the disease is lipid metabolism abnormality.

27. A compound of claim 1 that is 4-{3-[2-(4-hydroxyphenyl)thiazol-5-yl]-2-fluoropropanoyl}amino-1-ethylpyrrole-3-carboxylic acid or a pharmaceutically salt thereof.

28. A potassium salt of 4-{3-[2-(4-hydroxyphenyl)thiazol-5-yl]-2-fluoropropanoyl}amino-1-ethylpyrrole-3-carboxylic acid.

29. A compound of claim 1 that is 4-{3-[(4-hydroxyphenyl)-4-methylisoxazol-5-yl]propanoyl}amino-1-ethylpyrrole-3-carboxylic acid or a pharmaceutically salt thereof.

30. A potassium salt of 4-{3-[(4-hydroxyphenyl)-4-methylisoxazol-5-yl]propanoyl}amino-1-ethylpyrrole-3-carboxylic acid.

31. A compound of claim 1 that is 4-{3-[3-(4-hydroxyphenyl)isoxazol-5-yl]-2,2-difluoropropanoyl}amino-1-ethylpyrrole-3-carboxylic acid or a pharmaceutically salt thereof.

32. A potassium salt of 4-{3-[3-(4-hydroxyphenyl)isoxazol-5-yl]-2,2-difluoropropanoyl}amino-1-ethylpyrrole-3-carboxylic acid.

33. A pharmaceutical composition comprising, as an active ingredient, the compound according to claim 27.

34. A pharmaceutical composition comprising, as an active ingredient, the compound according to claim 28.

35. A pharmaceutical composition comprising, as an active ingredient, the compound according to claim 29.

36. A pharmaceutical composition comprising, as an active ingredient, the compound according to claim 30.

37. A pharmaceutical composition comprising, as an active ingredient, the compound according to claim 31.

38. A pharmaceutical composition comprising, as an active ingredient, the compound according to claim 32.

39. A method for the treatment of hyperlipidemia, dyslipidemia, lipid metabolism abnormality, arteriosclerosis, or type II diabetes mellitus, which comprises administering a pharmaceutically effective amount of the compound according to claim 27 or a pharmacologically acceptable salt thereof to a warm-blooded animal.

40. A method for the treatment of hyperlipidemia, dyslipidemia, lipid metabolism abnormality, arteriosclerosis, or type II diabetes mellitus, which comprises administering a pharmaceutically effective amount of the compound according to claim 28 to a warm-blooded animal.

41. A method for the treatment of hyperlipidemia, dyslipidemia, lipid metabolism abnormality, arteriosclerosis, or type II diabetes mellitus, which comprises administering a pharmaceutically effective amount of the compound according to claim 29 or a pharmacologically acceptable salt thereof to a warm-blooded animal.

42. A method for the treatment of hyperlipidemia, dyslipidemia, lipid metabolism abnormality, arteriosclerosis, or type II diabetes mellitus, which comprises administering a pharmaceutically effective amount of the compound according to claim 30 to a warm-blooded animal.

43. A method for the treatment of hyperlipidemia, dyslipidemia, lipid metabolism abnormality, arteriosclerosis, or type II diabetes mellitus, which comprises administering a pharmaceutically effective amount of the compound according to claim 31 or a pharmacologically acceptable salt thereof to a warm-blooded animal.

44. A method for the treatment of hyperlipidemia, dyslipidemia, lipid metabolism abnormality, arteriosclerosis, or type II diabetes mellitus, which comprises administering a pharmaceutically effective amount of the compound according to claim 32 to a warm-blooded animal.

* * * * *